US007566805B2

(12) United States Patent
Hickey et al.

(10) Patent No.: US 7,566,805 B2
(45) Date of Patent: Jul. 28, 2009

(54) MODAFINIL COMPOSITIONS

(75) Inventors: Magali Bourghol Hickey, Medford, MA (US); Matthew Peterson, Hopkinton, MA (US); Orn Almarsson, Shrewsbury, MA (US); Mark Oliveira, Framingham, MA (US)

(73) Assignee: Cephalon, Inc., Frazer, PA (US)

( * ) Notice: Subject to any disclaimer, the term of this patent is extended or adjusted under 35 U.S.C. 154(b) by 107 days.

(21) Appl. No.: 10/570,405

(22) PCT Filed: Sep. 4, 2004

(86) PCT No.: PCT/US2004/029013

§ 371 (c)(1),
(2), (4) Date: Mar. 3, 2006

(87) PCT Pub. No.: WO2005/023198

PCT Pub. Date: Mar. 17, 2005

(65) Prior Publication Data

US 2007/0021510 A1    Jan. 25, 2007

Related U.S. Application Data

(60) Provisional application No. 60/508,208, filed on Oct. 2, 2003, provisional application No. 60/542,752, filed on Feb. 6, 2004, provisional application No. 60/560,411, filed on Apr. 6, 2004, provisional application No. 60/573,412, filed on May 21, 2004, provisional application No. 60/579,176, filed on Jun. 12, 2004, provisional application No. 60/581,992, filed on Jun. 22, 2004, provisional application No. 60/586,752, filed on Jul. 9, 2004, provisional application No. 60/588,236, filed on Jul. 15, 2004.

(30) Foreign Application Priority Data

Sep. 4, 2003   (WO) .................... PCT/US03/27772
Feb. 26, 2004  (WO) ............... PCT/US2004/006288

(51) Int. Cl.
*C07C 323/22* (2006.01)
*A61K 31/165* (2006.01)

(52) U.S. Cl. ..................................... 564/162; 514/618
(58) Field of Classification Search ...................... None
See application file for complete search history.

(56) References Cited

U.S. PATENT DOCUMENTS

| 4,927,855 A | 5/1990 | Lafon |
| 2003/0224006 A1 | 12/2003 | Zaworotko et al. |
| 2004/0019211 A1 | 1/2004 | Remenar |

FOREIGN PATENT DOCUMENTS

| WO | WO 02/056915 | 7/2002 |
| WO | WO 03/074474 | 9/2003 |

OTHER PUBLICATIONS

Database CAPLUS on STN, Acc. No. 2002:107306, Singer et al., WO 2002010125 (Feb. 7, 2002) (abstract).*
*FDA Approved Labeling Text for NDA* 20-717/S-005 & S-008 Approved Jan. 23, 2004, 2004, pp. 1-35.

* cited by examiner

*Primary Examiner*—Brian J Davis

(57) ABSTRACT

Co-crystals and solvates of racemic, enantiomerically pure, and enantiomerically mixed modafinil are formed and several important physical properties are modulated. The solubility, dissolution, bioavailability, dose response, and stability of modafinil can be modulated to improve efficacy in pharmaceutical compositions.

53 Claims, 56 Drawing Sheets

| Position: | 124.38 | Intensity: | 56488.199 |
| Position: | 1003.39 | Intensity: | 32065.602 |
| Position: | 190.78 | Intensity: | 19242.451 |
| Position: | 624.92 | Intensity: | 16043.604 |
| Position: | 1032.16 | Intensity: | 14613.689 |
| Position: | 267.46 | Intensity: | 13128.612 |
| Position: | 822.14 | Intensity: | 11636.112 |
| Position: | 1181.06 | Intensity: | 11607.680 |
| Position: | 1601.13 | Intensity: | 11005.503 |
| Position: | 725.91 | Intensity: | 9152.309 |
| Position: | 494.61 | Intensity: | 7458.328 |
| Position: | 362.59 | Intensity: | 6747.720 |
| Position: | 887.40 | Intensity: | 5256.710 |
| Position: | 1106.67 | Intensity: | 5119.203 |

MODAFINIL COMPOSITIONS

CROSS REFERENCE TO RELATED APPLICATIONS

This application is a §371 National Stage filing of PCT/US2004/029013 filed Sep. 4, 2004 and claims the benefit of PCT/US2004/006288 filed Feb. 26, 2004, PCT/US2003/027772 filed Sep. 4, 2003 and US provisional applications U.S. Ser. No. 60/542,752 filed Feb. 6, 2004, U.S. Ser. No. 60/560,411 filed Apr. 6, 2004, U.S. Ser. No. 60/573,412 filed May 21, 2004, 60/579,176 filed Jun. 12, 2004, U.S. Ser. No. 60/581,992 filed Jun. 22, 2004, U.S. Ser. No. 60/586,752 filed Jul. 9, 2004, U.S. Ser. No. 60/588,236 filed Jul. 15, 2004, U.S. Ser. No. 60/508,208 filed Oct. 2, 2003 and non-provisional application U.S. Ser. No. 10/660,202 filed Sep. 11, 2003.

This application is a 371 of PCT/US/04/29013, filed Sep. 4, 2003, which claims the benefit of PCT/US/03/2772, filed Sep. 4, 2003, U.S. Ser. No. 10/660,202, filed Sep. 11, 2003, U.S. Ser. No. 60/508,208, filed Oct. 2, 2003, U.S. Ser. No. 60/542,752, filed Feb. 6, 2004, PCT/US/04/06288, filed Feb. 26, 2004, U.S. Ser. No. 60/560,411, filed Apr. 6, 2004, U.S. Ser. No. 60/573,412, filed May 21, 2004, U.S. Ser. No. 60/579,176, filed Jun. 12, 2004, U.S. Ser. No. 60/581,992, filed Jun. 22, 2004, U.S. Ser. No. 60/586,752, filed Jul. 9, 2004, and U.S. Ser. No. 60/588,236, filed Jul. 15, 2004.

This application is also a continuation-in-part of U.S. application Ser. No. 10/660,202, filed Sep. 11, 2003, which claims the benefit of PCT/US03/27772, filed Sep. 4, 2003. Said U.S. application Ser. No. 10/660,202, filed Sep. 11, 2003 also claims the benefit of U.S. application Ser. No. 10/637,829, filed Aug. 8, 2003, which is a divisional of U.S. application Ser. No. 10/295,995, filed Nov. 18, 2002, which is a continuation of U.S. application Ser. No. 10/232,589, filed Sep. 3, 2002, which claims the benefit of U.S. Provisional Application No. 60/406,974, filed Aug. 30, 2002, U.S. Provisional Application No. 60/380,288, filed May 15, 2002, and U.S. Provisional Application No. 60/356,764, filed Feb. 15, 2002. Said U.S. application Ser. No. 10/660,202, filed Sep. 11, 2003, is also a continuation-in-part of U.S. application Ser. No. 10/449,307, filed May 30, 2003, which claims the benefit of U.S. Provisional Application No. 60/463,962, filed Apr. 18, 2003, U.S. Provisional Application No. 60/444,315, filed Jan. 31, 2003, U.S. Provisional Application No. 60/439,282, filed Jan. 10, 2003, and U.S. Provisional Application No. 60/384,152, filed May 31, 2002. Said U.S. application Ser. No. 10/660,202, filed Sep. 11, 2003, is also a continuation-in-part of U.S. application Ser. No. 10/601,092, filed Jun. 20, 2003. Said U.S. application Ser. No. 10/660,202, filed Sep. 11, 2003, also claims the benefit of U.S. Provisional Application No. 60/451,213, filed Feb. 28, 2003, U.S. Provisional Application No. 60/463,962, filed Apr. 18, 2003, and U.S. Provisional Application No. 60/487,064, filed Jul. 11, 2003.

This application is also a continuation-in-part of Application No. PCT/US04/06288, filed Feb. 26, 2004, which claims the benefit of U.S. Provisional Application No. 60/451,213, filed Feb. 28, 2003, U.S. Provisional Application No. 60/487,064, filed Jul. 11, 2003, Application No. PCT/US03/27772, filed Sep. 4, 2003, U.S. application Ser. No. 10/660,202, filed Sep. 11, 2003, Application No. PCT/US03/06662, filed Mar. 3, 2003, U.S. Provisional Application No. 60/508,208, filed Oct. 2, 2003, U.S. Provisional Application No. 60/542,752, filed Feb. 6, 2004, U.S. Provisional Application No. 60/463,962, filed Apr. 18, 2003, U.S. application Ser. No. 10/449,307, filed May 30, 2003, U.S. Provisional Application No. 60/456,027, filed Mar. 18, 2003, U.S. application Ser. No. 10/601,092, filed Jun. 20, 2003, Application No. PCT/US03/19574, filed Jun. 20, 2003, and Application No. PCT/US03/41273, filed Dec. 24, 2003.

This application also claims the benefit of U.S. Provisional Application No. 60/508,208, filed Oct. 2, 2003, U.S. Provisional Application No. 60/542,752, filed Feb. 6, 2004, U.S. Provisional Application No. 60/560,411, filed Apr. 6, 2004, U.S. Provisional Application No. 60/573,412, filed May 21, 2004, U.S. Provisional Application No. 60/579,176, filed Jun. 12, 2004, U.S. Provisional Application No. 60/581,992, filed Jun. 22, 2004, U.S. Provisional Application No. 60/586,752, filed Jul. 9, 2004, and U.S. Provisional Application No. 60/588,236, filed Jul. 15, 2004.

All of the applications above, to which a benefit is claimed, are herein incorporated by reference in their entireties.

FIELD OF THE INVENTION

The present invention relates to API-containing compositions, pharmaceutical compositions comprising such APIs, and methods for preparing the same.

BACKGROUND OF THE INVENTION

Active pharmaceutical ingredients (API or APIs (plural)) in pharmaceutical compositions can be prepared in a variety of different forms. Such APIs can be prepared so as to have a variety of different chemical forms including chemical derivatives, solvates, hydrates, co-crystals, or salts. Such APIs can also be prepared to have different physical forms. For example, the APIs may be amorphous, may have different crystalline polymorphs, or may exist in different solvation or hydration states. By varying the form of an API, it is possible to vary the physical properties thereof. For example, crystalline polymorphs typically have different solubilities from one another, such that a more thermodynamically stable polymorph is less soluble than a less thermodynamically stable polymorph. Pharmaceutical polymorphs can also differ in properties such as shelf-life, bioavailability, morphology, vapour pressure, density, colour, and compressibility. Accordingly, variation of the crystalline state of an API is one of many ways in which to modulate the physical properties thereof.

It would be advantageous to have new forms of these APIs that have improved properties, in particular, as oral formulations. Specifically, it is desirable to identify improved forms of APIs that exhibit significantly improved properties including increased aqueous solubility and stability. Further, it is desirable to improve the processability, or preparation of pharmaceutical formulations. For example, needle-like crystal forms or habits of APIs can cause aggregation, even in compositions where the API is mixed with other substances, such that a non-uniform mixture is obtained. Needle-like morphologies can also give rise to filtration problems (See e.g., Mirmehrabi et al. J. Pharm. Sci. Vol. 93, No. 7, pp. 1692-1700, 2004). It is also desirable to increase the dissolution rate of API-containing pharmaceutical compositions in water, increase the bioavailability of orally-administered compositions, and provide a more rapid onset to therapeutic effect. It is also desirable to have a form of the API which, when administered to a subject, reaches a peak plasma level faster, has a longer lasting therapeutic plasma concentration, and higher overall exposure when compared to equivalent amounts of the API in its presently-known form.

Modafinil, an API used to treat subjects with narcolepsy, is practically insoluble in water. Modafinil (CAS Registry Number: 68693-11-8) is represented by the structure (I):

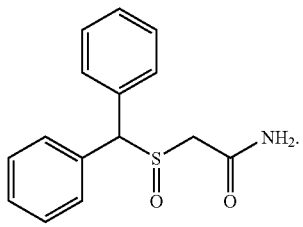

Modafinil is a chiral molecule due to the chiral S=O group. Therefore, modafinil exists as two isomers, R-(−)-modafinil and S-(+)-modafinil. It would be advantageous to have new forms of modafinil that have improved properties, in particular, as oral formulations. Specifically, it is desirable to identify improved forms of modafinil that exhibit significantly increased aqueous solubilities and both chemical and form stability. It is also desirable to increase the dissolution rate of API-containing pharmaceutical compositions in water, increase the bioavailability of orally-administered compositions, and provide a more rapid onset to therapeutic effect. It is also desirable to have a form of the API which, when administered to a subject, reaches a peak plasma level faster and/or has a longer lasting plasma concentration and higher overall exposure at high doses when compared to equivalent amounts of the API in its presently-known form.

SUMMARY OF THE INVENTION

It has now been found that co-crystals and solvates of modafinil can be obtained, many of which have different properties as compared to the free form of the API.

Accordingly, in a first aspect, the present invention provides a co-crystal of modafinil, wherein the co-crystal former is an ether, thioether, alcohol, thiol, aldehyde, ketone, thioketone, nitrate ester, phosphate ester, thiophosphate ester, ester, thioester, sulfate ester, carboxylic acid, phosphonic acid, phosphinic acid, sulfonic acid, amide, primary amine, secondary amine, ammonia, tertiary amine, sp2 amine, thiocyanate, cyanamide, oxime, nitrile, diazo, organohalide, nitro, S-heterocyclic ring, thiophene, N-heterocyclic ring, pyrrole, O-heterocyclic ring, furan, epoxide, hydroxamic acid, imidazole, or pyridine.

The invention further provides a pharmaceutical composition comprising a co-crystal of modafinil. Typically, the pharmaceutical composition further comprises one or more pharmaceutically-acceptable carriers, diluents or excipients. Pharmaceutical compositions according to the invention are described in further detail below.

In a further aspect, the present invention provides a process for the preparation of a co-crystal of modafinil, which comprises:
(a) providing modafinil;
(b) providing a co-crystal former compatible with a functional group of modafinil such that the co-crystal former and the modafinil can form a co-crystal;
(c) grinding, heating, co-subliming, co-melting, or contacting in solution the modafinil with the co-crystal former under crystallization conditions, so as to form a solid phase; and
(d) isolating co-crystals comprising modafinil and the co-crystal former.

In an embodiment, the co-crystal former has at least one functional group selected from the group consisting of ether, thioether, alcohol, thiol, aldehyde, ketone, thioketone, nitrate ester, phosphate ester, thiophosphate ester, ester, thioester, sulfate ester, carboxylic acid, phosphonic acid, phosphinic acid, sulfonic acid, amide, primary amine, secondary amine, ammonia, tertiary amine, sp2 amine, thiocyanate, cyanamide, oxime, nitrile, diazo, organohalide, nitro, S-heterocyclic ring, thiophene, N-heterocyclic ring, pyrrole, O-heterocyclic ring, furan, epoxide, hydroxamic acid, imidazole, or pyridine.

Embodiments of the present invention including, but not limited to, co-crystals, polymorphs, and solvates can comprise racemic modafinil, enantiomerically pure modafinil (i.e., R-(−)-modafinil or S-(+)-modafinil), or enriched modafinil (e.g., between about 55 and about 90 percent ee). Similarly, co-crystal formers and solvent molecules (e.g., in a solvate) can also exist as racemic, enantiomerically pure, or an enriched form in embodiments of the present invention.

In a further aspect, the present invention provides a process for increasing the solubility of modafinil in water, simulated gastric fluid (SGF), or simulated intestinal fluid (SIF) for use in a pharmaceutical composition or medicament, which process comprises:
(a) providing modafinil;
(b) providing a co-crystal former compatible with a functional group of modafinil such that the co-crystal former and the modafinil can form a co-crystal;
(c) grinding, heating, co-subliming, co-melting, or contacting in solution the modafinil with the co-crystal former under crystallization conditions, so as to form a solid phase; and
(d) isolating co-crystals comprising the modafinil and the co-crystal former.

In a further aspect, the present invention provides a process for modulating the dissolution of modafinil, whereby the aqueous dissolution rate or the dissolution rate in simulated gastric fluid or in simulated intestinal fluid, or in a solvent or plurality of solvents is increased, which process comprises:
(a) providing modafinil;
(b) providing a co-crystal former compatible with a functional group of modafinil such that the co-crystal former and the modafinil can form a co-crystal;
(c) grinding, heating, co-subliming, co-melting, or contacting in solution the modafinil with the co-crystal former under crystallization conditions, so as to form a solid phase; and
(d) isolating co-crystals comprising the modafinil and the co-crystal former.

In a further aspect, the present invention provides a process for modulating the bioavailability of modafinil, whereby the AUC is increased, the time to $T_{max}$ is reduced, the length of time the concentration of modafinil is above ½ $T_{max}$ is increased, or $C_{max}$ is increased, which process comprises:
(a) providing modafinil;
(b) providing a co-crystal former compatible with a functional group of modafinil such that the co-crystal former and the modafinil can form a co-crystal;
(c) grinding, heating, co-subliming, co-melting, or contacting in solution the modafinil with the co-crystal former under crystallization conditions, so as to form a solid phase; and
(d) isolating co-crystals comprising the modafinil and the co-crystal former.

In a further aspect, the present invention provides a process for modulating the dose response of modafinil for use in a pharmaceutical composition or medicament, which process comprises:

(a) providing modafinil;
(b) providing a co-crystal former compatible with a functional group of modafinil such that the co-crystal former and the modafinil can form a co-crystal;
(c) grinding, heating, co-subliming, co-melting, or contacting in solution the modafinil with the co-crystal former under crystallization conditions, so as to form a solid phase; and
(d) isolating co-crystals comprising the modafinil and the co-crystal former.

In a still further aspect the present invention provides a process for improving the stability of modafinil (as compared to a reference form such as its free form), which process comprises:
(a) providing modafinil;
(b) providing a co-crystal former compatible with a functional group of modafinil such that the co-crystal former and the modafinil can form a co-crystal;
(c) grinding, heating, co-subliming, co-melting, or contacting in solution the modafinil with the co-crystal former under crystallization conditions, so as to form a solid phase; and
(d) isolating co-crystals comprising the modafinil and the co-crystal former.

In a still further aspect the present invention provides a process for modifying the morphology of modafinil, which process comprises:
(a) providing modafinil;
(b) providing a co-crystal former compatible with a functional group of modafinil such that the co-crystal former and the modafinil can form a co-crystal;
(c) grinding, heating, co-subliming, co-melting, or contacting in solution the modafinil with the co-crystal former under crystallization conditions, so as to form a solid phase; and
(d) isolating co-crystals comprising the modafinil and the co-crystal former.

In a still further aspect, the present invention therefore provides a process of screening for co-crystal compounds, which comprises:
(a) providing (i) modafinil and (ii) a co-crystal former compatible with a functional group of modafinil such that the co-crystal former and the modafinil can form a co-crystal; and
(b) screening for co-crystals of modafinil with a co-crystal former by subjecting each combination of modafinil and co-crystal former to a procedure comprising:
  (i) grinding, heating, co-subliming, co-melting, or contacting in solution the modafinil with the co-crystal former under crystallization conditions, so as to form a solid phase; and
  (ii) isolating co-crystals comprising the modafinil and the co-crystal former.

An alternative embodiment is drawn to a process of screening for co-crystal compounds, which comprises:
(a) providing (i) modafinil and (ii) a plurality of different co-crystal formers compatible with a functional group of modafinil such that each co-crystal former and the modafinil can form a co-crystal; and
(b) screening for co-crystals of modafinil with co-crystal formers by subjecting each combination of modafinil and co-crystal former to a procedure comprising:
  (i) grinding, heating, co-subliming, co-melting, or contacting in solution the modafinil with the co-crystal former under crystallization conditions, so as to form a solid phase; and
  (ii) isolating co-crystals comprising the modafinil and the co-crystal former.

In a further aspect, the present invention provides a co-crystal composition comprising a co-crystal, wherein said co-crystal comprises modafinil and a co-crystal former. In further embodiments the co-crystal has an improved property as compared to the free form (which includes hydrates and solvates). In further embodiments, the improved property is selected from the group consisting of: increased solubility, increased dissolution, increased bioavailability, increased dose response, or other property described herein.

In another embodiment, the present invention provides a co-crystal comprising modafinil and a co-crystal former selected from the group consisting of: malonic acid, glycolic acid, fumaric acid, tartaric acid, citric acid, succinic acid, gentisic acid, oxalic acid, 1-hydroxy-2-naphthoic acid, orotic acid, glutaric acid, L-tartaric acid, palmitic acid, L-proline, salicylic acid, lauric acid, L-malic acid, and maleic acid.

In further embodiments, the present invention provides the following co-crystals: modafinil:malonic acid, modafinil:glycolic acid, modafinil:maleic acid, modafinil:L-tartaric acid, modafinil:citric acid, modafinil:succinic acid, modafinil:DL-tartaric acid, modafinil:fumaric acid (Form I), modafinil:fumaric acid (Form II), modafinil:gentisic acid, modafinil:oxalic acid, modafinil:1-hydroxy-2-naphthoic acid, R-(−)-modafinil:malonic acid, R-(−)-modafinil:succinic acid, R-(−)-modafinil:citric acid, R-(−)-modafinil:DL-tartaric acid, R-(−)-modafinil:1-hydroxy-2-naphthoic acid, R-(−)-modafinil:orotic acid, R-(−)-modafinil:glutaric acid, R-(−)-modafinil:L-tartaric acid, R-(−)-modafinil:palmitic acid, R-(−)-modafinil:L-proline, R-(−)-modafinil:salicylic acid, R-(−)-modafinil:lauric acid, R-(−)-modafinil:L-malic acid, and R-(−)-modafinil:gentisic acid.

In another embodiment, the present invention provides a novel polymorph or co-crystal of racemic modafinil (form VII).

In another embodiment, the present invention provides the following modafinil solvates: acetic acid, tetrahydrofuran, 1,4-dioxane, methanol, nitromethane, acetone, o-xylene, benzene, ethanol, benzyl alcohol, isopropanol, acetonitrile, and toluene.

The processes according to the present invention may each comprise a further step or steps in which the modafinil co-crystal produced thereby is incorporated into a pharmaceutical composition.

In another embodiment, a pharmaceutical composition comprises a modified release profile of one or more of racemic modafinil, R-(−)-modafinil, and S-(+)-modafinil. The modified release profile can comprise, for example, two or more maxima of plasma concentration, such as a dual-release profile.

The invention further provides a medicament comprising a co-crystal of modafinil and methods of making the same. Typically, the medicament further comprises one or more pharmaceutically-acceptable carriers, diluents or excipients. Medicaments according to the invention are described in further detail below.

The processes according to the present invention may each comprise a further step or steps in which the modafinil co-crystal produced thereby is incorporated into a medicament.

In a still further aspect of the invention, a method is provided for treating a subject, preferably a human subject, suffering from excessive daytime sleepiness associated with narcolepsy, multiple sclerosis related fatigue, infertility, eating disorders, attention deficit hyperactivity disorder (ADHD), Parkinson's disease, incontinence, sleep apnea, or myopathies where modafinil is an effective active pharmaceutical for said disorder. The method comprises administering to the subject a therapeutically-effective amount of a co-crystal or a solvate comprising modafinil, or a polymorph of modafinil.

DETAILED DESCRIPTION OF THE INVENTION

Figure 1:
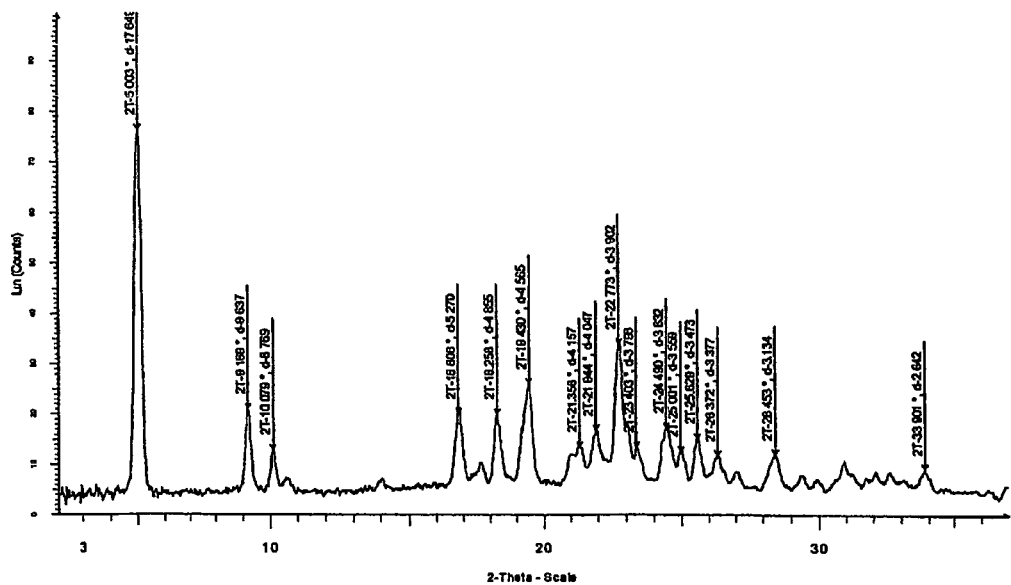
FIG. 1—PXRD diffractogram of a co-crystal comprising modafinil and malonic acid.

The structure of modafinil includes a stereocenter and, therefore, can exist as a racemate, one of two pure isomers, or any ratio of the two isomeric pairs. The chemical name of racemic modafinil is (±)-2-[(Diphenylmethyl)sulfinyl]acetamide. The isomeric pairs of racemic modafinil are R-(−)-2-[(Diphenylmethyl)sulfinyl]acetamide or R-(−)-modafinil and S-(+)-2-[(Diphenylmethyl)sulfinyl]acetamide or S-(+)-modafinil.

As used herein and unless otherwise specified, the term "enantiomerically pure" includes a composition which is substantially enantiomerically pure and includes, for example, a composition with greater than or equal to about 90, 91, 92, 93, 94, 95, 96, 97, 98, or 99 percent enantiomeric excess. Enantiomeric excess is defined by percent enantiomer A-percent enantiomer B, or by the formula: ee percent=100*([R]−[S]/([R]+[S]), where R is moles of R-(−)-modafinil and S is moles of S-(+)-modafinil.

As used herein, the term "modafinil" includes the racemate, other mixtures of R- and S-isomers, and single enantiomers, but may be specifically set forth as the racemate, R-isomer, S-isomer, or any mixture of both R- and S-isomers.

As used herein and unless otherwise specified, the term "racemic co-crystal" refers to a co-crystal which is comprised of an equimolar mixture of the enantiomers of modafinil, the co-crystal former, or both. For example, a co-crystal comprising modafinil and a non-stereoisomeric co-crystal former is a "racemic co-crystal" only when there is present an equimolar mixture of the modafinil enantiomers. Similarly, a co-crystal comprising modafinil and a stereoisomeric co-crystal former is a "racemic co-crystal" only when there is present an equimolar mixture of the modafinil enantiomers and of the co-crystal former enantiomers.

As used herein and unless otherwise specified, the term "enantiomerically pure co-crystal" refers to a co-crystal which is comprised of modafinil and a stereoisomeric or non-stereoisomeric co-crystal former where the enantiomeric excess of the stereoisomeric species is greater than or equal to about 90 percent ee (enantiomeric excess).

The term "co-crystal" as used herein means a crystalline material comprised of two or more unique solids at room temperature (22 degrees C.), each containing distinctive physical characteristics, such as structure, melting point, and heats of fusion, with the exception that, if specifically stated, the API may be a liquid at room temperature. The co-crystals of the present invention comprise a co-crystal former H-bonded to modafinil or a derivative thereof. The co-crystal former may be H-bonded directly to modafinil or may be H-bonded to an additional molecule which is bound to modafinil. The additional molecule may be H-bonded to modafinil or bound ionically to modafinil. The additional molecule could also be a different API. Solvates of modafinil compounds that do not further comprise a co-crystal former are not co-crystals according to the present invention. The co-crystals may however, include one or more solvate molecules in the crystalline lattice. That is, a solvate of co-crystal, or a co-crystal further comprising a solvent or compound that is a liquid at room temperature, is a co-crystal according to the present invention, but crystalline material comprised of only modafinil and one or more liquids (at room temperature) are not co-crystals for purposes of the present invention. Other modes of molecular recognition may also be present including, pi-stacking, guest-host complexation and van der Waals interactions. Of the interactions listed above, hydrogen-bonding is the dominant interaction in the formation of the co-crystal, (and a required interaction according to the present invention) whereby a non-covalent bond is formed between a hydrogen bond donor of one of the moieties and a hydrogen bond acceptor of the other. Hydrogen bonding can result in several different intermolecular configurations. For example, hydrogen bonds can result in the formation of dimers, linear chains, or cyclic structures. These configurations can further include extended (two-dimensional) hydrogen bond networks and isolated triads. An alternative embodiment provides for a co-crystal wherein the co-crystal former is a second API. In another embodiment, the co-crystal former is not an API.

For purposes of the present invention, the chemical and physical properties of modafinil in the form of a co-crystal may be compared to a reference compound that is modafinil in a different form. The reference compound may be specified as a free form, or more specifically, an anhydrate or hydrate of a free form, or more specifically, for example, a hemihydrate, monohydrate, dihydrate, trihydrate, quadrahydrate, pentahydrate; or a solvate of a free form. For example, the reference compound for modafinil in free form co-crystallized with a co-crystal former can be modafinil in free form. The reference compound may also be specified as crystalline or amorphous. The reference compound may also be specified as the most stable polymorph known of the specified form of the reference compound.

The ratio of modafinil to co-crystal former may be stoichiometric or non-stoichiometric according to the present invention. Non-limiting examples such as, 1:1, 1:1.5, 1.5:1, 1:2, and 2:1 ratios of modafinil:co-crystal former are acceptable. In addition, co-crystals with vacancies within the crystalline lattice are included in the present invention. For example, a co-crystal with less than or about 0.01, 0.1, 1, 2, 3, 4, 5, 6, 7, 8, 9, 10, 11, 12, 13, 14, 15, 16, 17, 18, 19, or 20 percent vacancies within the crystalline lattice are included in the present invention. The vacancies can be due to missing modafinil molecules or missing co-crystal former molecules from the crystalline lattice, or both.

It has surprisingly been found that when modafinil and a selected co-crystal former are allowed to form co-crystals, the resulting co-crystals often give rise to improved properties of modafinil, as compared to modafinil in the free form, particularly with respect to: solubility, dissolution, bioavailability, stability, $C_{max}$, $T_{max}$, processability (including compressibility), longer lasting therapeutic plasma concentration, etc. For example, a co-crystal form of modafinil is particularly advantageous due to the low solubility of modafinil in water. Additionally, the co-crystal properties conferred upon modafinil are also useful because the bioavailability of modafinil can be improved and the plasma concentration and/or serum concentration of modafinil can be improved. This is particularly advantageous for orally-administrable formulations. Moreover, the dose response of modafinil can be improved, for example by increasing the maximum attainable response and/or increasing the potency of modafinil by increasing the biological activity per dosing equivalent.

Accordingly, in a first aspect, the present invention provides a pharmaceutical composition (or medicament) comprising a co-crystal of modafinil and a co-crystal former, such that the modafinil and the co-crystal former are capable of co-crystallizing from a solution phase under crystallization conditions or from the solid-state, for example, through grinding or heating. In another aspect, the co-crystal former which has at least one functional group selected from the group consisting of ether, thioether, alcohol, thiol, aldehyde, ketone, thioketone, nitrate ester, phosphate ester, thiophosphate ester, ester, thioester, sulfate ester, carboxylic acid, phosphonic acid, phosphinic acid, sulfonic acid, amide, primary amine, secondary amine, ammonia, tertiary amine, sp2 amine, thiocyanate, cyanamide, oxime, nitrile, diazo, organohalide, nitro, S-heterocyclic ring, thiophene, N-heterocyclic ring, pyrrole, O-heterocyclic ring, furan, epoxide, hydroxamic acid, imidazole, and pyridine, or a functional group in a Table herein, such that the modafinil and co-crystal former are capable of co-crystallizing from a solution phase under crystallization conditions.

In another embodiment, the use of an excess (more than 1 molar equivalent for a 1:1 co-crystal) of a co-crystal former can be used to drive the formation of stoichiometric co-crystals. For example, co-crystals with stoichiometries of 1:1, 2:1, or 1:2 can be produced by adding co-crystal former in an amount that is 2, 3, 4, 5, 6, 7, 8, 9, 10, 15, 20, 25, 50, 75, 100 times or more than the stoichiometric amount for a given co-crystal. Such an excessive use of a co-crystal former to form a co-crystal can be employed in solution or when grinding modafinil and a co-crystal former to cause co-crystal formation.

In another embodiment of the present invention, a modafinil co-crystal further comprises a co-crystal former which is hydrogen bonded via a preferred interaction between two or more functional groups. For example, modafinil and malonic acid co-crystallize through the interaction of a carboxylic acid functional group of the co-crystal former with sulfoxide and amide functional groups of modafinil.

In another embodiment of the present invention, the co-crystal comprises modafinil wherein the modafinil forms a dimeric primary amide structure via hydrogen bonds with an $R^2_2$ (8) motif. See e.g., J. Bernstein, *Polymorphism in Molecular Crystals*, Oxford University Press, 2002, pp. 55-59, or M. C. Etter, *Acct. Chem. Res.*, 1990, 23, 120, or M. C. Etter, *J. Phys. Chem.*, 1991, 95, 4601. In such a structure, the $NH_2$ moiety can also participate in a hydrogen bond with a donor or an acceptor moiety from, for example, a co-crystal former or an additional (third) molecule, and the C=O moiety can participate in a hydrogen bond with a donor moiety from the co-crystal former or the additional molecule. In a further embodiment, the dimeric primary amide structure (formed by two modafinil molecules) further comprises one, two, three, or four hydrogen bond donors (from one, two, three, or four co-crystal formers). In a further embodiment, the dimeric primary amide structure further comprises one or two hydrogen bond acceptors (from one or two co-crystal formers). In a further embodiment, the dimeric primary amide structure further comprises a combination of hydrogen bond donors and acceptors. For example, the dimeric primary amide structure can further comprise one hydrogen bond donor and one hydrogen bond acceptor, one hydrogen bond donor and two hydrogen bond acceptors, two hydrogen bond donors and one hydrogen bond acceptor, two hydrogen bond donors and two hydrogen bond acceptors, or three hydrogen bond donors and one hydrogen bond acceptor.

The co-crystals of the present invention are formed where modafinil and the co-crystal former are bonded together through hydrogen bonds. Other non-covalent interactions, including pi-stacking and van der Waals interactions, may also be present.

In one embodiment, the co-crystal former is selected from the co-crystal formers of Table I and Table II. In other embodiments, the co-crystal former of Table I is specified as a Class 1, Class 2, or Class 3 co-crystal former (see column labeled "class" Table I). Table I lists multiple $pK_a$ values for co-crystal formers having multiple functionalities. It is readily apparent to one skilled in the art the particular functional group corresponding to a particular $pK_a$ value.

In another embodiment the particular functional group of a co-crystal former interacting with modafinil is specified (see for example Table I, columns labeled "Functionality" and "Molecular Structure" and the column of Table II labeled "Co-Crystal Former Functional Group").

In another embodiment, the co-crystal comprises more than one co-crystal former. For example, two, three, four, five, or more co-crystal formers can be incorporated in a co-crystal with modafinil. Co-crystals which comprise two or more co-crystal formers and an API are bound together via hydrogen bonds. In one embodiment, incorporated co-crystal formers are hydrogen bonded to modafinil molecules. In another embodiment, co-crystal formers are hydrogen bonded to either the modafinil molecules or the incorporated co-crystal formers.

In each process according to the invention, there is a need to contact modafinil with the co-crystal former. This may involve grinding the two solids together or melting one or both components and allowing them to recrystallize. This may also involve either solubilizing modafinil and adding the co-crystal former, or solubilizing the co-crystal former and adding modafinil. Crystallization conditions are applied to modafinil and the co-crystal former. This may entail altering a property of the solution, such as pH or temperature and may require concentration of the solute, usually by removal of the solvent, typically by drying the solution. Solvent removal results in the concentration of both modafinil and the co-crystal former increasing over time so as to facilitate crystallization. For example, evaporation, cooling, or the addition of an antisolvent may be used to crystallize co-crystals. In another embodiment, a slurry comprising modafinil and a co-crystal former is used to form co-crystals. Once the solid phase comprising any crystals is formed, this may be tested as described herein.

The co-crystals obtained as a result of such process steps may be readily incorporated into a pharmaceutical composition (or medicament) by conventional means. Pharmaceutical compositions and medicaments in general are discussed in further detail below and may further comprise a pharmaceutically-acceptable diluent, excipient or carrier.

In a further aspect, the present invention provides a process for the preparation of a co-crystal of modafinil, which comprises:
 (a) providing modafinil;
 (b) providing a co-crystal former compatible with a functional group of modafinil such that the co-crystal former and the modafinil can form a co-crystal;
 (c) grinding, heating, co-subliming, co-melting, or contacting in solution the modafinil with the co-crystal former under crystallization conditions, so as to form a solid phase; and
 (d) isolating co-crystals comprising modafinil and the co-crystal former.

In an embodiment, the co-crystal former has at least one functional group selected from the group consisting of ether, thioether, alcohol, thiol, aldehyde, ketone, thioketone, nitrate ester, phosphate ester, thiophosphate ester, ester, thioester, sulfate ester, carboxylic acid, phosphonic acid, phosphinic acid, sulfonic acid, amide, primary amine, secondary amine, ammonia, tertiary amine, sp2 amine, thiocyanate, cyanamide, oxime, nitrile, diazo, organohalide, nitro, S-heterocyclic ring, thiophene, N-heterocyclic ring, pyrrole, O-heterocyclic ring, furan, epoxide, hydroxamic acid, imidazole, or pyridine.

In a further aspect, the present invention provides a process for the production of a pharmaceutical composition or medicament, which process comprises:
 (a) providing modafinil;
 (b) providing a co-crystal former compatible with a functional group of modafinil such that the co-crystal former and the modafinil can form a co-crystal;
 (c) grinding, heating, co-subliming, co-melting, or contacting in solution the modafinil with the co-crystal former under crystallization conditions;
 (d) isolating co-crystals formed thereby; and
 (e) incorporating the co-crystals into a pharmaceutical composition or medicament.

In another embodiment, a process for the formation of co-crystals includes a meta-stable form of modafinil, the co-crystal former, or both. A meta-stable form can be for example, but not limited to, a polymorph, solvate, or hydrate of modafinil or the co-crystal former. While not bound by theory, the incorporation of a meta-stable form may facilitate co-crystal formation via increasing the thermodynamic driving force.

Assaying the solid phase for the presence of co-crystals of modafinil and the co-crystal former may be carried out by conventional methods known in the art. For example, it is convenient and routine to use powder X-ray diffraction techniques to assess the presence of co-crystals. This may be affected by comparing the diffractograms of modafinil, the crystal former and putative co-crystals in order to establish whether or not true co-crystals had been formed. Other techniques, used in an analogous fashion, include differential scanning calorimetry (DSC), thermogravimetric analysis (TGA), infrared spectroscopy (IR), and Raman spectroscopy. Single crystal X-ray diffraction is especially useful in identifying co-crystal structures.

In a further aspect, the present invention therefore provides a process of screening for co-crystal compounds, which comprises:
 (a) providing (i) modafinil and (ii) a co-crystal former compatible with a functional group of modafinil such that the co-crystal former and the modafinil can form a co-crystal; and
 (b) screening for co-crystals of the modafinil with the co-crystal former by subjecting each combination of modafinil and co-crystal former to a procedure comprising:
  (i) grinding, heating, co-subliming, co-melting, or contacting in solution the modafinil with the co-crystal former under crystallization conditions so as to form a solid phase; and
  (ii) isolating co-crystals comprising the modafinil and the co-crystal former.

An alternative embodiment is drawn to a process of screening for co-crystal compounds, which comprises:
 (a) providing (i) modafinil and (ii) a plurality of different co-crystal formers compatible with a functional group of modafinil such that the co-crystal former and the modafinil can form a co-crystal; and
 (b) screening for co-crystals of the modafinil with the co-crystal formers by subjecting each combination of the modafinil and the co-crystal formers to a procedure comprising:
  (i) grinding, heating, co-subliming, co-melting, or contacting in solution the modafinil with each co-crystal former under crystallization conditions so as to form a solid phase; and
  (ii) isolating co-crystals comprising the modafinil and the co-crystal former.

The present invention includes several co-crystals comprising modafinil and a carboxylic acid co-crystal former. Some examples include modafinil co-crystals comprising malonic acid, tartaric acid (L- and DL-), succinic acid, citric acid, fumaric acid, gentisic acid, oxalic acid, and 1-hydroxy-2-naphthoic acid. These examples represent mono-, di- and tri-carboxylic acid co-crystal formers. Other acids, including carboxylic acids, may be used as co-crystal formers with modafinil including, but not limited to, palmitic acid, orotic acid, and adipic acid etc. These co-crystal formers may comprise one, two, three, or more carboxylic acid functional groups. Co-crystal formers can also include non-carboxylic acid molecules such as, but not limited to, urea, saccharin, and caffeine.

In another embodiment, a co-crystal comprises modafinil and a carboxylic acid as a co-crystal former. In another embodiment, the carboxylic acid co-crystal former has one, two, three, or more carboxylic acid functional groups.

Several co-crystals may exhibit one or more particular interactions between modafinil and a carboxylic acid co-crystal former. For example, a carboxylic acid functional group can interact with the primary amide and/or the S=O functional group of modafinil via a hydrogen bond. In another embodiment, a carboxylic acid functional group from the co-crystal former interacts with the primary amide functional group or the S=O functional group of modafinil via a hydrogen bond. In another embodiment, a carboxylic acid functional group from the co-crystal former interacts with the periphery of the amide dimer of modafinil via a hydrogen bond. In another embodiment, a carboxylic acid functional group from the co-crystal former interacts with the amide dimer and the S=O functional group of modafinil via a hydrogen bond. In another embodiment, a carboxylic acid functional group from the co-crystal former interacts with two amide dimers of modafinil via a hydrogen bond.

Modafinil and some co-crystal formers of the present invention have one or more chiral centers and may exist in a variety of stereoisomeric configurations. As a consequence of these chiral centers, modafinil and several co-crystal formers of the present invention occur as racemates, mixtures of enantiomers and as individual enantiomers, as well as diastereomers and mixtures of diastereomers. All such racemates, enantiomers, and diastereomers are within the scope of the present invention including, for example, cis- and trans-isomers, R- and S-enantiomers, and (D)- and (L)-isomers. Co-crystals of the present invention can include isomeric forms of either modafinil or the co-crystal former or both. Isomeric forms of modafinil and co-crystal formers include, but are not limited to, stereoisomers such as enantiomers and diastereomers. In one embodiment, a co-crystal can comprise racemic modafinil and/or a co-crystal former. In another embodiment, a co-crystal can comprise enantiomerically pure R- or S-modafinil and/or a co-crystal former. In another embodiment, a co-crystal of the present invention can comprise modafinil or a co-crystal former with an enantiomeric excess of about 1 percent, 2 percent, 3 percent, 4 percent, 5 percent, 10 percent, 15 percent, 20 percent, 25 percent, 30 percent, 35 percent, 40 percent, 45 percent, 50 percent, 55 percent, 60 percent, 65 percent, 70 percent, 75 percent, 80 percent, 85 percent, 90 percent, 95 percent, 96 percent, 97 percent, 98 percent, 99 percent, greater than 99 percent, or any intermediate value. Several non-limiting examples of stereoisomeric co-crystal formers include tartaric acid and malic acid. In another embodiment, a polymorph or a solvate of the present invention can comprise modafinil with an enantiomeric excess of about 1 percent, 2 percent, 3 percent, 4 percent, 5 percent, 10 percent, 15 percent, 20 percent, 25 percent, 30 percent, 35 percent, 40 percent, 45 percent, 50 percent, 55 percent, 60 percent, 65 percent, 70 percent, 75 percent, 80 percent, 85 percent, 90 percent, 95 percent, 96 percent, 97 percent, 98 percent, 99 percent, greater than 99 percent, or any intermediate value.

"Enriched" modafinil, according to the present invention, comprises both the R-(−)- and S-(+)-isomers of modafinil in amounts greater than or equal to about 5, 6, 7, 8, 9, or 10 percent by weight and less than or equal to about 90, 91, 92, 93, 94, or 95 percent by weight. For example, a composition comprising 67 percent by weight R-(−)-modafinil and 33 percent by weight S-(+)-modafinil is an enriched modafinil composition. In such an example, the composition is neither racemic nor enantiomerically pure. The term "enriched R-(−)-modafinil" may be used to describe a composition of modafinil with greater than 50 percent R-(−)-modafinil and less than 50 percent S-(+)-modafinil. Likewise, the term "enriched S-(+)-modafinil" may be used to describe a composition of modafinil with greater than 50 percent S-(+)-modafinil and less than 50 percent R-(−)-modafinil.

The terms "R-(−)-modafinil" and "S-(+)-modafinil" can be used to describe enriched modafinil, enantiomerically pure modafinil, or substantially enantiomerically pure modafinil, but may also specifically exclude enriched modafinil, enantiomerically pure modafinil, and/or substantially enantiomerically pure modafinil.

Co-crystals, solvates, and polymorphs comprising enantiomerically pure and/or enantiomerically enriched components (e.g., modafinil or co-crystal former) can give rise to chemical and/or physical properties which are modulated with respect to those of the corresponding co-crystal comprising a racemic component. For example, the modafinil:malonic acid co-crystal from Example 1 comprises racemic modafinil. Enantiomerically pure R-(−)-modafinil:malonic acid is included in the scope of the invention. Likewise, enantiomerically pure S-(+)-modafinil:malonic acid is included in the scope of the invention. A co-crystal comprising an enantiomerically pure component can give rise to a modulation of, for example, activity, bioavailability, or solubility, with respect to the corresponding co-crystal comprising a racemic component. As an example, the co-crystal R-(−)-modafinil:malonic acid can have modulated properties as compared to the racemic modafinil:malonic acid co-crystal.

Polymorphs and solvates of modafinil can also be prepared with racemic modafinil, enantiomerically pure modafinil, or with any mixture of R-(−)- and S-(+)-modafinil according to the present invention.

In another embodiment, the present invention includes a pharmaceutical composition or medicament comprising a co-crystal with enantiomerically pure modafinil and/or co-crystal former wherein the bioavailability is modulated with respect to the racemic co-crystal. In another embodiment, the present invention includes a pharmaceutical composition or medicament comprising a co-crystal with enantiomerically pure modafinil and/or co-crystal former wherein the activity is modulated with respect to the racemic co-crystal. In another embodiment, the present invention includes a pharmaceutical composition or medicament comprising a co-crystal with enantiomerically pure modafinil and/or co-crystal former wherein the solubility is modulated with respect to the racemic co-crystal.

In another embodiment, a pharmaceutical composition or medicament can be formulated to contain modafinil in co-crystal form as micronized or nano-sized particles. More specifically, another embodiment couples the processing of pure modafinil to a co-crystal form with the process of making a controlled particle size for manipulation into a pharmaceutical dosage form. This embodiment combines two processing steps into a single step via techniques such as, but not limited to, grinding, alloying, or sintering (i.e., heating a powder mix). The coupling of these processes overcomes a serious limitation of having to isolate and store the bulk drug that is required for a formulation, which in some cases can be difficult to isolate (e.g., amorphous, chemically or physically unstable).

Solubility Modulation

In a further aspect, the present invention provides a process for increasing the solubility of modafinil in water, simulated gastric fluid (SGF), or simulated intestinal fluid (SIF) for use in a pharmaceutical composition or medicament, which process comprises:

(a) providing modafinil;

(b) providing a co-crystal former compatible with a functional group of modafinil such that the co-crystal former and the modafinil can form a co-crystal;

(c) grinding, heating, co-subliming, co-melting, or contacting in solution the modafinil with the co-crystal former under crystallization conditions, so as to form a solid phase; and (d) isolating co-crystals comprising the modafinil and the co-crystal former.

In one embodiment, the solubility of modafinil is modulated such that the aqueous solubility (mg/mL) is increased by at least 1.1, 1.2, 1.3, 1.5, 2.0, 5.0, 10.0, 20.0, 25.0, 50.0, 75.0, or 100.0 times or more than the free form. Solubility of modafinil may be measured by any conventional means such as chromatography (e.g., HPLC) or spectroscopic determination of the amount of modafinil in a saturated solution, such as UV-spectroscopy, IR-spectroscopy, Raman spectroscopy, quantitative mass spectroscopy, or gas chromatography.

In another embodiment, the compositions or medicaments including co-crystals, solvates, and polymorphs of the present invention can be compared with free form modafinil as found in PROVIGIL® (Cephalon, Inc.). (See U.S. Reissued Pat. No. RE37,516) For example, the bioavailability of a composition or medicament of the present invention can be compared with that of PROVIGIL. As embodiments of the present invention, solubility can be increased 2, 3, 4, 5, 7, 10, 15, 20, 25, 50, 75, or 100 times by making a co-crystal of the reference form (e.g., crystalline or amorphous free form, hydrate or solvate). Further aqueous solubility can be measured in simulated gastric fluid (SGF) or simulated intestinal fluid (SIF) rather than water. SGF (non-diluted) of the present invention is made by combining 1 g/L Triton X-100 and 2 g/L NaCl in water and adjusting the pH with 20 mM HCl to obtain a solution with a final pH=1.7 SIF is 0.68% monobasic potassium phosphate, 1% pancreatin, and sodium hydroxide where the pH of the final solution is 7.5. The pH of the solvent used may also be specified as 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 11.5, or 12, or any pH in between successive values.

Examples of embodiments includes: co-crystal compositions with an aqueous solubility, at 37 degrees C. and a pH of 7.0, that is increased at least 5 fold over the reference form, co-crystal compositions with a solubility in SGF that is increased at least 5 fold over the reference form, co-crystal compositions with a solubility in SIF that is increased at least 5 fold over the reference form.

Dissolution Modulation

In another aspect of the present invention, the dissolution profile of modafinil is modulated whereby the aqueous dissolution rate or the dissolution rate in simulated gastric fluid or in simulated intestinal fluid, or in a solvent or plurality of solvents is increased. Dissolution rate is the rate at which API solids dissolve in a dissolution medium. For APIs whose absorption rates are faster than the dissolution rates (e.g., steroids), the rate-limiting step in the absorption process is often the dissolution rate. Because of a limited residence time at the absorption site, APIs that are not dissolved before they are removed from intestinal absorption site are considered useless. Therefore, the rate of dissolution has a major impact on the performance of APIs that are poorly soluble. Because of this factor, the dissolution rate of APIs in solid dosage forms is an important, routine, quality control parameter used in the API manufacturing process. The following equation is an approximation, $$\text{Dissolution rate} = KS(C_s - C)$$

where K is dissolution rate constant, S is the surface area, $C_s$ is the apparent solubility, and C is the concentration of API in the dissolution medium.

For rapid API absorption, $C_s - C$ is approximately equal to $C_s$

The dissolution rate of modafinil may be measured by conventional means known in the art.

The increase in the dissolution rate of a co-crystal, as compared to the reference form (e.g., free form), may be specified, such as by 10, 20, 30, 40, 50, 60, 70, 80, 90, or 100%, or by 2, 3, 4, 5, 6, 7, 8, 9, 10, 15, 20, 25, 30, 40, 50, 75, 100, 125, 150, 175, 200, 250, 300, 350, 400, 500, 1000, 10,000, or 100,000 fold greater than the reference form (e.g., free form) in the same solution. Conditions under which the dissolution rate is measured are the same as discussed above. The increase in dissolution may be further specified by the time the composition remains supersaturated before reaching equilibrium solubility.

In a further aspect, the present invention provides a process for modulating the dissolution of modafinil, whereby the aqueous dissolution rate or the dissolution rate in simulated gastric fluid or in simulated intestinal fluid, or in a solvent or plurality of solvents is increased, which process comprises:

(a) providing modafinil;

(b) providing a co-crystal former compatible with a functional group of modafinil such that the co-crystal former and the modafinil can form a co-crystal;

(c) grinding, heating, co-subliming, co-melting, or contacting in solution the modafinil with the co-crystal former under crystallization conditions, so as to form a solid phase; and (d) isolating co-crystals comprising the modafinil and the co-crystal former.

Examples of above embodiments include: co-crystal compositions with a dissolution rate in aqueous solution, at 37 degrees C. and a pH of 7.0, that is increased at least 5 fold over the reference form, co-crystal compositions with a dissolution rate in SGF that is increased at least 5 fold over the reference form, co-crystal compositions with a dissolution rate in SIF that is increased at least 5 fold over the reference form.

Bioavailability Modulation

The methods of the present invention are used to make a pharmaceutical modafinil formulation with greater solubility, dissolution, and bioavailability. Bioavailability can be improved via an increase in AUC, reduced time to $T_{max}$, (the time to reach peak blood serum levels), or increased $C_{max}$. The present invention can result in higher plasma concentrations of modafinil when compared to the free form (reference form).

AUC is the area under the plot of plasma concentration of API (not logarithm of the concentration) against time after API administration. The area is conveniently determined by the "trapezoidal rule": The data points are connected by straight line segments, perpendiculars are erected from the abscissa to each data point, and the sum of the areas of the triangles and trapezoids so constructed is computed. When the last measured concentration ($C_n$, at time $t_n$) is not zero, the AUC from $t_n$ to infinite time is estimated by $C_n/k_{el}$.

The AUC is of particular use in estimating bioavailability of APIs, and in estimating total clearance of APIs ($Cl_T$). Following single intravenous doses, AUC D/$Cl_T$, for single compartment systems obeying first-order elimination kinetics, where D is the dose; alternatively, $AUC=C_0/k_{el}$, where $k_{el}$ is the API elimination rate constant. With routes other than the intravenous, $AUC=F·D/Cl_T$, where F is the absolute bioavailability of the API.

In a further aspect, the present invention provides a process for modulating the bioavailability of modafinil, whereby the AUC is increased, the time to $T_{max}$ is reduced, the length of time the concentration of modafinil is above ½ $T_{max}$ is increased, or $C_{max}$ is increased, which process comprises:
  (a) providing modafinil;
  (b) providing a co-crystal former compatible with a functional group of modafinil such that the co-crystal former and the modafinil can form a co-crystal;
  (c) grinding, heating, co-subliming, co-melting, or contacting in solution the modafinil with the co-crystal former under crystallization conditions, so as to form a solid phase; and
  (d) isolating co-crystals comprising the modafinil and the co-crystal former.

Examples of the above embodiments include: co-crystal compositions with a time to $T_{max}$ that is increased by at least 5% as compared to the reference form, co-crystal compositions with a time to $T_{max}$ that is increased by at least 10% over the reference form, co-crystal compositions with a time to $T_{max}$ that is increased by at least 15% over the reference form, co-crystal compositions with a time to $T_{max}$ that is increased by at least 20% over the reference form, co-crystal compositions with a $T_{max}$ that is increased by at least 25% over the reference form, co-crystal compositions with a $T_{max}$ that is increased by at least 30% over the reference form, co-crystal compositions with a $T_{max}$ that is increased by at least 35% over the reference form, co-crystal compositions with a $T_{max}$ that is increased by at least 40% over the reference form, co-crystal compositions with an AUC that is increased by at least 5% over the reference form, co-crystal compositions with an AUC that is increased by at least 10% over the reference form, co-crystal compositions with an AUC that is increased by at least 15% over the reference form, co-crystal compositions with an AUC that is increased by at least 20% over the reference form, co-crystal compositions with an AUC that is increased by at least 25% over the reference form, co-crystal compositions with an AUC that is increased by at least 30% over the reference form, co-crystal compositions with an AUC that is increased by at least 35% over the reference form, co-crystal compositions with an AUC that is increased by at least 40% over the reference form. Other examples include wherein the reference form is crystalline, wherein the reference form is amorphous, or wherein the reference form is an anhydrous crystal form of modafinil.

Dose Response Modulation

In a further aspect, the present invention provides a process for modulating the dose response of modafinil for use in a pharmaceutical composition or medicament, which process comprises:
  (a) providing modafinil;
  (b) providing a co-crystal former compatible with a functional group of modafinil such that the co-crystal former and the modafinil can form a co-crystal;
  (c) grinding, heating, co-subliming, co-melting, or contacting in solution the modafinil with the co-crystal former under crystallization conditions, so as to form a solid phase; and
  (d) isolating co-crystals comprising the modafinil and the co-crystal former.

Dose response is the quantitative relationship between the magnitude of response and the dose inducing the response and may be measured by conventional means known in the art. The curve relating effect (as the dependent variable) to dose (as the independent variable) for an API-cell system is the "dose-response curve". Typically, the dose-response curve is the measured response to an API plotted against the dose of the API (mg/kg) given. The dose response curve can also be a curve of AUC against the dose of the API given.

In an embodiment of the present invention, a co-crystal of the present invention has an increased dose response curve or a more linear dose response curve than the corresponding reference compound.

Increased Stability

In a still further aspect the present invention provides a process for improving the stability of modafinil (as compared to a reference form such as its free form), which process comprises:
  (a) providing modafinil;
  (b) providing a co-crystal former compatible with a functional group of modafinil such that the co-crystal former and the modafinil can form a co-crystal;
  (c) grinding, heating, co-subliming, co-melting or contacting in solution the modafinil with the co-crystal former under crystallization conditions, so as to form a solid phase; and
  (d) isolating co-crystals comprising the modafinil and the co-crystal former.

In a preferred embodiment, the compositions of the present invention, including modafinil co-crystals, solvates, and formulations comprising modafinil, are suitably stable for pharmaceutical use. Preferably, modafinil or formulations thereof, of the present invention, are stable such that when stored at 30 degrees C. for 2 years, less than 0.2% of any one degradant is formed. The term degradant refers herein to product(s) of a single type of chemical reaction. For example, if a hydrolysis event occurs that cleaves a molecule into two products, for the purpose of the present invention, it would be considered a single degradant. More preferably, when stored at 40 degrees C. for 2 years, less than 0.2% of any one degradant is formed. Alternatively, when stored at 30 degrees C. for 3 months, less than 0.2% or 0.15%, or 0.1% of any one degradant is formed, or when stored at 40 degrees C. for 3 months, less than 0.2% or 0.15%, or 0.1% of any one degradant is formed. Further alternatively, when stored at 60 degrees C. for 4 weeks, less than 0.2% or 0.15%, or 0.1% of any one degradant is formed. The relative humidity (RH) may be specified as ambient RH, 75% RH, or as any single integer between 1 to 99% RH. In another embodiment, a single dose of the present invention comprises less than 0.5%, 0.2%, or 0.1% degradants upon administration to a subject.

Morphology Modulation

In a still further aspect the present invention provides a process for modifying the morphology of modafinil, which process comprises:
  (a) providing modafinil;
  (b) providing a co-crystal former compatible with a functional group of modafinil such that the co-crystal former and the modafinil can form a co-crystal;
  (c) grinding, heating, co-subliming, co-melting, or contacting in solution the modafinil with the co-crystal former under crystallization conditions, so as to form a solid phase; and
  (d) isolating co-crystals comprising the modafinil and the co-crystal former.

In an embodiment the co-crystal comprises or consists of modafinil and a co-crystal former wherein the interaction between the two, e.g., H-bonding, occurs between the amino group of modafinil and a co-crystal former with a corresponding interacting group of Table III. In a further embodiment, the co-crystal comprises modafinil and a co-crystal former of Table I or II. In an aspect of the invention, only co-crystals having an H-bond acceptor on the first molecule and an H-bond donor on the second molecule, where the first and second molecules are either co-crystal former and modafinil respectively, or modafinil and co-crystal former respectively, are included in the present invention.

A co-crystal can comprise more than two chemical entities within its co-crystalline structure. For example, a co-crystal can further comprise a solvent molecule, a water molecule, a salt, etc. In addition, a co-crystal can comprise an API and two or more co-crystal formers, a co-crystal former and two or more APIs, two or more APIs, or two or more co-crystal formers.

As defined herein, a ternary co-crystal is a co-crystal which comprises three distinct chemical entities in a stoichiometric ratio, where each is a solid at room temperature (with the exception that the API may be a liquid at room temperature). Specifically, a ternary co-crystal comprises three distinct chemical entities such as API:co-crystal former(1):co-crystal former(2), where the ratio of components can be, for example, but not limited to, 1:1:1, 2:1:1, 2:1:2, 2:1:0.5, 2:2:1, etc. Ternary co-crystals can also comprise other combinations of components such as, but not limited to, API(1):API(2):co-crystal former, API(1):API(2):API(3), and co-crystal former (1):co-crystal former(2):co-crystal former(3).

In another embodiment, the present invention provides a co-crystal comprising modafinil and a co-crystal former selected from the group consisting of: malonic acid, glycolic acid, fumaric acid, tartaric acid, citric acid, succinic acid, gentisic acid, oxalic acid, 1-hydroxy-2-naphthoic acid, orotic acid, glutaric acid, L-tartaric acid, palmitic acid, L-proline, salicylic acid, lauric acid, L-malic acid, and maleic acid.

In further embodiments, the present invention provides the following co-crystals: modafinil:malonic acid, modafinil:glycolic acid, modafinil:maleic acid, modafinil:L-tartaric acid, modafinil:citric acid, modafinil:succinic acid, modafinil:DL-tartaric acid, modafinil:fumaric acid (Form I), modafinil:fumaric acid (Form II), modafinil:gentisic acid, modafinil:oxalic acid, modafinil:1-hydroxy-2-naphthoic acid, R-(−)-modafinil:malonic acid, R-(−)-modafinil:succinic acid, R-(−)-modafinil:citric acid, R-(−)-modafinil:DL-tartaric acid, R-(−)-modafinil:1-hydroxy-2-naphthoic acid, R-(−)-modafinil:orotic acid, R-(−)-modafinil:glutaric acid, R-(−)-modafinil:L-tartaric acid, R-(−)-modafinil:palmitic acid, R-(−)-modafinil:L-proline, R-(−)-modafinil:salicylic acid, R-(−)-modafinil:lauric acid, R-(−)-modafinil:L-malic acid, and R-(−)-modafinil:gentisic acid.

In another embodiment, the present invention provides a novel polymorph or co-crystal of racemic modafinil (form VII).

In another embodiment, the present invention provides the following modafinil solvates: acetic acid, tetrahydrofuran, 1,4-dioxane, methanol, nitromethane, acetone, o-xylene, benzene, and toluene.

Pharmaceutically acceptable co-crystals can be administered by controlled- or delayed-release means. Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Cherng-ju, Controlled Release Dosage Form Design, 2 Technomic Publishing, Lancaster, Pa.: 2000).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under dosing a drug (i.e., going below the minimum therapeutic levels) as well as exceeding the toxicity level for the drug.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the co-crystals and compositions of the invention. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed co-crystals and thus effect controlled delivery of the drug. Examples of specific anion exchangers include, but are not limited to, Duolite® A568 and Duolite® AP143 (Rohm & Haas, Spring House, Pa. USA).

One embodiment of the invention encompasses a unit dosage form which comprises a pharmaceutically acceptable co-crystal, or a solvate, hydrate, dehydrate, anhydrous, or amorphous form thereof, and one or more pharmaceutically acceptable excipients or diluents, wherein the pharmaceutical composition, medicament or dosage form is formulated for controlled-release. Specific dosage forms utilize an osmotic drug delivery system.

A particular and well-known osmotic drug delivery system is referred to as OROS® (Alza Corporation, Mountain View, Calif. USA). This technology can readily be adapted for the delivery of compounds and compositions of the invention. Various aspects of the technology are disclosed in U.S. Pat. Nos. 6,375,978 B1; 6,368,626 B1; 6,342,249 B1; 6,333,050 B2; 6,287,295 B1; 6,283,953 B1; 6,270,787 B1; 6,245,357 B1; and 6,132,420; each of which is incorporated herein by reference. Specific adaptations of OROS® that can be used to administer compounds and compositions of the invention include, but are not limited to, the OROS® Push-Pull™, Delayed Push-Pull™, Multi-Layer Push-Pull™, and Push-Stick™ Systems, all of which are well known. See, e.g., http://www.alza.com. Additional OROS® systems that can be used for the controlled oral delivery of compounds and compositions of the invention include OROS®-CT and L-OROS®. Id.; see also, Delivery Times, vol. II, issue II (Alza Corporation).

Conventional OROS® oral dosage forms are made by compressing a drug powder (e.g. co-crystal) into a hard tablet, coating the tablet with cellulose derivatives to form a semipermeable membrane, and then drilling an orifice in the coating (e.g., with a laser). Kim, Cherng-ju, Controlled Release Dosage Form Design, 231-238 (Technomic Publishing, Lancaster, Pa.: 2000). The advantage of such dosage forms is that the delivery rate of the drug is not influenced by physiological or experimental conditions. Even a drug with a pH-dependent solubility can be delivered at a constant rate regardless of the pH of the delivery medium. But because these advantages are provided by a build-up of osmotic pressure within the dosage form after administration, conventional OROS® drug delivery systems cannot be used to effectively deliver drugs with low water solubility. Id. at 234. Because co-crystals of this invention can be far more soluble in water than modafinil itself, they are well suited for osmotic-based delivery to patients. This invention does, however, encompass the incorporation of conventional crystalline modafinil (e.g. pure modafinil without co-crystal former), and isomers and isomeric mixtures thereof, into OROS® dosage forms.

A specific dosage form of the invention comprises: a wall defining a cavity, the wall having an exit orifice formed or formable therein and at least a portion of the wall being semipermeable; an expandable layer located within the cavity remote from the exit orifice and in fluid communication with the semipermeable portion of the wall; a dry or substantially dry state drug layer located within the cavity adjacent to the exit orifice and in direct or indirect contacting relationship with the expandable layer; and a flow-promoting layer interposed between the inner surface of the wall and at least the external surface of the drug layer located within the cavity, wherein the drug layer comprises a co-crystal, or a solvate, hydrate, dehydrate, anhydrous, or amorphous form thereof. See U.S. Pat. No. 6,368,626, the entirety of which is incorporated herein by reference.

Another specific dosage form of the invention comprises: a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; the drug layer comprising a liquid, active agent formulation absorbed in porous particles, the porous particles being adapted to resist compaction forces sufficient to form a compacted drug layer without significant exudation of the liquid, active agent formulation, the dosage form optionally having a placebo layer between the exit orifice and the drug layer, wherein the active agent formulation comprises a co-crystal, or a solvate, hydrate, dehydrate, anhydrous, or amorphous form thereof. See U.S. Pat. No. 6,342,249, the entirety of which is incorporated herein by reference.

In another embodiment, a pharmaceutical composition or medicament comprises a mixture of a novel form of modafinil of the present invention (e.g., a co-crystal) and the free form of modafinil. This embodiment can be used, for example, as a controlled-, sustained-, or extended-release dosage form. In another embodiment, an extended-release dosage form comprises free form modafinil and a co-crystal or a solvate of the present invention. Such an extended-release dosage form contains modafinil in a form (e.g. modafinil:malonic acid co-crystal) which has a greater bioavailability than that of free form modafinil. In addition, the $C_{max}$ of such a form can be greater than that of free form modafinil, facilitating a therapeutic effect with longer duration than free form modafinil alone.

In another embodiment, a pharmaceutical composition or medicament comprises a modified release profile of one or more of racemic modafinil, R-(−)-modafinil, and S-(+)-modafinil. The modified release profile can comprise, for example, two or more maxima of plasma concentration, such as a dual-release profile. Such a modified release profile may aid a patient treated with a composition or medicament of the present invention who experiences loss of wakefulness in the afternoon, for example. A second "burst" or release of API at least 2, 3, 4, 5, or 6 hours after administration may help to overcome such an effect. In another embodiment, a pharmaceutical composition or medicament comprising a small loading dose released immediately following administration can be employed, followed by an approximate zero-order release profile over the following 2, 3, 4, 5, or 6 hours. In such a composition, peak plasma levels can be reached at about midday.

In another embodiment, a pharmaceutical composition or medicament comprising a modified release profile of modafinil can comprise R-(−)-modafinil and S-(+)-modafinil wherein the R-(−)-modafinil provides an initial increase (initial $C_{max}$ due to R-(−)-modafinil) in plasma concentration and the S-(+)-modafinil provides a delayed increase (subsequent $C$, due to S-(+)-modafinil) in plasma concentration. The delayed increase in $C_{max}$ due to S-(+)-modafinil can be 2, 3, 4, 5, 6 hours or more after the initial $C_{max}$ due to R-(−)-modafinil. In another embodiment, the delayed $C_{max}$ is approximately equal to the initial $C_{max}$. In another embodiment, the delayed $C_{max}$ is greater than the initial $C_{max}$. In another embodiment, the delayed $C_{max}$ is less than the initial $C_{max}$. In another embodiment, the delayed $C_{max}$ is due to racemic modafinil, instead of S-(+)-modafinil. In another embodiment, the delayed $C_{max}$ is due to R-(−)-modafinil, instead of S-(+)-modafinil. In another embodiment, the initial $C_{max}$ is due to racemic modafinil, instead of R-(−)-modafinil. In another embodiment, the initial $C_{max}$ is due to S-(+)-modafinil, instead of R-(−)-modafinil. In another embodiment, the modified release profile has 3, 4, 5, or more "bursts" in plasma concentration.

In another embodiment, a pharmaceutical composition or medicament comprising a modified release profile of modafinil wherein one or more of racemic modafinil, R-(−)-modafinil, or S-(+)-modafinil are present in the form of a co-crystal, solvate, free form, or a polymorph thereof.

In another embodiment, a pharmaceutical composition or medicament comprising a modified release profile wherein R-(−)-modafinil is used in an oral formulation. Such a composition can minimize first-pass metabolism of modafinil to the sulfone. In another embodiment, a pharmaceutical composition or medicament comprising a modified release profile wherein racemic modafinil is used in an oral formulation. In another embodiment, a pharmaceutical composition or medicament comprising a modified release profile wherein S-(+)-modafinil is used in an oral formulation. In another embodiment, a pharmaceutical composition or medicament comprising a modified release profile wherein racemic modafinil and R-(−)-modafinil are used in an oral formulation. In another embodiment, a pharmaceutical composition or medicament comprising a modified release profile wherein racemic modafinil and S-(+)-modafinil are used in an oral formulation. In another embodiment, a pharmaceutical composition or medicament comprising a modified release profile wherein S-(+)-modafinil and R-(−)-modafinil are used in an oral formulation. In another embodiment, a pharmaceutical composition or medicament comprising a modified release profile wherein racemic modafinil, S-(+)-modafinil and R-(−)-modafinil are used in an oral formulation.

In another embodiment, a pharmaceutical composition or medicament comprising a modified release profile of modafinil is administered transdermally. Such a transdermal (TD) delivery can avoid first-pass metabolism. Additionally, a "pill-and-patch" strategy can be taken, where only a fraction of the daily dose is delivered through the skin to generate basal systemic levels, onto which oral therapy is added to ensure the wakefulness effect.

Excipients employed in pharmaceutical compositions and medicaments of the present invention can be solids, semi-solids, liquids or combinations thereof. Preferably, excipients are solids. Compositions and medicaments of the invention containing excipients can be prepared by known technique of pharmacy that comprises admixing an excipient with an API or therapeutic agent. A pharmaceutical composition or medicament of the invention contains a desired amount of API per dose unit and, if intended for oral administration, can be in the form, for example, of a tablet, a caplet, a pill, a hard or soft capsule, a lozenge, a cachet, a dispensable powder, granules, a suspension, an elixir, a dispersion, a liquid, or any other form reasonably adapted for such administration. If intended for parenteral administration, it can be in the form, for example, of a suspension or transdermal patch. If intended for rectal administration, it can be in the form, for example, of a suppository. Presently preferred are oral dosage forms that are discrete dose units each containing a predetermined amount of the API, such as tablets or capsules.

Non-limiting examples follow of excipients that can be used to prepare pharmaceutical compositions or medicaments of the invention.

Pharmaceutical compositions and medicaments of the invention optionally comprise one or more pharmaceutically acceptable carriers or diluents as excipients. Suitable carriers or diluents illustratively include, but are not limited to, either individually or in combination, lactose, including anhydrous lactose and lactose monohydrate; starches, including directly compressible starch and hydrolyzed starches (e.g., Celutab™ and Emdex™); mannitol; sorbitol; xylitol; dextrose (e.g., Cerelose™ 2000) and dextrose monohydrate; dibasic calcium phosphate dihydrate; sucrose-based diluents; confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of alpha- and amorphous cellulose (e.g., RexcelJ), powdered cellulose, hydroxypropylcellulose (HPC) and hydroxypropylmethylcellulose (HPMC); calcium carbonate; glycine; bentonite; block co-polymers; polyvinylpyrrolidone; and the like. Such carriers or diluents, if present, constitute in total about 5% to about 99%, preferably about 10% to about 85%, and more preferably about 20% to about 80%, of the total weight of the composition. The carrier, carriers, diluent, or diluents selected preferably exhibit suitable flow properties and, where tablets are desired, compressibility.

Lactose, mannitol, dibasic sodium phosphate, and microcrystalline cellulose (particularly Avicel PH microcrystalline cellulose such as Avicel PH 101), either individually or in combination, are preferred diluents. These diluents are chemically compatible with APIs. The use of extragranular microcrystalline cellulose (that is, microcrystalline cellulose added to a granulated composition) can be used to improve hardness (for tablets) and/or disintegration time. Lactose, especially lactose monohydrate, is particularly preferred. Lactose typically provides compositions having suitable release rates of APIs, stability, pre-compression flowability, and/or drying properties at a relatively low diluent cost. It provides a high density substrate that aids densification during granulation (where wet granulation is employed) and therefore improves blend flow properties and tablet properties.

Pharmaceutical compositions and medicaments of the invention optionally comprise one or more pharmaceutically acceptable disintegrants as excipients, particularly for tablet formulations. Suitable disintegrants include, but are not limited to, either individually or in combination, starches, including sodium starch glycolate (e.g., Explotab™ of PenWest) and pregelatinized corn starches (e.g., National™ 1551 of National Starch and Chemical Company, National™ 1550, and Colocorn™ 1500), clays (e.g., Veegum™ HV of R. T. Vanderbilt), celluloses such as purified cellulose, microcrystalline cellulose, methylcellulose, carboxymethylcellulose and sodium carboxymethylcellulose, croscarmellose sodium (e.g., Ac-Di-Sol™ of FMC), alginates, crospovidone, and gums such as agar, guar, locust bean, karaya, pectin and tragacanth gums.

Disintegrants may be added at any suitable step during the preparation of the composition, particularly prior to granulation or during a lubrication step prior to compression. Such disintegrants, if present, constitute in total about 0.2% to about 30%, preferably about 0.2% to about 10%, and more preferably about 0.2% to about 5%, of the total weight of the composition.

Croscarmellose sodium is a preferred disintegrant for tablet or capsule disintegration, and, if present, preferably constitutes about 0.2% to about 10%, more preferably about 0.2% to about 7%, and still more preferably about 0.2% to about 5%, of the total weight of the composition. Croscarmellose sodium confers superior intragranular disintegration capabilities to granulated pharmaceutical compositions and medicaments of the present invention.

Pharmaceutical compositions and medicaments of the invention optionally comprise one or more pharmaceutically acceptable binding agents or adhesives as excipients, particularly for tablet formulations. Such binding agents and adhesives preferably impart sufficient cohesion to the powder being tableted to allow for normal processing operations such as sizing, lubrication, compression and packaging, but still allow the tablet to disintegrate and the composition to be absorbed upon ingestion. Such binding agents may also prevent or inhibit crystallization or recrystallization of an API of the present invention once the salt has been dissolved in a solution. Suitable binding agents and adhesives include, but are not limited to, either individually or in combination, acacia; tragacanth; sucrose; gelatin; glucose; starches such as, but not limited to, pregelatinized starches (e.g., National™ 1511 and National™ 1500); celluloses such as, but not limited to, methylcellulose and carmellose sodium (e.g., Tylose™); alginic acid and salts of alginic acid; magnesium aluminum silicate; PEG; guar gum; polysaccharide acids; bentonites; povidone, for example povidone K-15, K-30 and K-29/32; polymethacrylates; HPMC; hydroxypropylcellulose (e.g., Klucel™ of Aqualon); and ethylcellulose (e.g., Ethocel™ of the Dow Chemical Company). Such binding agents and/or adhesives, if present, constitute in total about 0.5% to about 25%, preferably about 0.75% to about 15%, and more preferably about 1% to about 10%, of the total weight of the pharmaceutical composition or medicament.

Many of the binding agents are polymers comprising amide, ester, ether, alcohol or ketone groups and, as such, are preferably included in pharmaceutical compositions and medicaments of the present invention. Polyvinylpyrrolidones such as povidone K-30 are especially preferred. Polymeric binding agents can have varying molecular weight, degrees of crosslinking, and grades of polymer. Polymeric binding agents can also be copolymers, such as block co-polymers that contain mixtures of ethylene oxide and propylene oxide units. Variation in these units' ratios in a given polymer affects properties and performance. Examples of block co-polymers with varying compositions of block units are Poloxamer 188 and Poloxamer 237 (BASF Corporation).

Pharmaceutical compositions and medicaments of the invention optionally comprise one or more pharmaceutically acceptable wetting agents as excipients. Such wetting agents are preferably selected to maintain the API in close association with water, a condition that is believed to improve bioavailability of the composition.

Non-limiting examples of surfactants that can be used as wetting agents in pharmaceutical compositions and medicaments of the invention include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and octoxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefosse), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of ICI), propylene glycol fatty acid esters, for example propylene glycol laurate (e.g., Lauroglycol™ of Gattefosse), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. Such wetting agents, if present, constitute in total about 0.25% to about 15%, preferably about 0.4% to about 10%, and more preferably about 0.5% to about 5%, of the total weight of the pharmaceutical composition or medicament.

Wetting agents that are anionic surfactants are preferred. Sodium lauryl sulfate is a particularly preferred wetting agent. Sodium lauryl sulfate, if present, constitutes about 0.25% to about 7%, more preferably about 0.4% to about 4%, and still more preferably about 0.5% to about 2%, of the total weight of the pharmaceutical composition or medicament.

Pharmaceutical compositions and medicaments of the invention optionally comprise one or more pharmaceutically acceptable lubricants (including anti-adherents and/or glidants) as excipients. Suitable lubricants include, but are not limited to, either individually or in combination, glyceryl behapate (e.g., Compritol™ 888 of Gattefosse); stearic acid and salts thereof, including magnesium, calcium and sodium stearates; hydrogenated vegetable oils (e.g., Sterotex™ of Abitec); colloidal silica; talc; waxes; boric acid; sodium benzoate; sodium acetate; sodium fumarate; sodium chloride; DL-leucine; PEG (e.g., Carbowax™ 4000 and Carbowax™ 6000 of the Dow Chemical Company); sodium oleate; sodium lauryl sulfate; and magnesium lauryl sulfate. Such lubricants, if present, constitute in total about 0.1% to about 10%, preferably about 0.2% to about 80%, and more preferably about 0.25% to about 5%, of the total weight of the pharmaceutical composition or medicament.

Magnesium stearate is a preferred lubricant used, for example, to reduce friction between the equipment and granulated mixture during compression of tablet formulations.

Suitable anti-adherents include, but are not limited to, talc, cornstarch, DL-leucine, sodium lauryl sulfate and metallic stearates. Talc is a preferred anti-adherent or glidant used, for example, to reduce formulation sticking to equipment surfaces and also to reduce static in the blend. Talc, if present, constitutes about 0.1% to about 10%, more preferably about 0.25% to about 5%, and still more preferably about 0.5% to about 2%, of the total weight of the pharmaceutical composition or medicament.

Glidants can be used to promote powder flow of a solid formulation. Suitable glidants include, but are not limited to, colloidal silicon dioxide, starch, talc, tribasic calcium phosphate, powdered cellulose and magnesium trisilicate. Colloidal silicon dioxide is particularly preferred.

Other excipients such as colorants, flavors and sweeteners are known in the pharmaceutical art and can be used in pharmaceutical compositions and medicaments of the present invention. Tablets can be coated, for example with an enteric coating, or uncoated. Compositions of the invention can further comprise, for example, buffering agents.

Optionally, one or more effervescent agents can be used as disintegrants and/or to enhance organoleptic properties of pharmaceutical compositions and medicaments of the invention. When present in pharmaceutical compositions and medicaments of the invention to promote dosage form disintegration, one or more effervescent agents are preferably present in a total amount of about 30% to about 75%, and preferably about 45% to about 70%, for example about 60%, by weight of the pharmaceutical composition or medicament.

According to a particularly preferred embodiment of the invention, an effervescent agent, present in a solid dosage form in an amount less than that effective to promote disintegration of the dosage form, provides improved dispersion of the API in an aqueous medium. Without being bound by theory, it is believed that the effervescent agent is effective to accelerate dispersion of the API, from the dosage form in the gastrointestinal tract, thereby further enhancing absorption and rapid onset of therapeutic effect. When present in a pharmaceutical composition or medicament of the invention to promote intragastrointestinal dispersion but not to enhance disintegration, an effervescent agent is preferably present in an amount of about 1% to about 20%, more preferably about 2.5% to about 15%, and still more preferably about 5% to about 10%, by weight of the pharmaceutical composition or medicament.

An "effervescent agent" herein is an agent comprising one or more compounds which, acting together or individually, evolve a gas on contact with water. The gas evolved is generally oxygen or, most commonly, carbon dioxide. Preferred effervescent agents comprise an acid and a base that react in the presence of water to generate carbon dioxide gas. Preferably, the base comprises an alkali metal or alkaline earth metal carbonate or bicarbonate and the acid comprises an aliphatic carboxylic acid.

Non-limiting examples of suitable bases as components of effervescent agents useful in the invention include carbonate salts (e.g., calcium carbonate), bicarbonate salts (e.g., sodium bicarbonate), sesquicarbonate salts, and mixtures thereof. Calcium carbonate is a preferred base.

Non-limiting examples of suitable acids as components of effervescent agents and/or solid acids useful in the invention include citric acid, tartaric acid (as D-, L-, or D/L-tartaric acid), malic acid, maleic acid, fumaric acid, adipic acid, succinic acid, acid anhydrides of such acids, acid salts of such acids, and mixtures thereof. Citric acid is a preferred acid.

In a preferred embodiment of the invention, where the effervescent agent comprises an acid and a base, the weight ratio of the acid to the base is about 1:100 to about 100:1, more preferably about 1:50 to about 50:1, and still more preferably about 1:10 to about 10:1. In a further preferred embodiment of the invention, where the effervescent agent comprises an acid and a base, the ratio of the acid to the base is approximately stoichiometric.

Excipients which solubilize metal salts of APIs typically have both hydrophilic and hydrophobic regions, or are preferably amphiphilic or have amphiphilic regions. One type of amphiphilic or partially-amphiphilic excipient comprises an amphiphilic polymer or is an amphiphilic polymer. A specific amphiphilic polymer is a polyalkylene glycol, which is commonly comprised of ethylene glycol and/or propylene glycol subunits. Such polyalkylene glycols can be esterified at their termini by a carboxylic acid, ester, acid anhyride or other suitable moiety. Examples of such excipients include poloxamers (symmetric block copolymers of ethylene glycol and propylene glycol; e.g., poloxamer 237), polyalkyene glycolated esters of tocopherol (including esters formed from a di- or multi-functional carboxylic acid; e.g., d-alpha-tocopherol polyethylene glycol-1000 succinate), and macrogolglycerides (formed by alcoholysis of an oil and esterification of a polyalkylene glycol to produce a mixture of mono-, di- and tri-glycerides and mono- and di-esters; e.g., stearoyl macrogol-32 glycerides). Such pharmaceutical compositions and medicaments are advantageously administered orally.

Pharmaceutical compositions and medicaments of the present invention can comprise about 10% to about 50%, about 25% to about 50%, about 30% to about 45%, or about 30% to about 35% by weight of API; about 10% to about 50%, about 25% to about 50%, about 30% to about 45%, or about 30% to about 35% by weight of a an excipient which inhibits crystallization; and about 5% to about 50%, about 10% to about 40%, about 15% to about 35%, or about 30% to about 35% by weight of a binding agent. In one example, the weight ratio of the API to the excipient which inhibits crystallization to binding agent is about 1 to 1 to 1.

Solid dosage forms of the invention can be prepared by any suitable process, not limited to processes described herein.

An illustrative process comprises (a) a step of blending a salt of the invention with one or more excipients to form a blend, and (b) a step of tableting or encapsulating the blend to form tablets or capsules, respectively.

In a preferred process, solid dosage forms are prepared by a process comprising (a) a step of blending an API salt of the invention with one or more excipients to form a blend, (b) a step of granulating the blend to form a granulate, and (c) a step of tableting or encapsulating the blend to form tablets or capsules respectively. Step (b) can be accomplished by any dry or wet granulation technique known in the art, but is preferably a dry granulation step. A salt of the present invention is advantageously granulated to form particles of about 1 micrometer to about 100 micrometer, about 5 micrometer to about 50 micrometer, or about 10 micrometer to about 25 micrometer. One or more diluents, one or more disintegrants and one or more binding agents are preferably added, for example in the blending step, a wetting agent can optionally be added, for example in the granulating step, and one or more disintegrants are preferably added after granulating but before tableting or encapsulating. A lubricant is preferably added before tableting. Blending and granulating can be performed independently under low or high shear. A process is preferably selected that forms a granulate that is uniform in API content, that readily disintegrates, that flows with sufficient ease so that weight variation can be reliably controlled during capsule filling or tableting, and that is dense enough in bulk so that a batch can be processed in the selected equipment and individual doses fit into the specified capsules or tablet dies.

In an alternative embodiment, solid dosage forms are prepared by a process that includes a spray drying step, wherein the API is suspended with one or more excipients in one or more sprayable liquids, preferably a non-protic (e.g., non-aqueous or non-alcoholic) sprayable liquid, and then is rapidly spray dried over a current of warm air.

A granulate or spray dried powder resulting from any of the above illustrative processes can be compressed or molded to prepare tablets or encapsulated to prepare capsules. Conventional tableting and encapsulation techniques known in the art can be employed. Where coated tablets are desired, conventional coating techniques are suitable.

Excipients for tablet compositions of the invention are preferably selected to provide a disintegration time of less than about 30 minutes, preferably about 25 minutes or less, more preferably about 20 minutes or less, and still more preferably about 15 minutes or less, in a standard disintegration assay.

In another embodiment of the present invention, a pharmaceutical composition or medicament comprising modafinil and an additional API can be prepared. The modafinil and the additional API can be in the form of a co-crystal, or may be included as a mixture or a combination of active pharmaceutical ingredients. For example, a composition can comprise modafinil and caffeine as a combination. A composition comprising modafinil and caffeine can be used as a therapeutic agent to treat the same conditions as modafinil. In such a composition comprising modafinil and caffeine, the caffeine can yield a quick release characteristic (small $T_{max}$ relative to modafinil) to the dissolution profile while the modafinil causes the therapeutic effect to be present for hours after administration. For example, the $T_{max}$ of caffeine may be 0.001, 0.01, 0.05, 0.1, 0.2, 0.3, 0.4, 0.5, 0.6, 0.7, or 0.8 times that of modafinil. Combination therapies comprise the administration of two or more APIs in the same formulation, or in two or more co-administered formulations. The APIs can be administered together at the same time, or individually at specified intervals.

Uses for modafinil are well known in the art and include the treatment of narcolepsy, multiple sclerosis related fatigue, infertility, eating disorders, attention deficit hyperactivity disorder (ADHD), Parkinson's disease, incontinence, sleep apnea, or myopathies. In another embodiment, any one or more of the modafinil compositions of the present invention may be used in the treatment of one or more of the above conditions. The dosage and administration for modafinil compositions of the present invention can be determined using routine methods in the art but will generally fall between about 50 and about 700 mg/day.

In another embodiment, a composition of the present invention can be administered to a mammal via an injection. Injections include, but are not limited to, intravenous, subcutaneous, and intramuscular injections. In another embodiment, a composition of the present invention is formulated for injection into a mammal in need of therapeutic effect.

EXAMPLES

General Methods for the Preparation of Co-Crystals a) High Throughput Crystallization Using the CrystalMax® Platform CrystalMax® comprises a sequence of automated, integrated high throughput robotic stations capable of rapid generation, identification and characterization of polymorphs, salts, and co-crystals of APIs and API candidates. Worksheet generation and combinatorial mixture design is carried out using proprietary design software Architect™. Typically, an API or an API candidate is dispensed from an organic solvent into tubes and dried under a stream of nitrogen. Salts and/or co-crystal formers may also be dispensed and dried in the same fashion. Water and organic solvents may be combinatorially dispensed into the tubes using a multi-channel dispenser. Each tube in a 96-tube array is then sealed within 15 seconds of combinatorial dispensing to avoid solvent evaporation. The mixtures are then rendered supersaturated by heating to 70 degrees C. for 2 hours followed by a 1 degree C./minute cooling ramp to 5 degrees C. Optical checks are then conducted to detect crystals and/or solid material. Once a solid has been identified in a tube, it is isolated through aspiration and drying. Raman spectra are then obtained on the solids and cluster classification of the spectral patterns is performed using proprietary software (Inquire™).

b) Crystallization from Solution

Co-crystals may be obtained by dissolving the separate components in a solvent and adding one to the other. The co-crystal may then precipitate or crystallize as the solvent mixture is evaporated slowly. The co-crystal may also be obtained by dissolving the two components in the same solvent or a mixture of solvents. The co-crystal may also be obtained by seeding a saturated solution of the two components and seeding with a ground mixture of the co-crystal.

c) Crystallization from the Melt (Co-Melting)

A co-crystal may be obtained by melting the two components together (i.e., co-melting) and allowing recrystallization to occur. In some cases, an anti-solvent may be added to facilitate crystallization.

d) Thermal Microscopy

A co-crystal may be obtained by melting the higher melting component on a glass slide and allowing it to recrystallize. The second component is then melted and is also allowed to recrystallize. The co-crystal may form as a separated phase/band in between the eutectic bands of the two original components.

e) Mixing and/or Grinding

A co-crystal may be obtained by mixing or grinding two components together in the solid state. For example, Example 12 describes the synthesis of a modafinil:1-hydroxy-2-naphthoic acid co-crystal obtained by milling with the addition of a small amount of an appropriate solvent (wet grinding). Similarly, Example 5 describes the synthesis of a modafinil: citric acid monohydrate co-crystal obtained by milling both with and without the addition of a small amount of an appropriate solvent. In one embodiment, a co-crystal is prepared via milling or grinding modafinil with a co-crystal former (dry grinding). In another embodiment, a co-crystal is prepared via milling or grinding modafinil, a co-crystal former, and a small amount of solvent (wet grinding).

In another embodiment, a co-crystal is prepared with the addition of solvent, without the addition of solvent, or both. Solvents used in such a co-crystallization process can be, for example, but not limited to, acetone, methanol, ethanol, isopropyl alcohol, ethyl acetate, isopropyl acetate, nitromethane, dichloromethane, chloroform, toluene, propylene glycol, dimethyl sulfoxide (DMSO), dimethyl formamide (DMF), diethyl ether (ether), ethyl formate, hexane, acetonitrile, benzyl alcohol, water, or another organic solvent including alcohols.

f) Co-sublimation

A co-crystal may be obtained by co-subliming a mixture of an API and a co-crystal former in the same sample cell as an intimate mixture either by heating, mixing or placing the mixture under vacuum. A co-crystal may also be obtained by co-sublimation using a Kneudsen apparatus where the API and the co-crystal former are contained in separate sample cells, connected to a single cold finger, each of the sample cells is maintained at the same or different temperatures under a vaccum atmosphere in order to co-sublime the two components onto the cold-finger forming the desired co-crystal.

Analytical Methods

Differential scanning calorimetric (DSC) analysis of the samples was performed using a Q1000 Differential Scanning Calorimeter (TA Instruments, New Castle, Del., U.S.A.), which uses Advantage for QW-Series, version 1.0.0.78, Thermal Advantage Release 2.0 (2001 TA Instruments-Water LLC). In addition, the analysis software used was Universal Analysis 2000 for Windows 95/98/2000/NT, version 3.1E; Build 3.1.0.40 (2001 TA Instruments-Water LLC).

For the DSC analysis, the purge gas used was dry nitrogen, the reference material was an empty aluminum pan that was crimped, and the sample purge was 50 mL/minute.

DSC analysis of the sample was performed by placing the modafinil sample in an aluminum pan with a crimped pan closure. The starting temperature was typically 20 degrees C. with a heating rate of 10 degrees C./minute, and the ending temperature was 200 degrees C. All reported DSC transitions represent the temperature of endothermic or exothermic transition at their respective peaks with an error of +/−2 degrees C., unless otherwise indicated.

Thermogravimetric analysis (TGA) of samples was performed using a Q500 Thermogravimetric Analyzer (TA Instruments, New Castle, Del., U.S.A.), which uses Advantage for QW-Series, version 1.0.0.78, Thermal Advantage Release 2.0 (2001 TA Instruments-Water LLC). In addition, the analysis software used was Universal Analysis p000 for Windows 95/98/2000/NT, version 3.1E; Build 3.1.0.40 (2001 TA Instruments-Water LLC).

For the TGA experiments, the purge gas used was dry nitrogen, the balance purge was 40 mL/minute $N_2$, and the sample purge was 60 mL/minute $N_2$.

TGA was performed on the sample by placing the modafinil sample in a platinum pan. The starting temperature was typically 20 degrees C. with a heating rate of 10 degrees C./minute, and the ending temperature was 300 degrees C.

A powder X-ray diffraction (PXRD) pattern for the samples was obtained using a D/Max Rapid, Contact (Rigaku/MSC, The Woodlands, Tex., U.S.A.), which uses as its control software RINT Rapid Control Software, Rigaku Rapid/XRD, version 1.0.0 (1999 Rigaku Co.). In addition, the analysis software used were RINT Rapid display software, version 1.18 (Rigaku/MSC), and JADE XRD Pattern Processing, versions 5.0 and 6.0 ((1995-2002, Materials Data, Inc.).

For the PXRD analysis, the acquisition parameters were as follows: source was Cu with a K line at 1.5406 Å; x-y stage was manual; collimator size was 0.3 mm; capillary tube (Charles Supper Company, Natick, Mass., U.S.A.) was 0.3 mm ID; reflection mode was used; the power to the X-ray tube was 46 kV; the current to the X-ray tube was 40 mA; the omega-axis was oscillating in a range of 0-5 degrees at a speed of 1 degree/minute; the phi-axis was spinning at an angle of 360 degrees at a speed of 2 degrees/second; 0.3 mm collimator; the collection time was 60 minutes; the temperature was room temperature; and the heater was not used. The sample was presented to the X-ray source in a boron rich glass capillary.

In addition, the analysis parameters were as follows: the integration 2-theta range was 2-60 degrees; the integration chi range was 0-360 degrees; the number of chi segments was 1; the step size used was 0.02; the integration utility was cylint; normalization was used; dark counts were 8; omega offset was 180; and chi and phi offsets were 0.

PXRD diffractograms were also acquired via the Bruker AXS D8 Discover X-ray Diffractometer. This instrument was equipped with GADDS™ (General Area Diffraction Detection System), a Bruker AXS HI-STAR Area Detector at a distance of 15.05 cm as per system calibration, a copper source (Cu/K$_\alpha$ 1.54056 angstroms), automated x-y-z stage, and 0.5 mm collimator. The sample was compacted into pellet form and mounted on the x-y-z stage. A diffractogram was acquired under ambient conditions (25 degrees C.) at a powder setting of 40 kV and 40 mA in reflection mode while the sample remained stationary. The exposure time was varied and specified for each sample. The diffractogram obtained underwent a spatial remapping procedure to account for the geometrical pincushion distortion of the area detector then integrated along chi from −118.8 to −61.8 degrees and 2-theta 2.1-37 degrees at a step size of 0.02 degrees with normalization set to bin normalize.

The relative intensity of peaks in a diffractogram is not necessarily a limitation of the PXRD pattern because peak intensity can vary from sample to sample, e.g., due to crystalline impurities. Further, the angles of each peak can vary by about +/−0.1 degrees, preferably +/−0.05. The entire pattern or most of the pattern peaks may also shift by about +/−0.1 degrees to about +/−0.2 degrees due to differences in calibration, settings, and other variations from instrument to instrument and from operator to operator. All reported PXRD peaks in the Figures, Examples, and elsewhere herein are reported with an error of about ±0.1 degrees 2-theta.

For PXRD data herein, including Tables and Figures, each composition of the present invention may be characterized by any one, any two, any three, any four, any five, any six, any seven, or any eight or more of the 2 theta angle peaks. Any one, two, three, four, five, or six DSC transitions can also be used to characterize the compositions of the present invention. The different combinations of the PXRD peaks and the DSC transitions can also be used to characterize the compositions.

Thermal (hotstage) microscopy was completed on a Zeiss Axioplan 2 microscope equipped with a Mettler Toledo FP90 controller. The hotstage used was a Mettler Toledo FP82HT. All melting point determinations were completed by placing the sample on a microscope slide and covered with a coverslip. The initial temperature was set at 30 degrees C. and the temperature was increased at a rate of 10 degrees C./minute. Melting was observed through a 5× microscope objective.

HPLC Method: (adapted from Donovan et al. *Therapeutic Drug Monitoring* 25:197-202.

Column: Astec Cyclobond I 2000 RSP 250×4.6 mm (Part No. 411121)

Mobile Phase A: 20 mM sodium phosphate, pH 3.0
   B: 70:30 mobile phase A:acetonitrile
   Flow Rate: 1.0 mL/min (~1500 PSI)

Flow Program: gradient

Run Time: 35 minutes

Detection: UV @ 225 nm

Injection Volume: 10 microliters

Column Temperature: 30+/−1 degrees C.

Standard diluent: 90:10 (v/v) Mobile Phase A:acetonitrile

Needle wash: acetonitrile

Purge solvent & seal wash: 90:10 (v/v) water:acetonitrile

Mobile Phase Preparation:
1. Prep 1 M sodium phosphate monobasic: dissolve 120 g of sodium phosphate monobasic in water and make up to 1000 mL; filter.
2. Prep Mobile Phase A (20 mM sodium phosphate, pH 3.0): for each liter, dilute 20 mL 1 M sodium phosphate to 1000 mL with water; adjust pH to 3.0 with phosphoric acid.
3. Prep Mobile Phase B (70:30 (v/v) 20 mM sodium phosphate, pH 3.0:acetonitrile): for each liter, mix 700 mL Mobile Phase A and 300 mL of acetonitrile.

Sample Prep:
1. Dissolve samples in 90:10 (v/v) 20 mM sodium phosphate, pH 3.0:acetonitrile to an approximate concentration of 20 micrograms/mL Raman Acquisitions The sample was either left in the glass vial in which it was processed or an aliquot of the sample was transferred to a glass slide. The glass vial or slide was positioned in the sample chamber. The measurement was made using an Almega™ Dispersive Raman (Almega™ Dispersive Raman, Thermo-Nicolet, 5225 Verona Road, Madison, Wis. 53711-4495) system fitted with a 785 nm laser source. The sample was manually brought into focus using the microscope portion of the apparatus with a 10× power objective (unless otherwise noted), thus directing the laser onto the surface of the sample. The spectrum was acquired using the parameters, outlined in Table A. Exposure times and number of exposures may vary; changes to parameters will be indicated for each acquisition.)

TABLE A

Raman Spectral acquisition parameters

| Parameter | Setting Used |
| --- | --- |
| Exposure time (s) | 2.0 |
| Number of exposures | 10 |
| Laser source wavelength (nm) | 785 |
| Laser power (%) | 100 |
| Aperture shape | pin hole |
| Aperture size (um) | 100 |
| Spectral range | 104-3428 |
| Grating position | Single |
| Temperature at acquisition (degrees C.) | 24.0 |

IR Acquisitions

IR spectra were obtained using Nexus™ 470 FT-IR, Thermo-Nicolet, 5225 Verona Road, Madison, Wis. 53711-4495 and were analyzed with Control and Analysis software: OMNIC, Version 6.0a, (C) Thermo-Nicolet, 1995-2004.

Data for the co-crystals are shown in Table IV and in the Figures.

Example 1

Racemic Modafinil:Malonic Acid Co-crystal

Figure 2:
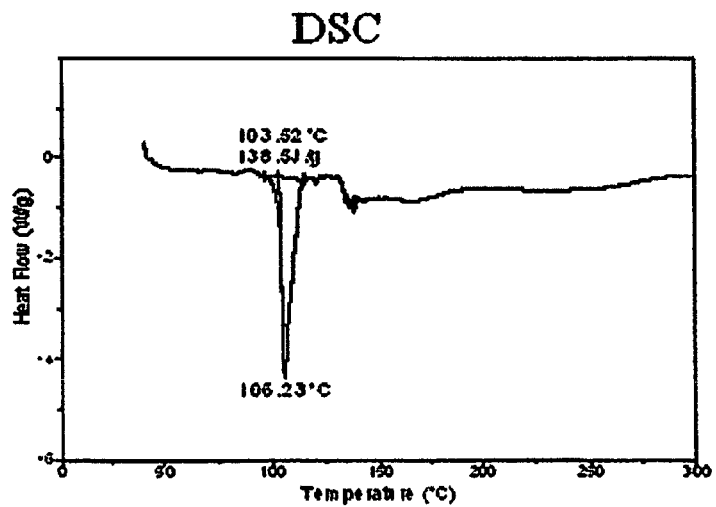
FIG. 2—DSC thermogram of a co-crystal comprising modafinil and malonic acid.
Figure 3:
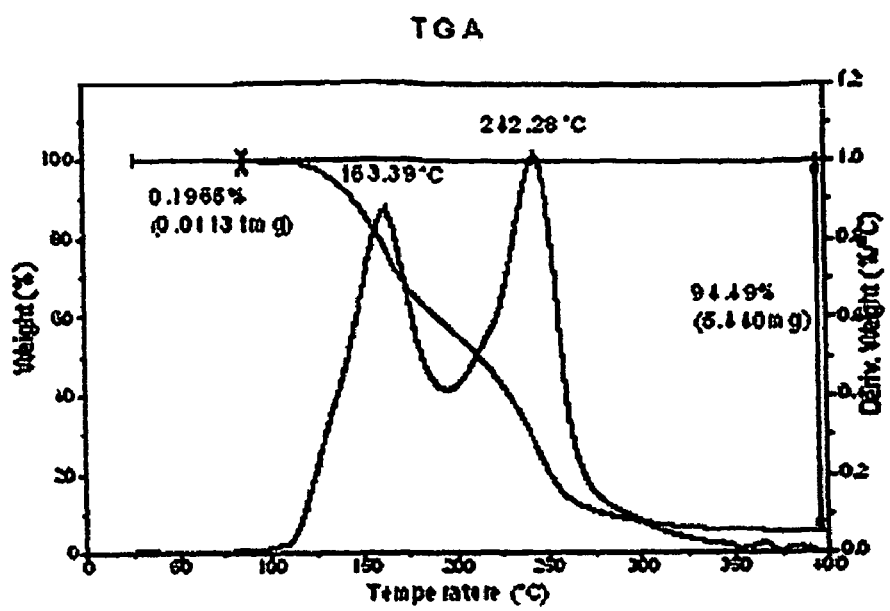
FIG. 3—TGA thermogram of a co-crystal comprising modafinil and malonic acid.
Figure 4A:
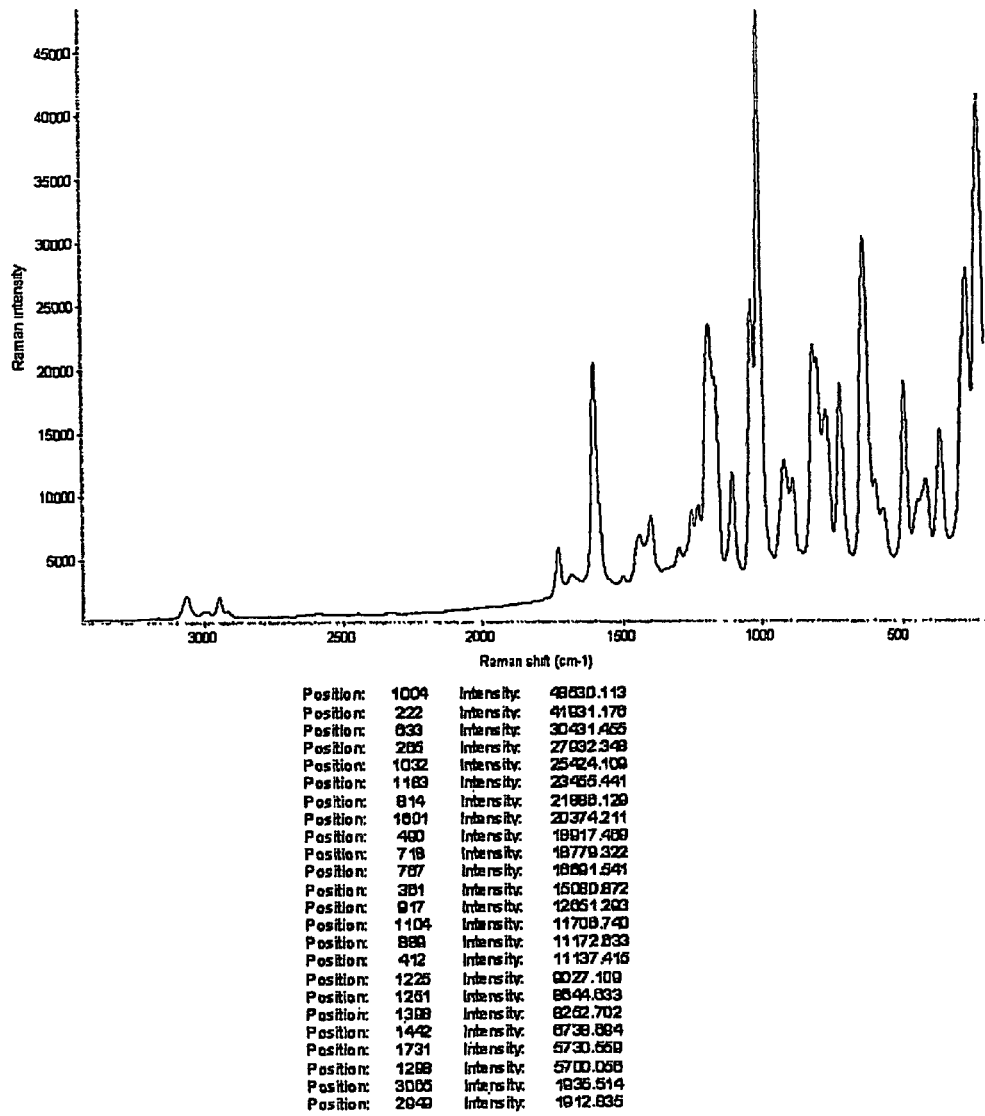
FIGS. 4A and 4B—Raman spectrum of a co-crystal comprising modafinil and malonic acid (FIG. 4A), and three Raman spectra of modafinil (bottom spectrum), malonic acid (middle spectrum), and a co-crystal comprising modafinil and malonic acid (top spectrum) (FIG. 4B).
Figure 4B:
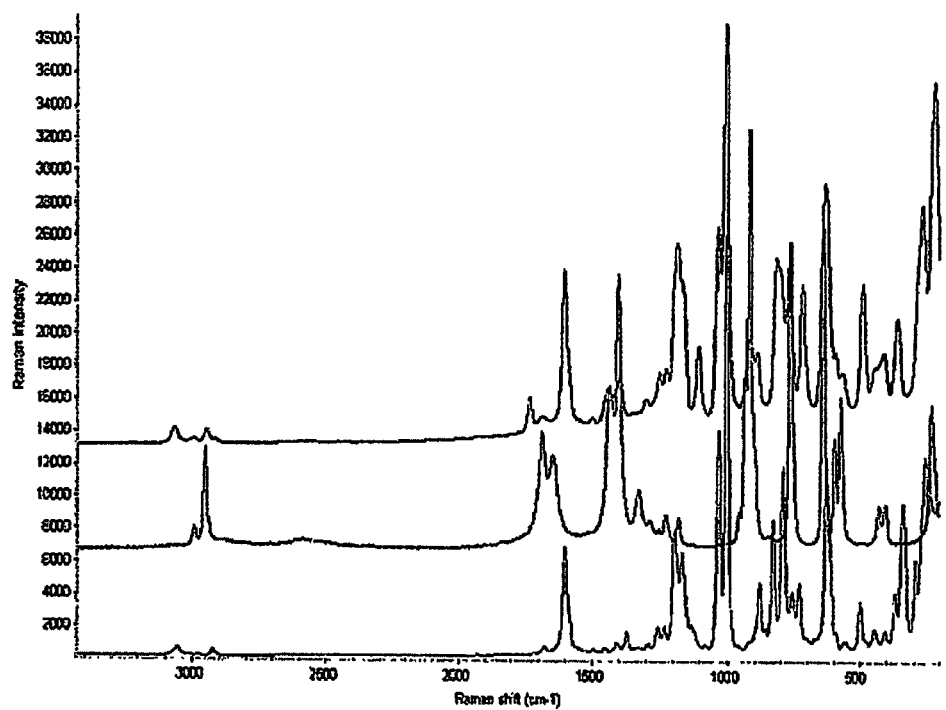
Figure 5A:
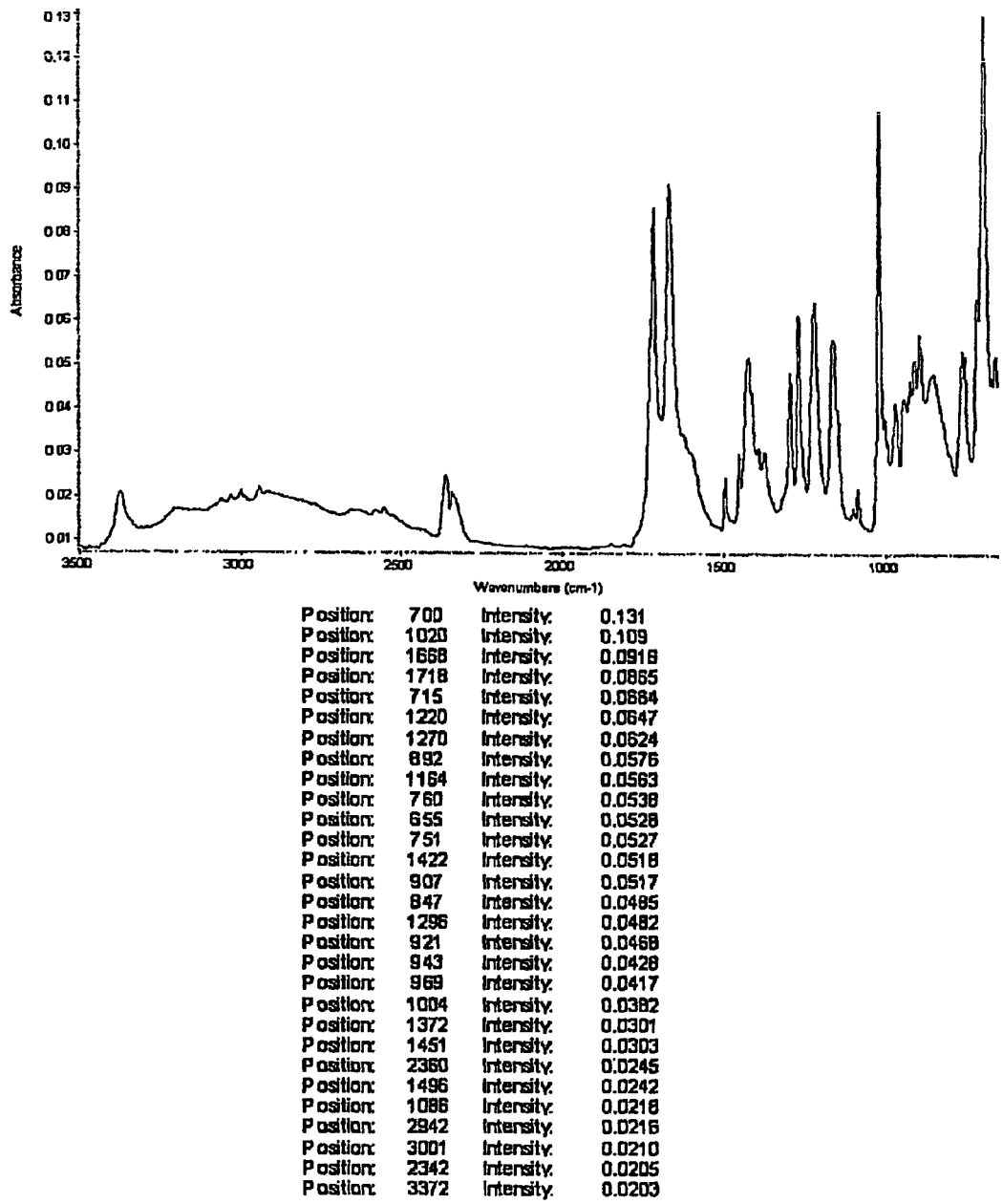
FIGS. 5A and 5B—Infrared spectrum of a co-crystal comprising modafinil and malonic acid (FIG. 5A), and three Infrared spectra of modafinil (top spectrum), malonic acid (middle spectrum), and a co-crystal comprising modafinil and malonic acid (bottom spectrum) (FIG. 5B).
Figure 5B:
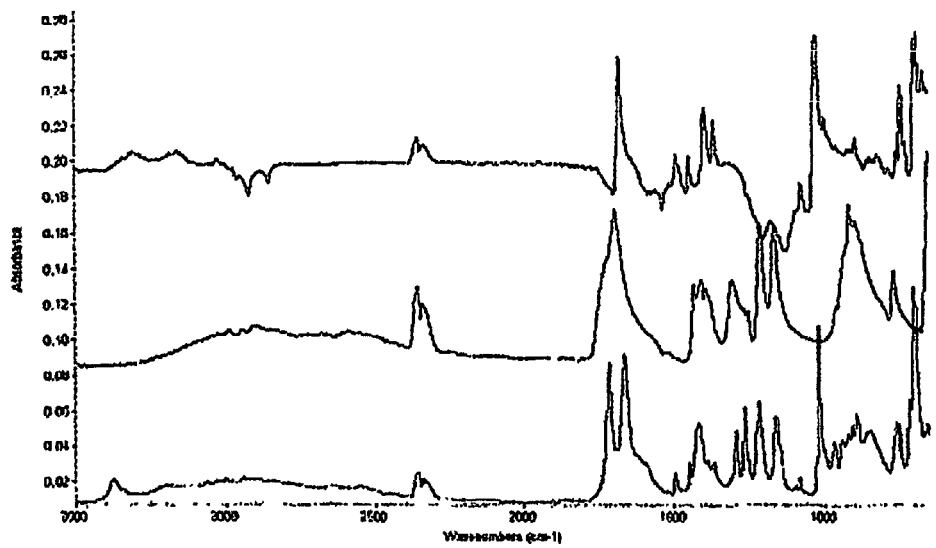

To a solution containing racemic modafinil (150 mg, 0.549 mmol) in acetic acid (600 microliters) was added malonic acid (114.9 mg, 1.104 mmol). The mixture was then heated on a hotplate at 67 degrees C. until all material dissolved. The solution was then dried under a flow of nitrogen to give a 1:1 modafinil:malonic acid co-crystal as a colorless solid. The solid material was characterized using PXRD. The material was then dried further under a flow of nitrogen overnight to give the same material with a slight excess of malonic acid. The colorless solid was characterized using PXRD (Bruker), DSC, TGA, IR and Raman spectroscopy. PXRD data for the modafinil:malonic acid (1:1) co-crystal are listed in Table IV, and the diffractogram is shown in FIG. 1 (Data as collected/received). DSC showed an endothermic transition at about 106 degrees C., and the thermogram is shown in FIG. 2. TGA thermogram is shown in FIG. 3. FIGS. 4A and 4B show a Raman spectrum of the modafinil:malonic acid co-crystal and three Raman spectra of modafinil, malonic acid, and the co-crystal, respectively. FIGS. 5A and 5B show an IR spectrum of the modafinil:malonic acid co-crystal and three IR spectra of modafinil, malonic acid, and the co-crystal, respectively. The modafinil:malonic acid co-crystal can be characterized by any one, any two, any three, any four, any five, or any six or more of the peaks in FIG. 1 including, but not limited to, 5.00, 9.17, 10.08, 16.81, 18.26, 19.43, 21.36, 21.94, 22.77, 24.49, 25.63, 26.37, and 28.45 degrees 2-theta.

Figure 6A:
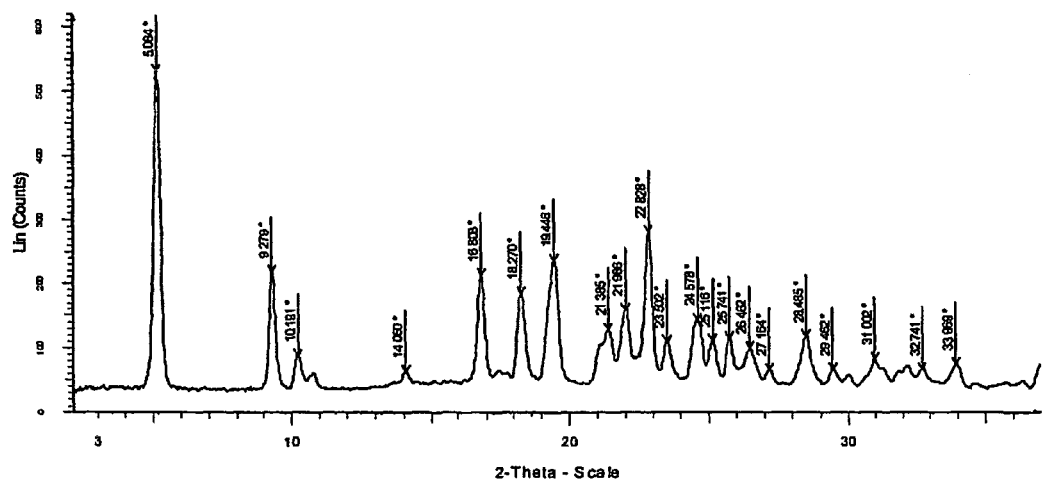
FIG. 6A—PXRD diffractogram of a co-crystal comprising modafinil and malonic acid.
Figure 6B:
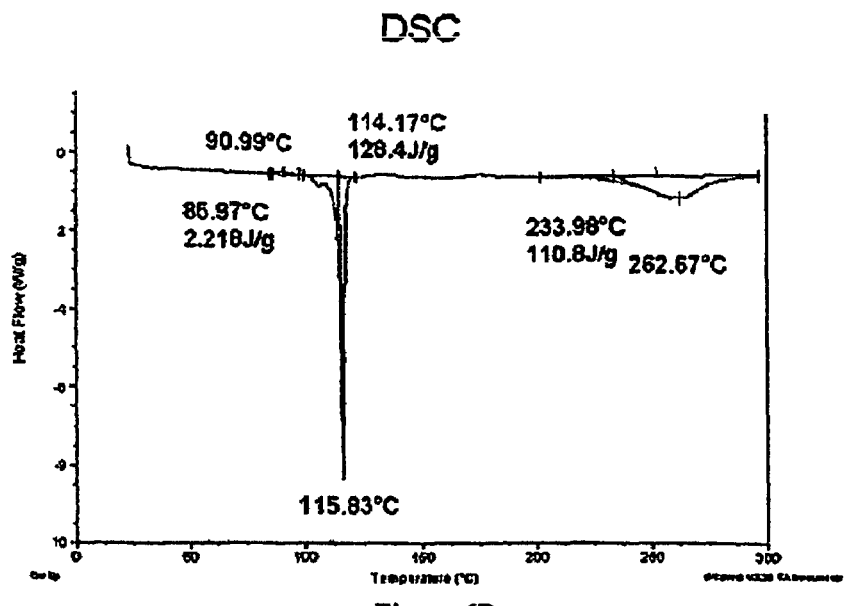
FIG. 6B—DSC thermogram of a co-crystal comprising modafinil and malonic acid (from grinding).
Figure 7:
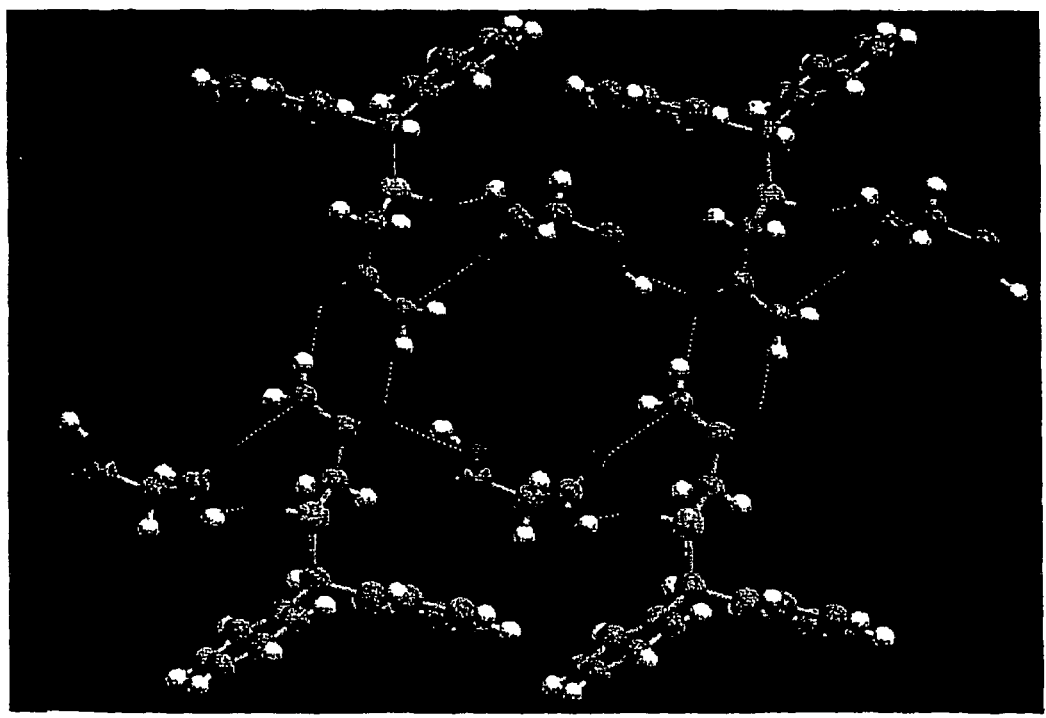
FIG. 7—Packing diagram for modafinil:malonic acid co-crystal.

The modafinil:malonic acid co-crystal was also prepared by grinding the API and co-crystal former together. Racemic modafinil (2.50 g, 0.009 mol) and malonic acid (1.01 g, 0.0097 mmol) were mixed in a large mortar and pestle over a period of seven days (malonic acid added in increments over 7 days with about a 1:1.05 ratio made on the first day and increments added over the next seven days which resulted in a 1:2 modafinil:malonic acid ratio). The mixture was ground for 45 minutes initially and 20 minutes each time more malonic acid was added. On the seventh day the mixture of co-crystal and starting components was heated in a sealed 20 mL vial at 80 degrees C. for about 35 minutes to facilitate completion of the co-crystal formation. PXRD analysis (Bruker) of the resultant material was completed, and is shown in FIG. 6A (data as received). The modafinil:malonic acid co-crystal can be characterized by any one, any two, any three, any four, any five, or any six or more of the peaks in FIG. 6A including, but not limited to, 5.08, 9.28, 16.81, 18.27, 19.45, 21.39, 21.99, 22.83, 23.50, 24.58, 25.12, and 28.49 degrees 2-theta. DSC thermogram for the co-crystal shows, in FIG. 6B, an endothermic transition at about 116 degrees C. Single crystal data of the modafinil:malonic acid co-crystal were acquired and are reported below. FIG. 7 shows a packing diagram of the modafinil:malonic acid.

Crystal data: $C_{18}H_{19}NO_6S$, M=377.40, monoclinic C2/c; a=18.728(8) angstroms, b=5.480(2) angstroms, c=33.894(13) angstroms, alpha=90 degrees, beta=91.864(9) degrees, gamma=90 degrees, T=100(2) K, Z=8, $D_c$=1.442 $Mg/m^3$, V=3477(2) cubic angstroms, λ=0.71073 angstroms, 6475 reflections measured, 3307 unique ($R_{int}$=0.1567). Final residuals were $R_1$=0.1598, $wR_2$=0.3301 for I>2sigma(I), and $R_1$=0.2544, $wR_2$=0.3740 for all 3307 data.

Other methods were also used to prepare the modafinil:malonic acid co-crystal. A third preparation was performed by placing modafinil (30 mg, 0.0001 mol) and excess malonic acid in a stainless steel vial. 20 microliters of acetone was added to the vial. The vial was then placed in a grinder (wig-1-bug, Bratt Technologies, 115V/60 Hz) and the solid mixture was milled for 5 minutes. The resultant powder was then collected and characterized using PXRD and DSC. In yet another preparation of the modafinil:malonic acid co-crystal, the third preparation above was completed without the addition of solvent. All of the above methods with malonic acid were shown to yield the same co-crystal via PXRD and DSC analysis.

Example 2

Racemic Modafinil:Glycolic Acid Co-crystal

Figure 8A:
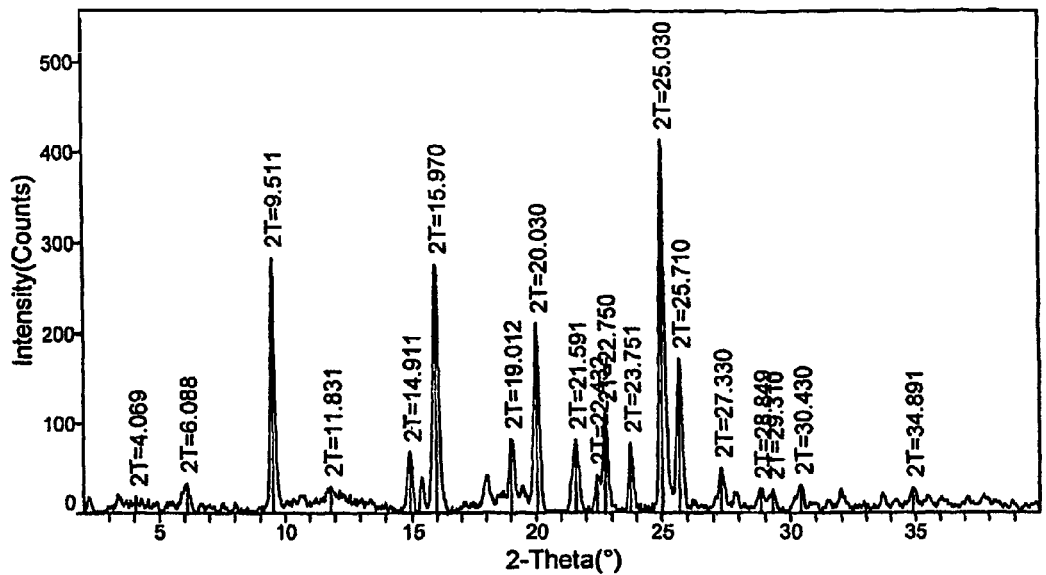
FIGS. 8A and 8B—PXRD diffractograms of a co-crystal comprising modafinil and glycolic acid, background removed and as collected, respectively.
Figure 8B:
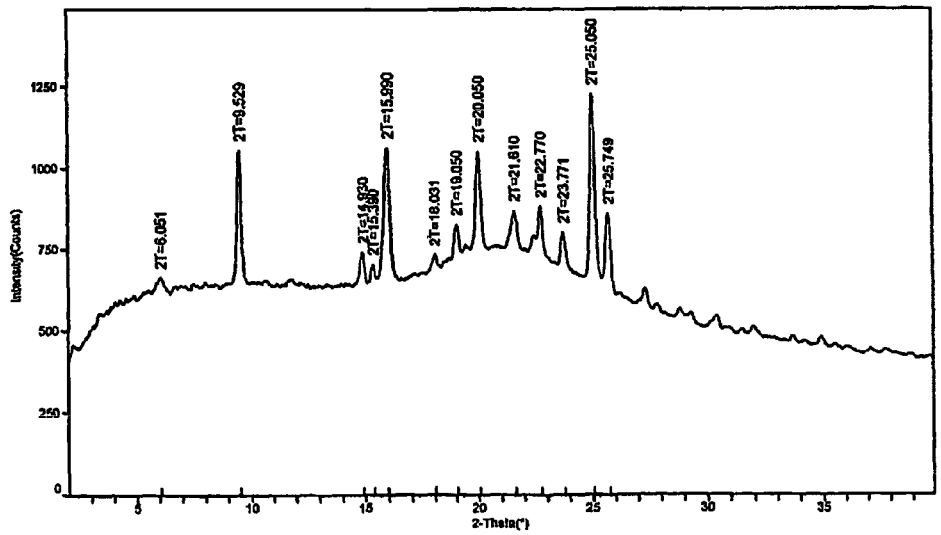

Racemic modafinil (1 mg, 0.0037 mmol) and glycolic acid (0.30 mg, 0.0037 mmol) were dissolved in acetone (400 microliters). The solution was allowed to evaporate to dryness and the resulting solid was characterized using PXRD (Rigaku). PXRD data for the modafinil:glycolic acid co-crystal are listed in Table IV. See FIGS. 8A and 8B. FIG. 5A shows the PXRD diffractogram after subtraction of background noise. FIG. 8B shows the raw PXRD data as collected.

An alternative method for the preparation of modafinil:glycolic acid co-crystals was also completed. To a solution of modafinil (1 mg, 0.0037 mmol) dissolved in a mixture of acetone and methanol (3:1, 100 microliters) was added glycolic acid (0.28 mg, 0.0037 mmol) dissolved in methanol (50 microliters). The solvent was then evaporated to dryness under a flow of nitrogen to give a mixture of the two starting components. Acetone (200 microliters) was then added to the mixture and it was heated to 70 degrees C. and maintained at 70 degrees C. for 2 hours. The sample was then cooled to 5 degrees C. and maintained at that temperature for 1 day. After 1 day, the cap was removed from the vial and the solvent was evaporated to dryness to give a modafinil:glycolic acid co-crystal as a colorless solid. The modafinil:glycolic acid co-crystal was characterized by PXRD. The modafinil:glycolic acid co-crystal can be characterized by any one, any two, any three, any four, any five, or any six or more of the peaks in FIG. 8A including, but not limited to, 9.51, 14.91, 15.97, 19.01, 20.03, 21.59, 22.75, 25.03, and 25.71 degrees 2-theta. The modafinil:glycolic acid co-crystal can, likewise, be characterized by any one, any two, any three, any four, any five, or any six or more of the peaks in FIG. 8B including, but not limited to, 9.53, 14.93, 15.99, 19.05, 20.05, 21.61, 22.77, and 25.05 degrees 2-theta.

Example 3

Racemic Modafinil:Maleic Acid Co-crystal

Figure 9A:
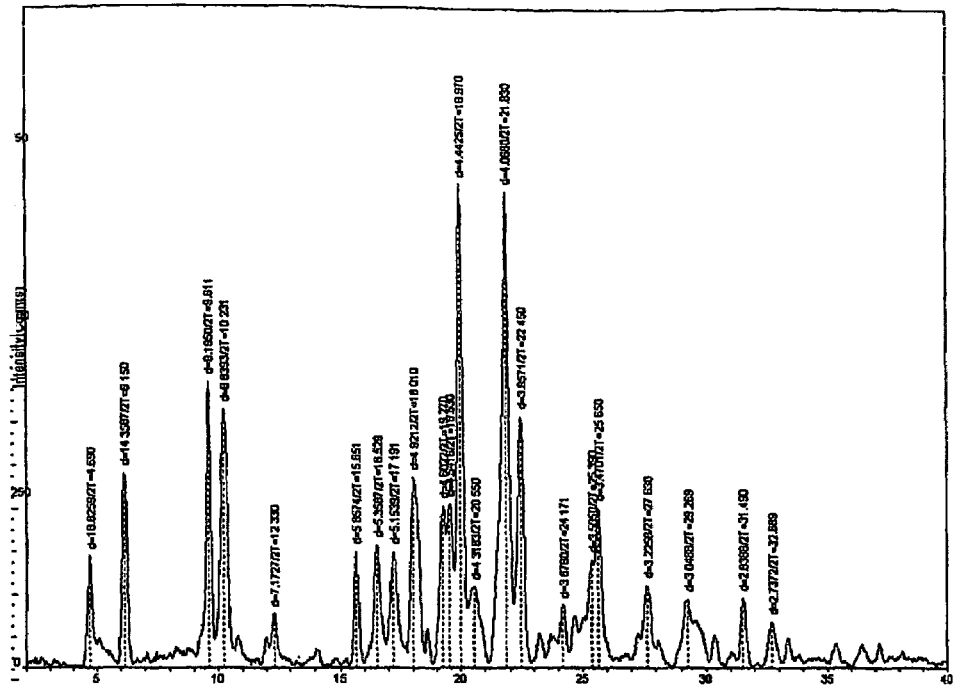
FIGS. 9A and 9B—PXRD diffractograms of a co-crystal comprising modafinil and maleic acid, background removed and as collected, respectively.
Figure 9B:
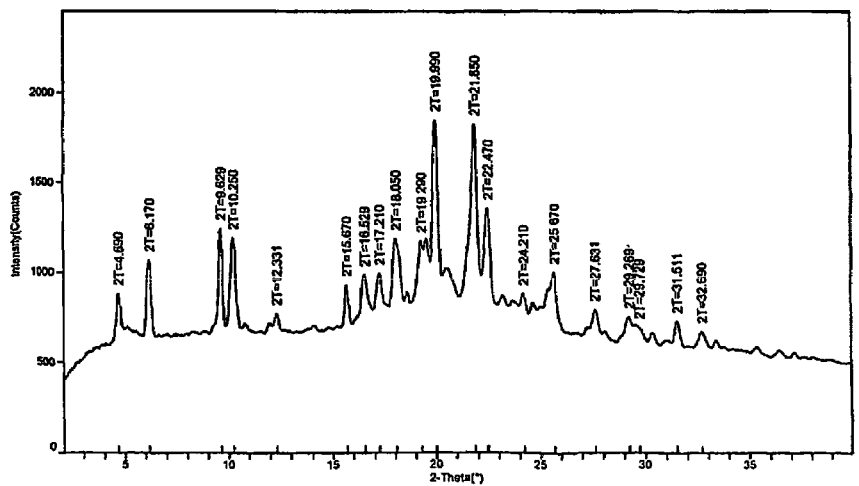

To a solution containing modafinil (150 mg, 0.549 mmol) in acetic acid (600 microliters) was added maleic acid (30.7 mg, 0.264 mmol). The mixture was then heated on a hotplate at 67 degrees C. until all material dissolved. The solution was then dried under a flow of nitrogen to give a clear amorphous material. The amorphous material was stored in a sealed vial at room temperature. After 2 days, a solid material began to form and and was collected and characterized to be a modafinil:maleic acid co-crystal using PXRD (Rigaku), as shown in FIGS. 9A and 9B. FIG. 9A shows the PXRD diffractogram after subtraction of background noise. FIG. 9B shows the raw PXRD data. PXRD data for the modafinil:maleic acid co-crystal are listed in Table IV. The modafinil:maleic acid co-crystal can be characterized by any one, any two, any three, any four, any five, or any six or more of the peaks in FIG. 9A including, but not limited to, 4.69, 6.15, 9.61, 10.23, 15.65, 16.53, 17.19, 18.01, 19.97, 21.83, and 22.45 degrees 2-theta. The modafinil:maleic acid co-crystal can, likewise, be characterized by any one, any two, any three, any four, any five, or any six or more of the peaks in FIG. 9B including, but not limited to, 4.69, 6.17, 9.63, 10.25, 15.67, 16.53, 17.21, 18.05, 19.99, 21.85, and 22.47 degrees 2-theta.

Example 4

Racemic Modafinil:L-Tartaric Acid Co-crystal

Figure 10:
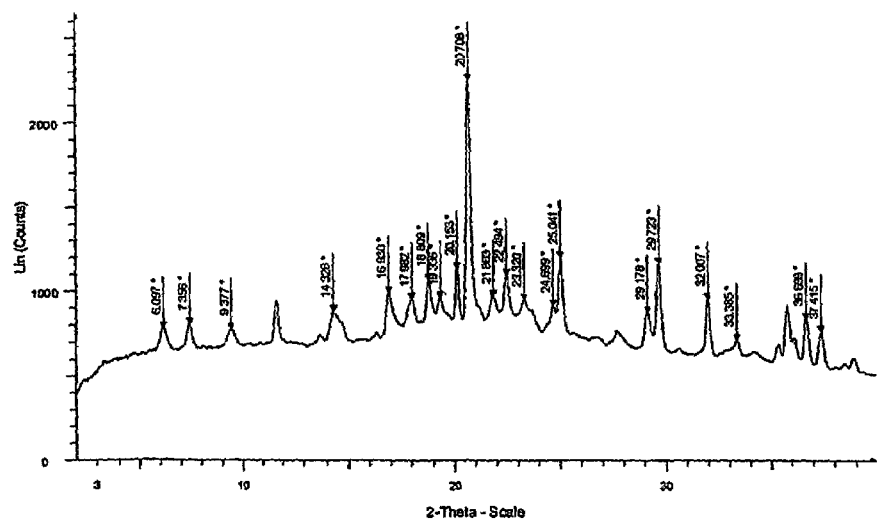
FIG. 10—PXRD diffractogram of a co-crystal comprising modafinil and L-tartaric acid.

To a solution of racemic modafinil (10.12 mg, 0.037 mmol) in methanol (2 mL) was added L-tartaric acid (5.83 mg, 0.039 mmol). The solution was then left to evaporate at room temperature to give a clear, viscous material. The material was dried further under flowing nitrogen for 2 days, and then placed in a vial and capped. After 6 days, a small amount of colorless solid formed. One day after the first solids are seen approximately 60% of the remaining clear amorphous volume converted to the solid form. A sample of this material was analyzed by PXRD (Bruker), as shown in FIG. 10. The modafinil:L-tartaric acid co-crystal can be characterized by any one, any two, any three, any four, any five, or any six or more of the peaks in FIG. 10 including, but not limited to, 6.10, 7.36, 9.38, 14.33, 16.93, 17.98, 18.81, 20.15, 20.71, 22.49, and 25.04 degrees 2-theta.

Example 5

Racemic Modafinil:Citric Acid Co-crystal

Figure 11A:
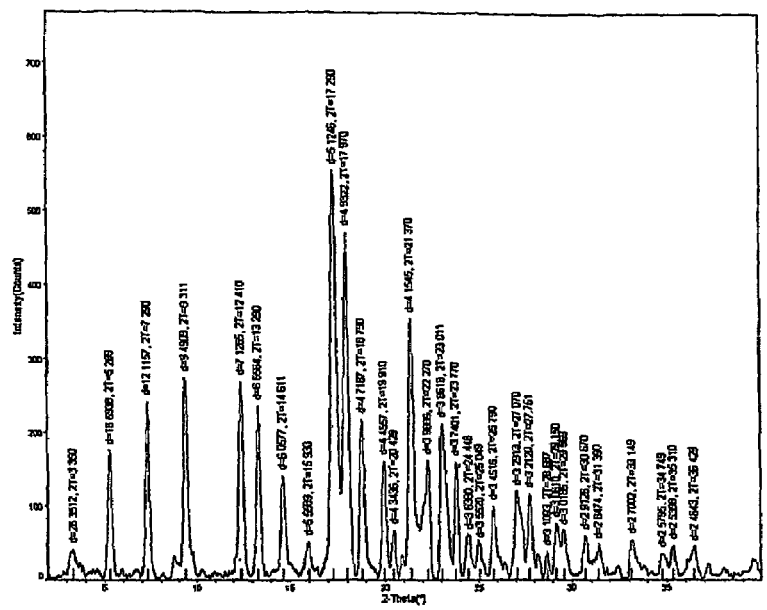
FIG. 11A—PXRD diffractogram of a co-crystal comprising modafinil and citric acid.

Racemic modafinil (25.3 mg, 93 mmol) and citric acid monohydrate (26.8 mg, 128 mmol) were ground together for 3 minutes. 1 mg of the resulting mixture was then dissolved in acetone (100 microliters) and heated to 70 degrees C. and maintained at that temperature for 2 hours. The solution was then cooled to 5 degrees C. and was left at that temperature for 2 days. After 2 days the cap was removed from the vial and one drop of water was added. The solvent was then evaporated to give a modafinil:citric acid monohydrate co-crystal as a colorless solid. The modafinil:citric acid monohydrate co-crystal was characterized by PXRD (Rigaku), as shown in FIG. 11A (background subtracted). The modafinil:citric acid co-crystal can be characterized by any one, any two, any three, any four, any five, or any six or more of the peaks in FIG. 11A including, but not limited to, 5.29, 7.29, 9.31, 12.41, 13.29, 17.29, 17.97, 18.79, 21.37, and 23.01 degrees 2-theta.

Figure 11B:
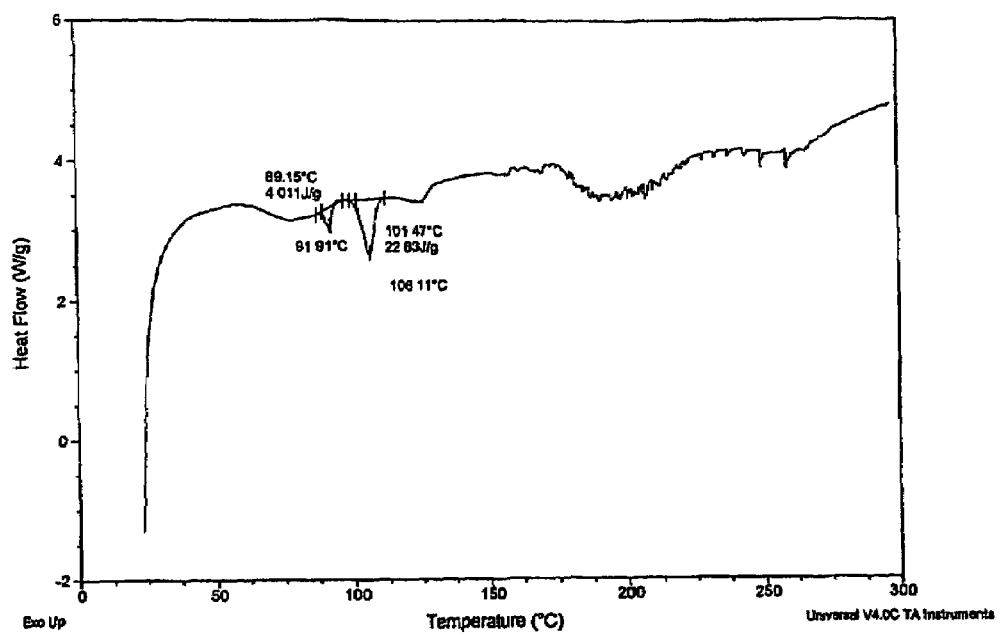
FIG. 11B—DSC thermogram of a co-crystal comprising modafinil and citric acid.

Other methods were also used to prepare the modafinil:citric acid monohydrate co-crystal. A second preparation was performed by placing modafinil (30 mg, 0.0001 mol) and excess citric acid monohydrate in a stainless steel vial. 20 microliters of acetone was added to the vial. The vial was then placed in a grinder (wig-1-bug, Bratt Technologies, II 5V/60 Hz) and the solid mixture was milled for 5 minutes. The resultant powder was then collected and characterized using PXRD and DSC. The DSC thermogram is shown in FIG. 11B. In yet another preparation of the modafinil:citric acid monohydrate co-crystal, the second preparation above was completed without the addition of solvent. All of the above methods with citric acid monohydrate were shown to yield the same co-crystal via PXRD and DSC analysis.

Example 6

Racemic Modafinil:Succinic Acid Co-crystal

Figure 12A:
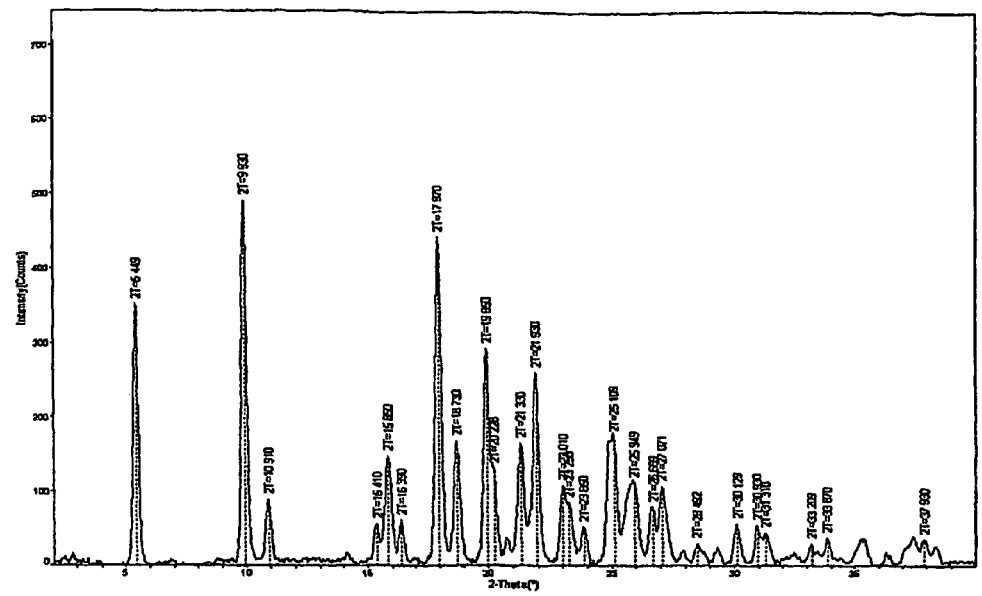
FIGS. 12A and 12B—PXRD diffractogram of a co-crystal comprising modafinil and succinic acid, background removed and as collected, respectively.
Figure 12B:
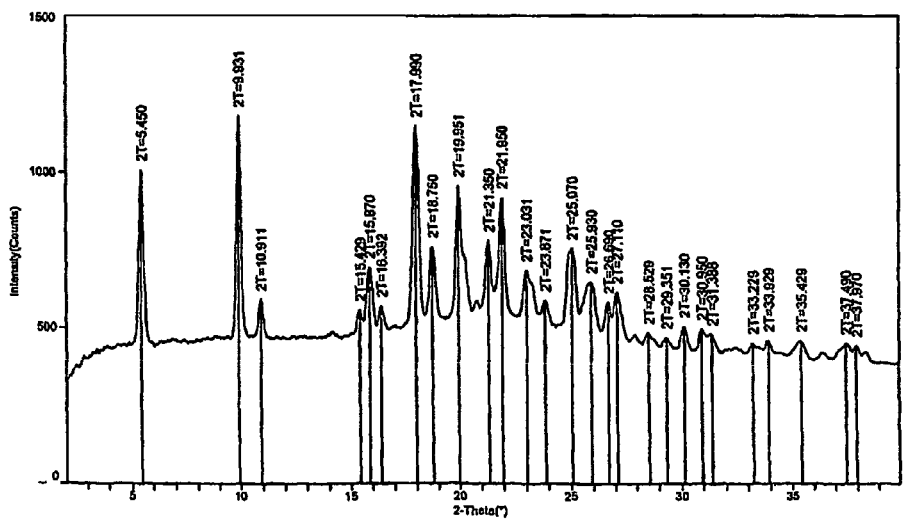
Figure 13:
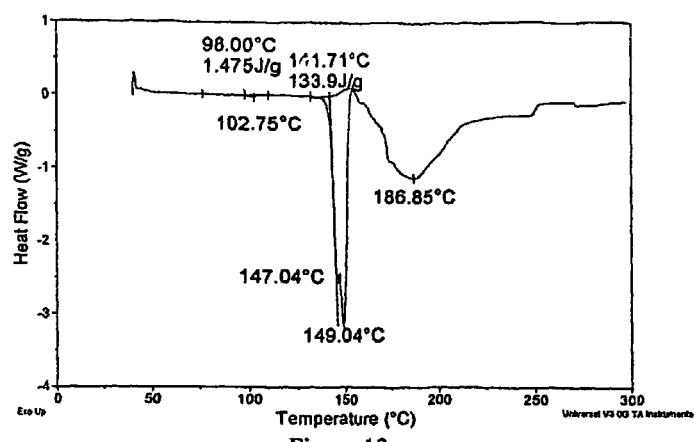
FIG. 13—DSC thermogram of a co-crystal comprising modafinil and succinic acid.

Racemic modafinil (25 mg, 90 mmol) and succinic acid (10.6 mg, 90 mmol) were placed in a glass vial and dissolved in methanol (20 microliters). The resulting solution was heated at 70 degrees C. for 2 hours and then cooled to 5 degrees C. and maintained at that temperature for 2 days. After 2 days, the cap was removed from the vial and the solvent was evaporated at 65 degrees C. to give a 2:1 modafinil:succinic acid co-crystal as a colorless solid. The co-crystal is a 2:1 co-crystal comprising two moles of modafinil for every mole of succinic acid. The modafinil:succinic acid co-crystal was characterized by PXRD (Rigaku) and DSC, as shown in FIGS. 12A, 12B, and 13. FIG. 12A shows the PXRD diffractogram after subtraction of background noise. FIG. 12B shows the raw PXRD data. FIG. 13 shows the DSC thermogram.

Figure 14:
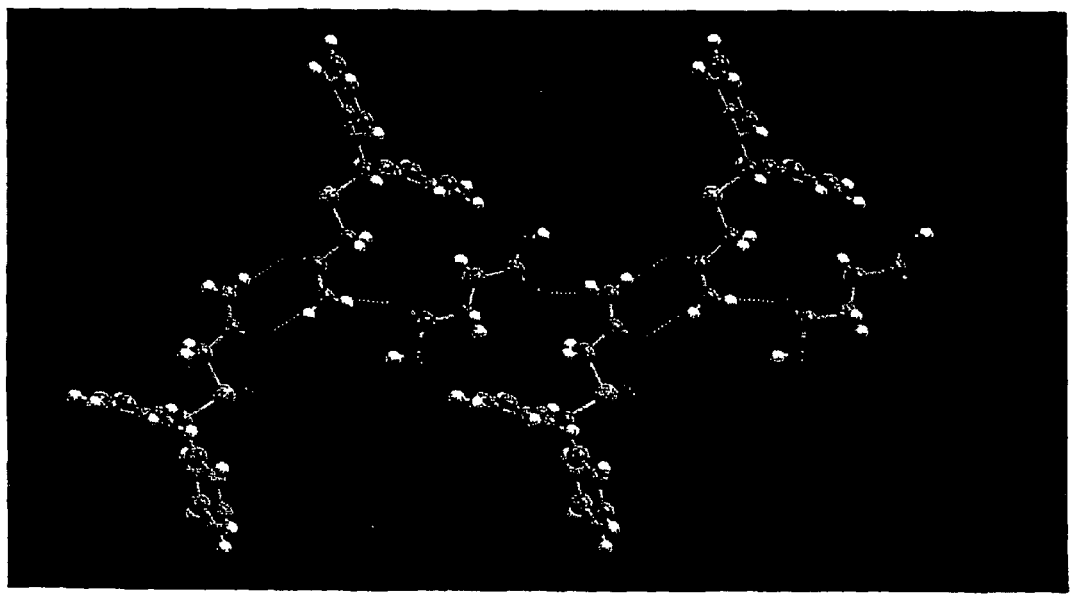
FIG. 14—Packing diagram of a co-crystal comprising modafinil and succinic acid.

An alternative method for the preparation of modafinil:succinic acid co-crystals was also completed. To racemic modafinil (49.7 mg, 0.182 mmol) and succinic acid (21.6 mg, 0.182 mmol) in a round bottom flask was added methanol (1.5 mL). The mixture was then dissolved on a hotplate at 65 degress C. Seed crystals of modafinil:succinic acid co-crystal from the above preparation were then added to the flask. The methanol was then evaporated using a rotary evaporator and a 65 degrees C. hot water bath to give the modafinil:succinic acid co-crystal as a colorless solid. PXRD (Rigaku) of the collected solid confirms the synthesis of the modafinil:succinic acid co-crystal. The modafinil:succinic acid co-crystal can be characterized by any one, any two, any three, any four, any five, or any six or more of the peaks in FIG. 12A including, but not limited to, 5.45, 9.93, 15.85, 17.97, 18.73, 19.95, 21.33, 21.93, 23.01, and 25.11 degrees 2-theta. The modafinil:succinic acid co-crystal can, likewise, be characterized by any one, any two, any three, any four, any five, or any six or more of the peaks in FIG. 12B including, but not limited to, 5.45, 9.93, 15.87, 17.99, 18.75, 19.95, 21.95, 23.03, and 25.07 degrees 2-theta. Single crystal data of the modafinil:succinic acid co-crystal were acquired and are reported below. FIG. 14 shows a packing diagram of the modafinil:succinic acid co-crystal.

Crystal data: $C_{17}H_{18}NO_4S$, triclinic P-1; a=5.672(4) angstroms, b=8.719(6) angstroms, c=16.191(11) angstroms, alpha=93.807(14) degrees, beta=96.471(17) degrees, gamma=92.513(13) degrees, T=100(2) K, Z=2, $D_c$=1.392 Mg/m³, V=792.8(9) cubic angstroms, λ=0.71073 angstroms, 2448 reflections measured, 1961 unique ($R_{int}$=0.0740). Final residuals were $R_1$=0.1008, $wR_2$=0.2283 for I>2sigma(I), and $R_1$=0.1593, $wR_2$=0.2614 for all 1961 data.

A third method was also used to prepare the modafinil:succinic acid co-crystal. This method was performed by placing modafinil (30 mg, 0.0001 mol) and excess succinic acid in a stainless steel vial. 20 microliters of acetone was added to the vial. The vial was then placed in a grinder (wig-1-bug, Bratt Technologies, 115V/60 Hz) and the solid mixture was milled for 5 minutes. The resultant powder was then collected and characterized using PXRD and DSC. All of the above methods with succinic acid were shown to yield the same co-crystal via PXRD and DSC analysis.

Example 7

Racemic Modafinil:DL-Tartaric Acid Co-crystal

Figure 15:
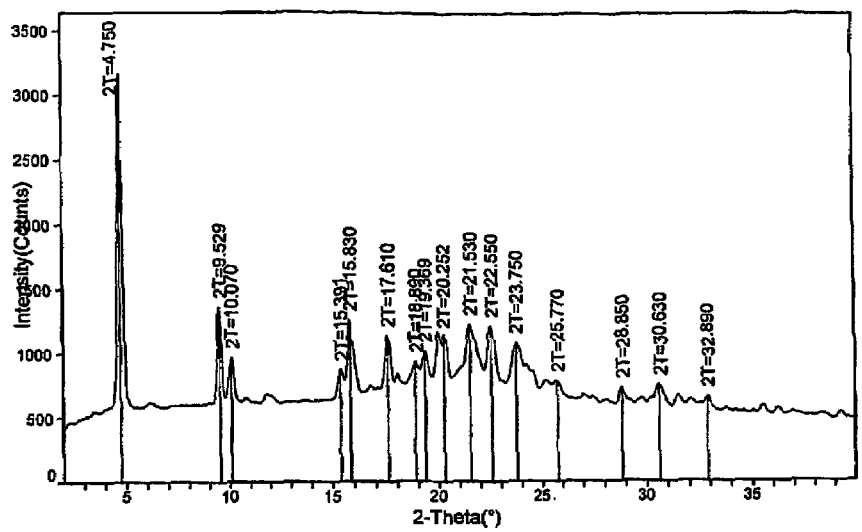
FIG. 15—PXRD diffractogram of a co-crystal comprising modafinil and DL-tartaric acid.

A suspension of racemic modafinil (162 mg; 0.591 mmol) and DL-tartaric acid (462 mg; 3.08 mmol) in acetone (10 mL) was heated to reflux for 1 minute. The undissolved DL-tartaric acid was filtered off while the suspension was still hot through a 0.2 micrometer PTFE filter. The remaining solution was allowed to cool to room temperature then to 0 degrees C. for 1 hour. After 1 hour, large colorless crystals were observed. The mother liquor was decanted and the solid was allowed to air dry and was characterized by PXRD (Rigaku), as shown in FIG. 15. The modafinil:DL-tartaric acid co-crystal can be characterized by any one, any two, any three, any four, any five, or any six or more of the peaks in FIG. 15 including, but not limited to, 4.75, 9.53, 10.07, 15.83, 17.61, 19.37, 20.25, 21.53, 22.55, and 23.75 degrees 2-theta (as collected).

Example 8

Racemic Modafinil:Fumaric Acid Co-crystal (Form I)

Figure 16:
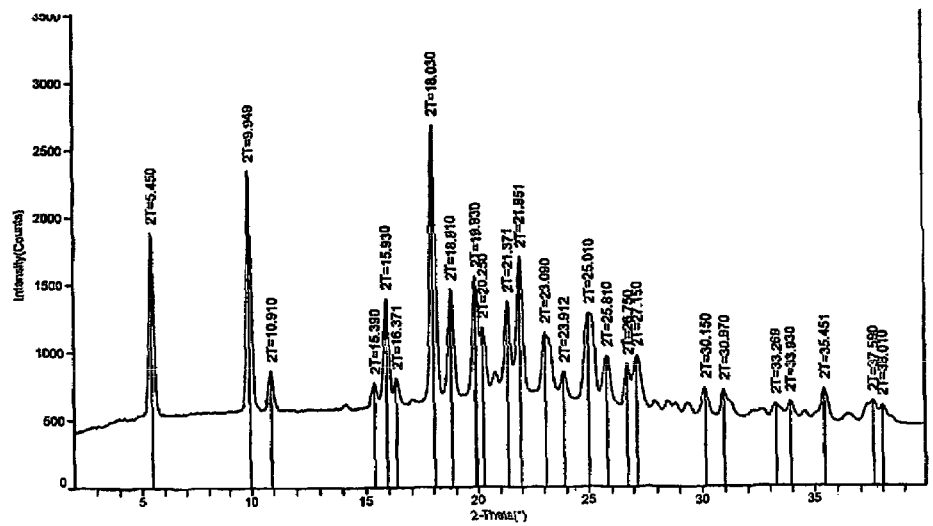
FIG. 16—PXRD diffractogram of a co-crystal comprising modafinil and fumaric acid (Form I).
Figure 17:
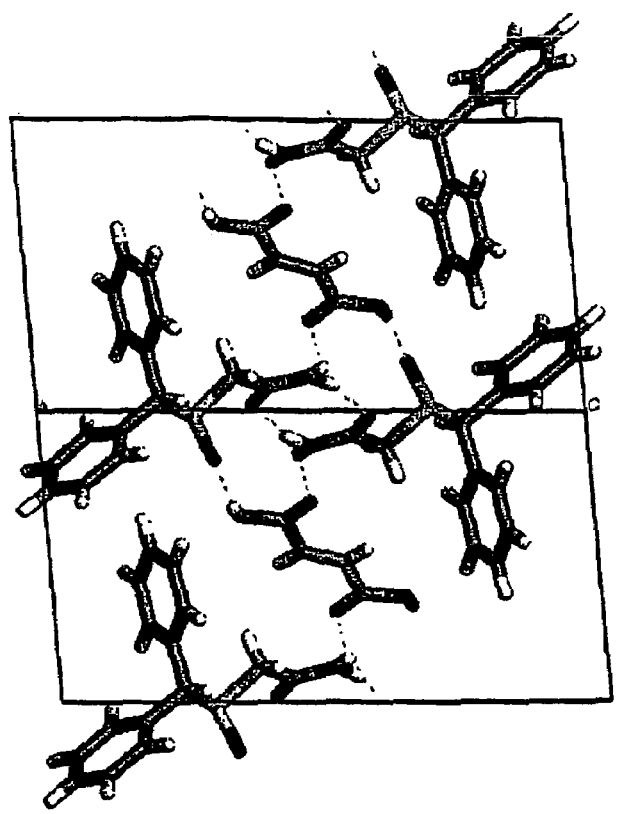
FIG. 17—Packing diagram of a co-crystal comprising modafinil and fumaric acid (Form I).

Racemic modafinil (30 mg, 0.0001 mol) and fumaric acid (2.3 mg, 0.0002 mol) were placed in a stainless steel vial. 20 microliters of acetone was added to the vial. The vial was then placed in a grinder (wig-1-bug, Bratt Technologies, 115V/60 Hz) and the solid mixture was milled for 5 minutes. The resultant powder was then collected and characterized as modafinil:fumaric acid co-crystal (Form I) using PXRD (Rigaku), as shown in FIG. 16. The co-crystal is a 2:1 co-crystal comprising two moles of modafinil for every mole of fumaric acid. The modafinil:fumaric acid co-crystal (Form I) can be characterized by any one, any two, any three, any four, any five, or any six or more of the peaks in FIG. 16 including, but not limited to, 5.45, 9.95, 10.91, 15.93, 18.03, 18.81, 19.93, 20.25, 21.37, 21.95, 23.09, and 25.01 degrees 2-theta (as collected). Single crystal data of the modafinil:fumaric acid co-crystal (Form I) were acquired and are reported below. FIG. 17 shows a packing diagram of the modafinil: fumaric acid co-crystal (Form I).

Crystal data: $C_{17}H_{17}NO_4S$, M=331.38, triclinic P-1; a=5.7000(15) angstroms, b=8.735(2) angstroms, c=16.204 (4) angstroms, alpha=93.972(6) degrees, beta=97.024(6) degrees, gamma=93.119(7) degrees, T=100(2) K, Z=2, $D_c$=1.381 Mg/m$^3$, V=797.2(4) cubic angstroms, λ=0.71073 angstroms, 4047 reflections measured, 2615 unique ($R_{int}$=0.0475). Final residuals were $R_1$=0.0784, $wR_2$=0.1584 for I>2sigma(I), and $R_1$=0.1154, $wR_2$=0.1821 for all 2615 data.

Example 9

Racemic Modafinil:Fumaric Acid Co-crystal (Form II)

Figure 18:
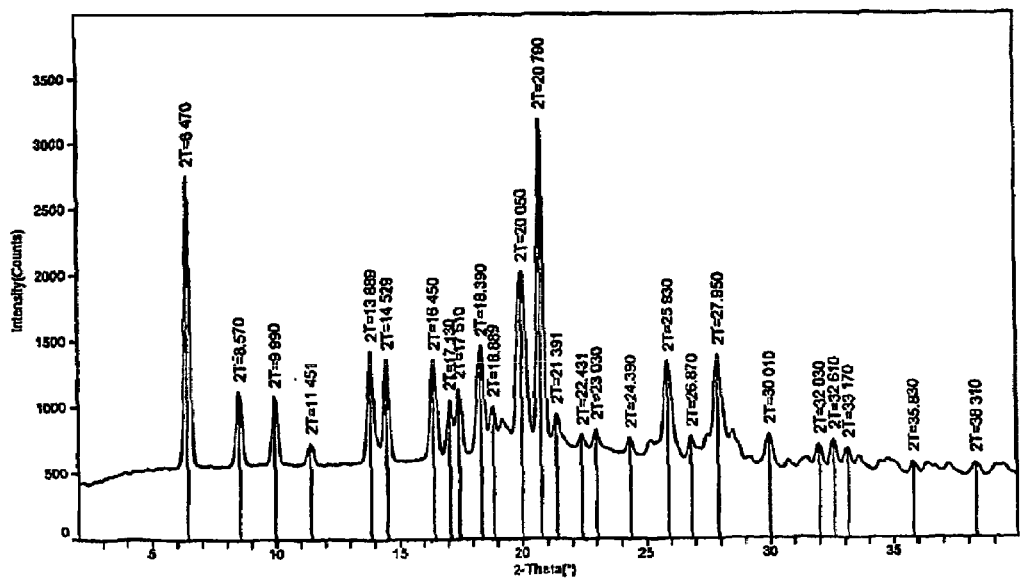
FIG. 18—PXRD diffractogram of a co-crystal comprising modafinil and fumaric acid (Form II).

Racemic modafinil (30 mg, 0.0001 mol) and fumaric acid (1.2 mg, 0.0001 mol) were placed in a stainless steel vial. 20 microliters of acetone was added to the vial. The vial was then placed in a grinder (wig-1-bug, Bratt Technologies, 115V/60 Hz) and the solid mixture was milled for 5 minutes. The resultant powder was then collected and characterized as modafinil:fumaric acid co-crystal (Form II) using PXRD (Rigaku), as shown in FIG. 18. The modafinil:fumaric acid co-crystal (Form II) can be characterized by any one, any two, any three, any four, any five, or any six or more of the peaks in FIG. 18 including, but not limited to, 6.47, 8.57, 9.99, 13.89, 14.53, 16.45, 17.13, 17.51, 18.39, 20.05, 20.79, 25.93, and 27.95 degrees 2-theta (as collected).

Example 10

Racemic Modafinil:Gentisic Acid Co-crystal

Figure 19:
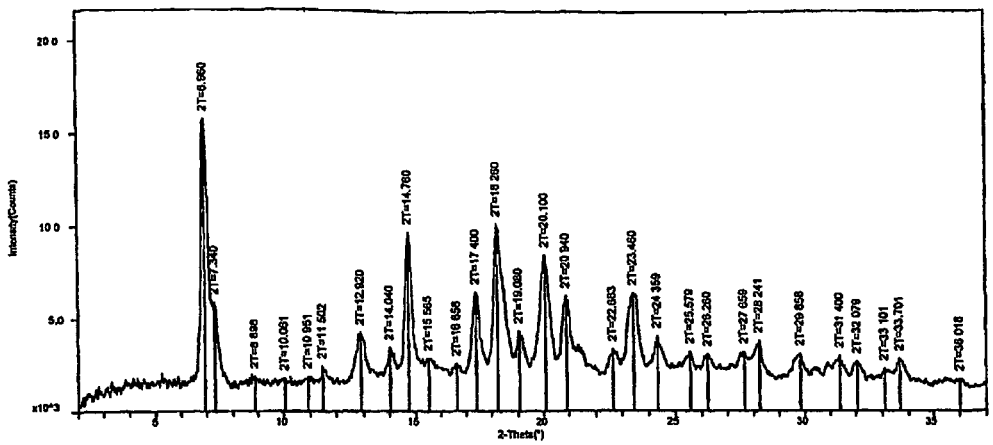
FIG. 19—PXRD diffractogram of a co-crystal comprising modafinil and gentisic acid.

Racemic modafinil (30 mg, 0.0001 mol) and gentisic acid (1.5 mg, 0.0001 mol) were placed in a stainless steel vial. 20 microliters of acetone was added to the vial. The vial was then placed in a grinder (wig-1-bug, Bratt Technologies, 115V/60 Hz) and the solid mixture was milled for 5 minutes. The resultant powder was then collected and characterized using PXRD (Bruker), as shown in FIG. 19. The modafinil:gentisic acid co-crystal can be characterized by any one, any two, any three, any four, any five, or any six or more of the peaks in FIG. 19 including, but not limited to, 6.96, 12.92, 14.76, 17.40, 18.26, 20.10, 20.94, 23.46, and 24.36 degrees 2-theta (as collected).

Example 11

Racemic Modafinil:Oxalic Acid Co-crystal

Figure 20:
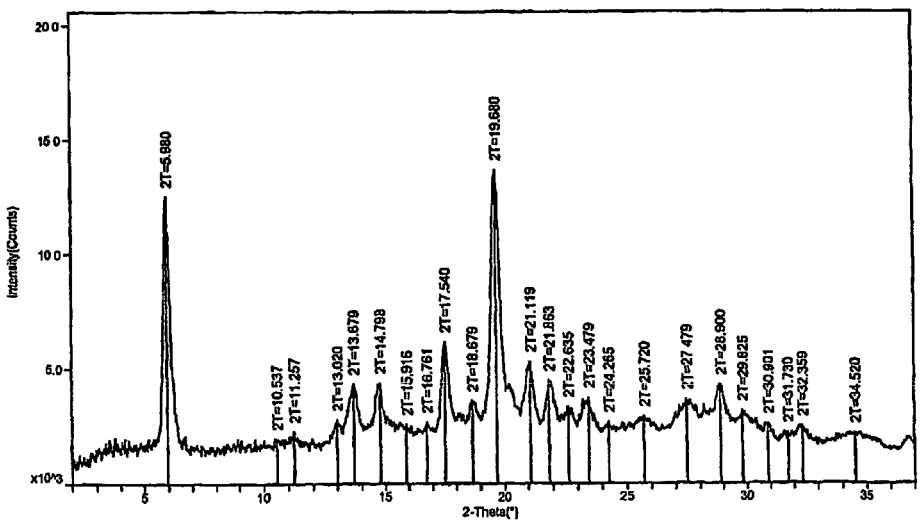
FIG. 20—PXRD diffractogram of a co-crystal comprising modafinil and oxalic acid.

A preparation of modafinil:oxalic acid co-crystal was performed by placing racemic modafinil (30 mg, 0.0001 mol) and oxalic acid (1-2 mg, 0.0001-0.0002 mol) in a stainless steel vial. 20 microliters of acetone was added to the vial. The vial was then placed in a grinder (wig-1-bug, Bratt Technologies, 11 5V/60 Hz) and the solid mixture was milled for 5 minutes. The resultant powder was then collected and characterized using PXRD (Bruker), as shown in FIG. 20. In another preparation of the modafinil:oxalic acid co-crystal, the preparation above was completed without the addition of solvent. Both methods were shown to yield the same co-crystal via PXRD analysis. The modafinil:oxalic acid co-crystal can be characterized by any one, any two, any three, any four, any five, or any six or more of the peaks in FIG. 20 including, but not limited to, 5.98, 13.68, 14.80, 17.54, 19.68, 21.12, 21.86, and 28.90 degrees 2-theta (as collected).

Example 12

Racemic Modafinil:1-hydroxy-2-naphthoic Acid Co-crystal

Figure 21:
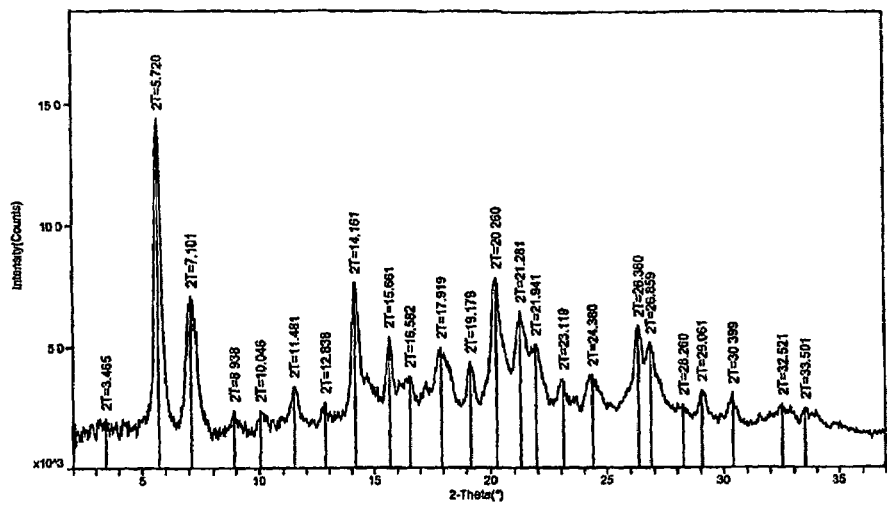
FIG. 21—PXRD diffractogram of a co-crystal comprising modafinil and 1-hydroxy-2-naphthoic acid.

Racemic modafinil (30 mg, 0.0001 mol) and 1-hydroxy-2-naphthoic acid (21 mg, 0.0001 mol) were placed in a stainless steel vial. 20 microliters of acetone was added to the vial. The vial was then placed in a grinder (wig-1-bug, Bratt Technologies, 115V/60 Hz) and the solid mixture was milled for 5 minutes. The resultant powder was then collected and characterized using PXRD (Bruker), as shown in FIG. 21. The modafinil:1-hydroxy-2-naphthoic acid co-crystal can be characterized by any one, any two, any three, any four, any five, or any six or more of the peaks in FIG. 21 including, but not limited to, 5.72, 7.10, 11.48, 14.16, 15.66, 17.92, 19.18, 20.26, 21.28, 21.94, 24.38, and 26.86 degrees 2-theta (as collected). PXRD peaks at 10.05 and 26.36 degrees 2-theta may be from excess co-crystal former.

Example 13

R-(−)-Modafinil:Malonic Acid Co-crystal

Figure 22:
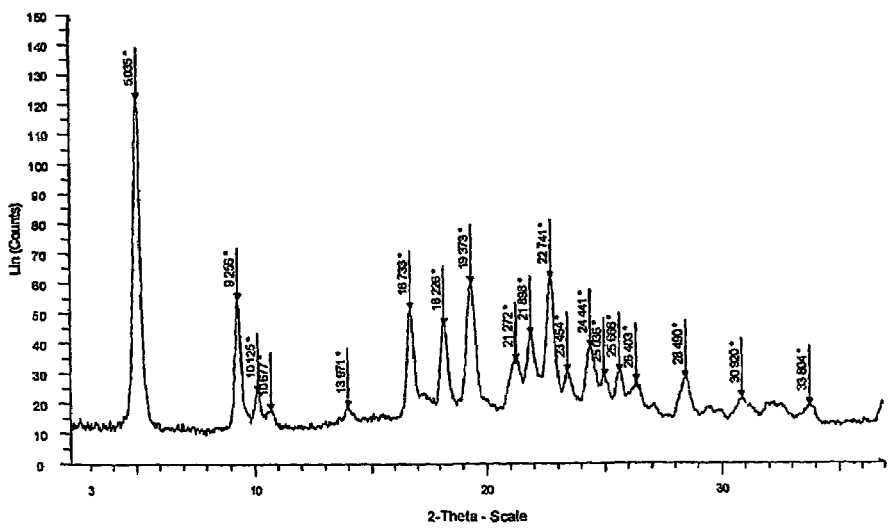
FIG. 22—PXRD diffractogram of a co-crystal comprising R-(−)-modafinil and malonic acid.
Figure 23:
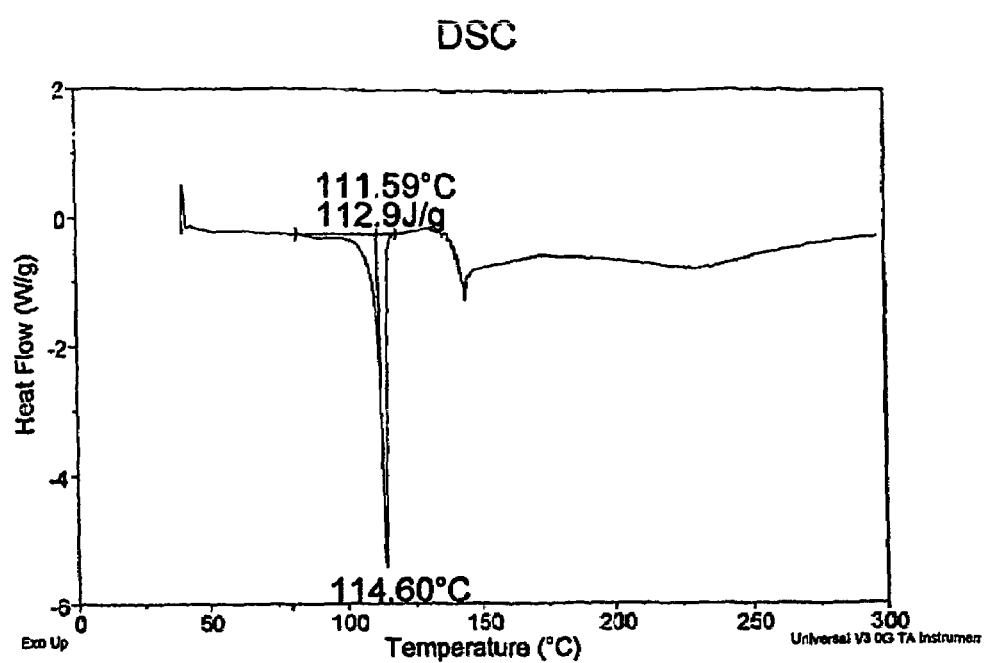
FIG. 23—DSC thermogram of a co-crystal comprising R-(−)-modafinil and malonic acid.

R-(−)-modafinil:malonic acid co-crystal was prepared by grinding R-(−)-modafinil (29.7 mg, 0.109 mmol, 82.2 percent R-isomer) with malonic acid (11.9 mg, 0.114 mmol). The ground mixture was then heated to 80 degrees C. for 10 minutes. The powder was analyzed by PXRD (Bruker) and DSC, as shown in FIGS. 22 and 23, respectively. The PXRD pattern confirms that the co-crystal was made and shows many similarities to the PXRD pattern for the racemic modafinil:malonic acid co-crystal. The R-(−)-modafinil:malonic acid co-crystal can be characterized by any one, any two, any three, any four, any five, or any six or more of the peaks in FIG. 22 including, but not limited to, 5.04, 9.26, 16.73, 18.23, 19.37, 21.90, 22.74, 24.44, and 25.67 degrees 2-theta (data as collected). The DSC showed a melting range of 111.5-114.7 degrees C. with a heat of fusion of 112.9 J/g.

Example 14

R-(−)-Modafinil:Succinic Acid Co-crystal

Figure 24:
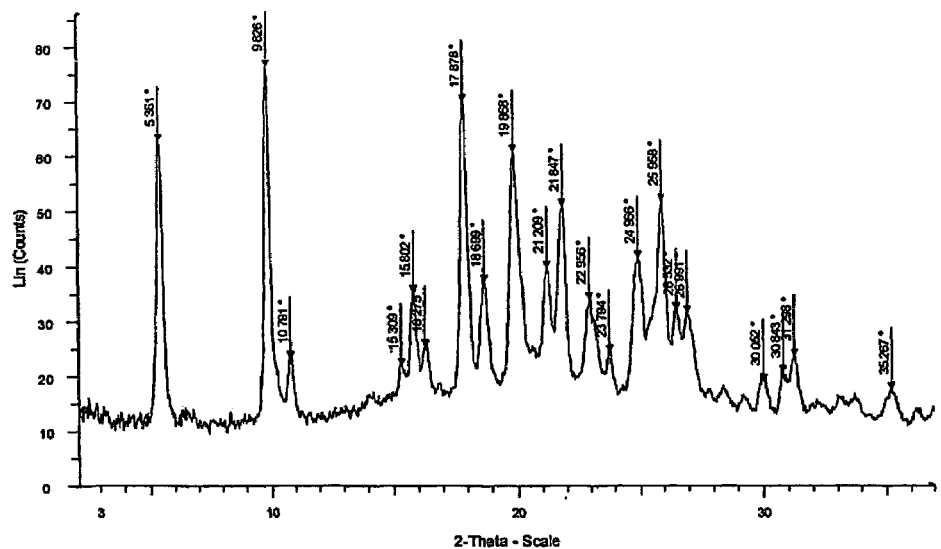
FIG. 24—PXRD diffractogram of a co-crystal comprising R-(−)-modafinil and succinic acid.
Figure 25:
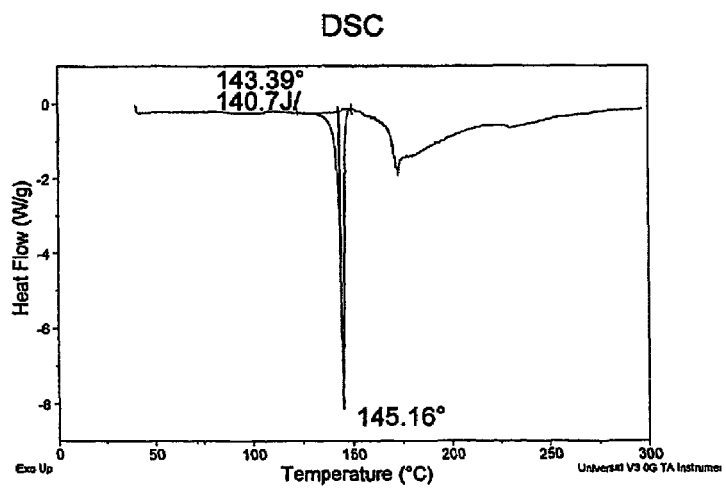
FIG. 25—DSC thermogram of a co-crystal comprising R-(−)-modafinil and succinic acid.

R-(−)-modafinil:succinic acid co-crystal was prepared by grinding R-(−)-modafinil (30.9 mg, 0.113 mmol, 82.2 percent R-isomer) with succinic acid (14.8 mg, 0.125 mmol). The ground mixture was then heated to 145 degrees C. for 5 minutes. The powder was analyzed by PXRD (Bruker) and DSC, as shown in FIGS. 24 and 25, respectively. The PXRD pattern confirms that the co-crystal was made and shows many similarities to the PXRD pattern for the racemic modafinil:succinic acid co-crystal made from solution. The R-(−)-modafinil:succinic acid co-crystal can be characterized by any one, any two, any three, any four, any five, or any six or more of the peaks in FIG. 24 including, but not limited to, 5.36, 9.83, 15.80, 17.88, 18.70, 19.87, 21.21, 21.85, and 25.96 degrees 2-theta (data as collected). The DSC showed a melting range of 143.3-145.2 degrees C. with a heat of fusion of 140.7 J/g.

Example 15

R-(−)-Modafinil:Citric Acid Co-crystal

Figure 26:
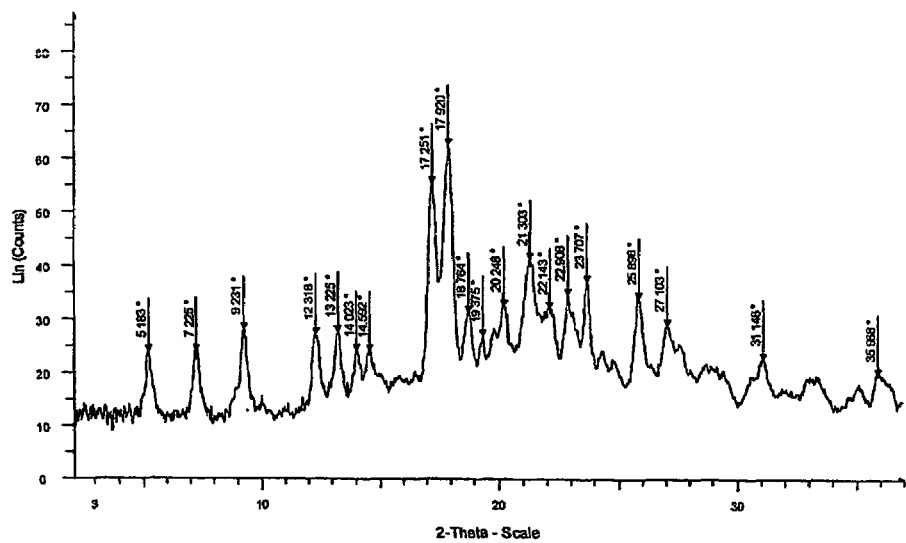
FIG. 26—PXRD diffractogram of a co-crystal comprising R-(−)-modafinil and citric acid.
Figure 27:
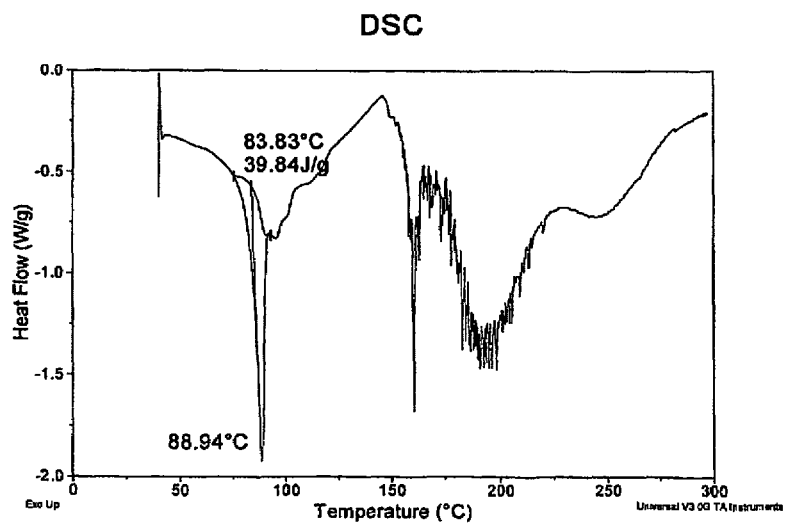
FIG. 27—DSC thermogram of a co-crystal comprising R-(−)-modafinil and citric acid.

R-(−)-modafinil:citric acid co-crystal was prepared by grinding R-(−)-modafinil (30.0 mg, 0.110 mmol, 82.2 percent R-isomer) with citric acid monohydrate (27.1 mg, 0.129 mmol). The powder was analyzed by PXRD (Bruker) and DSC, as shown in FIGS. 26 and 27, respectively. The PXRD pattern confirms that the co-crystal was made and shows many similarities to the PXRD pattern for the racemic modafinil:citric acid co-crystal. The R-(−)-modafinil:citric acid co-crystal can be characterized by any one, any two, any three, any four, any five, or any six or more of the peaks in FIG. 26 including, but not limited to, 5.18, 7.23, 9.23, 12.32, 13.23, 17.25, 17.92, 18.76, 20.25, 21.30, and 23.71 degrees 2-theta (data as collected). The DSC showed a melting range of 83.5-89.0 degrees C. with a heat of fusion of 39.8 J/g.

Example 16

R-(−)-Modafinil:DL-tartaric Acid Co-crystal

Figure 28:
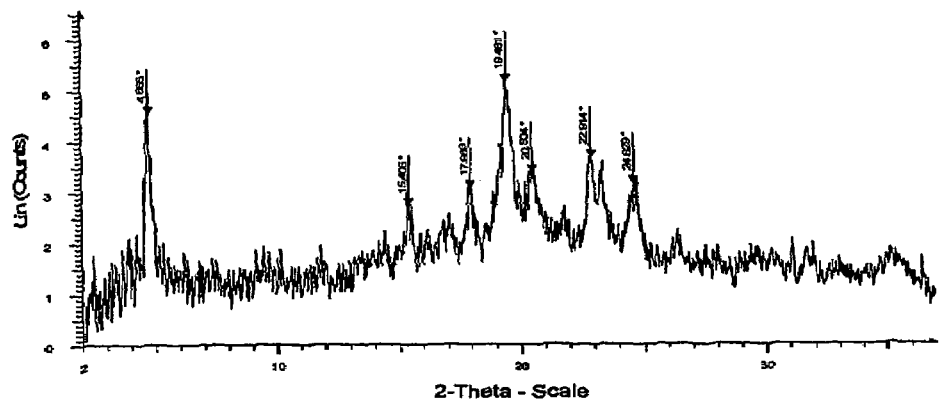
FIG. 28—PXRD diffractogram of a co-crystal comprising R-(−)-modafinil and DL-tartaric acid.
Figure 29:
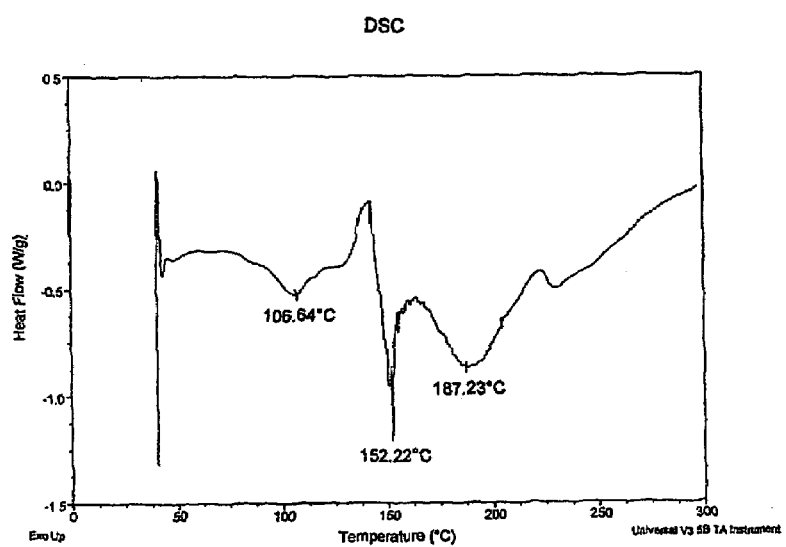
FIG. 29—DSC thermogram of a co-crystal comprising R-(−)-modafinil and DL-tartaric acid.

The R-(−)-modafinil:DL-tartaric acid co-crystal was found from a high throughput crystallization experiment from dichloromethane. The vial contained a 1:2 mixture of R-(−)-modafinil (greater than 98 percent R-isomer) and DL-tartaric acid. The co-crystal was also found from a 1:1 mixture of R-(−)-modafinil (greater than 98 percent R-isomer) and DL-tartaric acid in nitromethane. The solid materials were collected and characterized using PXRD (Bruker) and DSC, as shown in FIGS. 28 and 29, respectively. The R-(−)-modafinil:DL-tartaric acid co-crystal can be characterized by any one, any two, any three, any four, any five, or any six or more of the peaks in FIG. 28 including, but not limited to, 4.67, 15.41, 17.97, 19.46, 20.50, 22.91, and 24.63 degrees 2-theta (as collected). Endothermic transitions were present at about 107, 152, and 187 degrees C.

Example 17

R-(−)-Modafinil:1-hydroxy-2-naphthoic Acid Co-crystal

Figure 30:
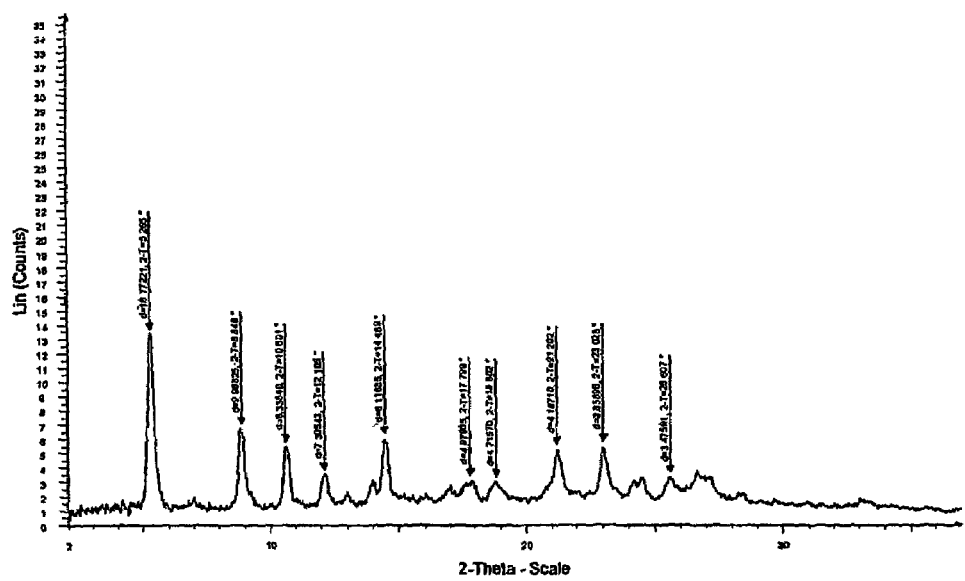
FIG. 30—PXRD diffractogram of a co-crystal comprising R-(−)-modafinil and 1-hydroxy-2-naphthoic acid.

To a solid mixture of R-(−)-modafinil (98.6 mg; 0.361 mmol, greater than 98 percent R-isomer) and 1-hydroxy-2-naphthoic acid (71.2 mg; 0.378 mmol) was added o-xylene (4.5 mL). The mixture was heated to reflux for less than one minute at which point both solids dissolved. The solution was then slowly cooled to room temperature at which point a solid crystallized. The solid was collected via filtration and air-dried. The powder was characterized using PXRD (Bruker), as shown in FIG. 30. The same material has been prepared from benzene, toluene, and acetone using the above procedure. The R-(−)-modafinil:1-hydroxy-2-naphthoic acid co-crystal can be characterized by any one, any two, any three, any four, any five, or any six or more of the peaks in FIG. 30 including, but not limited to, 5.27, 8.85, 10.60, 12.11, 14.47, 17.80, 18.80, 21.20, 23.03, and 25.61 degrees 2-theta (as collected).

Figure 31:
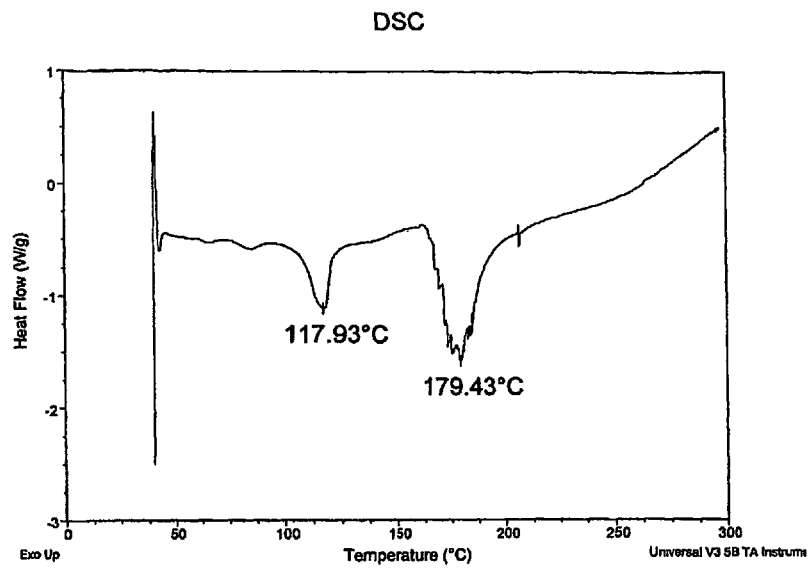
FIG. 31—DSC thermogram of a co-crystal comprising R-(−)-modafinil and 1-hydroxy-2-naphthoic acid.
Figure 32:
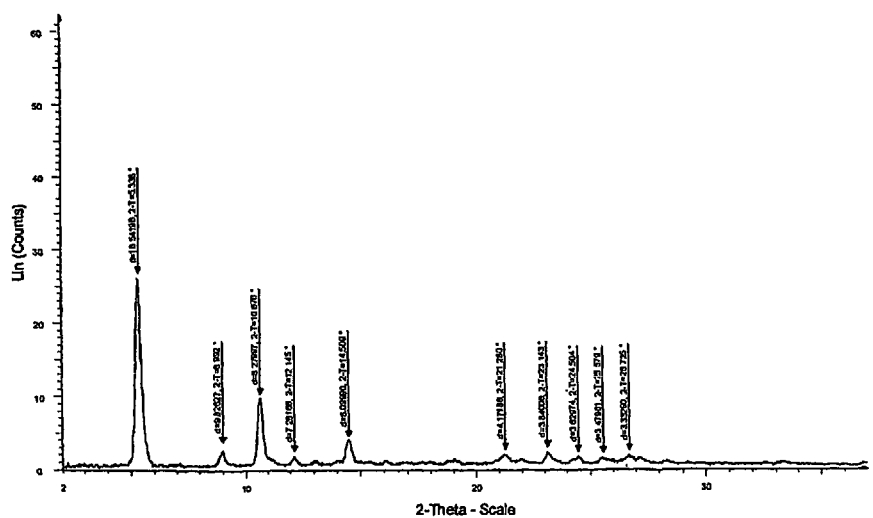
FIG. 32—PXRD diffractogram of a co-crystal comprising R-(−)-modafinil and 1-hydroxy-2-naphthoic acid obtained from a high throughput experiment.

The R-(−)-modafinil:1-hydroxy-2-naphthoic co-crystal was also obtained from a high throughput crystallization experiment from a vial containing a 1:1 mixture of R-(−)-modafinil (greater than 98 percent R-isomer) and 1-hydroxy-2-naphthoic acid in nitromethane. The solid material was collected and characterized using DSC and PXRD (Bruker), as shown in FIGS. 31 and 32, respectively. The R-(−)-modafinil:1-hydroxy-2-naphthoic acid co-crystal can be characterized by any one, any two, any three, any four, any five, or any six or more of the peaks in FIG. 32 including, but not limited to 5.34, 8.99, 10.68, 12.15; 14.51, 21.28, 23.14, and 24.50 degrees 2-theta (as collected). DSC shows endothermic transitions at about 118 and 179 degrees C.

Example 18

R-(−)-Modafinil:Orotic Acid Co-crystal

Figure 33:
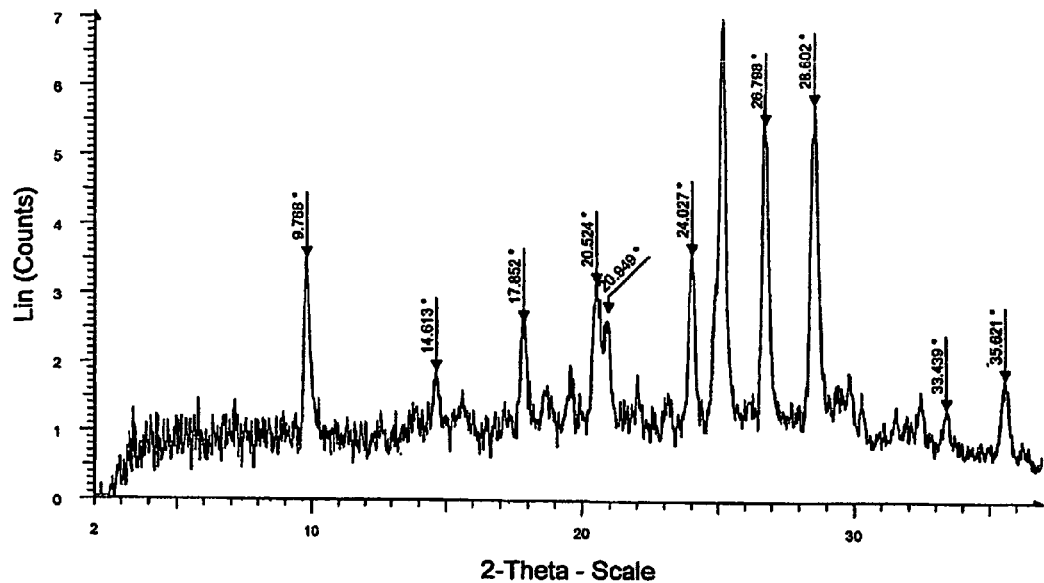
FIG. 33—PXRD diffractogram of a co-crystal comprising R-(−)-modafinil and orotic acid.
Figure 34:
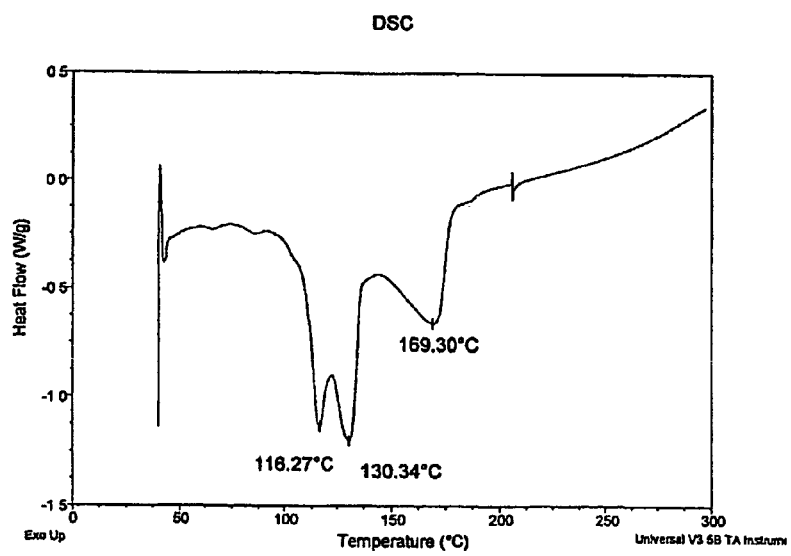
FIG. 34—DSC thermogram of a co-crystal comprising R-(−)-modafinil and orotic acid.
Figure 35:
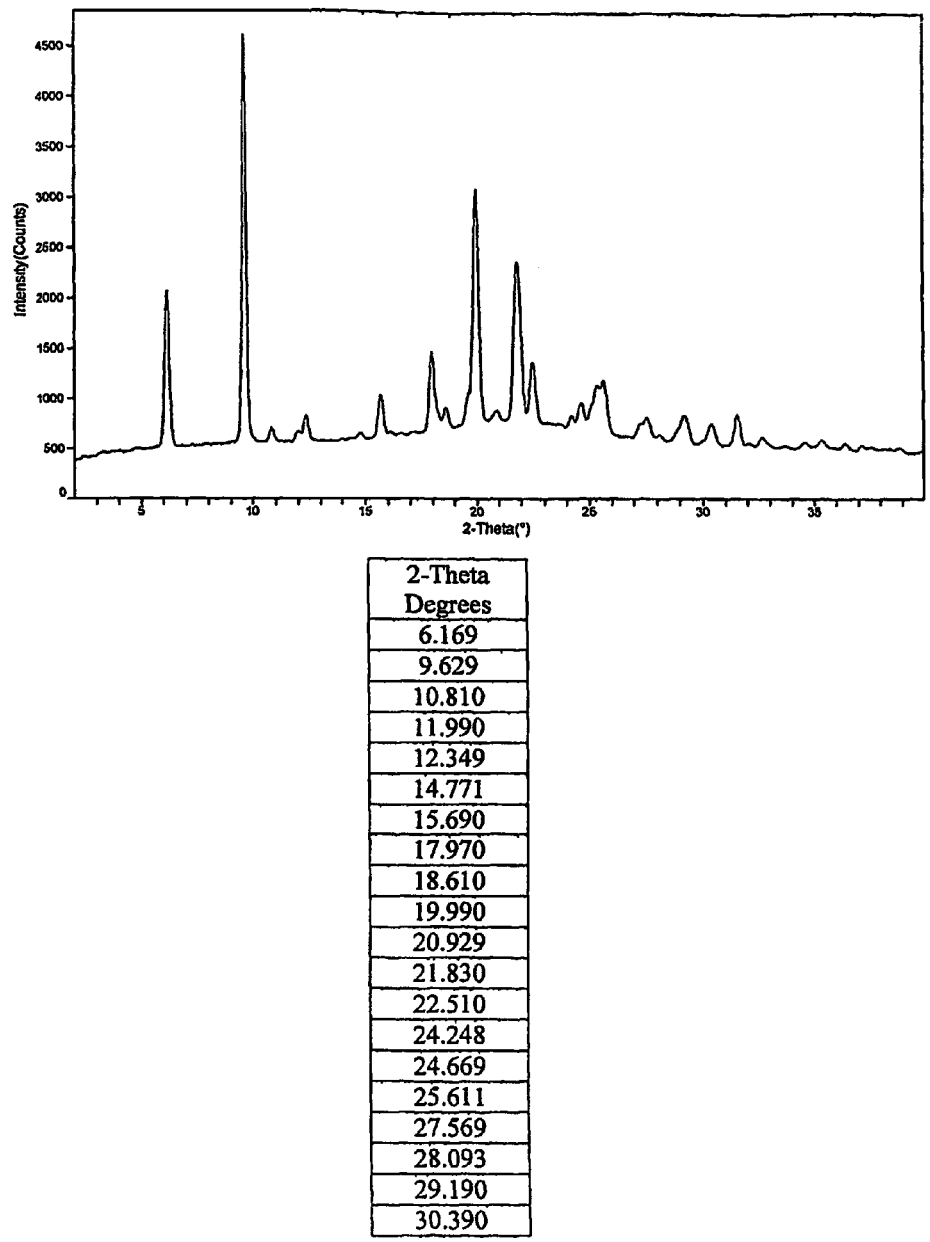
FIG. 35—PXRD diffractogram of a solvate comprising modafinil and acetic acid.
Figure 36:
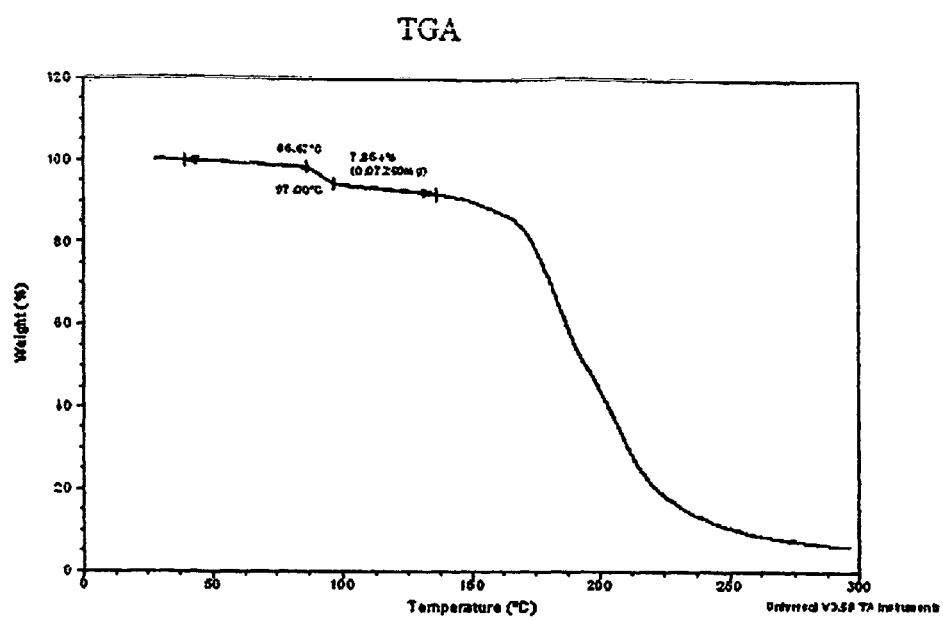
FIG. 36—TGA thermogram of a solvate comprising modafinil and acetic acid.
Figure 37:
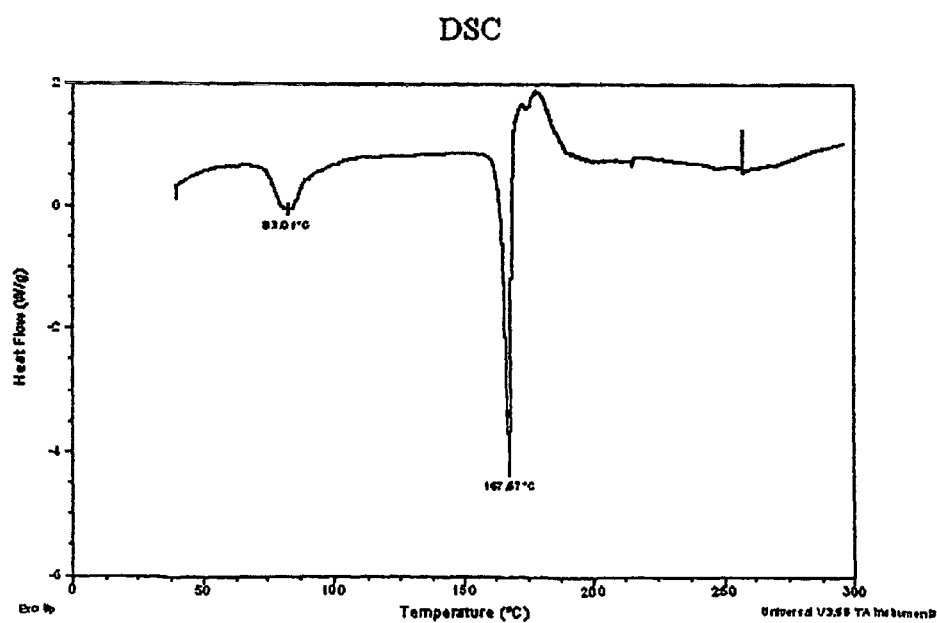
FIG. 37—DSC thermogram of a solvate comprising modafinil and acetic acid.
Figure 38:
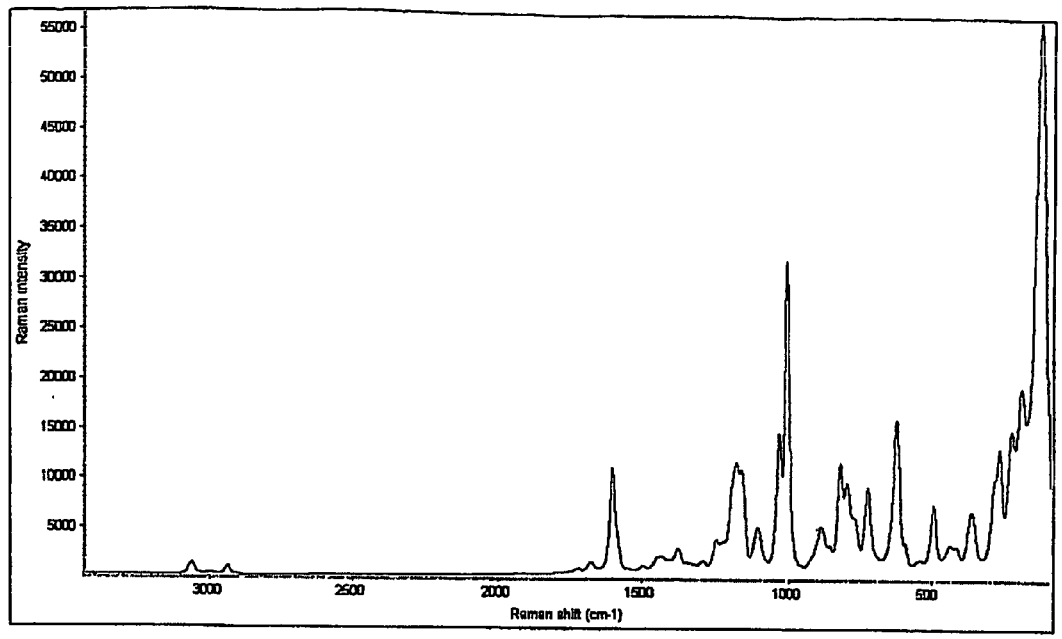
FIG. 38—Raman spectrum of a solvate comprising modafinil and acetic acid.

The R-(−)-modafinil:orotic acid co-crystal was obtained from a high throughput crystallization experiment from a vial containing R-(−)-modafinil (1 mg, 0.0036 mmol, greater than 98 percent R-isomer) and orotic acid (1.14 mg, 0.0073 mmol) in acetone (100 microliters). The solid material obtained was characterized using PXRD (Bruker) and DSC, as shown in FIGS. 33 and 34, respectively. The R-(−)-modafinil:orotic acid co-crystal can be characterized by any one, any two, any three, any four, any five, or any six or more of the peaks in FIG. 33 including, but not limited to, 9.77, 17.85, 20.52, 20.95, 24.03, and 26.80 degrees 2-theta (as collected). PXRD peaks at 14.61 and 28.60 may correspond to excess co-crystal former. Endothermic transitions were present at about 116, 130, and 169 degrees C.

TABLE IV

Co-crystals of Modafinil

| Co-Crystal former | Representative PXRD Peaks (degrees 2-theta) |
| --- | --- |
| Malonic acid | 5.00, 9.17, 10.08, 16.81, 18.26, 19.43, 21.36, 21.94, 22.77, 24.49, 25.63, 26.37, 28.45 |
| Glycolic acid | 9.53, 14.93, 15.99, 19.05, 20.05, 21.61, 22.77, 25.05 |
| Maleic acid | 4.69, 6.17, 9.63, 10.25, 15.67, 16.53, 17.21, 18.05, 19.99, 21.85, 22.47 |
| L-tartaric acid | 6.10, 7.36, 9.38, 14.33, 16.93, 17.98, 18.81, 20.15, 20.71, 22.49, 25.04 |
| Citric acid | 5.29, 7.29, 9.31, 12.41, 13.29, 17.29, 17.97, 18.79, 21.37, 23.01 |
| Succinic acid | 5.45, 9.93, 15.87, 17.99, 18.75, 19.95, 21.95, 23.03, 25.07 |
| DL-tartaric acid | 4.75, 9.53, 10.07, 15.83, 17.61, 19.37, 20.25, 21.53, 22.55, 23.75 |
| Fumaric acid (Form I) | 5.45, 9.95, 10.91, 15.93, 18.03, 18.81, 19.93, 20.25, 21.37, 21.95, 23.09, 25.01 |
| Fumaric acid (Form II) | 6.47, 8.57, 9.99, 13.89, 14.53, 16.45, 17.13, 17.51, 18.39, 20.05, 20.79, 25.93, 27.95 |
| Gentisic acid | 6.96, 12.92, 14.76, 17.40, 18.26, 20.10, 20.94, 23.46, 24.36 |
| Oxalic acid | 5.98, 13.68, 14.80, 17.54, 19.68, 21.12, 21.86, 28.90 |
| 1-hydroxy-2-naphthoic acid | 5.72, 7.10, 11.48, 14.16, 15.66, 17.92, 19.18, 20.26, 21.28, 21.94, 24.38, 26.86 |
| *Malonic acid | 5.04, 9.26, 16.73, 18.23, 19.37, 21.90, 22.74, 24.44, 25.67 |
| *Succinic acid | 5.36, 9.83, 15.80, 17.88, 18.70, 19.87, 21.21, 21.85, 25.96 |
| *Citric acid | 5.18, 7.23, 9.23, 12.32, 13.23, 17.25, 17.92, 18.76, 20.25, 21.30, 23.71 |
| **DL-tartaric acid | 4.67, 15.41, 17.97, 19.46, 20.50, 22.91, 24.63 |
| **1-hydroxy-2-naphthoic acid | 5.27, 8.88, 10.60, 12.11, 14.47, 17.80, 18.80, 21.20, 23.03, 25.61 |
| **Orotic acid | 9.77, 17.85, 20.52, 20.95, 24.03, 26.80 |
| **Gentisic acid | 7.07, 7.51, 9.07, 12.31, 16.03, 17.63, 18.39, 19.83, 21.27, 23.57, 26.93, 28.85 |

*= API is R-(−)-modafinil with 82.2 percent (purity) R-(−)-modafinil (17.8 percent S-(+)-modafinil)
**= API is R-(−)-modafinil with greater than 98 percent (purity) R-(−)-modafinil (less than 2 percent S-(+)-modafinil
All other co-crystals comprise racemic modafinil Example 19

Acetic Acid Solvate of Racemic Modafinil

To racemic modafinil (12.9 mg, 0.047 mmol) was added acetic acid (40 microliters). The mixture was heated at 50 degrees C. to completely dissolve the solid. The solution was allowed to cool to room temperature, and left overnight, which yielded no precipitation. The solution was then evaporated under flowing nitrogen until precipitation was observed. The resulting solid was further dried under flowing nitrogen. Characterization of the product has been achieved via PXRD (Rigaku), TGA, DSC, and Raman spectroscopy, as shown in FIGS. 35-38, respectively. An alternative method for the preparation of the acetic acid solvate of modafinil was also completed. A sample of modafinil acetic acid solvate was prepared by dissolving racemic modafinil (12.9 mg, 0.047 mmol) in acetic acid (40 microliters) and incubating at 65 degrees C. for 30 minutes to dissolve, then cooling to 25 degrees C. to incubate overnight. The sample was then evaporated to approximately ⅓ volume. After centrifugation of the sample, rapid nucleation and growth of crystals was observed. An additional 20 microliters of acetic acid was then added. The sample was heated at 50 degrees C. until partial dissolution of the crystals was observed. The sample was then cooled to room temperature over a 1 hour period, then to 5 degrees C. for 3 hours in an attempt to induce crystal growth. The sample was then dried under nitrogen gas. Rapid appearance of crystals was observed. The modafinil acetic acid solvate can be characterized by any one, any two, any three, any four, any five, or any six or more of the peaks in FIG. 35 including, but not limited to, 6.17, 9.63, 15.69, 17.97, 19.99, and 21.83 degrees 2-theta (data as collected).

Example 20

Tetrahydrofuran Solvate of Racemic Modafinil

Figure 39:
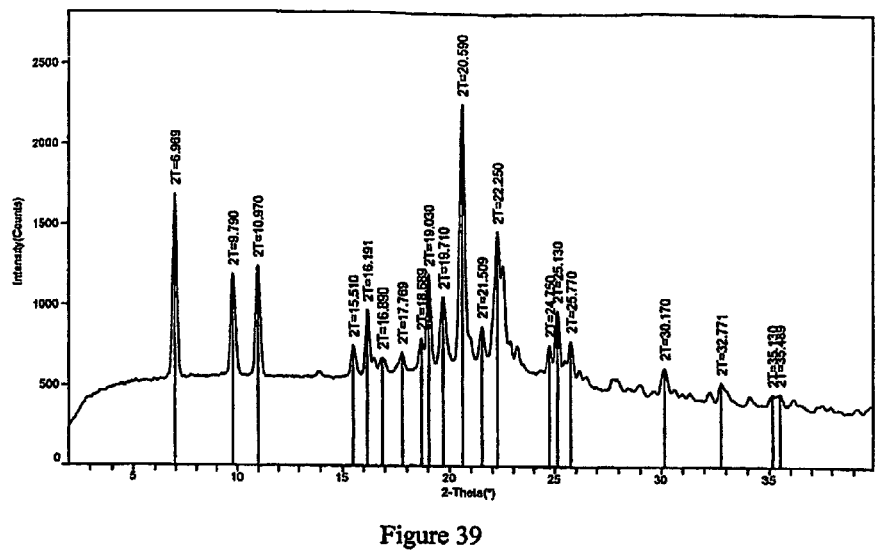
FIG. 39—PXRD diffractogram of a solvate comprising modafinil and tetrahydrofuran.

The tetrahydrofuran (THF) solvate of modafinil was prepared by placing racemic modafinil (10.4 mg, 0.038 mmol) in tetrahydrofuran (1 mL). The powder did not completely dissolve in THF and converted overnight into long, fine, needle shaped crystals which were collected and analyzed by PXRD (Rigaku), as shown in FIG. 39. The modafinil tetrahydrofuran solvate can be characterized by any one, any two, any three, any four, any five or any six or more of the peaks in FIG. 39 including, but not limited to, 6.97, 9.79, 10.97, 16.19, 19.03, 19.71, 20.59, 22.25, and 25.13 degrees 2-theta (data as collected).

Example 21

1,4-Dioxane Solvate of Racemic Modafinil

Figure 40:
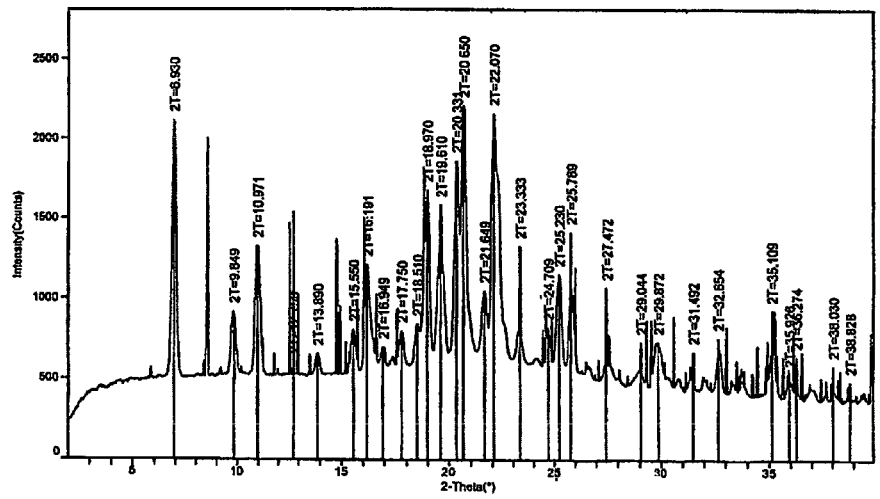
FIG. 40—PXRD diffractogram of a solvate comprising modafinil and 1,4-dioxane.

To racemic modafinil (11.6 mg, 0.042 mmol) was added 1,4-dioxane (1 mL). The mixture was then left overnight and converted to long, fine, needle shaped crystals which were collected and analyzed by PXRD (Rigaku), as shown in FIG. 40. The modafinil 1,4-dioxane solvate can be characterized by any one, any two, any three, any four, any five, or any six or more of the peaks in FIG. 40 including, but not limited to, 6.93, 9.85, 10.97, 16.19, 18.97, 19.61, 20.33, 20.65, and 22.07 degrees 2-theta (data as collected). PXRD pattern also contains several spikes which were a result of instrument error and could not be removed.

Example 22

Methanol Solvate of Racemic Modafinil

Figure 41:
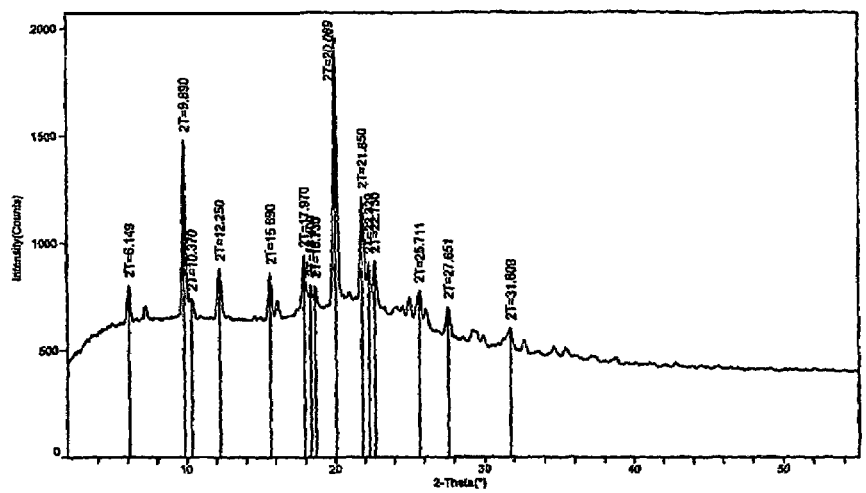
FIG. 41—PXRD diffractogram of a solvate comprising modafinil and methanol.
Figure 42:
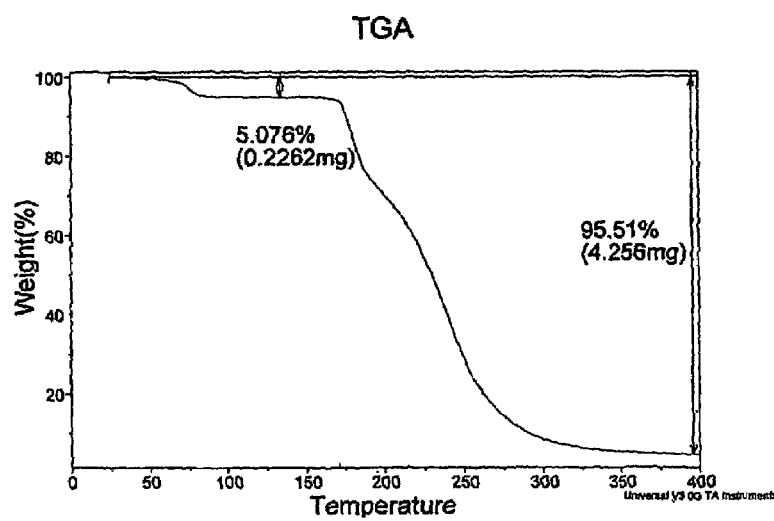
FIG. 42—TGA thermogram of a solvate comprising modafinil and methanol.
Figure 43:
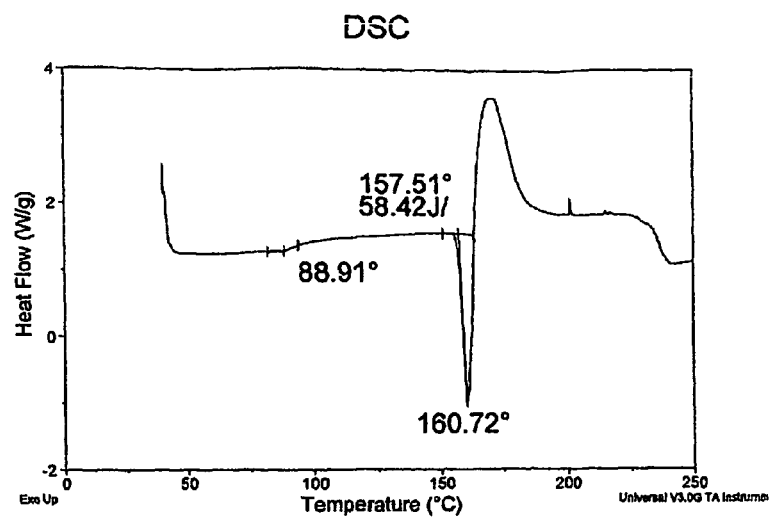
FIG. 43—DSC thermogram of a solvate comprising modafinil and methanol.

The methanol solvate of modafinil is obtained by evaporating 2 mL of a 30 mg/mL racemic modafinil solution in methanol under flowing nitrogen overnight. The methanol solvate was characterized by PXRD (Rigaku), TGA, and DSC, as shown in FIGS. 41, 42, and 43, respectively. The modafinil methanol solvate can be characterized by any one, any two, any three, any four, any five, or any six or more of the peaks in FIG. 41 including, but not limited to, 6.15, 9.89, 12.25, 15.69, 17.97, 20.07, 21.85, and 22.73 degrees 2-theta (data as collected).

Example 23

Figure 44:
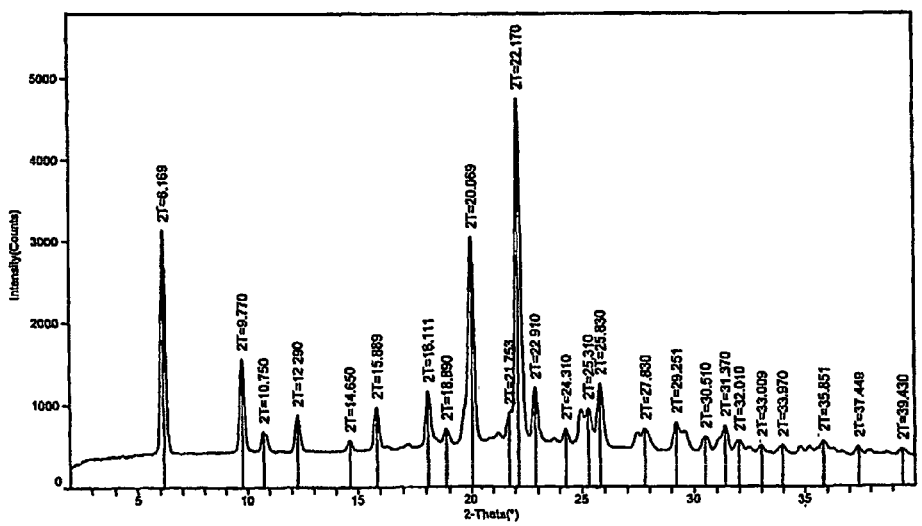
FIG. 44—PXRD diffractogram of a solvate comprising modafinil and nitromethane.

Nitromethane Solvate of Racemic Modafinil To racemic modafinil (12.9 mg, 0.047 mmol) was added nitromethane (1 mL). The mixture which did not fully dissolve was left overnight and converted to large rectangular crystals. The solid was collected and analyzed by PXRD (Rigaku), as shown in FIG. 44. The modafinil nitromethane solvate can be characterized by any one, any two, any three, any four, any five, or any six or more of the peaks in FIG. 44 including, but not limited to, 6.17, 9.77, 15.89, 18.11, 20.07, 22.17, 22.91, 25.31, and 25.83 degrees 2-theta (data as collected).

Example 24

Acetone Solvate of Racemic Modafinil

Figure 45:
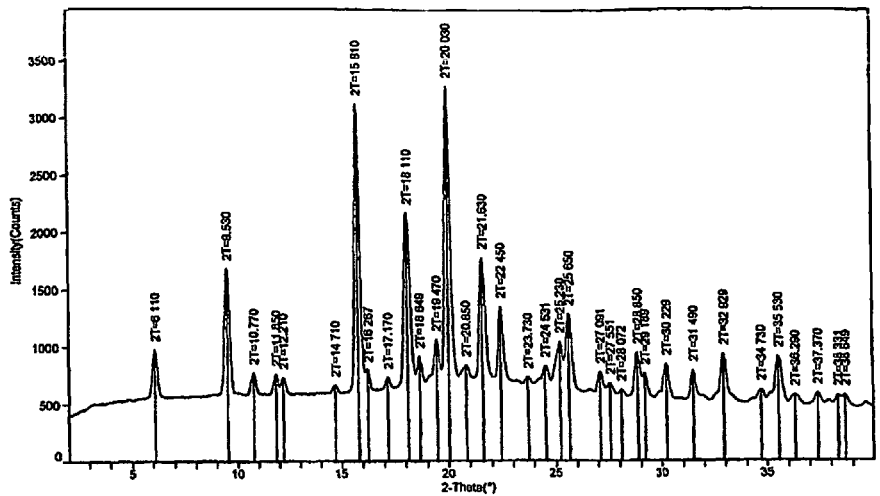
FIG. 45—PXRD diffractogram of a solvate comprising modafinil and acetone.

A solution containing racemic modafinil (300 mg, 0.001 mol) and glutaric acid (150 mg, 0.001 mol) in acetone (3 mL) was heated until it was boiling in order to dissolve all solid material. Once the solids dissolved, the solution was placed on an aluminum block at 5 degrees C. After 15 minutes of sitting at 5 degrees C., crystals began to form at the bottom of the vial. The solution was then decanted and the single crystals were collected and analyzed using PXRD (Rigaku), as shown in FIG. 45. The crystals were determined to be an acetone solvate of modafinil. The acetone solvate of modafinil can be characterized by any one, any two, any three, any four, any five, or any six or more of the peaks in FIG. 45 including, but not limited to, 6.11, 9.53, 15.81, 18.11, 20.03, 21.63, 22.45, 25.23, 25.65, 28.85, 30.23, and 32.93 degrees 2-theta (as collected). The acetone solvate may also be obtained following the procedure above with several other co-crystal formers including adipic acid, lactobionic acid, maleic acid, and glycolic acid.

Example 25

Figure 46:
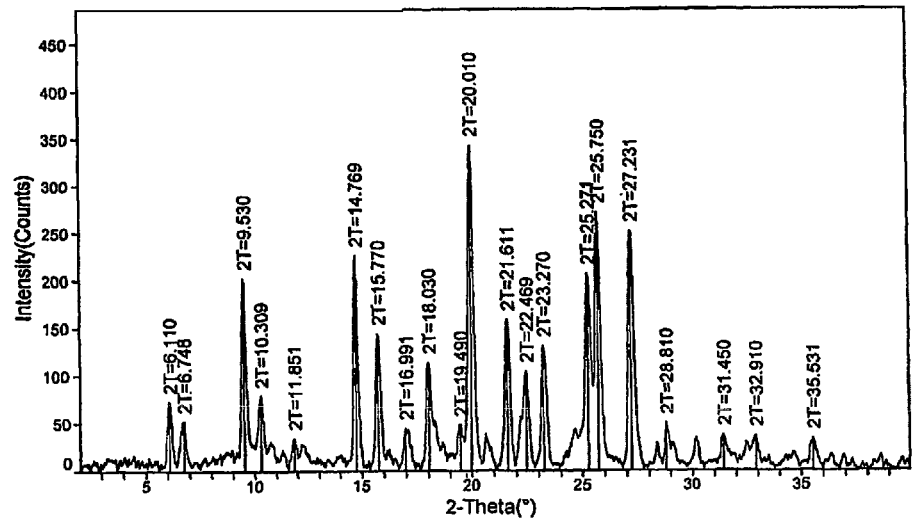
FIG. 46—PXRD diffractogram of a possible solvate comprising modafinil and acetone.

Racemic modafinil (1 mg, 0.0037 mmol) and mandelic acid (0.55 mg, 0.0037 mmol) were dissolved in acetone (400 microliters). The solution was allowed to evaporate to dryness and the resulting solid was characterized using PXRD (Rigaku), as shown in FIG. 46. The obtained solid is a mixture of the acetone solvate and another product of modafinil. The form can be characterized by any one, any two, any three, any four, any five, or any six or more of the peaks in FIG. 46 including, but not limited to, 6.11, 9.53, 15.77, 18.03, 20.01, and 21.61 degrees 2-theta (background removed). Other peaks including 6.75, 10.31, 14.77, and 23.27 may correspond to a modafinil polymorph.

Example 26

Figure 47:
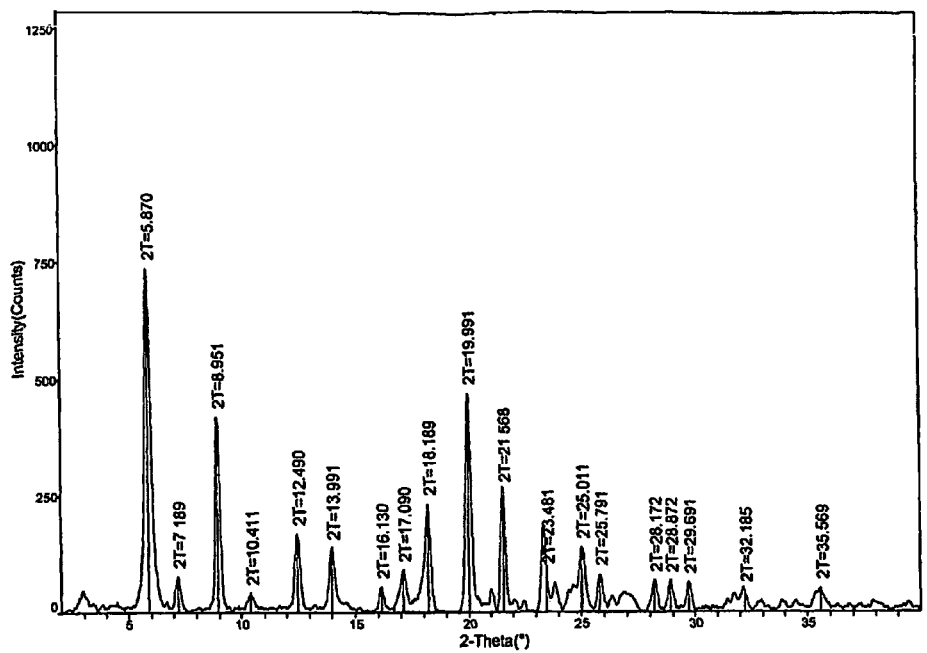
FIG. 47—PXRD diffractogram of a possible solvate comprising modafinil and 1,2-dichloroethane.

Racemic modafinil (1 mg, 0.0037 mmol) and fumaric acid (0.42 mg, 0.0037 mmol) were dissolved in 1,2-dichloroethane (400 microliters). The solution was allowed to evaporate to dryness and the resulting solid was characterized using PXRD (Rigaku), as shown in FIG. 47. The obtained solid may be a solvate of modafinil. The form can be characterized by any one, any two, any three, any four, any five, or any six or more of the peaks in FIG. 47 including, but not limited to, 5.87, 8.95, 12.49, 13.99, 18.19, 19.99, 21.57, and 25.01 degrees 2-theta (background removed).

Example 27

Novel form of Racemic Modafinil

Figure 48:
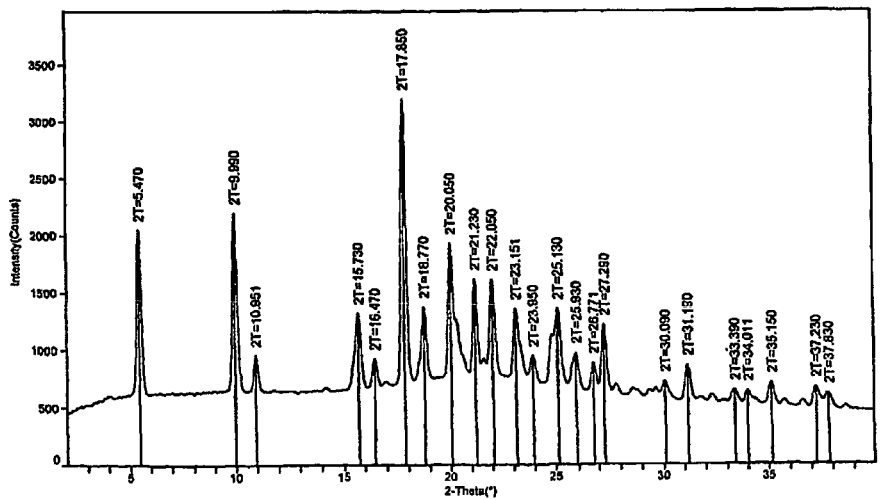
FIG. 48—PXRD diffractogram of a polymorph of modafinil (Form VI).

Racemic modafinil was dispensed from a stock solution containing 50 mg of modafinil in 20 mL of a 15:5 acetone/methanol mixture. The solution was then evaporated to dryness under a flow of nitrogen. Benzoic acid was dispensed from an acetone solution and the mixture was again evaporated to dryness. 200 microliters of isopropyl alcohol or methanol was then added and the vials were capped. After standing at room temperature for one day, the caps were removed and the solvent was allowed to evaporate. PXRD (Rigaku) was carried out on the sample, as shown in FIG. 48. The novel form of racemic modafinil, which may be a polymorph or a co-crystal, is denoted as form VII. Form VII can be characterized by any one, any two, any three, any four, any five, or any six or more of the peaks in FIG. 48 including, but not limited to, 5.47, 9.99, 15.73, 17.85, 18.77, 20.05, 21.23, 22.05, 23.15, and 25.13 degrees 2-theta (data as collected).

Example 28

Racemic Modafinil:Malonic Acid Co-crystal Pharmacokinetic Study in Dogs

The racemic modafinil:malonic acid co-crystal (from Example 1) was administered to dogs in a pharmacokinetic study. Particles of modafinil:malonic acid co-crystal with a median particle size of about 16 micrometers were administered in the study. As a reference, micronized modafinil with a median particle size of about 2 micrometers was also administered in the study. The AUC of the modafinil:malonic acid co-crystal was determined to be 40 to 60 percent higher than that of the pure modafinil. Such a higher bioavailability illustrates the modulation of an important pharmacokinetic parameter due to an embodiment of the present invention. A compilation of important pharmacokinetic parameters measured during the animal study are included in Table V.

TABLE V

Pharmacokinetic parameters of modafinil: malonic acid co-crystal and pure modafinil in dogs

| Parameter | Pure Modafinil | Modafinil: malonic acid co-crystal |
|---|---|---|
| Median particle size | 2 micrometers | 16 micrometers |
| $C_{max}$ (ng/mL) | 11.0 ± 5.9 | 10.3 ± 3.4 |
| $T_{max}$ (hours) | 1.3 ± 0.6 | 1.7 ± 0.6 |
| AUC (relative) | 1.0 | 1.4-1.6 |
| Half-life (hours) | 2.1 ± 0.7 | 5.1 ± 2.4 |

Example 29

Racemic Modafinil:Malonic Acid Co-crystal Solid-State Stability

The stability of the racemic modafinil:malonic acid co-crystal was measured at various temperatures and relative humidities over a four week period. No degradation was found to occur at 20 or 40 degrees C. At 60 degrees C., about 0.14 percent degradation per day was determined based on a simple exponential model. At 80 degrees C., about 8 percent degradation per day was determined.

Figure 49:
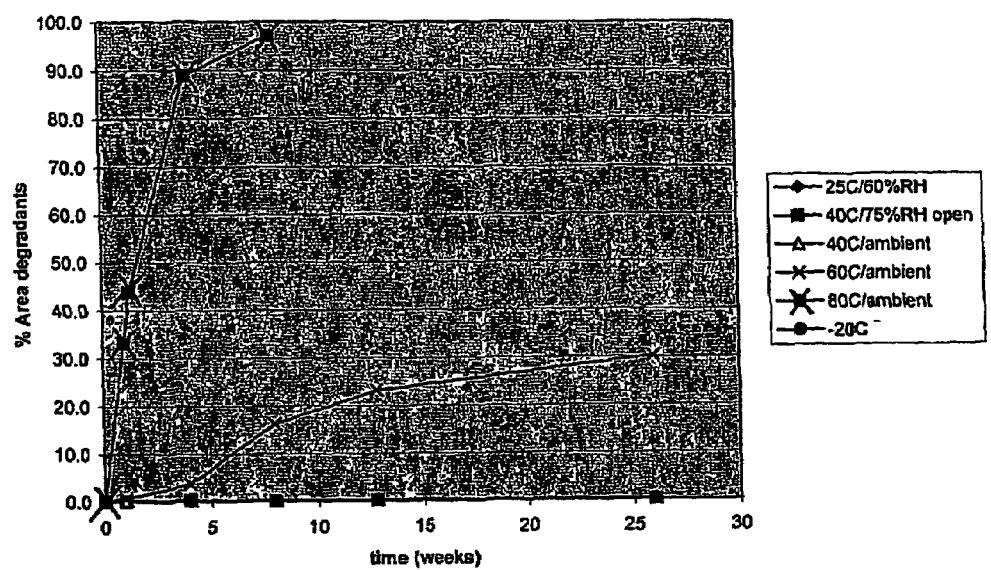
FIG. 49—Stability plot of modafinil:malonic acid co-crystal over a 26 week period.
Figure 50:
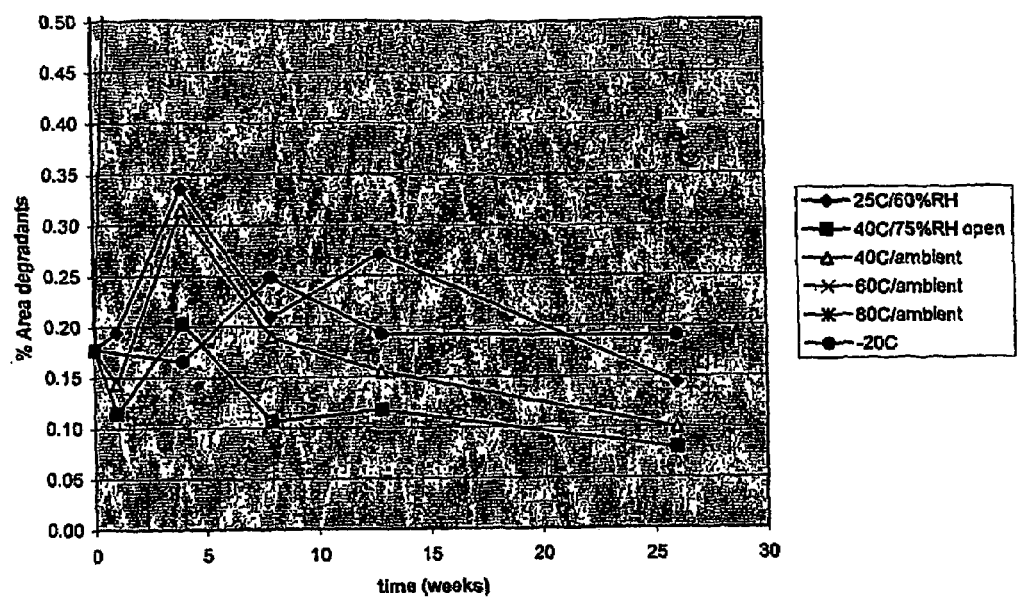
FIG. 50—Closer view of stability plot of modafinil:malonic acid co-crystal over a 26 week period.
Figure 51:
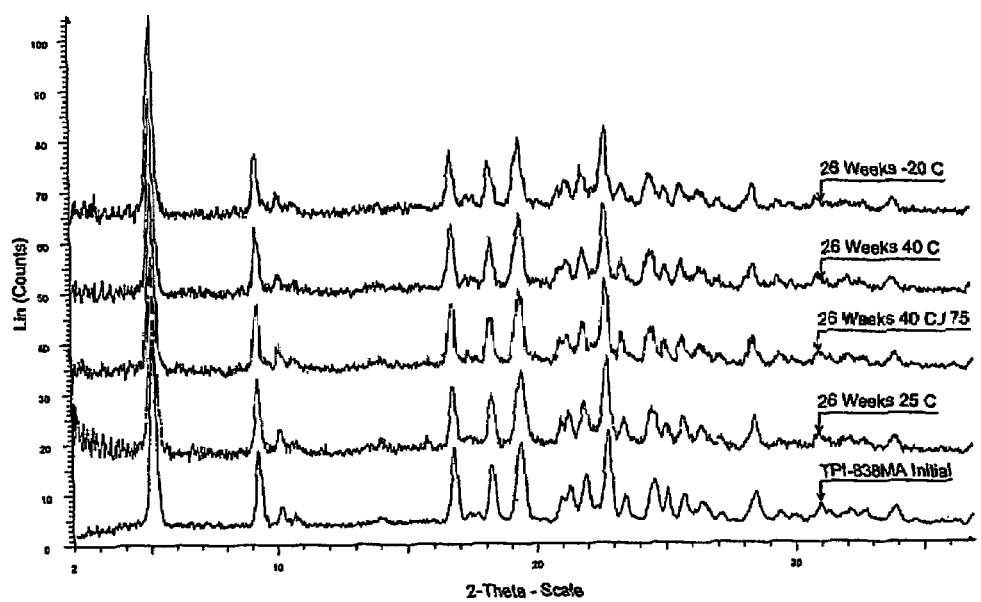
FIG. 51—PXRD diffractogram comparison of modafinil:malonic acid co-crystal after several environmental conditions are endured.

The stability of the modafinil:malonic acid co-crystal was also measured at various temperatures and relative humidities over a 26 week period. FIGS. 49 and 50 show the % area impurities as measured via HPLC versus time (weeks) for samples stored at various conditions including: 25 degrees C., 60% RH; 40 degrees C., 75 percent RH; 40 degrees C., ambient RH; 60 degrees C., ambient RH; 80 degrees C., ambient RH; and −20 degrees C. These data show that the compound is stable when stored at or below 40 degrees C. for at least 26 weeks. FIG. 51 compares PXRD patterns of initial and 26 week old samples of the modafinil:malonic acid co-crystal for several temperatures and RH levels.

Example 30

Formulation of Racemic Modafinil:Malonic Acid Co-crystal

The formulation of a racemic modafinil:malonic acid co-crystal was completed using lactose. Two mixtures, one of modafinil and lactose, and the second of modafinil:malonic acid co-crystal and lactose, were ground together in a mortar an pestle. The mixtures targeted a 1:1 weight ratio of modafinil to lactose. In the modafinil and lactose mixture, 901.2 mg of modafinil and 901.6 mg of lactose were ground together. In the modafinil:malonic acid co-crystal and lactose mixture, 1221.6 mg of co-crystal and 871.4 mg of lactose were ground together. The resulting powders were analyzed by PXRD and DSC. The PXRD patterns and DSC thermograms of the mixtures showed virtually no change upon comparison with both individual components. The DSC of the co-crystal mixture showed only the co-crystal melting peak at 113.6 degrees C. with a heat of fusion of 75.9 J/g. This heat of fusion is 59.5% of that found for the co-crystal alone (127.5 J/g). This result is consistent with a 58.4% weight ratio of co-crystal in the mixture. The DSC of the modafinil and lactose mixture had a melting point of 165.7 degrees C. This is slightly lower then the measured melting point of modafinil (168.7 degrees C.). The heat of fusion of the mixture (59.3 J/g) is 46.9% that of the modafinil alone (126.6 J/g), which is consistent with the estimated value of 50%.

Figure 52:
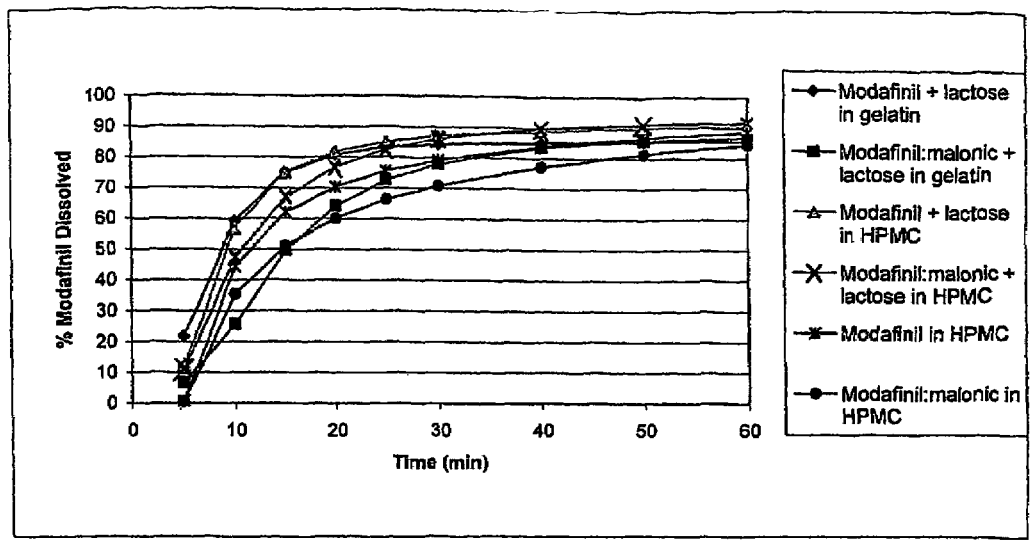
FIG. 52—Dissolution profile of several formulations of modafinil free form and modafinil:malonic acid.

The in vitro dissolution of both the modafinil:malonic acid co-crystal and pure modafinil were tested in capsules. Both gelatin and hydroxypropylmethyl cellulose (HPMC) capsules were used in the dissolution study. The capsules were formulated with and without lactose. All formulations were ground in a mortar and pestle prior to transfer into a capsule. The dissolution of the capsules was tested in 0.01 M HCl (See FIG. 52).

In 0.01N HCl, Using Sieved and Ground Materials in Gelatin Capsules:

Modafinil and the modafinil:malonic acid co-crystal were passed through a 38 micrometer sieve. Gelatin capsules (Size 0, B&B Pharmaceuticals, Lot # 15-01202) were filled with 200.0 mg sieved modafinil, 280.4 mg sieved modafinil:malonic acid co-crystal, 200.2 mg ground modafinil, or 280.3 mg ground modafinil:malonic acid co-crystal. Dissolution studies were performed in a Vankel VK 7000 Benchsaver Dissolution Testing Apparatus with the VK750D heater/circulator set at 37 degrees C. At 0 minutes, the capsules were dropped into vessels containing 900 mL 0.01 M HCl and stirred by paddles.

Absorbance readings were taken using a Cary 50 Spectrophotometer (wavelength set at 260 nm) at the following time points: 0, 5, 10, 15, 20, 25, 30, 40, 50, and 60 minutes. The absorbance values were compared to those of standards and the modafinil concentrations of the solutions were calculated.

In 0.01N HCl, Using Ground Materials in Gelatin or HPMC Capsules, with and without Lactose:

Modafinil and the modafinil:malonic acid co-crystal were mixed with equivalent amounts of lactose (Spectrum, Lot QV0460) for approximately 5 minutes. Gelatin capsules (Size 0, B&B Pharmaceuticals, Lot # 15-01202) were filled with 400.2 mg modafinil and lactose (approximately 200 mg modafinil), or 561.0 mg modafinil:malonic acid co-crystal and lactose (approximately 200 mg modafinil). HPMC capsules (Size O, Shionogi, Lot # A312A6) were filled with 399.9 mg modafinil and lactose, 560.9 mg modafinil:malonic acid co-crystal and lactose, 199.9 mg modafinil, or 280.5 mg modafinil:malonic acid co-crystal. The dissolution study was carried out as described above.

Example 31

In Vitro Dissolution

Figure 53:
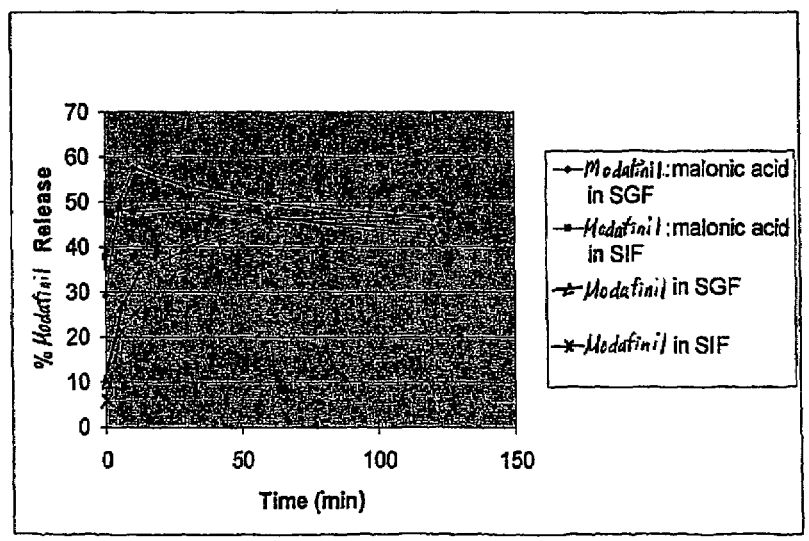
FIG. 53—In Vitro dissolution profile of modafinil:malonic acid co-crystal in SGF and SIF.
Figure 54:
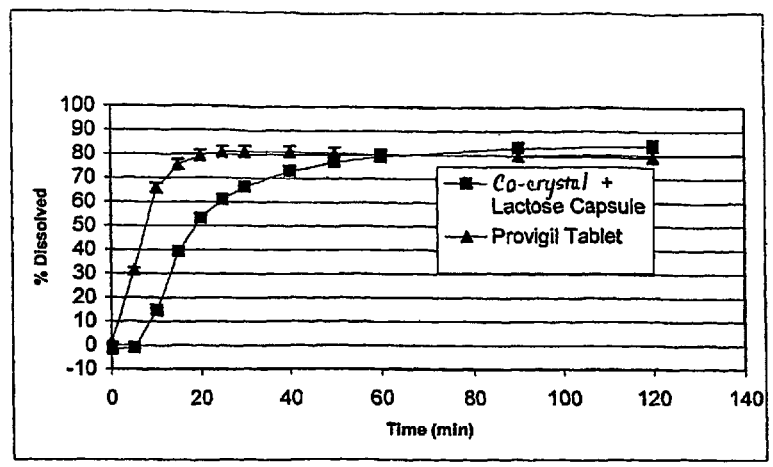
FIG. 54—In Vitro dissolution profile of modafinil:malonic acid co-crystal in HCl.
Figure 55:
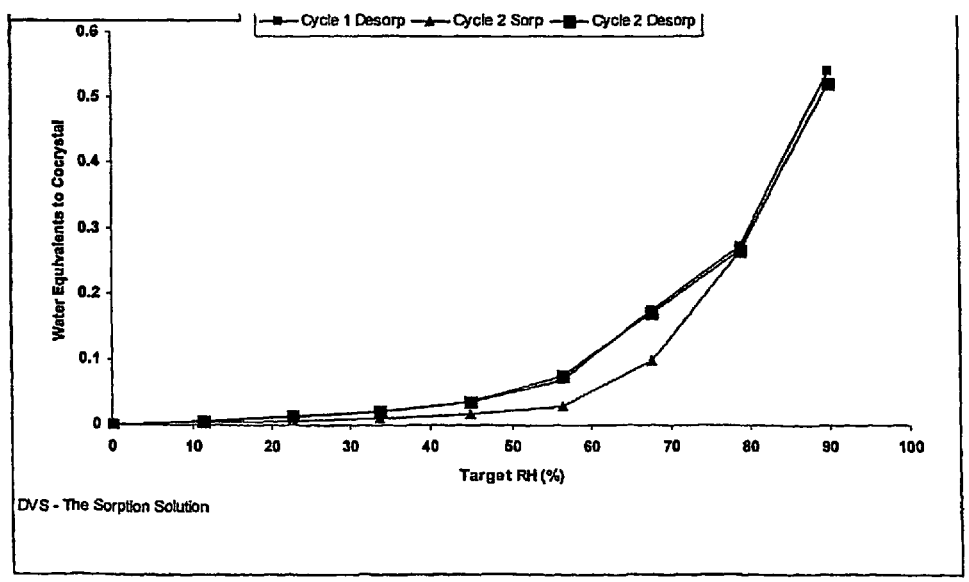
FIG. 55—DVS plot of modafinil:malonic acid co-crystal.

FIG. 53 shows in vitro dissolution data of micronized racemic modafinil:malonic acid co-crystal and of micronized modafinil in simulated gastric fluid (SGF) and in simulated intestinal fluid (SIF). Both samples were blended with lactose and filled into HPMC capsules. The co-crystal releases modafinil into solution more quickly in both SGF and SIF than does the free form of modafinil. FIG. 54 compares the dissolution of an HPMC capsule filled with the modafinil:malonic acid co-crystal blended with lactose and that of a PROVIGIL tablet. FIG. 55 shows a dynamic vapor sorption (IVS) isotherm plot of the modafinil:malonic acid co-crystal. This plot shows no appreciable water adsorption up to at least 40 percent RH at 26 degrees C.

Example 32

In Vivo Studies

Figure 56:
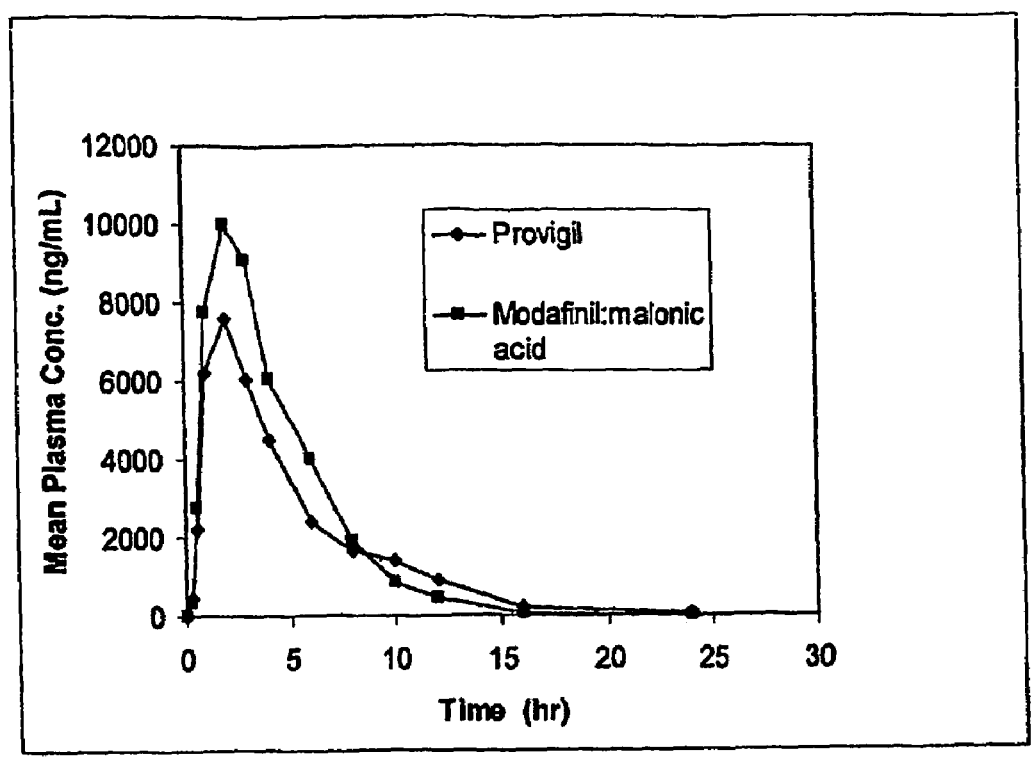
FIG. 56—Pharmacokinetics of modafinil:malonic acid co-crystal in dogs.

A pharmacokinetic study was completed with dogs using both racemic modafinil:malonic acid formulated with lactose and PROVIGIL tablets (200 mg). Seven capsules were filled with the modafinil:malonic acid co-crystal and lactose to 476.24+/−2 mg, each containing 200 mg modafinil. FIG. 56 shows the co-crystal formulation has an increased $C_{max}$ and an increased bioavailability. Severel important pharmacokinetic parameters are described in Table VI. In Table VI, "$C_{max}$" is the maximum blood plasma concentration, "AUC (inf)" is the extrapolated area under the curve, "$t_{1/2}$" is the amount of time for the blood plasma level to decrease to half of the $C_{max}$ level beginning at administration, "$T_{max}$" is the time to maximum blood plasma concentration from administration, "CL" is the clearance rate of modafinil, and "F %" is the percent bioavailability.

TABLE VI

PK parameters of modafinil: malonic acid co-crystal and PROVIGIL from In Vivo study

|  | Cmax | AUC (inf) | $t_{1/2}$ | Tmax | CL | F % |
|---|---|---|---|---|---|---|
| | | PROVIGIL (200 mg) | | | | |
| Mean | 7838.33 | 41193.33 | 1.76 | 2.00 | 524.17 | 66.48 |
| SD | 2734.35 | 8104.32 | 0.88 | 0.63 | 146.98 | 13.08 |
| % CV | 34.9 | 19.7 | 49.7 | 31.6 | 28.0 | 19.7 |

TABLE VI-continued

PK parameters of modafinil: malonic acid co-crystal and PROVIGIL from In Vivo study

| | Cmax | AUC (inf) | $t_{1/2}$ | Tmax | CL | F % |
|---|---|---|---|---|---|---|
| Modafinil: malonic acid (200 mg modafinil) | | | | | | |
| Mean | 11246.67 | 50545.00 | 1.63 | 2.00 | 368.33 | 81.57 |
| SD | 1662.13 | 10635.46 | 0.64 | 0.89 | 165.60 | 17.16 |
| % CV | 14.8 | 21.0 | 39.5 | 44.7 | 45.0 | 21.0 |

Example 33

R-(−)-modafinil:Gentisic Acid Co-crystal

Figure 57:
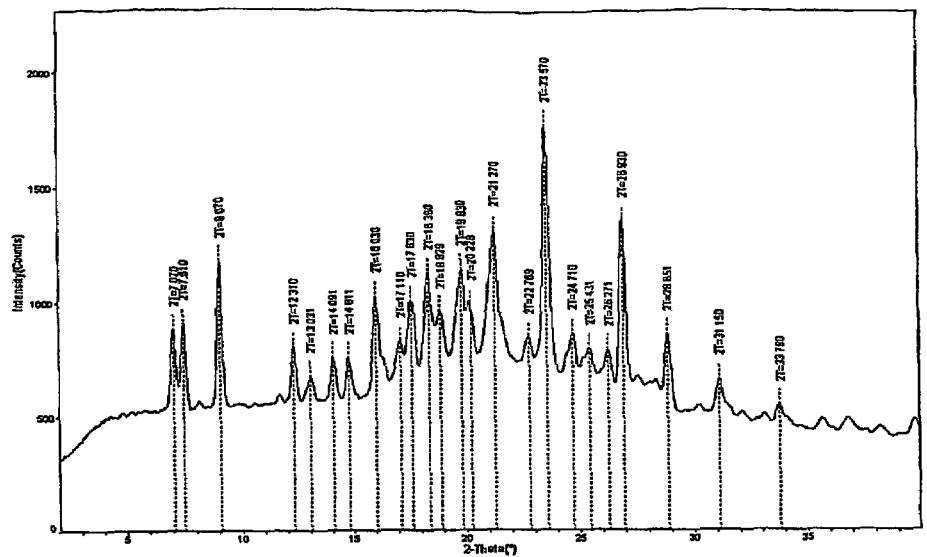
FIG. 57—PXRD diffractogram of a co-crystal comprising R-(−)-modafinil and gentisic acid.

R-(−)-modafinil (50 mg, 0.183 mmol, greater than 98 percent R-isomer) and gentisic acid (28.2 mg, 0.183 mmol) were placed in a stainless steel vial. 10 microliters of acetone was added to the vial. The vial was then placed in a grinder (wig-l-bug, Bratt Technologies, 115V/60 Hz) and the solid mixture was milled for 5 minutes. The resultant powder was then collected and characterized using PXRD (Rigaku), as shown in FIG. 57. The R-(−)-modafinil:gentisic acid co-crystal can be characterized by any one, any two, any three, any four, any five, or any six or more of the peaks in FIG. 57 including, but not limited to, 7.07, 9.07, 12.31, 13.03, 14.09, 18.93, 19.83, and 21.27 degrees 2-theta (as collected). Other PXRD peaks at 7.51, 16.03, 17.63, 18.39, 23.57, 26.93, and 28.85 degrees 2-theta correspond to excess co-crystal former.

Example 34

Channel Solvates of Racemic Modafinil

Figure 58:
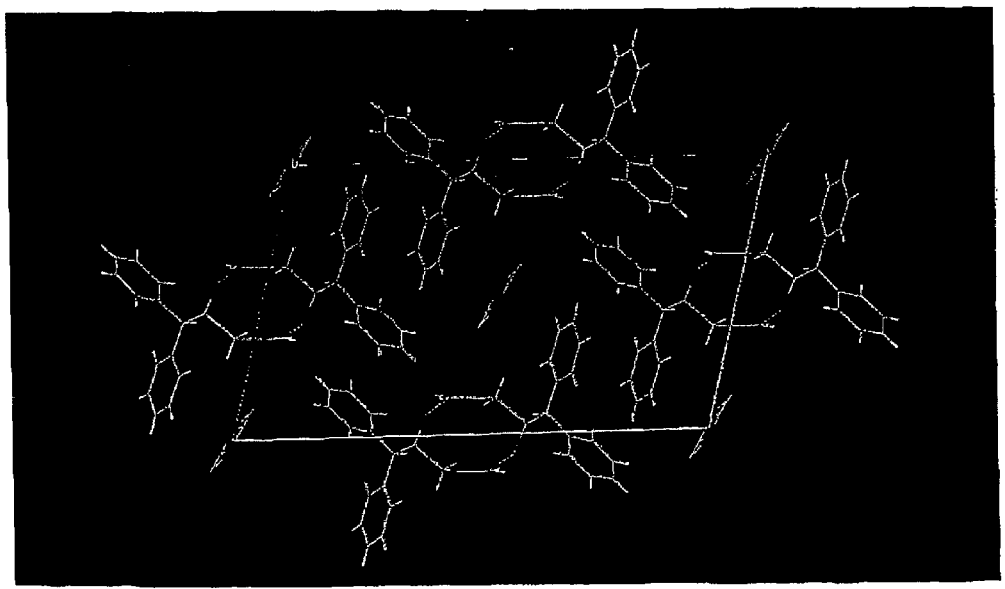
FIG. 58—Packing diagram of acetone channel solvate of modafinil.
Figure 59:
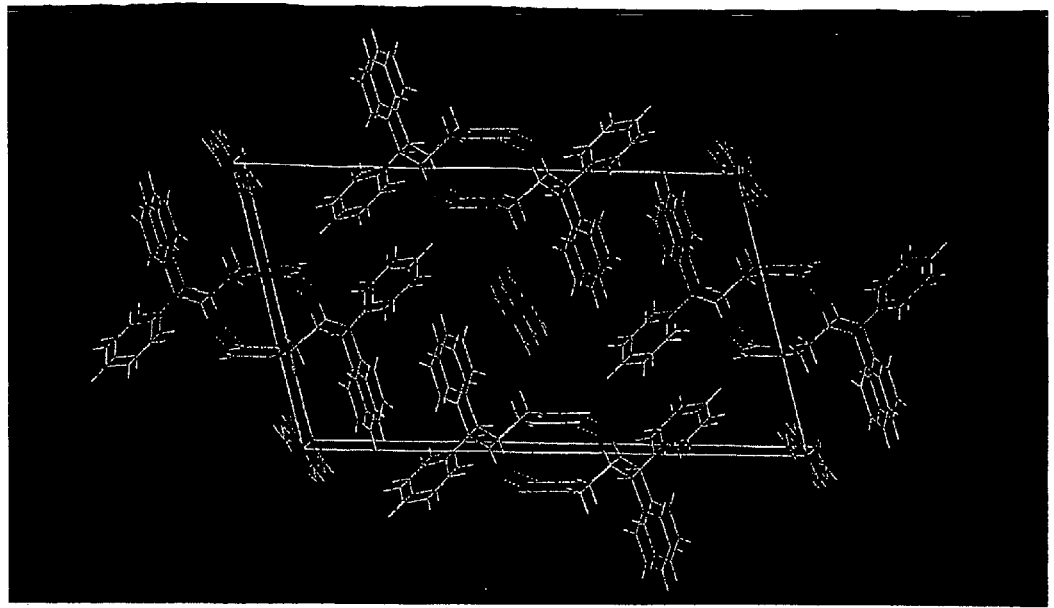
FIG. 59—Additional packing diagram of acetone channel solvate of modafinil.

Channel solvates of modafinil have been unexpectedly discovered. The channel solvate was made from a solution of racemic modafinil (97.9 mg, 0.358 mmol) and 1-hydroxy-2-napthoic acid (68.8 mg, 0.366 mmol) in acetone (3.15 mL), dissolved over a 60 degrees C. hotplate. The solution was then evaporated under flowing nitrogen while hot to 1.6 mL total volume. Once cooled, the solution was seeded with ground racemic modafinil:1-hydroxy-2-naphtoic acid co-crystal. Single crystals were obtained and characterized using single x-ray analysis. Single-crystal x-ray parameters: P2(1)/n, a=12.737(3) angstroms, b=5.5945(11) angstroms, c=22.392 (5) angstroms, alpha=90 degrees, beta=104.140(4) degrees, gamma=90 degrees, V=1547.3(5) cubic angstroms, Z=2. FIGS. 58 and 59 show packing diagrams of the acetone channel solvate of modafinil. The packing diagrams show acetone with a variable position within the channel structure. An ethyl acetate channel solvate has also been prepared according to the method above using ethyl acetate in place of acetone.

Example 35 o-Xylene Hemisolvate of Racemic Modafinil

Figure 60:
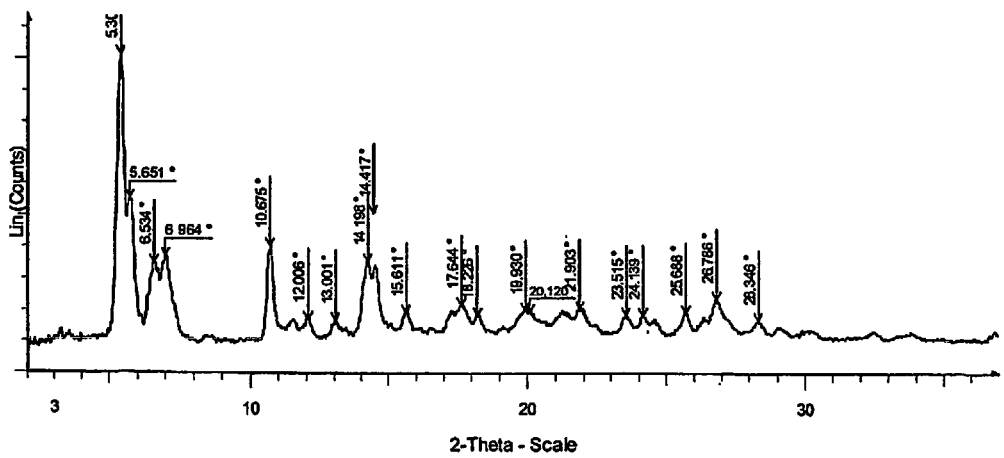
FIG. 60—PXRD diffractogram of o-xylene solvate.
Figure 61:
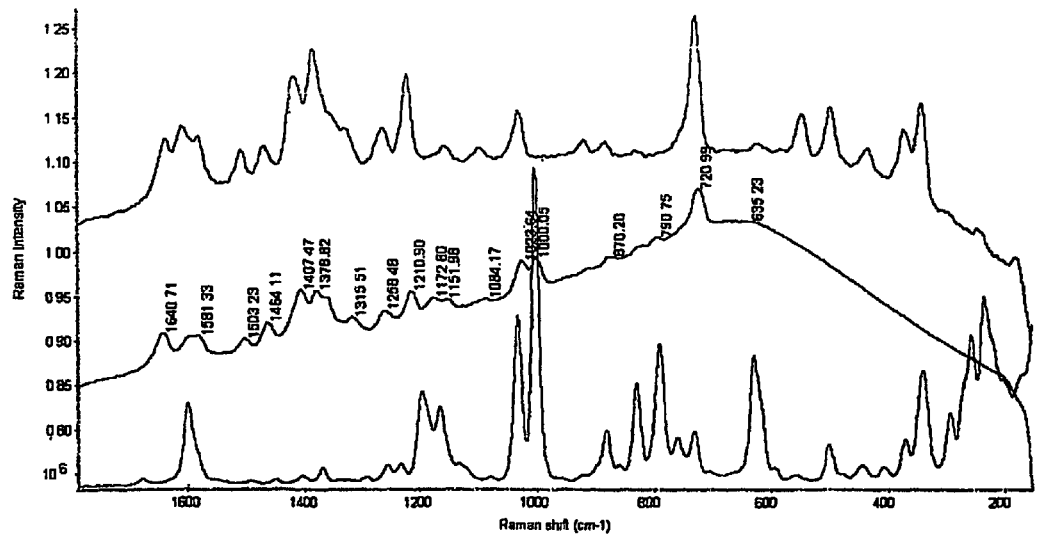
FIG. 61—Raman spectrum of o-xylene solvate (middle spectrum).
Figure 62:
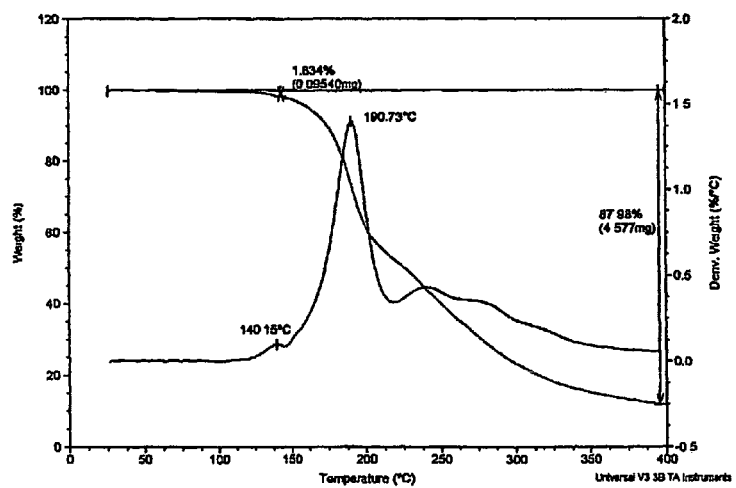
FIG. 62—TGA thermogram of o-xylene solvate.
Figure 63:
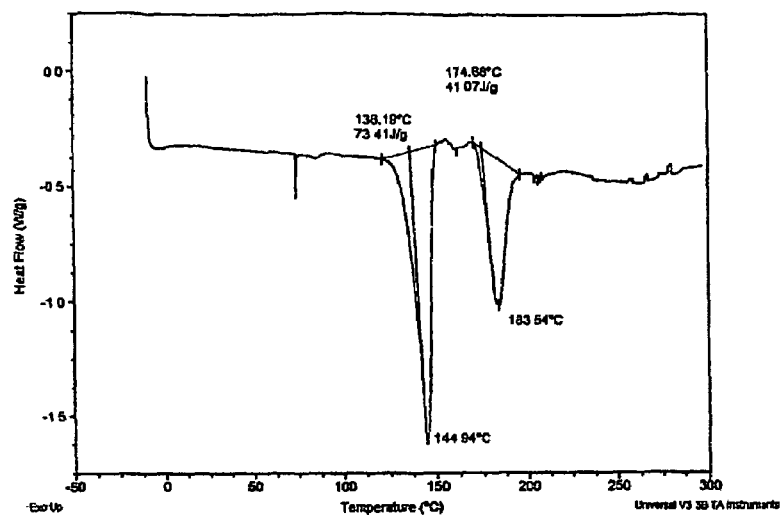
FIG. 63—DSC thermogram of o-xylene solvate.

An o-xylene hemisolvate was formed by preparing a 1:2 solution of racemic modafinil (49.6 mg, 0.181 mmol) and 1-hydroxy-2-napthoic acid (68.3 mg, 0.363 mmol) in o-xylene (4.5 mL). The mixture was heated on a hotplate with swirling until all solids were dissolved. The solution was then left to crystallize in a sealed vial. The resulting powder was collected in a centrifuge filter and analyzed by PXRD (Bruker), as shown in FIG. 60. Raman spectroscopy (FIG. 61), TGA (FIG. 62), and DSC (FIG. 63) were also used to analyze and characterize the hemisolvate. The o-xylene solvate can be characterized by any one, any two, any three, any four, any five, or any six or more of the peaks in FIG. 60 including, but not limited to, 5.31, 6.53, 6.96, 10.68, 14.20, 17.64, 19.93, 25.69, and 26.79 degrees 2-theta. The o-xylene solvate can be characterized by any one, any two, any three, any four, any five, or any six or more of the peaks in FIG. 61 (middle spectrum) including, but not limited to, 1641, 1407, 1379, 1211, 1024, and 721 $cm^{-1}$.

Example 36

Benzene Hemisolvate of Racemic Modafinil

Figure 64:
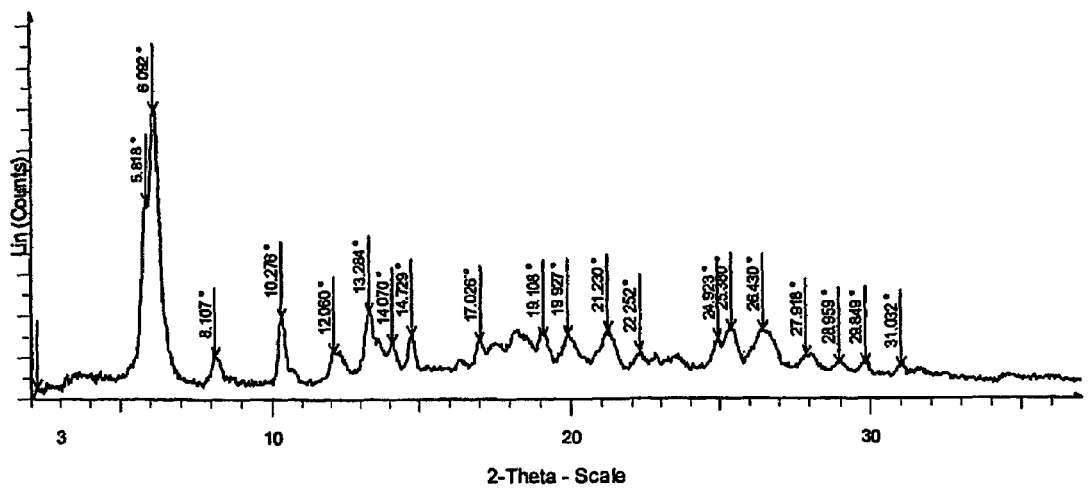
FIG. 64—PXRD diffractogram of benzene solvate.
Figure 65:
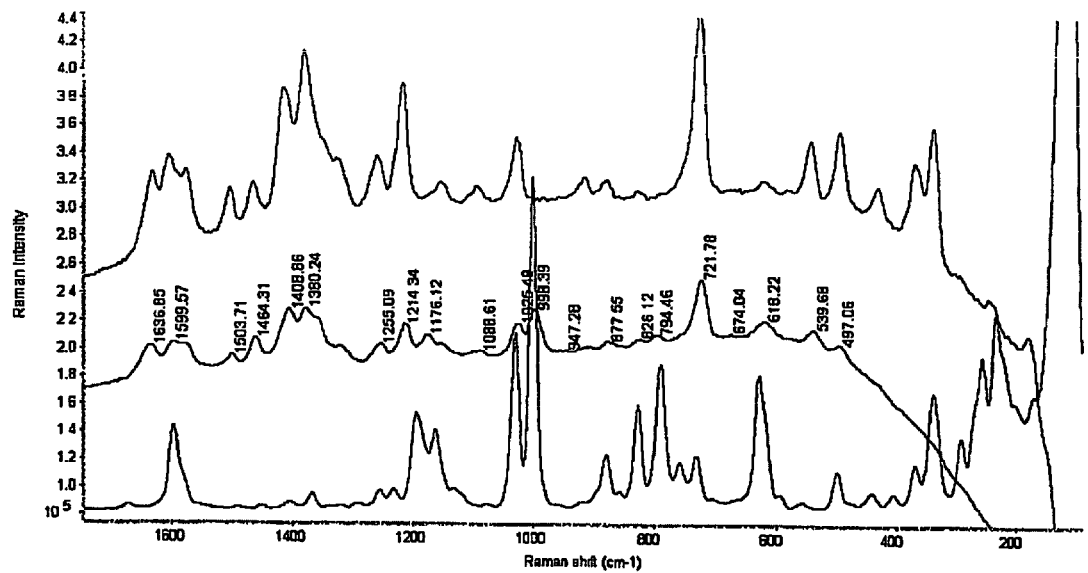
FIG. 65—Raman spectrum of benzene solvate (middle spectrum).
Figure 66:
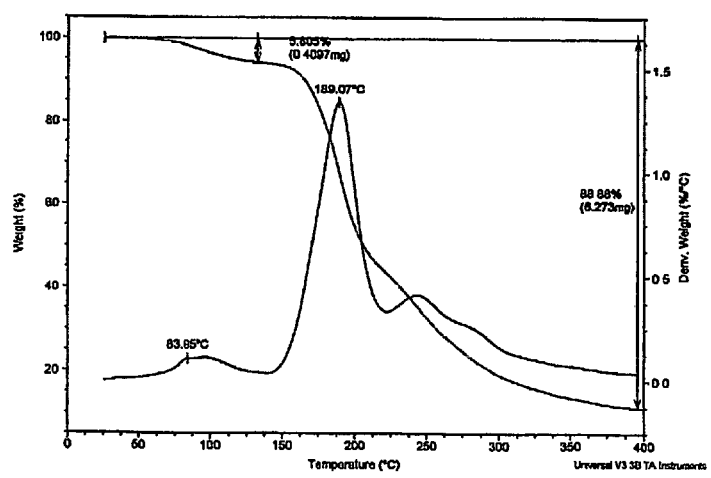
FIG. 66—TGA thermogram of benzene solvate.
Figure 67:
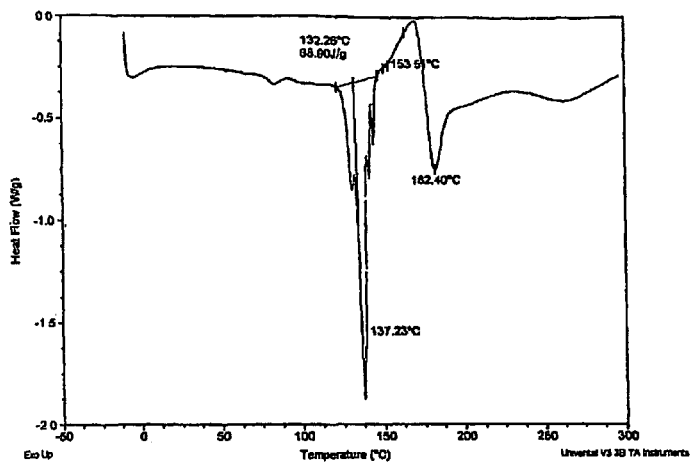
FIG. 67—DSC thermogram of benzene solvate.

A benzene hemisolvate was formed by preparing a 1:2 solution of racemic modafinil (50.6 mg, 0.181 mmol) and 1-hydroxy-2-napthoic acid (70.1 mg, 0.373 mmol) in benzene (1.8 mL). The mixture was heated on a hotplate with swirling until all solids were dissolved. The solution was then left to crystallize in a sealed vial. The resulting powder was collected in a centrifuge filter and analyzed by PXRD (Bruker), as shown in FIG. 64. Raman spectroscopy (FIG. 65), TGA (FIG. 66), and DSC (FIG. 67) were also used to analyze and characterize the hemisolvate. The benzene solvate can be characterized by any one, any two, any three, any four, any five, or any six or more of the peaks in FIG. 64 including, but not limited to, 5.82, 6.09, 8.11, 10.28, 12.06, 13.28, 14.73, 17.03, 19.11, 19.93, 21.23, 25.38, and 26.43 degrees 2-theta. The benzene solvate can be characterized by any one, any two, any three, any four, any five, or any six or more of the peaks in FIG. 65 (middle spectrum) including, but not limited to, 1637, 1600, 1409, 1380, 1214, 1025, 998, and 721 $cm^{-1}$.

Example 37

Toluene Hemisolvate of Racemic Modafinil

Figure 68:
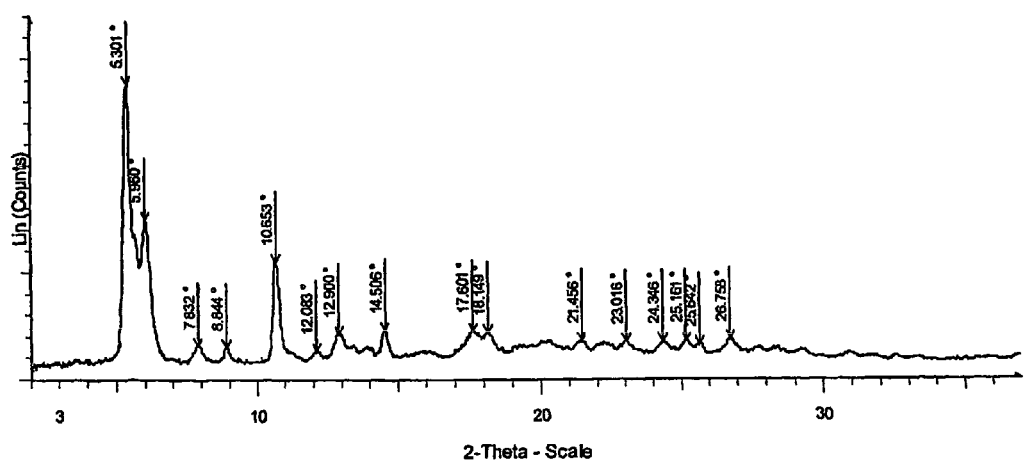
FIG. 68—PXRD diffractogram of toluene solvate.
Figure 69:
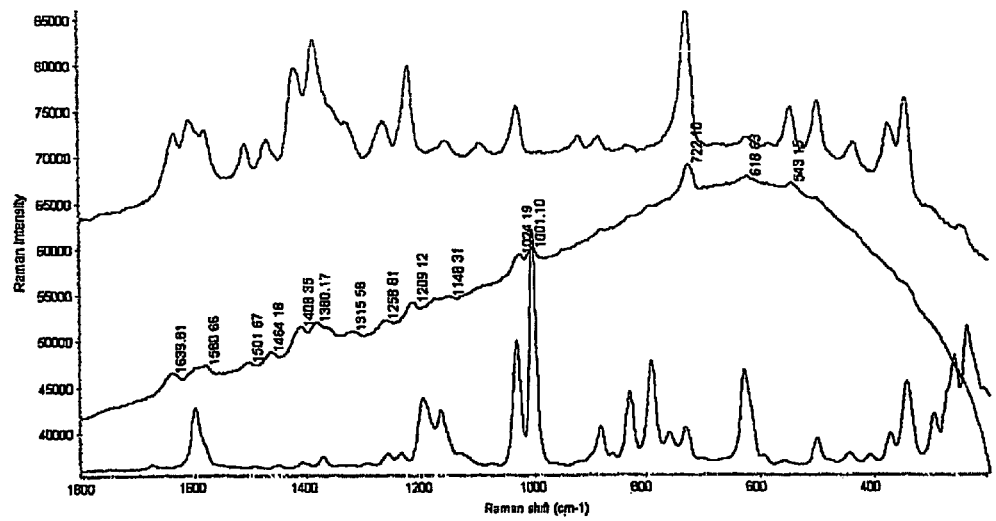
FIG. 69—Raman spectrum of toluene solvate (middle spectrum).
Figure 70:
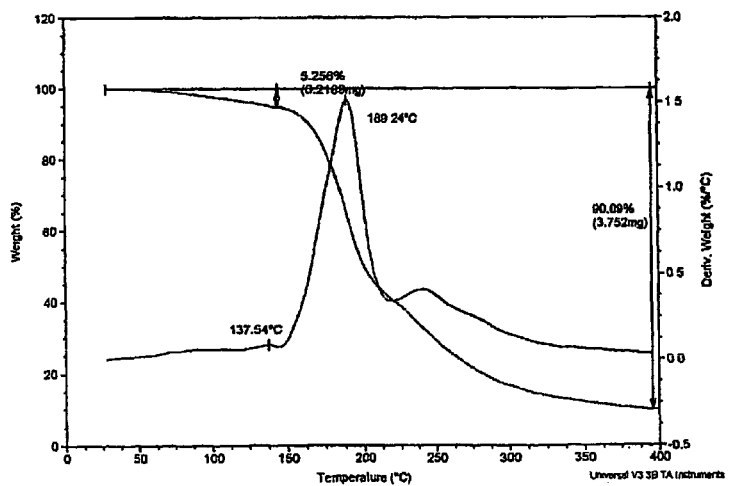
FIG. 70—TGA thermogram of toluene solvate.
Figure 71:
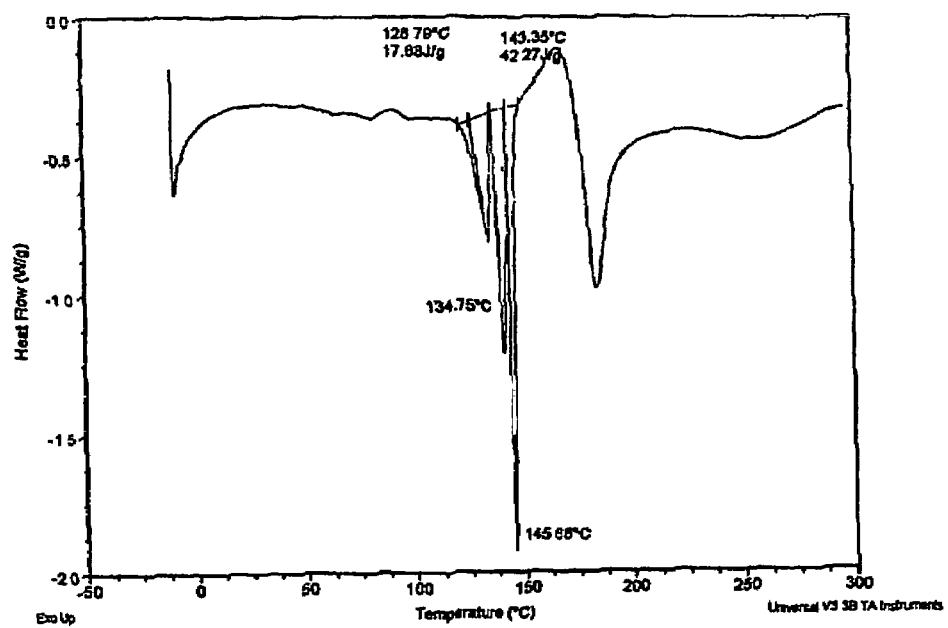
FIG. 71—DSC thermogram of toluene solvate.

A toluene hemisolvate was formed by making a 1:2 solution of racemic modafinil (37.3 mg, 0.136 mmol) and 1-hydroxy-2-napthoic acid (51.3 mg, 0.273 mmol) in toluene (1 mL). The mixture was heated on a hotplate with swirling until all solids were dissolved. The solution was then left to crystallize in a sealed vial. The resulting powder was collected in a centrifuge filter and analyzed by PXRD (Bruker), as shown in FIG. 68. Raman spectroscopy (FIG. 69), TGA (FIG. 70), and DSC (FIG. 71) were also used to analyze and characterize the hemisolvate. The toluene solvate can be characterized by any one, any two, any three, any four, any five, or any six or more of the peaks in FIG. 68 including, but not limited to, 5.30, 5.96, 10.65, 12.90, 14.51, 17.60, and 18.15 degrees 2-theta. The toluene solvate can be characterized by any one, any two, any three, any four, any five, or any six or more of the peaks in FIG. 69 (middle spectrum) including, but not limited to, 1640, 1581, 1408, 1380, 1209, 1024, 1001, and 722 $cm^{-1}$.

Example 38

Pharmacokinetics of Isomers of Modafinil

A dog pharmacokinetic study (N=6) of a single intravenous dose of R-(−)-modafinil was completed. The purity of the R-(−)-modafinil in the administered formulation was ca 80 percent. This formulation was compared to a formulation of racemic modafinil, also administered by the intravenous route to the same dogs in a crossover design. Results are reported in Table VII. Ir. Table VII, "$C_{max}$" is the maximum blood plasma concentration, "AUC (inf)" is the extrapolated area under the curve, "$t_{1/2}$" is the amount of time for the blood plasma level to decrease to half of the $C_{max}$ level beginning at administration, "$V_d$" is the volume of distribution, and "CL" is the clearance rate of modafinil.

TABLE VII

PK parameters of racemic modafinil and R-(−)-modafinil from In Vivo study

|  | $C_{max}$ (ng/mL) | AUC (inf) (ng/mL × hr) | $t_{1/2}$ (hr) | $V_d$ (mL/kg) | CL (mL/hr × kg) |
|---|---|---|---|---|---|
| Racemic Modafinil (5 mg/kg IV) | | | | | |
| Mean | 8682.83 | 15117.50 | 1.05 | 588.83 | 341.00 |
| SD | 1413.71 | 2870.24 | 0.16 | 96.41 | 65.63 |
| % CV | 16.3 | 19.0 | 15.4 | 16.4 | 19.2 |
| R-(−)-modafinil (5 mg/kg IV) | | | | | |
| Mean | 7806.67 | 15905.17 | 1.53 | 646.67 | 340.33 |
| SD | 827.97 | 4958.47 | 1.11 | 68.10 | 102.39 |
| % CV | 10.6 | 31.2 | 72.5 | 10.5 | 30.1 |

These results suggest that there is no significant difference between the pharmacokinetics of R-(−)-modafinil and racemic modafinil following intravenous administration.

These results are in contrast to the pharmacokinetics of the isomers when administered by the oral route (See U.S. Pat. No. 4,927,855, which is herein incorporated by reference in its entirety). In said study, four dogs were administered 30 mg/kg oral dose of either R-(−)-modafinil (40-982), S-(+)-modafinil (40-983), or racemic modafinil (40-476). The AUC values were calculated from plasma concentration of both forms (40476) and the sulfone metabolite measured from 2 to 9 hours post-dose administration. Table VIII shows the pharmacokinetic data.

TABLE VIII

PK parameters of racemic modafinil, R-(−)-modafinil, and S-(+)-modafinil from In Vivo study

| Compound administered (30 mg/kg) | Mean AUC (racemate) (mg/L × hr) | Mean AUC (sulfone) (mg/L × hr) |
|---|---|---|
| 40-476 (racemate) | 46.76 +/− 6.95 | 35.12 +/− 6.93 |
| 40-982 (R-(−)-modafinil) | 97.22 +/− 12.58 | 8.69 +/− 1.22 |
| 40-983 (S-(+)-modafinil) | 50.94 +/− 8.77 | 83.12 +/− 21.66 |

These results suggest striking differences in the metabolism of both isomers of modafinil, leading to differences in the formation of the inactive sulfone metabolite therefore resulting in higher exposure to the API when administered as R-(−)-modafinil. The different profile observed between the intravenous and the oral route could be explained by the fact that the formation of the sulfone metabolite is primarily catalyzed by cytochrome CYP3A4 which is both present at the intestinal and hepatic level, and that the affinity of CYP3A4 to S-(+)-modafinil is higher (stereoselective metabolism) than that to R-(−)-modafinil. This can result in faster metabolite formation with S-(+)-modafinil which can reduce the exposure to the API.

Example 39

R-(−)-modafinil Ethanol Solvate

A solution containing R-(−)-modafinil (100 mg, 0.366 mmol, 85.4 percent R-isomer) and racemic modafinil (40 mg, 0.146 mmol) in ethanol (3 mL) was prepared. The mixture was heated to reflux in order to dissolve the entire solid and was then cooled to room temperature (25 degrees C.). After remaining at room temperature for 15 minutes, the solution was placed at 5 degrees C. overnight. A solid precipitate was observed after 1 day and was collected, dried, and characterized using PXRD and TGA FIGS. 72 and 73). The solid was determined to be an ethanol solvate of R-(−)-modafinil.

Figure 72:
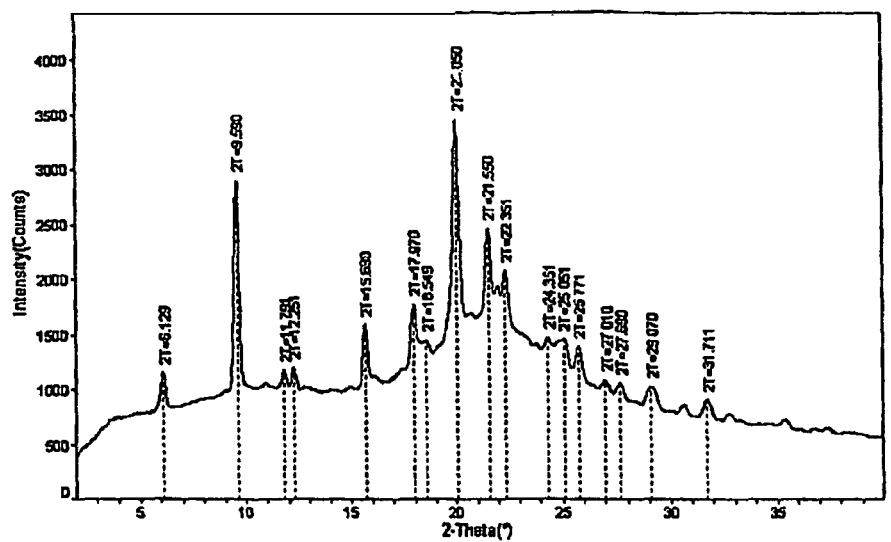
FIG. 72—PXRD diffractogram of R-(−)-modafinil ethanol solvate.

R-(−)-modafinil ethanol solvate can be characterized by any one, any two, any three, any four, any five, or any six or more of the peaks in FIG. 72 including, but not limited to, 6.13, 9.59, 15.69, 17.97, 20.05, 21.55, 22.35, 25.77, and 29.07 degrees 2-theta (Rigaku PXRD, data as collected).

Figure 73:
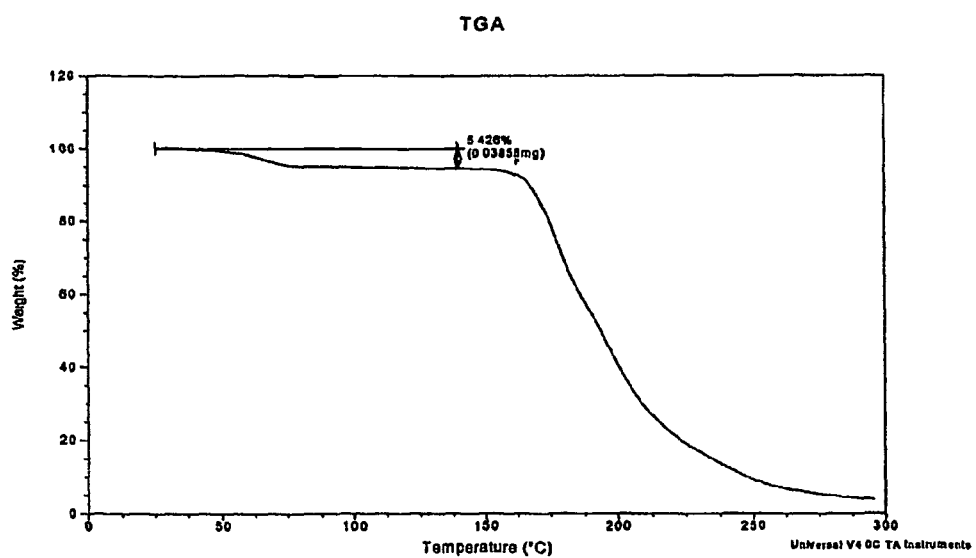
FIG. 73—TGA thermogram of R-(−)-modafinil ethanol solvate.

TGA of the R-(−)-modafinil ethanol solvate characterized in FIG. 73 showed about a 5.4 percent weight loss between about 25 and about 140 degrees C.

Example 40

R-(−)-modafinil Benzyl alcohol Solvate

Figure 74:
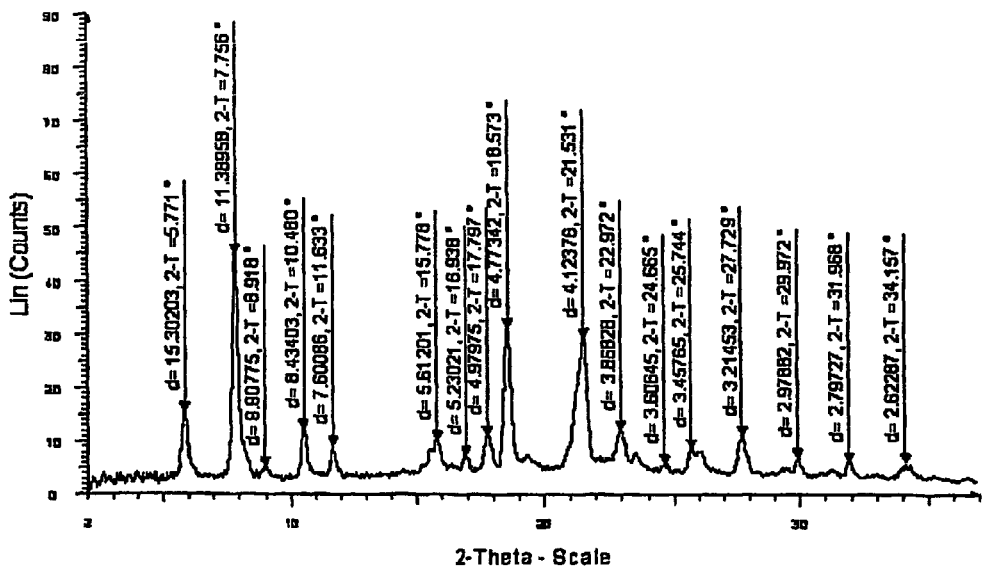
FIG. 74—PXRD diffractogram of R-(−)-modafinil benzyl alcohol solvate.
Figure 75:
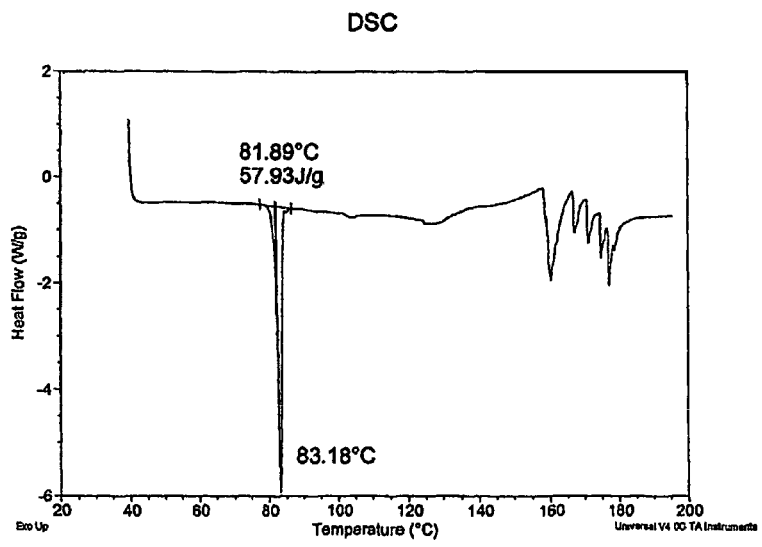
FIG. 75—DSC thermogram of R-(−)-modafinil benzyl alcohol solvate.
Figure 76:
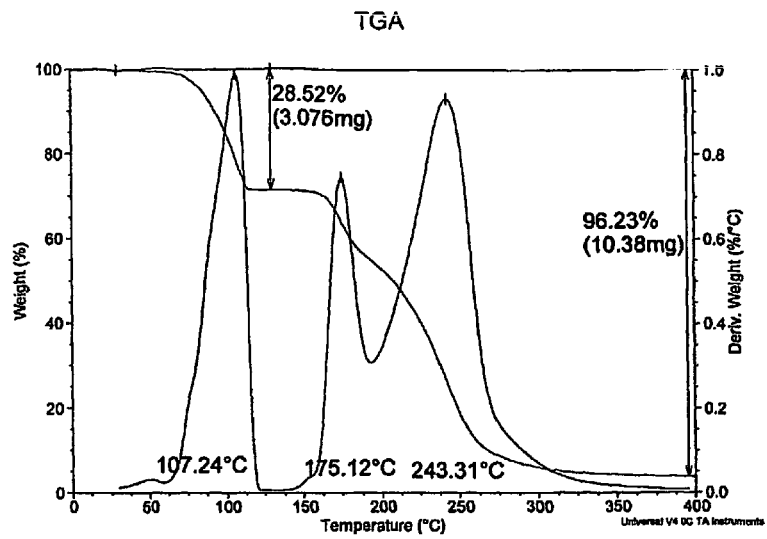
FIG. 76—TGA thermogram of R-(−)-modafinil benzyl alcohol solvate.

R-(−)-modafinil (100 mg, 0.366 mmol) was milled with benzyl alcohol (40 microliters) for 5 minutes. The milled powder was then analyzed by PXRD, DSC, and TGA (FIGS. 74, 75, and 76). The powder was determined to be a benzyl alcohol solvate of R-(−)-modafinil.

R-(−)-modafinil benzyl alcohol solvate can be characterized by any one, any two, any three, any four, any five, or any six or more of the peaks in FIG. 74 including, but not limited to, 5.77, 7.76, 10.48, 15.78, 17.80, 18.57, 21.53, 22.97, and 27.73 degrees 2-theta (Bruker PXRD, data as collected).

DSC of the R-(−)-modafinil benzyl alcohol solvate characterized in FIG. 75 showed an endothermic transition at about 83 degrees C.

TGA of the R-(−)-modafinil benzyl alcohol solvate characterized in FIG. 76 showed about a 28.5 percent weight loss between about 25 and about 125 degrees C.

Example 41

R-(−)-modafinil Isopropanol Solvate

R-(−)-modafinil was slurried overnight in isopropanol. The liquid was filtered out in a centrifuge filter, then dried under flowing nitrogen gas at 5 degrees C. The resulting solid was analyzed via PXRD.

Figure 77:
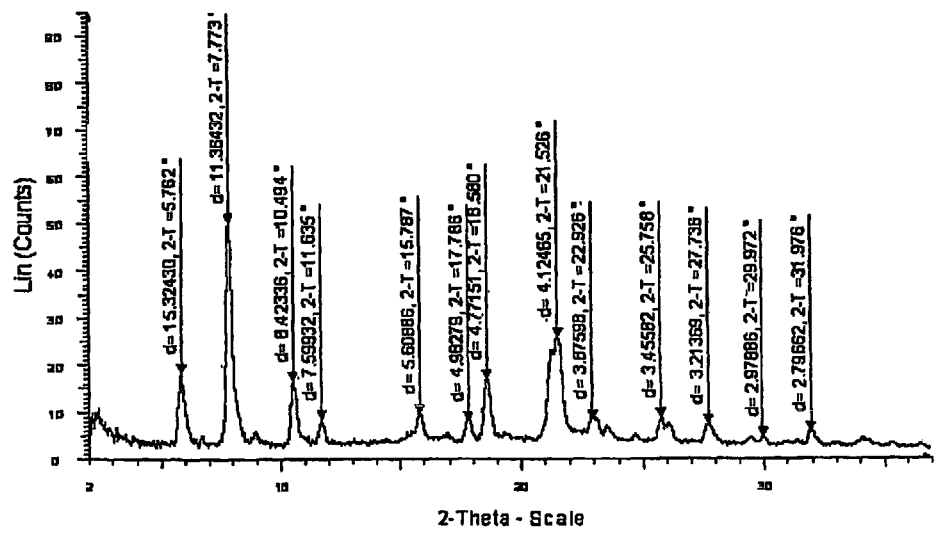
FIG. 77—PXRD diffractogram of R-(−)-modafinil isopropanol solvate.

R-(−)-modafinil isopropanol solvate can be characterized by any one, any two, any three, any four, any five, or any six or more of the peaks in FIG. 77 including, but not limited to, 5.76, 7.77, 10.49, 15.79, 18.58, 21.53, 25.76, and 27.74 degrees 2-theta (Bruker PXRD, data as collected).

Example 42

R-(−)-modafinil Acetonitrile Solvate 100 mg of R-(−)-modafinil was slurrie in acetonitrile for 2 days. The solid was filtered from the suspension and analyzed by PXRD.

Figure 78:
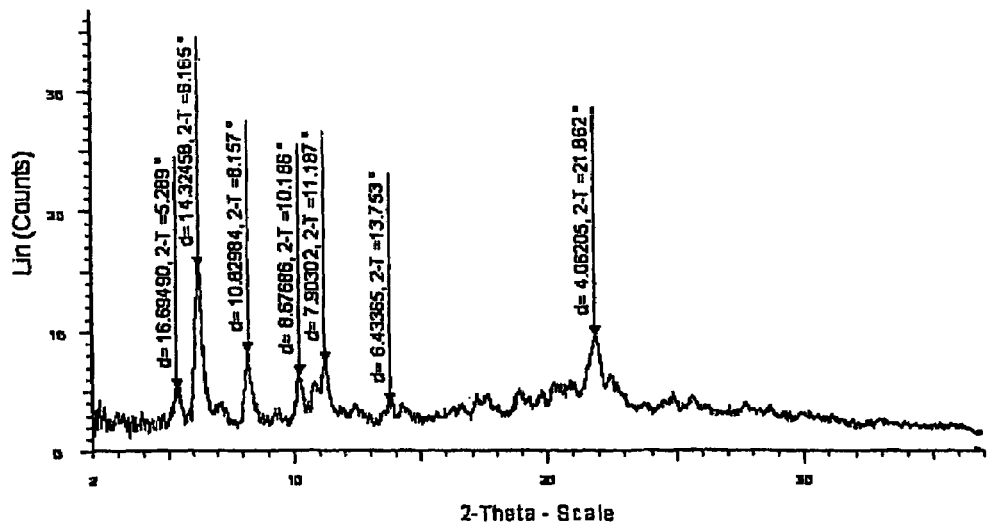
FIG. 78—PXRD diffractogram of R-(−)-modafinil acetonitrile solvate.

R-(−)-modafinil acetonitrile solvate can be characterized by any one, any two, any three, any four, any five, or any six or more of the peaks in FIG. 78 including, but not limited to, 5.29, 6.17, 8.16, 10.19, 11.19, and 21.86 degrees 2-theta (Bruker PXRD, data as collected).

Example 43

R-(−)-Modafinil:Glutaric Acid Co-crystal

R-(−)-modafinil (20 to 30 mg, greater than 98 percent R-isomer) and glutaric acid (15-20 mg) were ground together in the presence of one drop of benzyl alcohol.

Figure 79:
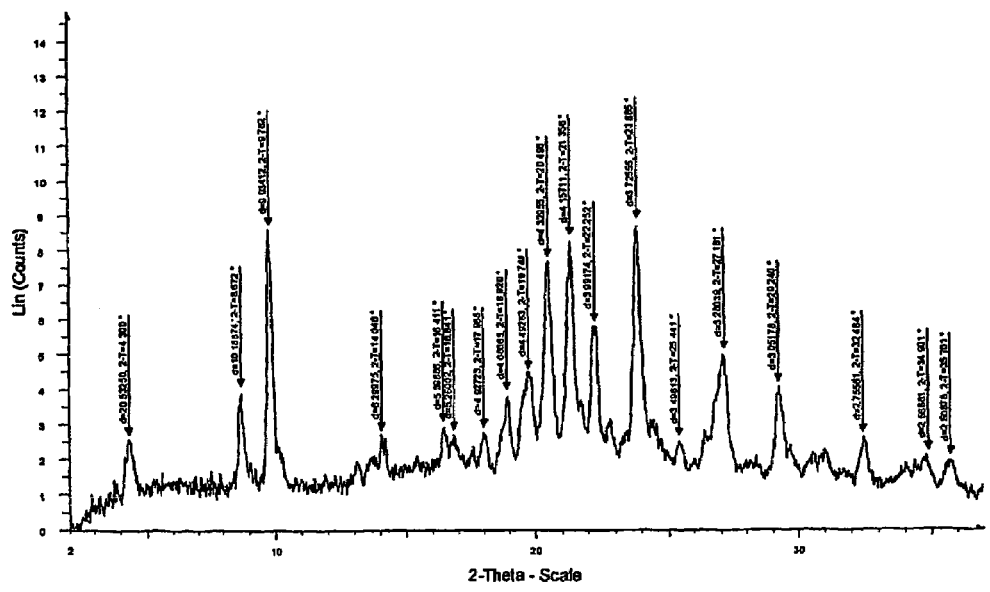
FIG. 79—PXRD diffractogram of R-(−)-modafinil:glutaric acid co-crystal.

The resultant solid was characterized by PXRD (See FIG. 79) and may comprise a co-crystal. The R-(−)-modafinil:glutaric acid co-crystal can be characterized by any one, any two, any three, any four, any five, or any six or more of the peaks in FIG. 79 including, but not limited to, 4.30, 8.67, 9.78, 17.99, 18.92, 19.74, 20.50, 21.36, 22.25, 23.87, 27.16, 29.24, and 32.46 degrees 2-theta (Bruker PXRD, data as collected).

Wet grinding was also used with acetone and with water, both of which resulted in the formation of the co-crystal.

Example 44

R-(−)-Modafinil:Citric Acid Co-crystal

R-(−)-modafinil (20 to 30 mg, greater than 98 percent R-isomer) and citric acid monohydrate (15-20 mg) were ground together in the presence of one drop of benzyl alcohol.

Figures 80, 81:
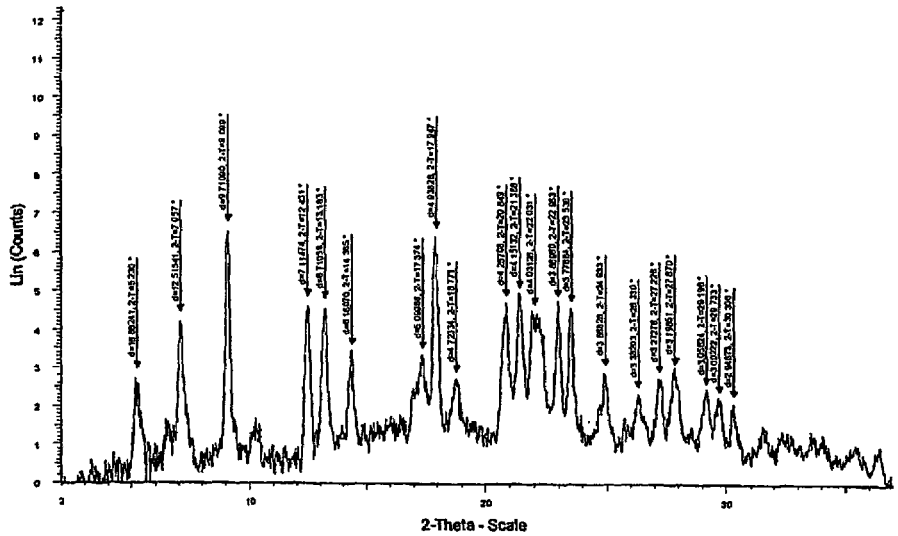
FIG. 80—PXRD diffractogram of R-(−)-modafinil:citric acid co-crystal.
FIG. 81—PXRD diffractogram of R-(−)-modafinil:L-tartaric acid co-crystal.

The resultant solid was characterized by PXRD (See FIG. 80) and may comprise a co-crystal. The R-(−)-modafinil:citric acid co-crystal can be characterized by any one, any two, any three, any four, any five, or any six or more of the peaks in FIG. 80 including, but not limited to, 5.23, 7.06, 9.10, 12.43, 13.18, 14.37, 17.34, 17.95, 20.85, 21.39, 22.03, 22.96, 23.54, and 24.93 degrees 2-theta (Bruker PXRD, data as collected).

Wet grinding was also used with acetone which resulted in the formation of the co-crystal.

Example 45

R-(−)-Modafinil:L-tartaric Acid Co-crystal

R-(−)-modafinil (20 to 30 mg, greater than 98 percent R-isomer) and L-tartaric acid (15-20 mg) were ground together in the presence of one drop of benzyl alcohol.

The resultant solid was characterized by PXRD (See FIG. 81) and may comprise a co-crystal. The R-(−)-modafinil:L-tartaric acid co-crystal can be characterized by any one, any two, any three, any four, any five, or any six or more of the peaks in FIG. 81 including, but not limited to, 4.56, 10.33, 14.45, 17.29, 19.91, 21.13, 23.10, 24.10, and 26.76 degrees 2-theta (Bruker PXRD, data as collected).

Wet grinding was also used with acetone and with water, both of which resulted in the formation of the co-crystal.

Example 46

R-(−)-Modafinil:Oxalic Acid Co-crystal

R-(−)-modafinil (20 to 30 mg, greater than 98 percent R-isomer) and oxalic acid (15-20 mg) were ground together in the presence of one drop of benzyl alcohol.

Figures 82A, 82B:
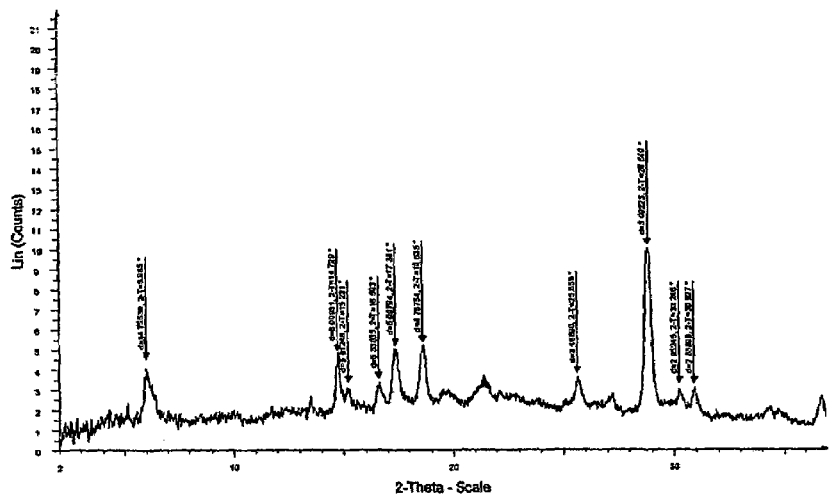
FIGS. 82A and 82B—PXRD diffractograms of R-(−)-modafinil:oxalic acid co-crystal.

The resultant solid was characterized by PXRD (See FIGS. 82A and 82B) and may comprise one or more co-crystals. The R-(−)-modafinil:oxalic acid (Form I) co-crystal can be characterized by any one, any two, any three, any four, any five, or any six or more of the peaks in FIG. 82A including, but not limited to, 5.99, 14.73, 16.59, 17.38, 18.64, 25.66, and 28.85 degrees 2-theta (Bruker PXRD, data as collected). The R-(−)-modafinil:oxalic acid (Form ED co-crystal can be characterized by any one, any two, any three, any four, any five, or any six or more of the peaks in FIG. 82B including, but not limited to, 5.66, 14.76, 17.20, 17.63, 19.60, 24.90, and 28.84 degrees 2-theta (Bruker PXRD, data as collected).

Wet grinding was also used with acetone and with water, both of which resulted in the formation of the co-crystal.

Example 47

R-(−)-Modafinil:Palmitic Acid Co-crystal

R-(−)-modafinil (20 to 30 mg, greater than 98 percent R-isomer) and palmitic acid (15-20 mg) were ground together in the presence of one drop of benzyl alcohol.

Figure 83:
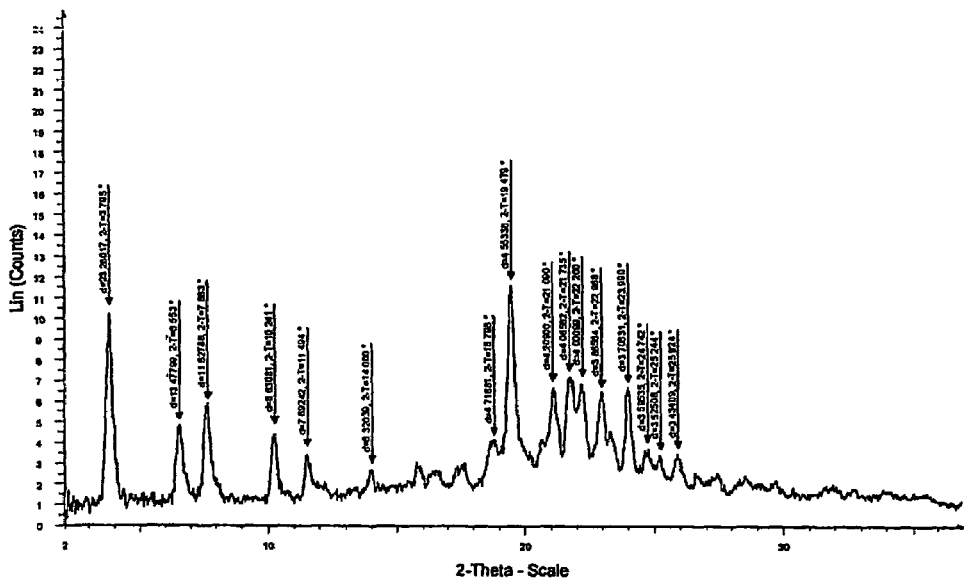
FIG. 83—PXRD diffractogram of R-(−)-modafinil:palmitic acid co-crystal.

The resultant solid was characterized by PXRD (See FIG. 83) and may comprise a co-crystal. The R-(−)-modafinil:palmitic acid co-crystal can be characterized by any one, any two, any three, any four, any five, or any six or more of the peaks in FIG. 83 including, but not limited to, 3.80, 6.55, 7.66, 10.24, 11.49, 19.48, 21.09, 21.74, 22.20, 22.97, and 23.99 degrees 2-theta (Bruker PXRD, data as collected).

Example 48

R-(−)-Modafinil:L-proline Co-crystal

R-(−)-modafinil (20 to 30 mg, greater than 98 percent R-isomer) and L-proline (15-20 mg) were ground together in the presence of one drop of benzyl alcohol.

Figure 84:
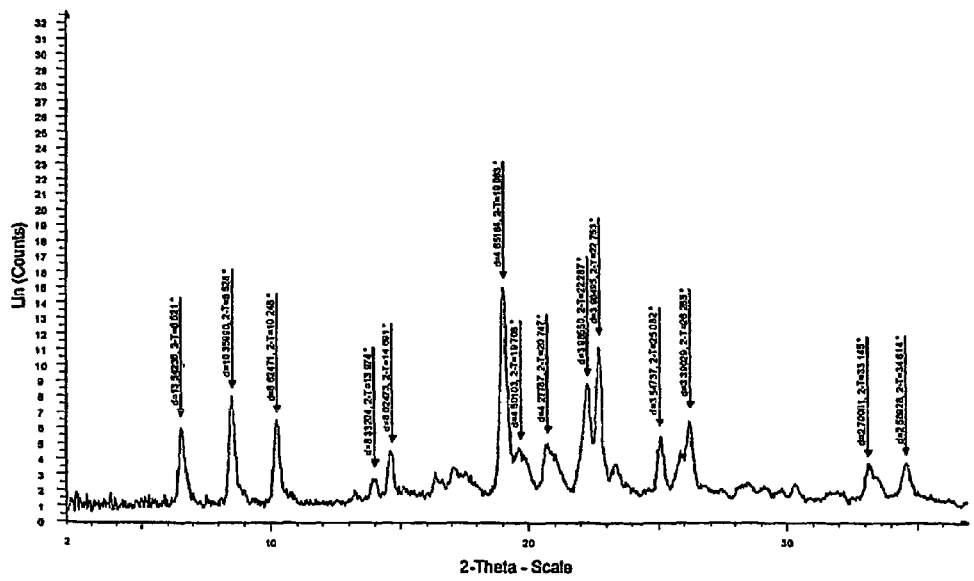
FIG. 84—PXRD diffractogram of R-(−)-modafinil:L-proline co-crystal.

The resultant solid was characterized by PXRD (See FIG. 84) and may comprise a co-crystal. The R-(−)-modafinil:L-proline co-crystal can be characterized by any one, any two, any three, any four, any five, or any six or more of the peaks in FIG. 84 including, but not limited to, 6.52, 8.53, 10.25, 14.69, 19.06, 19.71, 20.75, 22.29, 22.75, 25.08, and 26.27 degrees 2-theta (Bruker PXRD, data as collected).

Wet grinding was also used with acetone and with methanol, both of which resulted in the formation of the co-crystal.

Example 49

R-(−)-Modafinil:Salicylic Acid Co-crystal

R-(−)-modafinil (20 to 30 mg, greater than 98 percent R-isomer) and salicylic acid (15-20 mg) were ground together in the presence of one drop of benzyl alcohol.

Figure 85:
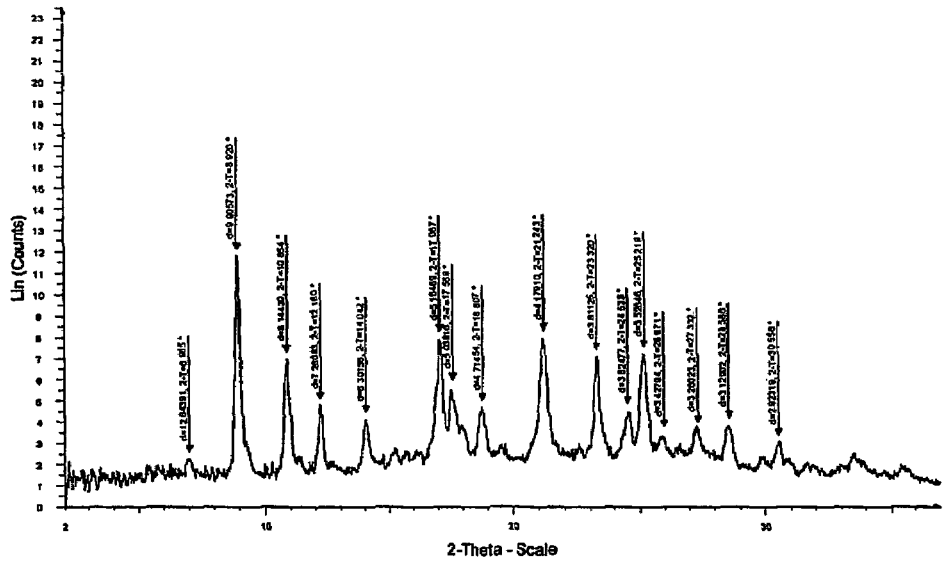
FIG. 85—PXRD diffractogram of R-(−)-modafinil:salicylic acid co-crystal.

The resultant solid was characterized by PXRD (See FIG. 85) and may comprise a co-crystal. The R-(−)-modafinil:salicylic acid co-crystal can be characterized by any one, any two, any three, any four, any five, or any six or more of the peaks in FIG. 85 including, but not limited to, 8.92, 10.85, 12.18, 14.04, 17.07, 17.59, 18.81, 21.24, 23.32, 25.22, and 28.59 degrees 2-theta (Bruker PXRD, data as collected).

Example 50

R-(−)-Modafinil:Lauric Acid Co-crystal

R-(−)-modafinil (20 to 30 mg, greater than 98 percent R-isomer) and lauric acid (15-20 mg) were ground together in the presence of one drop of benzyl alcohol.

Figure 86:
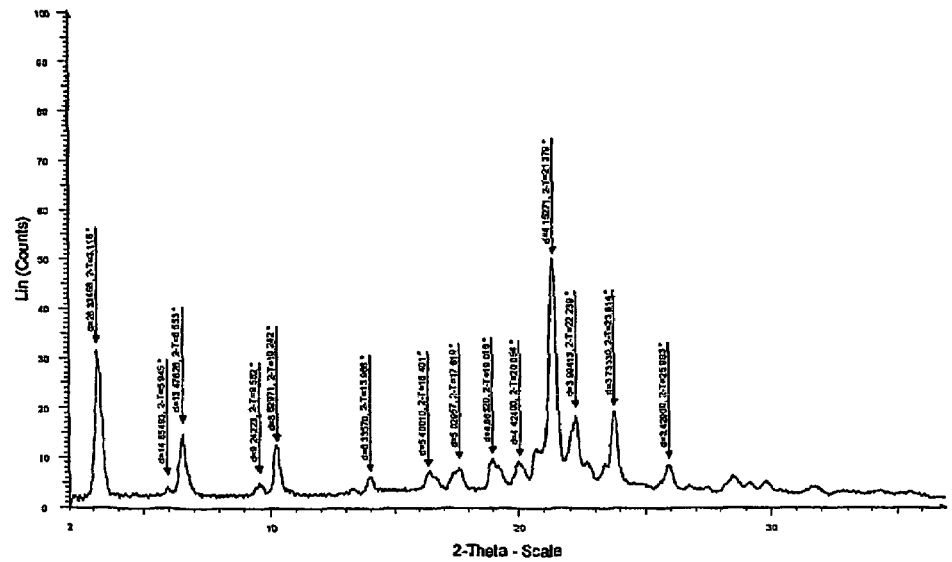
FIG. 86—PXRD diffractogram of R-(−)-modafinil:lauric acid co-crystal.

The resultant solid was characterized by PXRD (See FIG. 86) and may comprise a co-crystal. The R-(−)-modafinil:lauric acid co-crystal can be characterized by any one, any two, any three, any four, any five, or any six or more of the peaks in FIG. 86 including, but not limited to, 3.12, 6.55, 10.24, 13.97, 16.40, 17.62, 19.02, 20.05, 21.38, 22.24, 23.81, and 25.96 degrees 2-theta (Bruker PXRD, data as collected).

Wet grinding was also used with acetone and with methanol, both of which resulted in the formation of the co-crystal.

Example 51

R-(−)-Modafinil:L-malic Acid Co-crystal

R-(−)-modafinil (20 to 30 mg, greater than 98 percent R-isomer) and L-malic acid (15-20 mg) were ground together in the presence of one drop of acetone.

Figure 87:
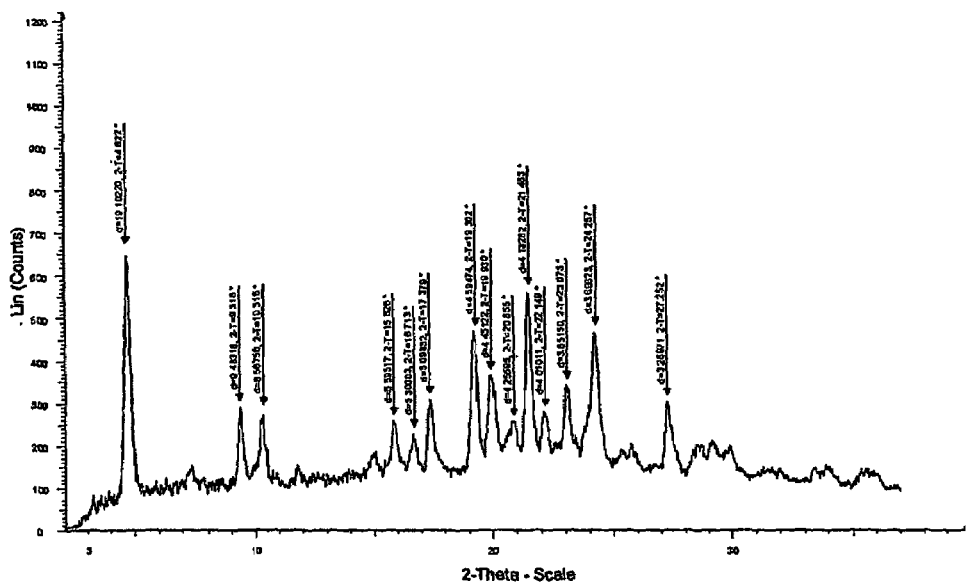
FIG. 87—PXRD diffractogram of R-(−)-modafinil:L-malic acid co-crystal.

The resultant solid was characterized by PXRD (See FIG. 87) and may comprise a co-crystal. The R-(−)-modafinil:L-malic acid co-crystal can be characterized by any one, any two, any three, any four, any five, or any six or more of the peaks in FIG. 87 including, but not limited to, 4.62, 9.32, 10.32, 15.83, 16.71, 17.38, 19.30, 19.93, 21.48, 23.07, 24.26, and 27.25 degrees 2-theta (Bruker PXRD, data as collected).

Example 52

Preparation of Benzhdrylthioacetic Acid from Benzhydrol

To a solution of benzhydrol (100 g, 0.542 mol) in trifluoroacetic acid (300 mL) at room temperature (about 22 degrees C.) was added thioglycolic acid (50 g, 0.542 mol) drop wise over 20 minutes. Reaction progress was monitored by thin layer chromatography (TLC). The reaction was complete within one hour at which point water (1000 mL) was added slowly into the reaction mixture causing the product to precipitate. The resulting precipitate was filtered, washed with water and dried overnight under high vacuum to give benzhydrylthioacetic acid (139.3 g, 99.3%) as a pale yellow solid. (See Prisinzano, T. et al, *Tetrahedron Asymm.*, 2004, 15, 1053-1058)

Example 53

Preparation of Benzhdrylthioacetic Acid from Bromodiphenylmethane (One Pot Procedure)

To a solution of thiourea (30.4 g, 0.399 mol) in water (200 mL) was added bromodiphenylmethane (98.8 g, 0.399 mol) at 42 degrees C. The mixture was heated gradually to reflux for 10 minutes. The reaction mixture was then cooled to 50 degrees C. and 5 N NaOH (200 mL) was subsequently added. The reaction mixture was then heated to reflux (101-102° C.) for 30 minutes and subsequently cooled to 60 degrees C. To this reaction mixture was slowly added a solution of chloroacetic acid (53.4 g, 0.565 mol) and NaOH (22.2 g) in water (150 mL) over 45 minutes. The reaction mixture was stirred for another 30 minutes. The reaction was then cooled to room temperature and washed with t-butylmethylether (200 ml) to remove any non carboxylic acid impurities. The aqueous layer was acidified (pH 2.0) using concentrated HCl (50 mL). The resulting precipitate was filtered, washed with water (2×200 mL) and heptane (200 mL) and allowed to air dry to give benzhydrylthioacetic acid (116.8 g, 100%) as a colorless solid. (See U.S. Pat. No. 4,066,686)

Example 54

Preparation of Benzhdrylthioacetic Acid from Benzhydrol Using Trifluoroacetic Acid in Dichloromethane To a solution of benzhydrol (90 g, 0.488 mol) and trifluoroacetic acid (90 mL) in dichloromethane (300 mL) was added thioglycolic acid (40 g, 0.488 mol) in dichloromethane (60 mL) drop wise over 20 minutes. The reaction was completed in one hour. The solvent was removed in vacuo to give a crude solid, which was dried overnight under high vacuum. The solid was treated with 2 N NaOH (1.0 L) and washed with t-butylmethylether (200 ml) to remove non carboxylic acid impurities. The aqueous solution was then acidified with concentrated HCl and the resulting precipitate was collected, washed with water and dried to give benzhydrylthioacetic acid (128.5 g) as a colorless solid.

Example 55

Preparation of Benzhydrylsulfinylacetic Acid from Benzhdrylthioacetic Acid

To a suspension of benzhydrylthioacetic acid (63.7 g, 0.246 mol) in methanol (250 mL) was added a solution of concentrated $H_2SO_4$ (1.6 mL) in isopropyl alcohol (65 mL) at room temperature (about 22 degrees C.). To this suspension was added 30% $H_2O_2$ in water (65 mL) drop wise over 25 minutes. The reaction was monitored by TLC and was completed within 2 hours. The solution was diluted with a solution of $NaHSO_3$ (125 mg) in water (700 mL). The resulting precipitate was filtered, washed with water, then methanol:water (1:1), and dried to give benzhydrylsulfinylacetic acid (47.6 g). $^1$H-NMR indicated the desired product was obtained along with ~10 percent starting material and some impurities. The compound was triturated with ethanol (100 mL), filtered and dried to give pure benzhydrylsulfinylacetic acid (33.4 g, 49.4%) as a colorless solid. (See Prisinzano, T. et al, *Tetrahedron Asymm.*, 2004, 15, 1053-1058)

Example 56

Oxidation of Benzhdrylthioacetic Acid

A 50 L three-necked round bottom flask equipped with a mechanical stirrer, a 2 L dropping funnel, a nitrogen inlet and an internal temperature probe was charged with benzhydrylthioacetic acid (3.5 kg, 13.54 mol), methanol (14 L) and $H_2SO_4$ (72 g) solution in isopropyl alcohol (6.5 L). To this mixture was added 30% $H_2O_2$ solution in water (3.75 L) drop wise over 80 minutes maintaining the temperature below 30 degrees C. Reaction mixture was further stirred for 7 hours, which resulted in formation of a crystalline solid. The reaction was monitored using TLC and HPLC. The resulting solid was filtered and washed with water (4.0 L) to give benzhydrylsulfinylacetic acid (2.5 kg) as a colorless solid. The peroxide was quenched with a $NaHSO_3$ solution.

Example 57

Resolution of Benzhydrylsulfinylacetic Acid Using S-(−)-α-methylbenzylamine

To a solution of (±)-benzhydrylsulfinylacetic acid (62.4 g, 0.227 mol) in water (300 mL) at 80 degrees C. was added S-(−)-α-methylbenzyl amine (30 mL, 0.236 mol) and stirred at reflux (101-102 degrees C.) for 10 minutes. The solution was gradually cooled to 40 degrees C. and the resulting precipitate was filtered, washed with water and dried to give a colorless solid (71.4 g). The salt was re-crystallized in water (500 ml) to give another colorless solid (53.5 g). The salt was then suspended in water (200 mL), acidified with concentrated HCl (50 mL), and stirred for 10 minutes. The resulting suspension was filtered and washed with water to give R-(−)-benzhydrylsulfinylacetic acid (21.5 g) as a colorless solid. Chiral purity as determined by HPLC was >99.9% ee. (See U.S. Pat. No. 4,927,855)

Example 58

Amidation of R-(−)-benzhydrylsulfinylacetic Acid to Give R-(−)-Modafinil Using N,N-Carbonyl Diimidazole

A 50 L, three-necked round bottom flask equipped with a mechanical stirrer, a nitrogen inlet and an internal temperature probe was charged with R-(−)-benzhydrylsulfinylacetic acid (1.32 kg, 4.81 mol) and tetrahydrofuran (7.0 L). To this slurry was added N,N-carbonyl diimidazole (1.215 kg, 7.49 mol) in tetrahydrofuran (7 L), which gave a clear solution. The solution was then stirred for 30 minutes and $NH_3$ gas (191 g, 2.5 eq.) was then bubbled through the reaction mixture for 3.5 hours. After that time, the volatiles were removed in vacuo to give a crude solid, which was triturated with a 20% methanol solution in t-butylmethylether (7.0 L) overnight. The solid material was then collected and purified further by refluxing of the solid in a 1:1 mixture of ethanol and t-butylmethylether (3 L). The reaction was then cooled to room temperature and the solid material was filtered and dried to give R-(−)-modafinil (501 g, 99.6% chemical purity and 100% ee) as a colorless solid.

Example 59

Preparation of Racemic Modafinil Via Activation Using N,N-Carbonyl Diimidazole (CDI)

To a suspension of (±)-benzhydrylsulfinylacetic acid (10.0 g, 0.036 mol) in tetrahydrofuran (100 mL) was added N,N-carbonyl diimidazole (7.1 g, 0.043 mol) resulting in a clear solution. The solution was stirred for 10 minutes and a precipitate formed upon evolution of $CO_2$. $NH_3$ gas was then bubbled through the reaction mixture for 10 minutes raising the reaction temperature from 16 to 33 degrees C. The reaction mixture was then diluted with water and extracted with ethyl acetate (3×50 mL). The organic layers were combined, washed with water, brine and dried over $Na_2SO_4$. The organic layer was then concentrated in vacuo to give crude modafinil (11.5 g). Recrystallization from 60% aqueous methanol gave pure modafinil (6.0 g) as a colorless solid.

Example 60

Synthesis of (±)-Modafinil from Benzhydrol

To a solution of benzhydrol (30 g, 0.162 mol) and trifluoroacetic acid (15 mL) in dichloromethane (120 ml) was added a solution of methyl thioglycolate (0.178 mol) in dichloromethane (30 ml) drop wise over 20 minutes. The reaction was stirred at room temperature for 1 hour and a saturated $NaHCO_3$ solution was added slowly. The organic layer was separated and concentrated in vacuo to give crude benzhydrylthioacetate (38.2 g, 89%).

To a solution of $NH_4Cl$ (0.29 mol, 2.0 eq) and $NH_4OH$ (300 ml) in methanol (200 mL) was added a solution of benzhydrylthioacetate (38.2 g, 0.145 mol) in methanol (50 ml) maintaining the temperature below 20° C. The reaction was stirred for 1 hour and diluted with water (100 ml) resulting in the formation of a precipitate. The precipitate was collected, washed with water and dried to give benzhydrylthioacetamide (31 g) as colorless solid.

Racemic modafinil was obtained from oxidation of benzhydrylthiacetamide using $H_2O_2$ following the same method used in the oxidation of benzhydrylthioacetic acid in the preparation of R-(−)-modafinil.

TABLE I

| Co-Crystal Former | MW (g/mol) | MP (° C.) | Class | Functionality | # acceptors | # donors | Molecular Structure | pKa Values |
|---|---|---|---|---|---|---|---|---|
| 1-Hydroxy-2-naphthoic acid | 188.18 | 191-192 | 2 | Carboxylic acid, alcohol | 1 | 2 | 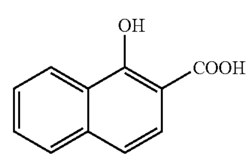 | 2.7, 13.5 |
| 4-aminobenzoic acid | 137.14 | 187-188 | 2 | Amine, carboxylic acid | 1 | 3 | 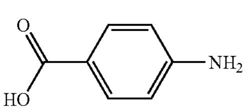 | 4.7, 4.8 |
| 4-aminopyridine | 94.11 | 158-159 | 3 | Amine, pyridine | 1 | 2 | 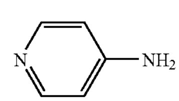 | 10 |
| 4-Chlorobenzenesulfonic acid | 192.63 | 67 | 1 | $SO_3H$ | 3 | 1 | 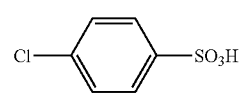 | 0-1 |
| 4-ethoxyphenyl urea | 180.2 | 173-174 | 3 | Amide, NH | 2 | 3 | 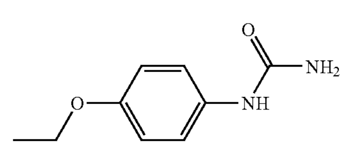 | ~7-9 |

TABLE I-continued

| Co-Crystal Former | MW (g/mol) | MP (° C.) | Class | Functionality | # acceptors | # donors | Molecular Structure | pKa Values |
|---|---|---|---|---|---|---|---|---|
| 7-oxo-DHEA | 303 | 190-192 | 1 | Alcohol, Ketoone | 3 | 1 | 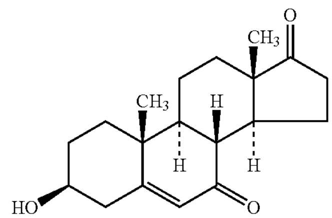 | |
| Acesulfame | 163.15 | 123-124 | 3 | $SO_2$, Amide | 4 | 1 | 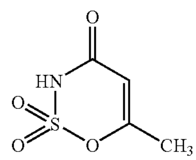 | ~5-7 |
| Acetohydroxamic acid | 75.05 | 89-92 | 3 | Amide, NH, OH | 2 | 2 | | 8.7 |
| Adenine | 135.13 | 220 (sub.) | 1 | Amine, NH | 3 | 3 | 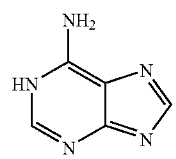 | 3.8 |
| Adipic Acid | 148.14 | 152 | 1 | Carboxylic acid | 2 | 2 | $HOOC(CH_2)_4COOH$ | 4.44, 5.44 |
| Alanine | 89.09 | 289-291 | 1 | Amine, carboxillic acid | 1 | 3 | 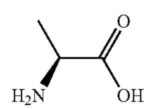 | 2.35, 9.87 |
| Allopurinaol | 136.11 | >350 | 3 | OH, NH | 4 | 2 | 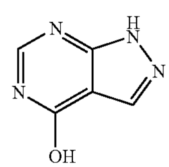 | 10.2 |
| Arginine | 174.2 | 244 | 1 | Amine, COOH | 2 | 7 | 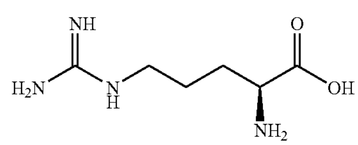 | 2.18, 9.09, 13.2 |
| Ascorbic acid | 176.12 | 190-192 | 1 | C═O, OH | 6 | 4 | 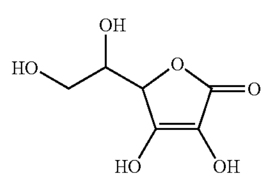 | 4.17, 11.57 |
| Asparagine | 132.12 | 234-235 | 1 | Amine, amide, COOH | 3 | 5 | 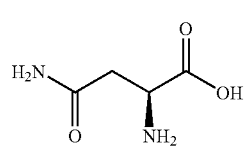 | 2.02, 8.5 |

TABLE I-continued

| Co-Crystal Former | MW (g/mol) | MP (° C.) | Class | Functionality | # acceptors | # donors | Molecular Structure | pKa Values |
|---|---|---|---|---|---|---|---|---|
| Aspartic acid | 133.1 | 270-271 | 1 | Amine, COOH | 2 | 4 | 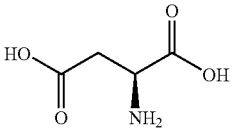 | 1.88, 3.65, 9.60 |
| Benzenesulfonic Acid | 158.18 | 43-44 | 1 | SO₃H | 2 | 1 | 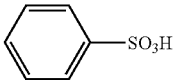 | 0.70, 1.58 |
| Benzoic acid* | 122.12 | 122-123 | 2 | COOH | 1 | 1 | 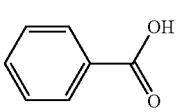 | 4.19 |
| Caffeine | 194.19 | 238 | 3 | C=O | 3 | 0 | 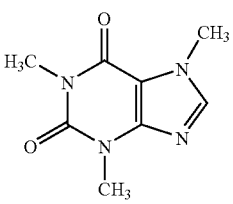 | |
| Camphoric acid | 200.23 | 186-189 | 2 | Carboxylic acid | 2 | 2 | 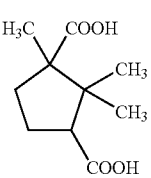 | 4.72, 5.83 |
| Capric acid | 172.27 | 31.4 | 1 | Carboxylic acid | 1 | 1 | CH$_3$(CH$_2$)$_8$COOH | 4.9 |
| Chrysin | 254.24 | 285 | 1 | Phenol, ether, ketone | 2 | 2 | 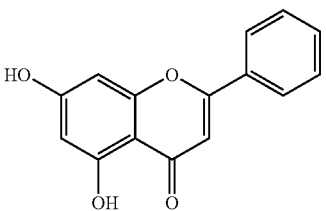 | |
| Cinnamic acid | 144.2 | 133 | 3 | Carboxylic acid | 1 | 1 | 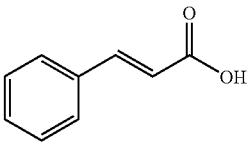 | 4.4 |
| Citric Acid | 192.12 | 153 | 1 | OH, COOH | 4 | 4 | 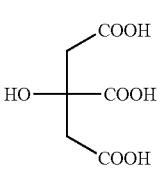 | 3.13, 4.76, 6.40 |
| Clemizole | 325.84 | 167 | 1 | Pyrrolidine | 3 | 0 | 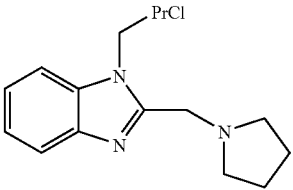 | |

TABLE I-continued

| Co-Crystal Former | MW (g/mol) | MP (° C.) | Class | Functionality | # acceptors | # donors | Molecular Structure | pKa Values |
|---|---|---|---|---|---|---|---|---|
| Cyclamic acid | 179.24 | 169-170 | 3 | NH, SO$_3$H | 2 | 2 | 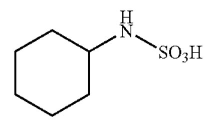 | −2 |
| Cysteine | 121.15 | — | 1 | Amine, COOH, SH | 2 | 4 | 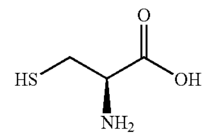 | 1.71, 8.33, 10.78 |
| Dimethyl-glycine | 103.1 | 178-192 | 1 | Amine, Carboxylic acid | 2 | 1 | 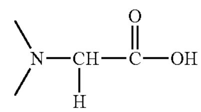 | 2.5 |
| D-Ribose | 150.13 | 87 | 1 | Alcohol, ether | 1 | 4 | 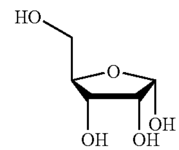 | |
| Fumaric acid | 116.07 | 287 | 1 | COOH | 2 | 2 | 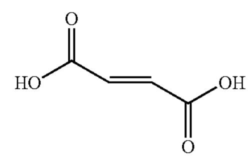 | 3.03, 4.38 |
| Galactaric acid | 210.14 (dec) | 255 | 1 | Carboxylic acid, alcohol | 2 | 6 | 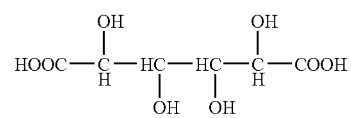 | 3.08, 3.63 |
| Genistein | 270.24 | 297-298 | 1 | Alcohol, Phenol, ether, ketone | 2 | 3 | 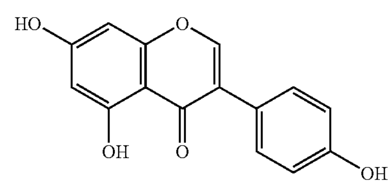 | |
| Gentisic acid | 154.12 | 199-200 form I, 205 form II | 2 | Carboxylic acid, alcohol, phenol | 1 | 3 | 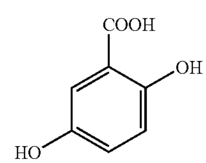 | 2.93 |
| Glucamine, N-Methyl | 195.22 | 128-129 | 1 | Alcohol, Amine | 5 | 6 | 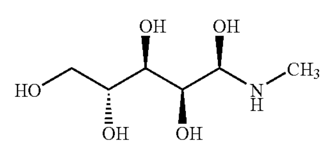 | 8.03(B) |
| Gluconic acid | 196.15 | 131 | 1 | OH, COOH | 6 | 6 | 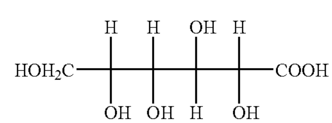 | 3.76 |

TABLE I-continued

| Co-Crystal Former | MW (g/mol) | MP (° C.) | Class | Functionality | # acceptors | # donors | Molecular Structure | pKa Values |
|---|---|---|---|---|---|---|---|---|
| Glucosamine | 179.17 | 88 | 1 | OH | 5 | 6 | 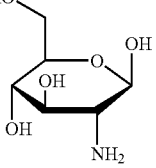 | 6.91 |
| Glucuronic acid | 194.14 | 165 | 1 | Carboxylic acid, alcohol, aldehyde | 2 | 5 | 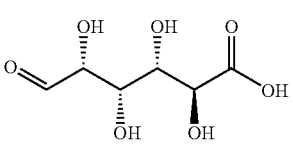 | 3.18 |
| Glutamic acid | 147.13 | 160 | 1 | Amine, COOH | 2 | 4 | 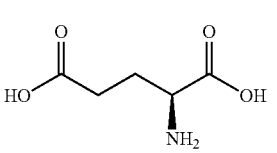 | 2.19, 4.25, 9.67 |
| Glutamine | 146.15 | 185-186 | 1 | Amine, Amide, COOH | 2 | 5 | 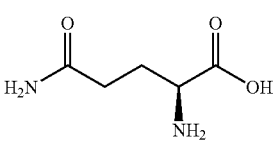 | 2.17, 9.13 |
| Glutaric acid | 132.11 | 98-98 | 1 | COOH | 2 | 2 | 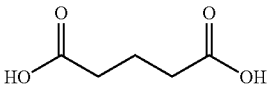 | 2.7, 4.5 |
| Glycine | 75.07 | 182 | 1 | Amine, COOH | 2 | 3 | 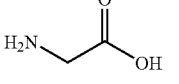 | 2.34, 9.8 |
| Glycolic acid | 76.05 | 80 | 1 | OH, COOH | 2 | 2 | 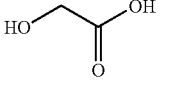 | 3.82 |
| Hippuric acid | 179.17 | 187-188 | 1 | Amide, NH, COOH | 2 | 2 | 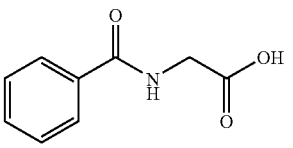 | 3.55 |
| Histidine | 155.16 | 287 | 1 | Amine, COOH, Imidazole | 2 | 4 | 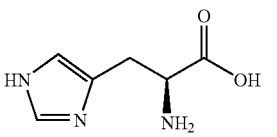 | 1.78, 5.97, 8.97 |
| Hydroquinone* | 110.11 | 170-171 | 2 | OH, Phenol | 2 | 2 | 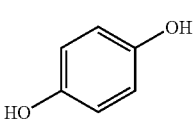 | ~10 |
| Imidazole | 68.08 | 90-91 | 1 | NH | 1 | 1 | 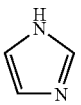 | 6.92 |

TABLE I-continued

| Co-Crystal Former | MW (g/mol) | MP (° C.) | Class | Functionality | # acceptors | # donors | Molecular Structure | pKa Values |
|---|---|---|---|---|---|---|---|---|
| Ipriflavone | 280.32 | 115-117 | 1 | Ketone, ether | 3 | 0 | 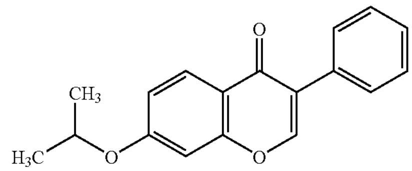 | |
| Isoleucine | 131.17 | 168-170 (sub.) | 1 | Amine, COOH | 1 | 3 | 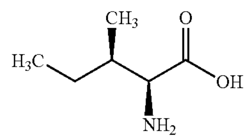 | 2.32, 9.76 |
| Lactobionic acid | 358.3 | 128-130 | 2 | Alcohol, carboxylic acid, ether | 1 | 9 | 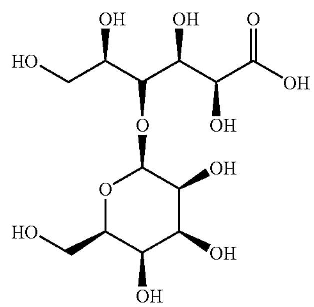 | 3.2 |
| Lauric acid | 200.32 | 44-48 | 1 | Carboxylic acid | 1 | 1 | $CH_3(CH_2)_{10}COOH$ | ~4.5 |
| Leucine | 131.17 | 145-148 (sub.) | 1 | Carboxylic acid, amine | 1 | 3 | 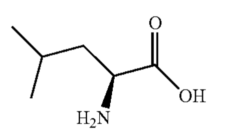 | 2.36, 9.6 |
| Lysine | 146.19 | 225 (dec.) | 1 | Amine, COOH | 1 | 5 | 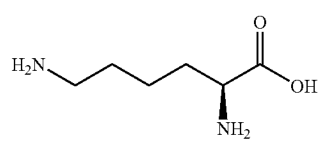 | 2.2, 8.9, 10.28 |
| Maleic | 116.07 | 138-139 | 1 | COOH | 2 | 2 | 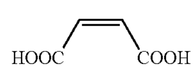 | 1.92, 6.23 |
| Malic acid | 134.09 | 131-132 | 1 | OH, COOH | 3 | 3 | 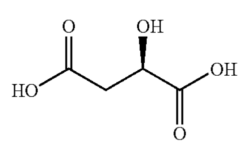 | 3.46, 5.1 |
| Malonic | 104.06 | 135 | 1 | COOH | 2 | 2 | 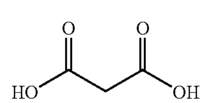 | 2.83, 5.70 |
| Mandelic acid | 152.15 | 119 | 1 | OH, COOH | 2 | 2 | 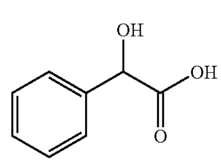 | 3.37 |

TABLE I-continued

| Co-Crystal Former | MW (g/mol) | MP (° C.) | Class | Functionality | # acceptors | # donors | Molecular Structure | pKa Values |
|---|---|---|---|---|---|---|---|---|
| Methionine | 149.21 | 280-282 (dec.) | 1 | Amine, COOH, S—Me | 2 | 3 | 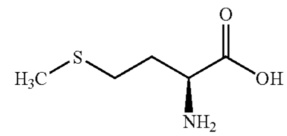 | 2-3, 9 |
| Nicotin-amide | 122.12 | 128-131 | 1 | Pyridine, amide | 2 | 2 | 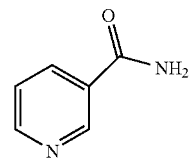 | 3.3 |
| Nicotinic acid | 123.11 | 236-237 | 2 | Carboxylic acid, pyridine | 2 | 1 | 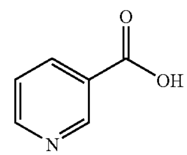 | 2.07(B), 4.85 |
| Orotic acid | 156.1 | 345-346 | 2 | Carboxilic acid, lactam | 3 | 3 | 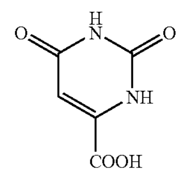 | 5.85, 8.95 |
| Oxalic acid | 90.04 | 189 | 2 | Carboxilic acid | 2 | 2 | 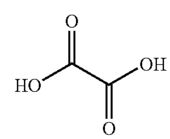 | 1.27, 4.27 |
| Palmitic acid | 256.43 | 63-64 | 1 | Carboxylic acid | 1 | 1 | $CH_3(CH_2)_{14}COOH$ | 4.9 |
| Pamoic | 388.38 | 280 | 2 | Carboxylic acid, phenol | 2 | 4 | 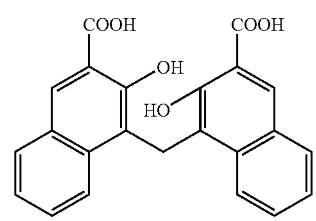 | 2.51, 3.1 |
| Phenyl-alanine | 165.19 | 283 (dec.) | 1 | Amine, COOH | 1 | 3 | 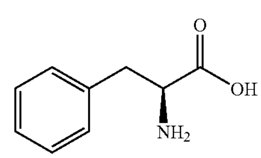 | ~2, ~9 |
| Piperazine | 86.14 | 106 | 1 | NH | 0 | 2 | 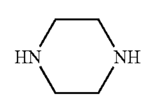 | 9.82(B) |
| Procaine | 236.31 | 61 | 1 | Amine, C═O | 2 | 2 | 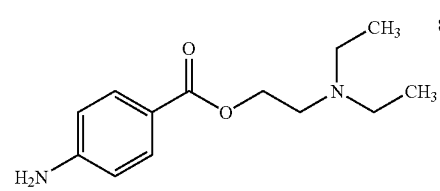 | 8.9(B) |

TABLE I-continued

| Co-Crystal Former | MW (g/mol) | MP (° C.) | Class | Functionality | # acceptors | # donors | Molecular Structure | pKa Values |
|---|---|---|---|---|---|---|---|---|
| Proline | 115.13 | 220-222 (dec.) | 1 | COOH, NH | 1 | 2 | 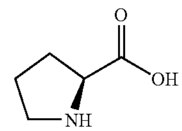 | 1.99, 10.6 |
| p-Toluene-sulfonic acid | 172.2 | 106-107 | 2 | Sulfonic acid | 2 | 1 | 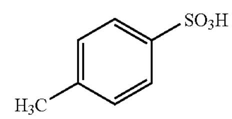 | −1.34 |
| Pyridox-amine | 168 | 193-194 | 2 | OH, Amine, Pyridine | 3 | 4 | 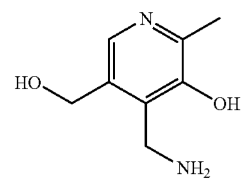 | ~9 |
| Pyridoxine | 170 | 160 | 2 | Alcohol, Pyridine | 3 | 3 | 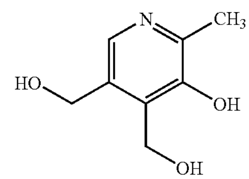 | ~9 |
| Pyroglutamic acid | 129.12 | 162 | 2 | Carboxylic acid, Lactam | 2 | 2 | 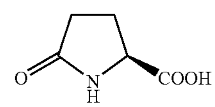 | 3.32 |
| Quercetin | 302.24 | 314 dec. | 1 | Phenol, ether, ketone | 2 | 5 | 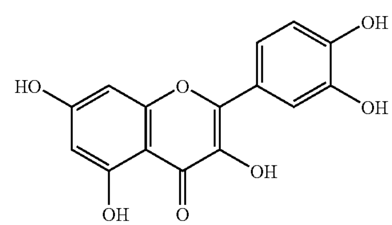 | |
| Resveratrol | 228.24 | 253-255 | 1 | Phenol | 0 | 3 | 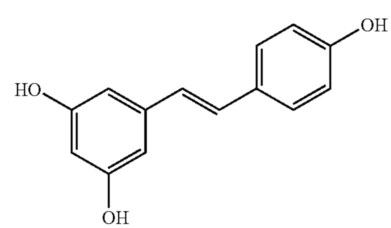 | |
| Saccharin | 183.19 | 228-230 | 1 | Amide, C=O, S=O, N—H | 3 | 1 | 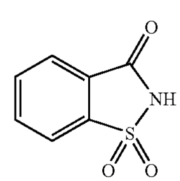 | 2 |
| Salicylic acid, 4-amino | 153.14 | 150-151 | 3 | COOH, OH, Analine | 1 | 4 | 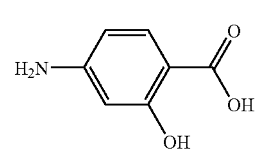 | 3.25, 10, 3.5(B) |

TABLE I-continued

| Co-Crystal Former | MW (g/mol) | MP (° C.) | Class | Functionality | # acceptors | # donors | Molecular Structure | pKa Values |
|---|---|---|---|---|---|---|---|---|
| Salicylic acid | 138.12 | 159 | 3 | COOH, OH | 2 | 2 | 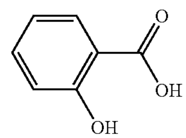 | 2.98, 13.82 |
| Sebacic acid | 202.25 | 134.5 | 1 | Carboxylic acid | 2 | 2 | $HOOC(CH_2)_8COOH$ | 4.59, 5.59 |
| Serine | 105.09 | 228 (dec.) | 1 | Carboxylic acid, amine, OH | 2 | 3 | 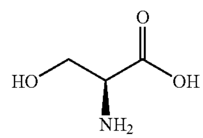 | 2.21, 9.15 |
| Stearic acid | 284.47 | 70-71 | 1 | Carboxylic acid | 1 | 1 | $CH_3(CH_2)_{16}COOH$ | 4.9 |
| Succinic acid | 118.09 | 185-187 | 1 | Carboxylic acid | 2 | 2 | 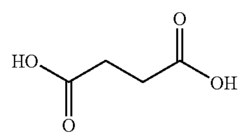 | 4.21, 5.64 |
| Tartaric acid | 150.09 | 205-206 | 1 | Carboxylic acid | 4 | 4 | 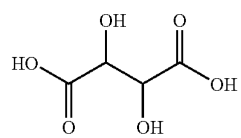 | 3.02, 4.36 |
| Threonine | 119.12 | 255-257 (dec.) | 1 | Amine, COOH, OH | 2 | 4 | 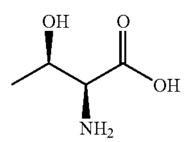 | 2.15, 9.12 |
| TRIS | 121.13 | 171-172 | 2 | Amine, OH | 3 | 5 | 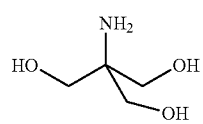 | 5.91, 8.3 |
| Tryptophan | 204.23 | 289 (dec.) | 1 | Amine, COOH, Indole | 1 | 4 | 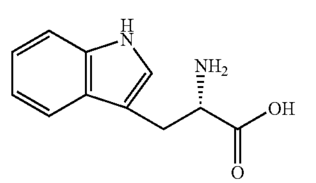 | 2.38, 9.39 |
| Tyrosine | 181.19 | 342-344 | 1 | Amine, COOH, OH | 2 | 3 | 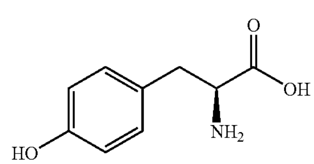 | 2.2, 9.11, 10.07 |
| Urea | 60.06 | Dec. | 1 | C=O, NH2 | 1 | 4 | 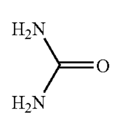 | ~8 |
| Valine | 117.15 | 315 | 1 | Amine, COOH | 1 | 3 | 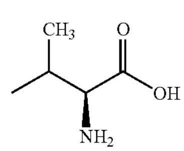 | ~4.5, ~9 |

TABLE I-continued

| Co-Crystal Former | MW (g/mol) | MP (° C.) | Class | Functionality | # acceptors | # donors | Molecular Structure | pKa Values |
|---|---|---|---|---|---|---|---|---|
| Vitamin K5 | 209.68 | 280-282 (dec.) | 3 | Amine, OH | 1 | 3 | (naphthalene with OH, CH3, NH2 substituents) | ~9 |
| Xylitol | 152.15 | 93-95 (I) | 2 | OH | 5 | 5 | HO–CH2–CH(OH)–CH(OH)–CH(OH)–CH2–OH | ~9 |

TABLE II

| Co-crystal Former | Co-crystal Former Functional Group | Interacting Group | | | | | | |
|---|---|---|---|---|---|---|---|---|
| 1,5-Napthalene-disulfonic Acid | Sulfonic Acid | pyridine | ketone | aldehyde | ether | ester | amide | Carboxylic Acid |
| 1-Hydroxy-2-naphthoic acid | Carboxylic Acid | alcohol | ketone | thiol | amide | amine | analine | phenol |
| 1-Hydroxy-2-naphthoic acid | alcohol | alcohol | ketone | thiol | amide | amine | analine | phenol |
| 4-Aminobenzoic Acid | Amine | alcohol | ketone | thiol | amide | amine | analine | phenol |
| 4-Aminobenzoic Acid | Carboxylic Acid | alcohol | ketone | thiol | amide | amine | analine | phenol |
| 4-aminopyridine | Amine | alcohol | ketone | thiol | amide | amine | analine | phenol |
| 4-aminopyridine | Pyridine | *alcohol | pyridinium | * | *amide | nitro | *amine | *Carboxylic Acid |
| 4-Chlorobenzene-Sulfonic Acid | Sulfonic Acid | pyridine | ketone | aldehyde | ether | ester | amide | Carboxylic Acid |
| 4-ethoxyphenyl Urea | Amide | alcohol | ketone | thiol | amide | amine | analine | phenol |
| 4-ethoxyphenyl Urea | Amine | alcohol | ketone | thiol | amide | amine | analine | phenol |
| 7-oxo-DHEA | alcohol | alcohol | ketone | thiol | amide | amine | analine | phenol |
| 7-oxo-DHEA | Ketone | alcohol | | thiol | amide | amine | analine | phenol |
| Acesulfame | Sulfone | pyridine | ketone | aldehyde | ether | ester | amide | carboxilic acid |
| Acesulfame | Amide | alcohol | ketone | thiol | amide | amine | analine | phenol |
| Acetohydroxamic Acid | Amide | alcohol | ketone | thiol | amide | amine | analine | phenol |
| Acetohydroxamic Acid | Amine | alcohol | ketone | thiol | amide | amine | analine | phenol |
| Acetohydroxamic Acid | Alcohol | alcohol | ketone | thiol | amide | amine | analine | phenol |
| Adenine | Amine | alcohol | ketone | thiol | amide | amine | analine | phenol |
| Adenine | N | *alcohol | pyridinium | * | *amide | nitro | *amine | *carboxilic acid |
| Adipic acid | Carboxylic Acid | alcohol | ketone | thiol | amide | amine | analine | phenol |
| Alanine | Amine | alcohol | ketone | thiol | amide | amine | analine | phenol |
| Alanine | Carboxylic Acid | alcohol | ketone | thiol | amide | amine | analine | phenol |
| Allopurinaol | Alcohol | alcohol | ketone | thiol | amide | amine | analine | phenol |
| Allopurinaol | Amine | alcohol | ketone | thiol | amide | amine | analine | phenol |
| Arginine | Amine | alcohol | ketone | thiol | amide | amine | analine | phenol |
| Arginine | Carboxylic Acid | alcohol | ketone | thiol | amide | amine | analine | phenol |
| Ascorbic Acid | Ketone | alcohol | | thiol | amide | amine | analine | phenol |
| Ascorbic Acid | Alcohol | alcohol | ketone | thiol | amide | amine | analine | phenol |
| Ascorbic Acid | Carboxylic Acid | alcohol | ketone | thiol | amide | amine | analine | phenol |
| Asparagine | Amine | alcohol | ketone | thiol | amide | amine | analine | phenol |
| Asparagine | Amide | alcohol | ketone | thiol | amide | amine | analine | phenol |
| Asparagine | Carboxylic Acid | alcohol | ketone | thiol | amide | amine | analine | phenol |
| Aspartic Acid | Amine | alcohol | ketone | thiol | amide | amine | analine | phenol |
| Aspartic Acid | Carboxylic Acid | alcohol | ketone | thiol | amide | amine | analine | phenol |
| Benzenesulfonic Acid | Sulfonic Acid | pyridine | ketone | aldehyde | ether | ester | amide | Carboxylic Acid |
| Benzoic Acid | Carboxylic Acid | alcohol | ketone | thiol | amide | amine | analine | phenol |
| Caffeine | Ketone | alcohol | | thiol | amide | amine | analine | phenol |
| Camphoric acid | Carboxylic Acid | alcohol | ketone | thiol | amide | amine | analine | phenol |
| Capric acid | Carboxylic Acid | alcohol | ketone | thiol | amide | amine | analine | phenol |
| Genistein | Ketone | alcohol | | thiol | amide | amine | analine | phenol |
| Genistein | Phenol | amine | amide | sulfoxide | n | pyridine | cyano | aldehyde |
| Genistein | Ether | aromatic-N | amide | amine | aromatic_s | Sp2 amine | sulfoxide | chlorate |
| Cinnamic acid | Carboxylic Acid | alcohol | ketone | thiol | amide | amine | analine | phenol |
| Citric Acid | Alcohol | alcohol | ketone | thiol | amide | amine | analine | phenol |

TABLE II-continued

| | | | | | | | | |
|---|---|---|---|---|---|---|---|---|
| Citric Acid | Carboxylic Acid | alcohol | ketone | thiol | amide | amine | analine | phenol |
| Clemizole | Pyrrolidine | *alcohol | pyridinium | * | *amide | nitro | *amine | *carboxilic acid |
| Cyclamic Acid | Amine | alcohol | ketone | thiol | amide | amine | analine | phenol |
| Cyclamic Acid | Sulfonic Acid | pyridine | ketone | aldehyde | ether | ester | amide | Carboxylic Acid |
| Cysteine | Amine | alcohol | ketone | thiol | amide | amine | analine | phenol |
| Cysteine | Carboxylic Acid | alcohol | ketone | thiol | amide | amine | analine | phenol |
| Cysteine | Thiol | carboxylic acid | sodium | aldehyde | ketone | -N | cadmium | |
| Dimethylglycine | Carboxylic Acid | alcohol | ketone | thiol | amide | amine | analine | phenol |
| Dimethylglycine | Amine | alcohol | ketone | thiol | amide | amine | analine | phenol |
| D-ribose | Ether | aromatic-N | amide | amine | aromatic_s | Sp2 amine | sulfoxide | chlorate |
| D-ribose | Alcohol | alcohol | ketone | thiol | amide | amine | analine | phenol |
| Fumaric Acid | Carboxylic Acid | alcohol | ketone | thiol | amide | amine | analine | phenol |
| Galactaric acid | Carboxylic Acid | alcohol | ketone | thiol | amide | amine | analine | phenol |
| Galactaric acid | alcohol | alcohol | ketone | thiol | amide | amine | analine | phenol |
| Chrysin | Ketone | alcohol | — | thiol | amide | amine | analine | phenol |
| Chrysin | Phenol | amine | amide | sulfoxide | n | pyridine | cyano | aldehyde |
| Chrysin | Ether | aromatic-N | amide | amine | aromatic_s | Sp2 amine | sulfoxide | chlorate |
| Gentisic acid | Carboxylic Acid | alcohol | ketone | thiol | amide | amine | analine | phenol |
| Gentisic acid | Phenol | amine | amide | sulfoxide | n | pyridine | cyano | aldehyde |
| Glucamine, N-methyl | alcohol | alcohol | ketone | thiol | amide | amine | analine | phenol |
| Glucamine, N-methyl | Amine | alcohol | ketone | thiol | amide | amine | analine | phenol |
| Gluconic Acid | Alcohol | alcohol | ketone | thiol | amide | amine | analine | phenol |
| Gluconic Acid | Carboxylic Acid | alcohol | ketone | thiol | amide | amine | analine | phenol |
| Glucosamine | alcohol | alcohol | ketone | thiol | amide | amine | analine | phenol |
| Glucuronic acid | Carboxylic Acid | alcohol | ketone | thiol | amide | amine | analine | phenol |
| Glucuronic acid | alcohol | alcohol | ketone | thiol | amide | amine | analine | phenol |
| Glucuronic acid | Aldehyde | alcohol | ketone | thiol | amide | amine | analine | phenol |
| Glutamic Acid | Amine | alcohol | ketone | thiol | amide | amine | analine | phenol |
| Glutamic Acid | Carboxylic Acid | alcohol | ketone | thiol | amide | amine | analine | phenol |
| Glutamine | Amine | alcohol | ketone | thiol | amide | amine | analine | phenol |
| Glutamine | Amide | alcohol | ketone | thiol | amide | amine | analine | phenol |
| Glutamine | Carboxylic Acid | alcohol | ketone | thiol | amide | amine | analine | phenol |
| Glutaric Acid | Carboxylic Acid | alcohol | ketone | thiol | amide | amine | analine | phenol |
| Glycine | Amine | alcohol | ketone | thiol | amide | amine | analine | phenol |
| Glycine | Carboxylic Acid | alcohol | ketone | thiol | amide | amine | analine | phenol |
| Glycolic Acid | Alcohol | alcohol | ketone | thiol | amide | amine | analine | phenol |
| Glycolic Acid | Carboxylic Acid | alcohol | ketone | thiol | amide | amine | analine | phenol |
| Hippuric Acid | Amide | alcohol | ketone | thiol | amide | amine | analine | phenol |
| Hippuric Acid | Amine | alcohol | ketone | thiol | amide | amine | analine | phenol |
| Hippuric Acid | Carboxylic Acid | alcohol | ketone | thiol | amide | amine | analine | phenol |
| Histidine | Amine | alcohol | ketone | thiol | amide | amine | analine | phenol |
| Histidne | Carboxylic Acid | alcohol | ketone | thiol | amide | amine | | phenol |
| Histidine | Imidazole | Imidazole | chlorine | acetamide | carboxylate | | thione | nitro |
| Hydraquinone | Alcohol | alcohol | ketone | thiol | amide | amine | analine | phenol |
| Hydraquinone | Phenol | amine | amide | sulfoxide | n | pyridine | cyano | aldehyde |
| Imidazole | Amine | alcohol | ketone | thiol | amide | amine | analine | phenol |
| Ipriflavone | Ether | aromatic-N | amide | amine | aromatic_s | Sp2 amine | sulfoxide | chlorate |
| Ipriflavone | Ketone | alcohol | | thiol | amide | amine | analine | phenol |
| Isoleucine | Amine | alcohol | ketone | thiol | amide | amine | analine | phenol |
| Isoleucine | Carboxylic Acid | alcohol | ketone | thiol | amide | amine | analine | phenol |
| lactobionic acid | Carboxylic Acid | alcohol | ketone | thiol | amide | amine | analine | phenol |
| Lactobionic acid | alcohol | alcohol | ketone | thiol | amide | amine | analine | phenol |
| Lactobionic acid | Ether | aromatic-N | amide | amine | aromatic_s | Sp2 amine | sulfoxide | chlorate |
| Lauric acid | Carboxylic Acid | alcohol | ketone | thiol | amide | amine | analine | phenol |
| Leucine | Carboxylic Acid | alcohol | ketone | thiol | amide | amine | analine | phenol |
| Leucine | Amine | alcohol | ketone | thiol | amide | amine | analine | phenol |
| Lysine | Amine | alcohol | ketone | thiol | amide | amine | analine | phenol |
| Lysine | Carboxylic Acid | alcohol | ketone | thiol | amide | amine | analine | phenol |
| Maleic | Carboxylic Acid | alcohol | ketone | thiol | amide | amine | analine | phenol |
| Malic Acid | Alcohol | alcohol | ketone | thiol | amide | amine | analine | phenol |
| Malic Acid | Carboxylic Acid | alcohol | ketone | thiol | amide | amine | analine | phenol |
| Malonic | Carboxylic Acid | alcohol | ketone | thiol | amide | amine | analine | phenol |
| Mandelic Acid | Alcohol | alcohol | ketone | thiol | amide | amine | analine | phenol |
| Mandelic Acid | Carboxylic Acid | alcohol | ketone | thiol | amide | amine | analine | phenol |
| Methionine | Amine | alcohol | ketone | thiol | amide | amine | analine | phenol |
| Methionine | Carboxylic Acid | alcohol | ketone | thiol | amide | amine | analine | phenol |
| Methionine | Thioether | -N | amide | amine | _s | Sp2 amine | sulfoxide | chlorate |
| Nicotinamide | Pyridine | *alcohol | | * | *amide | nitro | *amine | *Carboxylic Acid |
| Nicotinamide | Amide | alcohol | ketone | thiol | amide | amine | analine | phenol |
| Nicotinic Acid | Carboxylic Acid | alcohol | ketone | thiol | amide | amine | analine | phenol |
| Nicotinic Acid | Pyridine | *alcohol | | * | *amide | nitro | *amine | *Carboxylic Acid |
| Orotic acid | Carboxylic Acid | alcohol | ketone | thiol | amide | amine | analine | phenol |
| Orotic acid | Lactam | alcohol | ketone | thiol | amide | amine | analine | phenol |
| Oxalic acid | Carboxylic Acid | alcohol | ketone | thiol | amide | amine | analine | phenol |

TABLE II-continued

| | | | | | | | | |
|---|---|---|---|---|---|---|---|---|
| Palmitic acid | Carboxylic Acid | alcohol | ketone | thiol | amide | amine | analine | phenol |
| Pamoic acid | Carboxylic Acid | alcohol | ketone | thiol | amide | amine | analine | phenol |
| Pamoic acid | alcohol | alcohol | ketone | thiol | amide | amine | analine | phenol |
| Pamoic acid | Phenol | amine | amide | sulfoxide | n | pyridine | cyano | aldehyde |
| Phenylalanine | Amine | alcohol | ketone | thiol | amide | amine | analine | phenol |
| Phenylalanine | Carboxylic Acid | alcohol | ketone | thiol | amide | amine | analine | phenol |
| Piperazine | Amine | alcohol | ketone | thiol | amide | amine | analine | phenol |
| Procaine | Amine | alcohol | ketone | thiol | amide | amine | analine | phenol |
| Procaine | Ketone | alcohol | | thiol | amide | amine | analine | phenol |
| Proline | Carboxylic Acid | alcohol | ketone | thiol | amide | amine | analine | phenol |
| Proline | Amine | alcohol | ketone | thiol | amide | amine | analine | phenol |
| p-Toluenesulfonic acid | Sulfonic Acid | pyridine | ketone | aldehyde | ether | ester | amide | Carboxylic Acid |
| Pyridoxamine | Alcohol | alcohol | ketone | thiol | amide | amine | analine | phenol |
| Pyridoxamine | Amine | alcohol | ketone | thiol | amide | amine | analine | phenol |
| Pyridoxamine | Pyridine | *alcohol | | * | *amide | nitro | *amine | *Carboxylic Acid |
| Pyridoxine (4-Pyridoxic Acid) | Pyridine | *alcohol | pyridinium | * | *amide | nitro | *amine | *Carboxylic Acid |
| Pyridoxine (4-Pyridoxic Acid) | Alcohol | alcohol | ketone | thiol | amide | amine | analine | phenol |
| Pyroglutamic acid | Carboxylic Acid | alcohol | ketone | thiol | amide | amine | analine | phenol |
| Pyroglutamic acid | Lactam | alcohol | ketone | thiol | amide | amine | analine | phenol |
| Quercetin | Ketone | alcohol | | thiol | amide | amine | analine | phenol |
| Quercetin | Phenol | amine | amide | sulfoxide | n | pyridine | cyano | aldehyde |
| Quercetin | Ether | aromatic-N | amide | amine | aromatic_s | Sp2 amine | sulfoxide | chlorate |
| Resveratrol | Ketone | alcohol | | thiol | amide | amine | analine | phenol |
| Resveratrol | Phenol | amine | amide | sulfoxide | n | pyridine | cyano | aldehyde |
| Saccharin | Amide | alcohol | ketone | thiol | amide | amine | analine | phenol |
| Saccharin | Ketone | alcohol | | thiol | amide | amine | analine | phenol |
| Saccharin | Sulfoxide | pyridine | ketone | aldehyde | ether | ester | amide | Carboxylic Acid |
| Saccharin | Amine | alcohol | ketone | thiol | amide | | analine | phenol |
| Salicylic Acid | Carboxylic Acid | alcohol | ketone | thiol | amide | amine | analine | phenol |
| Salicylic Acid | Alcohol | alcohol | ketone | thiol | amide | amine | analine | phenol |
| Salicylic Acid, 4-amino | Carboxylic Acid | alcohol | ketone | thiol | amide | amine | analine | phenol |
| Salicylic Acid, 4-amino | alcohol | alcohol | ketone | thiol | amide | amine | analine | phenol |
| Salicylic Acid, 4-amino | Amine | alcohol | ketone | thiol | amide | amine | analine | phenol |
| Sebacic acid | Carboxylic Acid | alcohol | ketone | thiol | amide | amine | analine | phenol |
| Serine | Carboxylic Acid | alcohol | ketone | thiol | amide | amine | analine | phenol |
| Serine | Amine | alcohol | ketone | thiol | amide | amine | analine | phenol |
| Serine | Alcohol | alcohol | ketone | thiol | amide | amide | analine | phenol |
| Stearic acid | Carboxylic Acid | alcohol | ketone | thiol | amide | amine | analine | phenol |
| Succinic Acid | Carboxylic Acid | alcohol | ketone | thiol | amide | amine | analine | phenol |
| Tartaric Acid | Carboxylic Acid | alcohol | ketone | thiol | amide | amine | analine | phenol |
| Threonine | Amine | alcohol | ketone | thiol | amide | amine | analine | phenol |
| Threonine | Carboxylic Acid | alcohol | ketone | thiol | amide | amine | analine | phenol |
| Threonine | alcohol | alcohol | ketone | thiol | amide | amine | analine | phenol |
| Tris | Amine | alcohol | ketone | thiol | amide | amine | analine | phenol |
| Tris | Alcohol | alcohol | ketone | thiol | amide | amine | analine | phenol |
| Tryptophan | Amine | alcohol | ketone | thiol | amide | amine | analine | phenol |
| Tryptophan | Carboxylic Acid | alcohol | ketone | thiol | amide | amine | analine | phenol |
| Tryptophan | Indole | *alcohol | pyridinium | * | *amide | nitro | *amine | *carboxilic acid |
| Tyrosine | Amine | alcohol | ketone | thiol | amide | amine | analine | phenol |
| Tyrosine | Carboxylic Acid | alcohol | ketone | thiol | amide | amine | analine | phenol |
| Tyrosine | Alcohol | alcohol | ketone | thiol | amide | amine | analine | phenol |
| Urea | Ketone | alcohol | | thiol | amide | amine | analine | phenol |
| Urea | Amine | alcohol | ketone | thiol | amide | amine | analine | phenol |
| Urea | Amide | alcohol | ketone | thiol | amide | amine | analine | phenol |
| Valine | Amine | alcohol | ketone | thiol | amide | amine | analine | phenol |
| Valine | Carboxylic Acid | alcohol | ketone | thiol | amide | amine | analine | phenol |
| Vitamin K5 | Amine | alcohol | ketone | thiol | amide | amine | analine | phenol |
| Vitamin K5 | Alcohol | alcohol | ketone | thiol | amide | amine | analine | phenol |
| Xylitol | Alcohol | alcohol | ketone | thiol | amide | amine | analine | phenol |

| Co-crystal Former | Interacting Group | | | | | | | |
|---|---|---|---|---|---|---|---|---|
| 1,5-Napthalene-disulfonic Acid | amine | metals | thioether | | sulfate | alcohol | | |
| 1-Hydroxy-2-naphthoic acid | phosphate | sulfate | sulfone | nitrate | pyridine | carboxilic acid | metals | aldehyde | ester |
| 1-Hydroxy-2-naphthoic acid | phosphate | sulfate | sulfone | nitrate | pyridine | carboxilic acid | metals | aldehyde | ester |
| 4-Aminobenzoic Acid | phosphate | sulfate | sulfone | nitrate | pyridine | | carboxilic acid | metals | aldehyde |
| 4-Aminobenzoic Acid | phosphate | sulfate | sulfone | nitrate | pyridine | | Carboxylic Acid | metals | aldehyde |
| 4-aminopyridine | phosphate | sulfate | sulfone | nitrate | pyridine | | carboxilic acid | metals | aldehyde |
| 4-aminopyridine | *sulfonamide | *ketone | ether | triazole | | ammonium | oxime | *chlorine |
| 4-Chlorobenzene-Sulfonic Acid | amine | metals | thioether | | sulfate | alcohol | | |

TABLE II-continued

| | | | | | | | | | |
|---|---|---|---|---|---|---|---|---|---|
| 4-ethoxyphenyl Urea | phosphate | sulfate | sulfone | nitrate | pyridine | | Carboxylic Acid | metals | aldehyde |
| 4-ethoxyphenyl Urea | phosphate | sulfate | sulfone | nitrate | pyridine | | carboxilic acid | metals | aldehyde |
| 7-oxo-DHEA | phosphate | sulfate | sulfone | nitrate | pyridine | carboxilic acid | metals | aldehyde | ester |
| 7-oxo-DHEA | phosphate | sulfate | sulfone | nitrate | pyridine | | Carboxylic Acid | metals | aldehyde |
| Acesulfame | amine | metals | thioether | | sulfate | alcohol | | | |
| Acesulfame | phosphate | sulfate | sulfone | nitrate | pyridine | | Carboxylic Acid | metals | aldehyde |
| Acetohydroxamic Acid | phosphate | sulfate | sulfone | nitrate | pyridine | | carboxilic acid | metals | aldehyde |
| Acetohydroxamic Acid | phosphate | sulfate | sulfone | nitrate | pyridine | | carboxilic acid | metals | aldehyde |
| Acetohydroxamic Acid | phosphate | sulfate | sulfone | nitrate | pyridine | | Carboxylic Acid | metals | aldehyde |
| Adenine | phosphate | sulfate | sulfone | nitrate | pyridine | | carboxilic acid | metals | aldehyde |
| Adenine | *sulfonamide | *ketone | ether | triazole | | ammonium | oxime | *chlorine | |
| Adipic acid | phosphate | sulfate | sulfone | nitrate | pyridine | | carboxilic acid | metals | aldehyde |
| Alanine | phosphate | sulfate | sulfone | nitrate | pyridine | | carboxilic acid | metals | aldehyde |
| Alanine | phosphate | sulfate | sulfone | nitrate | pyridine | | carboxilic acid | metals | aldehyde |
| Allopurinaol | phosphate | sulfate | sulfone | nitrate | pyridine | | Carboxylic Acid | metals | aldehyde |
| Allopurinaol | phosphate | sulfate | sulfone | nitrate | pyridine | | carboxilic acid | metals | aldehyde |
| Arginine | phosphate | sulfate | sulfone | nitrate | pyridine | | carboxilic acid | metals | aldehyde |
| Arginine | phosphate | sulfate | sulfone | nitrate | pyridine | | carboxilic acid | metals | aldehyde |
| Ascorbic Acid | phosphate | sulfate | sulfone | nitrate | pyridine | | Carboxylic Acid | metals | aldehyde |
| Ascorbic Acid | phosphate | sulfate | sulfone | nitrate | pyridine | | Carboxylic Acid | metals | aldehyde |
| Ascorbic Acid | phosphate | sulfate | sulfone | nitrate | pyridine | | carboxilic acid | metals | aldehyde |
| Asparagine | phosphate | sulfate | sulfone | nitrate | pyridine | | carboxilic acid | metals | aldehyde |
| Asparagine | phosphate | sulfate | sulfone | nitrate | pyridine | | Carboxylic Acid | metals | aldehyde |
| Asparagine | phosphate | sulfate | sulfone | nitrate | pyridine | | carboxilic acid | metals | aldehyde |
| Aspartic Acid | phosphate | sulfate | sulfone | nitrate | pyridine | | carboxilic acid | metals | aldehyde |
| Aspartic Acid | phosphate | sulfate | sulfone | nitrate | pyridine | | carboxilic acid | metals | aldehyde |
| Benzenesulfonic Acid | amine | metals | thioether | | sulfate | alcohol | | | |
| Benzoic Acid | phosphate | sulfate | sulfone | nitrate | pyridine | | carboxilic acid | metals | aldehyde |
| Caffeine | phosphate | sulfate | sulfone | nitrate | pyridine | | Carboxylic Acid | metals | aldehyde |
| Camphoric acid | phosphate | sulfate | sulfone | nitrate | pyridine | | carboxilic acid | metals | aldehyde |
| Capric acid | phosphate | sulfate | sulfone | nitrate | pyridine | | carboxilic acid | metals | aldehyde |
| Genistein | phosphate | sulfate | sulfone | nitrate | pyridine | | Carboxylic Acid | metals | aldehyde |
| Genistein | | alchohol | | ester | ether | n-oxide | chlorine | fluorine | bromine |
| Genistein | chlorine | | cyano | ester | amine | nitro | nitrate | bromine | aldehyde |
| Cinnamic acid | phosphate | sulfate | sulfone | nitrate | pyridine | | carboxilic acid | metals | aldehyde |
| Citric Acid | phosphate | sulfate | sulfone | nitrate | pyridine | | Carboxylic Acid | metals | aldehyde |
| Citric Acid | phosphate | sulfate | sulfone | nitrate | pyridine | | carboxilic acid | metals | aldehyde |
| Clemizole | *sulfonamide | *ketone | ether | triazole | | ammonium | oxime | *chlorine | |
| Cyclamic Acid | phosphate | sulfate | sulfone | nitrate | pyridine | | carboxilic acid | metals | aldehyde |
| Cyclamic Acid | amine | metals | thioether | | sulfate | alcohol | | | |
| Cysteine | phosphate | sulfate | sulfone | nitrate | pyridine | | carboxilic acid | metals | aldehyde |
| Cysteine | phosphate | sulfate | sulfone | nitrate | pyridine | | carboxilic acid | metals | aldehyde |
| Cysteine | arsenic | chlorine | alcohol | potassium | Ru | | Rb | Sb | |
| Dimethylglycine | phosphate | sulfate | sulfone | nitrate | pyridine | | carboxilic acid | metals | aldehyde |
| Dimethylglycine | phosphate | sulfate | sulfone | nitrate | pyridine | | carboxilic acid | metals | aldehyde |
| D-ribose | chlorine | | cyano | ester | amine | nitro | nitrate | bromine | aldehyde |
| D-ribose | phosphate | sulfate | sulfone | nitrate | pyridine | | Carboxylic Acid | metals | aldehyde |
| Fumaric Acid | phosphate | sulfate | sulfone | nitrate | pyridine | | carboxilic acid | metals | aldehyde |
| Galactaric acid | phosphate | sulfate | sulfone | nitrate | pyridine | | carboxilic acid | metals | aldehyde |
| Galactaric acid | phosphate | sulfate | sulfone | nitrate | pyridine | carboxilic acid | metals | aldehyde | ester |
| Chrysin | phosphate | sulfate | sulfone | nitrate | pyridine | | Carboxylic Acid | metals | aldehyde |
| Chrysin | | alchohol | | ester | ether | n-oxide | chlorine | fluorine | bromine |
| Chrysin | chlorine | | cyano | ester | amine | nitro | nitrate | bromine | aldehyde |
| Gentisic acid | phosphate | sulfate | sulfone | nitrate | pyridine | | carboxilic acid | metals | aldehyde |
| Gentisic acid | | alchohol | | ester | ether | n-oxide | chlorine | fluorine | bromine |
| Glucamine, N-methyl | phosphate | sulfate | sulfone | nitrate | pyridine | carboxilic acid | metals | aldehyde | ester |
| Glucamine, N-methyl | phosphate | sulfate | sulfone | nitrate | pyridine | | carboxilic acid | metals | aldehyde |
| Gluconic Acid | phosphate | sulfate | sulfone | nitrate | pyridine | | Carboxylic Acid | metals | aldehyde |
| Gluconic Acid | phosphate | sulfate | sulfone | nitrate | pyridine | | carboxilic acid | metals | aldehyde |
| Glucosamine | phosphate | sulfate | sulfone | nitrate | pyridine | | Carboxylic Acid | metals | aldehyde |
| Glucuronic Acid | phosphate | sulfate | sulfone | nitrate | pyridine | | carboxilic acid | metals | aldehyde |

TABLE II-continued

| | | | | | | | | | |
|---|---|---|---|---|---|---|---|---|---|
| Glucuronic Acid | phosphate | sulfate | sulfone | nitrate | pyridine | carboxilic acid | metals | aldehyde | ester |
| Glucuronic Acid | phosphate | sulfate | sulfone | nitrate | pyridine aromatic | carboxilic acid | metals | aldehyde | |
| Glutamic Acid | phosphate | sulfate | sulfone | nitrate | pyridine | carboxilic acid | metals | aldehyde | |
| Glutamic Acid | phosphate | sulfate | sulfone | nitrate | pyridine | carboxilic acid | metals | aldehyde | |
| Glutamine | phosphate | sulfate | sulfone | nitrate | pyridine | carboxilic acid | metals | aldehyde | |
| Glutamine | phosphate | sulfate | sulfone | nitrate | pyridine | Carboxylic Acid | metals | aldehyde | |
| Glutamine | phosphate | sulfate | sulfone | nitrate | pyridine | carboxilic acid | metals | aldehyde | |
| Glutaric Acid | phosphate | sulfate | sulfone | nitrate | pyridine | carboxilic acid | metals | aldehyde | |
| Glycine | phosphate | sulfate | sulfone | nitrate | pyridine | carboxilic acid | metals | aldehyde | |
| Glycine | phosphate | sulfate | sulfone | nitrate | pyridine | carboxilic acid | metals | aldehyde | |
| Glycolic Acid | phosphate | sulfate | sulfone | nitrate | pyridine | Carboxylic Acid | metals | aldehyde | |
| Glycolic Acid | phosphate | sulfate | sulfone | nitrate | pyridine | carboxilic acid | metals | aldehyde | |
| Hippuric Acid | phosphate | sulfate | sulfone | nitrate | pyridine | carboxilic acid | metals | aldehyde | |
| Hippuric Acid | phosphate | sulfate | sulfone | nitrate | pyridine | carboxilic acid | metals | aldehyde | |
| Hippuric Acid | phosphate | sulfate | sulfone | nitrate | pyridine | carboxilic acid | metals | aldehyde | |
| Histidine | phosphate | sulfate | sulfone | nitrate | pyridine | carboxilic acid | metals | aldehyde | |
| Histidine | phosphate | sulfate | sulfone | nitrate | pyridine | carboxilic acid | metals | aldehyde | |
| Histidine | cyanamide | ketone | cyano | Carboxylic Acid | alcohol | thiol | amine | phosphinic acid hemi-hydrate | |
| Hydroquinone | phosphate | sulfate | sulfone | nitrate | pyridine | Carboxylic Acid | metals | aldehyde | |
| Hydroquinone | | alchohol | | ester | ether | n-oxide | chlorine | fluorine | bromine |
| Imidazole | phosphate | sulfate | sulfone | nitrate | pyridine | carboxilic acid | metals | aldehyde | |
| Ipriflavone | chlorine | | cyano | ester | amine | nitro | nitrate | bromine | aldehyde |
| Ipriflavone | phosphate | sulfate | sulfone | nitrate | pyridine | Carboxylic Acid | metals | aldehyde | |
| Isoleucine | phosphate | sulfate | sulfone | nitrate | pyridine | carboxilic acid | metals | aldehyde | |
| Isoleucine | phosphate | sulfate | sulfone | nitrate | pyridine | carboxilic acid | metals | aldehyde | |
| lactobionic acid | phosphate | sulfate | sulfone | nitrate | pyridine | carboxilic acid | metals | aldehyde | |
| Lactobionic acid | phosphate | sulfate | sulfone | nitrate | pyridine | carboxilic acid | metals | aldehyde | ester |
| Lactobionic acid | chlorine | | cyano | ester | amine | nitro | nitrate | bromine | aldehyde |
| Lauric acid | phosphate | sulfate | sulfone | nitrate | pyridine | carboxilic acid | | aldehyde | |
| Leucine | phosphate | sulfate | sulfone | nitrate | pyridine | Carboxylic Acid | metals | aldehyde | |
| Leucine | phosphate | sulfate | sulfone | nitrate | pyridine | carboxilic acid | metals | aldehyde | |
| Lysine | phosphate | sulfate | sulfone | nitrate | pyridine | carboxilic acid | metals | aldehyde | |
| Lysine | phosphate | sulfate | sulfone | nitrate | pyridine | carboxilic acid | metals | aldehyde | |
| Maleic | phosphate | sulfate | sulfone | nitrate | pyridine | carboxilic acid | metals | aldehyde | |
| Malic Acid | phosphate | sulfate | sulfone | nitrate | pyridine | Carboxylic Acid | metals | aldehyde | |
| Malic Acid | phosphate | sulfate | sulfone | nitrate | pyridine | carboxilic acid | metals | aldehyde | |
| Malonic | phosphate | sulfate | sulfone | nitrate | pyridine | carboxilic acid | metals | aldehyde | |
| Mandelic Acid | phosphate | sulfate | sulfone | nitrate | pyridine | Carboxylic Acid | metals | aldehyde | |
| Mandelic Acid | phosphate | sulfate | sulfone | nitrate | pyridine | carboxilic acid | metals | aldehyde | |
| Methionine | phosphate | sulfate | sulfone | nitrate | pyridine | carboxilic acid | metals | aldehyde | |
| Methionine | phosphate | sulfate | sulfone | nitrate | pyridine | carboxilic acid | metals | aldehyde | |
| Methionine | chlorine | | cyano | ester | amine | nitro | nitrate | bromine | aldehyde |
| Nicotinamide | *sulfonamide | *ketone | ether | triazole | | ammonium | oxime | *chlorine | |
| Nicotinamide | phosphate | sulfate | sulfone | nitrate | pyridine | Carboxylic Acid | metals | aldehyde | |
| Nicotinic Acid | phosphate | sulfate | sulfone | nitrate | pyridine | Carboxylic Acid | metals | aldehyde | |
| Nicotinic Acid | *sulfonamide | *ketone | ether | triazole | | ammonium | oxime | *chlorine | |
| Orotic acid | phosphate | sulfate | sulfone | nitrate | pyridine | carboxilic acid | | aldehyde | |
| Orotic acid | phosphate | sulfate | sulfone | nitrate | pyridine | Carboxylic Acid | metals | aldehyde | |
| Oxalic acid | phosphate | sulfate | sulfone | nitrate | pyridine | carboxilic acid | | aldehyde | |
| Palmitic acid | phosphate | sulfate | sulfone | nitrate | pyridine | carboxilic acid | | aldehyde | |
| Pamoic acid | phosphate | sulfate | sulfone | nitrate | pyridine | carboxilic acid | | aldehyde | |
| Pamoic acid | phosphate | sulfate | sulfone | nitrate | pyridine | carboxilic acid | metals | aldehyde | ester |
| Pamoic acid | | alchohol | | ester | ether | n-oxide | chlorine | fluorine | bromine |
| Phenylalanine | phosphate | sulfate | sulfone | nitrate | pyridine | carboxilic acid | metals | aldehyde | |
| Phenylalanine | phosphate | sulfate | sulfone | nitrate | pyridine | carboxilic acid | metals | aldehyde | |
| Piperazine | phosphate | sulfate | sulfone | nitrate | pyridine | carboxilic acid | metals | aldehyde | |
| Procaine | phosphate | sulfate | sulfone | nitrate | pyridine | carboxilic acid | metals | aldehyde | |
| Procaine | phosphate | sulfate | sulfone | nitrate | pyridine | Carboxylic Acid | metals | aldehyde | |
| Proline | phosphate | sulfate | sulfone | nitrate | pyridine | carboxilic acid | metals | aldehyde | |
| Proline | phosphate | sulfate | sulfone | nitrate | pyridine | carboxilic acid | metals | aldehyde | |
| p-Toluenesulfonic acid | amine | metals | thioether | | sulfate | alcohol | | | |

TABLE II-continued

| | | | | | | | | | |
|---|---|---|---|---|---|---|---|---|---|
| Pyridoxamine | phosphate | sulfate | sulfone | nitrate | pyridine | | Carboxylic Acid | metals | aldehyde |
| Pyridoxamine | phosphate | sulfate | sulfone | nitrate | pyridine | | carboxilic acid | metals | aldehyde |
| Pyridoxamine | *sulfonamide | *ketone | ether | triazole | | ammonium | oxime | *chlorine | |
| Pyridoxine (4-Pyridoxic Acid) | *sulfonamide | *ketone | ether | triazole | | ammonium | oxime | *chlorine | |
| Pyridoxine (4-Pyridoxic Acid) | phosphate | sulfate | sulfone | nitrate | pyridine | | Carboxylic Acid | metals | aldehyde |
| Pyroglutamic acid | phosphate | sulfate | sulfone | nitrate | pyridine | | carboxilic acid | metals | aldehyde |
| Pyroglutamic acid | phosphate | sulfate | sulfone | nitrate | pyridine | | Carboxylic Acid | metals | aldehyde |
| Quercetin | phosphate | sulfate | sulfone | nitrate | pyridine | | Carboxylic Acid | metals | aldehyde |
| Quercetin | | alchohol | | ester | ether | n-oxide | chlorine | fluorine | bromine |
| Quercetin | chlorine | | cyano | ester | amine | nitro | nitrate | bromine | aldehyde |
| Resveratrol | phosphate | sulfate | sulfone | nitrate | pyridine | | Carboxylic Acid | metals | aldehyde |
| Resveratrol | | alchohol | | ester | ether | n-oxide | chlorine | fluorine | bromine |
| Saccharin | phosphate | sulfate | sulfone | nitrate | pyridine | | Carboxylic Acid | metals | aldehyde |
| Saccharin | phosphate | sulfate | sulfone | nitrate | pyridine | | Carboxylic Acid | metals | aldehyde |
| Saccharin | amine | metals | thioether | | sulfate | alcohol | | | |
| Saccharin | phosphate | sulfate | sulfone | nitrate | pyridine | | Carboxylic Acid | metals | aldehyde |
| Salicylic Acid | phosphate | sulfate | sulfone | nitrate | pyridine | | carboxilic acid | metals | aldehyde |
| Salicylic Acid | phosphate | sulfate | sulfone | nitrate | pyridine | | Carboxylic Acid | metals | aldehyde |
| Salicylic Acid, 4-amino | phosphate | sulfate | sulfone | nitrate | pyridine | | carboxilic acid | metals | aldehyde |
| Salicylic Acid, 4-amino | phosphate | sulfate | sulfone | nitrate | pyridine | carboxilic acid | metals | aldehyde | ester |
| Salicylic Acid, 4-amino | phosphate | sulfate | sulfone | nitrate | pyridine | | carboxilic acid | metals | aldehyde |
| Sebacic acid | phosphate | sulfate | sulfone | nitrate | pyridine | | carboxilic acid | metals | aldehyde |
| Serine | phosphate | sulfate | sulfone | nitrate | pyridine | | Carboxylic Acid | metals | aldehyde |
| Serine | phosphate | sulfate | sulfone | nitrate | pyridine | | carboxilic acid | metals | aldehyde |
| Serine | phosphate | sulfate | sulfone | nitrate | pyridine | | Carboxylic Acid | metals | aldehyde |
| Stearic acid | phosphate | sulfate | sulfone | nitrate | pyridine | | carboxilic acid | metals | aldehyde |
| Succinic Acid | phosphate | sulfate | sulfone | nitrate | pyridine | | Carboxylic Acid | metals | aldehyde |
| Tartaric Acid | phosphate | sulfate | sulfone | nitrate | pyridine | | Carboxylic Acid | metals | aldehyde |
| Threonine | phosphate | sulfate | sulfone | nitrate | pyridine | | carboxilic acid | metals | aldehyde |
| Threonine | phosphate | sulfate | sulfone | nitrate | pyridine | | carboxilic acid | metals | aldehyde |
| Threonine | phosphate | sulfate | sulfone | nitrate | pyridine | | Carboxylic Acid | metals | aldehyde |
| Tris | phosphate | sulfate | sulfone | nitrate | pyridine | | carboxilic acid | metals | aldehyde |
| Tris | phosphate | sulfate | sulfone | nitrate | pyridine | | Carboxylic Acid | metals | aldehyde |
| Tryptophan | phosphate | sulfate | sulfone | nitrate | pyridine | | carboxilic acid | metals | aldehyde |
| Tryptophan | phosphate | sulfate | sulfone | nitrate | pyridine | | carboxilic acid | metals | aldehyde |
| Tryptophan | *sulfonamide | *ketone | ether | triazole | | ammonium | oxime | *chlorine | |
| Tyrosine | phosphate | sulfate | sulfone | nitrate | pyridine | | carboxilic acid | metals | aldehyde |
| Tyrosine | phosphate | sulfate | sulfone | nitrate | pyridine | | carboxilic acid | metals | aldehyda |
| Tyrosine | phosphate | sulfate | sulfone | nitrate | pyridine | | Carboxylic Acid | metals | aldehyde |
| Urea | phosphate | sulfate | sulfone | nitrate | pyridine | | Carboxylic Acid | metals | aldehyde |
| Urea | phosphate | sulfate | sulfone | nitrate | pyridine | | carboxilic acid | metals | aldehyde |
| Urea | phosphate | sulfate | sulfone | nitrate | pyridine | | Carboxylic Acid | metals | aldehyde |
| Valine | phosphate | sulfate | sulfone | nitrate | pyridine | | carboxilic acid | metals | aldehyde |
| Valine | phosphate | sulfate | sulfone | nitrate | pyridine | | carboxilic acid | metals | aldehyde |
| Vitamin K5 | phosphate | sulfate | sulfone | nitrate | pyridine | | carboxilic acid | metals | aldehyde |
| Vitamin K5 | phosphate | sulfate | sulfone | nitrate | pyridine | | Carboxylic Acid | metals | aldehyde |
| Xylitol | phosphate | sulfate | sulfone | nitrate | pyridine | | Carboxylic Acid | metals | aldehyde |

| Co-crystal Former | Interacting Group | | | | | | | |
|---|---|---|---|---|---|---|---|---|
| 1,5-Napthalene-disulfonic Acid | | | | | | | | |
| 1-Hydroxy-2-naphthoic acid | ether | cyano | | | furan | bromine | chlorine | s-heterocyclic | pyridine |
| 1-Hydroxy-2-naphthoic acid | ether | cyano | | | furan | bromine | chlorine | s-heterocyclic | pyridine |
| 4-Aminobenzoic Acid | ester | ether | cyano | | furan | bromine | chlorine | s-heterocyclic | |
| 4-Aminobenzoic Acid | ester | ether | cyano | | furan | bromine | chlorine | s-heterocyclic | |
| 4-aminopyridine | ester | ether | cyano | | furan | bromine | chlorine | s-heterocyclic | |

TABLE II-continued

| | | | | | | | | |
|---|---|---|---|---|---|---|---|---|
| 4-aminopyridine | thiol | n-heterocyclic ring | thione-disulfide | pyrro-lidindione | iodine | hydrazone | thiocyanate | *bromine |
| 4-Chlorobenzene-Sulfonic Acid | | | | | | | | |
| 4-ethoxyphenyl Urea | ester | ether | cyano | | furan | bromine | chlorine | s-heterocyclic |
| 4-ethoxyphenyl Urea | ester | ether | cyano | | furan | bromine | chlorine | s-heterocyclic |
| 7-oxo-DHEA | ether | cyano | | furan | bromine | chlorine | s-heterocyclic | pyridine |
| 7-oxo-DHEA | ester | ether | cyano | | furan | bromine | chlorine | s-heterocyclic |
| Acesulfame | | | | | | | | |
| Acesulfame | ester | ether | cyano | | furan | bromine | chlorine | s-heterocyclic |
| Acetohydroxamic Acid | ester | ether | cyano | | furan | bromine | chlorine | s-heterocyclic |
| Acetohydroxamic Acid | ester | ether | cyano | | furan | bromine | chlorine | s-heterocyclic |
| Acetohydroxamic Acid | ester | ether | cyano | | furan | bromine | chlorine | s-heterocyclic |
| Adenine | ester | ether | cyano | | furan | bromine | chlorine | s-heterocyclic |
| Adenine | thiol | n-heterocyclic ring | thione-disulfide | pyrro-lidindione | iodine | hydrazone | thiocyanate | *bromine |
| Adipic acid | ester | ether | cyano | | furan | bromine | chlorine | s-heterocyclic |
| Alanine | ester | ether | cyano | | furan | bromine | chlorine | s-heterocyclic |
| Alanine | ester | ether | cyano | | furan | bromine | chlorine | s-heterocyclic |
| Allopurinaol | ester | ether | cyano | | furan | bromine | chlorine | s-heterocyclic |
| Allopurinaol | ester | ether | cyano | | furan | bromine | chlorine | s-heterocyclic |
| Arginine | ester | ether | cyano | | furan | bromine | chlorine | s-heterocyclic |
| Arginine | ester | ether | cyano | | furan | bromine | chlorine | s-heterocyclic |
| Ascorbic Acid | ester | ether | cyano | | furan | bromine | chlorine | s-heterocyclic |
| Ascorbic Acid | ester | ether | cyano | | furan | bromine | chlorine | s-heterocyclic |
| Ascorbic Acid | ester | ether | cyano | | furan | bromine | chlorine | s-heterocyclic |
| Asparagine | ester | ether | cyano | | furan | bromine | chlorine | s-heterocyclic |
| Asparagine | ester | ether | cyano | | furan | bromine | chlorine | s-heterocyclic |
| Asparagine | ester | ether | cyano | | furan | bromine | chlorine | s-heterocyclic |
| Aspartic Acid | ester | ether | cyano | | furan | bromine | chlorine | s-heterocyclic |
| Aspartic Acid | ester | ether | cyano | | furan | bromine | chlorine | s-heterocyclic |
| Benzenesulfonic Acid | | | | | | | | |
| Benzoic Acid | ester | ether | cyano | | furan | bromine | chlorine | s-heterocyclic |
| Caffeine | ester | ether | cyano | | furan | bromine | chlorine | s-heterocyclic |
| Camphoric acid | ester | ether | cyano | | furan | bromine | chlorine | s-heterocyclic |
| Capric acid | ester | ether | cyano | | furan | bromine | chlorine | s-heterocyciic |
| Genistein | ester | ether | cyano | | furan | bromine | chlorine | s-heterocyclic |
| Genistein | iodine | ketone | sulfonic acid | sulfate | phosphate | phosphon-ic acid | carboxylic acid | nitro |
| Genistein | ketone | peroxide | epoxide | | | hetero-cyclic-S | iodine | ester |
| Cinnamic acid | ester | ether | cyano | | furan | bromine | chlorine | s-heterocyclic |
| Citric Acid | ester | ether | cyano | | furan | bromine | chlorine | s-heterocyclic |
| Citric Acid | ester | ether | cyano | | furan | bromine | chlorine | s-heterocyclic |
| Clemizole | thiol | n-heterocyclic ring | thione-disulfide | pyrro-lidindione | iodine | hydrazone | thiocyanate | *bromine |
| Cyclamic Acid | ester | ether | cyano | | furan | bromine | chlorine | s-heterocyclic |
| Cyclamic Acid | | | | | | | | |
| Cysteine | ester | ether | cyano | | furan | bromine | chlorine | s-heterocyclic |
| Cysteine | ester | ether | cyano | | furan | bromine | chlorine | s-heterocyclic |
| Cysteine | | | | | | | | |
| Dimethylglycine | ester | ether | cyano | | furan | bromine | chlorine | s-heterocyclic |
| Dimethylglycine | ester | ether | cyano | | furan | bromine | chlorine | s-heterocyclic |
| D-ribose | ketone | peroxide | epoxide | | | hetero-cyclic-S | iodine | ester |
| D-ribose | ester | ether | cyano | | furan | bromine | chlorine | s-heterocyclic |
| Fumaric Acid | ester | ether | cyano | | furan | bromine | chlorine | s-heterocyclic |
| Galactaric acid | ester | ether | cyano | | furan | bromine | chlorine | s-heterocyclic |
| Galactaric acid | ether | cyano | | furan | bromine | chlorine | s-heterocyclic | pyridine |
| Chrysin | ester | ether | cyano | | furan | bromine | chlorine | s-heterocyclic |
| Chrysin | iodine | ketone | sulfonic acid | sulfate | phosphate | phosphon-ic acid | carboxylic acid | nitro |
| Chrysin | ketone | peroxide | epoxide | | | hetero-cyclic-S | iodine | ester |
| Gentisic acid | ester | ether | cyano | | furan | bromine | chlorine | s-heterocyclic |
| Gentisic acid | iodine | ketone | sulfonic acid | sulfate | phosphate | phosphon-ic acid | carboxylic acid | nitro |
| Glucamine, N-methyl | ether | cyano | | furan | bromine | chlorine | s-heterocyclic | pyridine |
| Glucamine, N-methyl | ester | ether | cyano | | furan | bromine | chlorine | s-heterocyclic |
| Gluconic Acid | ester | ether | cyano | | furan | bromine | chlorine | s-heterocyclic |
| Gluconic Acid | ester | ether | cyano | | furan | bromine | chlorine | s-heterocyclic |
| Glucosamine | ester | ether | cyano | | furan | bromine | chlorine | s-heterocyclic |
| Glucuronic acid | ester | ether | cyano | | furan | bromine | chlorine | s-heterocyclic |
| Glucuronic acid | ether | cyano | | furan | bromine | chlorine | s-heterocyclic | pyridine |
| Glucuronic acid | ester | ether | cyano | | furan | bromine | chlorine | s-heterocyclic |
| Glutamic Acid | ester | ether | cyano | | furan | bromine | chlorine | s-heterocyclic |
| Glutamic Acid | ester | ether | cyano | | furan | bromine | chlorine | s-heterocyclic |
| Glutamine | ester | ether | cyano | | furan | bromine | chlorine | s-heterocyclic |
| Glutamine | ester | ether | cyano | | furan | bromine | chlorine | s-heterocyclic |
| Glutamine | ester | ether | cyano | | furan | bromine | chlorine | s-heterocyclic |

TABLE II-continued

| | | | | | | | | |
|---|---|---|---|---|---|---|---|---|
| Glutaric Acid | ester | ether | cyano | | furan | bromine | chlorine | s-heterocyclic |
| Glycine | ester | ether | cyano | | furan | bromine | chlorine | s-heterocyclic |
| Glycine | ester | ether | cyano | | furan | bromine | chlorine | s-heterocyclic |
| Glycolic Acid | ester | ether | cyano | | furan | bromine | chlorine | s-heterocyclic |
| Glycolic Acid | ester | ether | cyano | | furan | bromine | chlorine | s-heterocyclic |
| Hippuric Acid | ester | ether | cyano | | furan | bromine | chlorine | s-heterocyclic |
| Hippuric Acid | ester | ether | cyano | | furan | bromine | chlorine | s-heterocyclic |
| Hippuric Acid | ester | ether | cyano | | furan | bromine | chlorine | s-heterocyclic |
| Histidine | ester | ether | cyano | | furan | bromine | chlorine | s-heterocyclic |
| Histidine | ester | ether | cyano | | furan | bromine | chlorine | s-heterocyclic |
| Histidine | chlorine | sulfonyl | sulfoxide | amide | fluorine | sulfonate ester | | |
| Hydroquinone | ester | ether | cyano | | furan | bromine | chlorine | s-heterocyclic |
| Hydroquinone | iodine | ketone | sulfonic acid | sulfate | phosphate | phosphonic acid | carboxylic acid | nitro |
| Imidazole | ester | ether | cyano | | furan | bromine | chlorine | s-heterocyclic |
| Ipriflavone | ketone | peroxide | epoxide | | | heterocyclic-S | iodine | ester |
| Ipriflavone | ester | ether | cyano | | furan | bromine | chlorine | s-heterocyclic |
| Isoleucine | ester | ether | cyano | | furan | bromine | chlorine | s-heterocyclic |
| Isoleucine | ester | ether | cyano | | furan | bromine | chlorine | s-heterocyclic |
| lactobionic acid | ester | ether | cyano | | furan | bromine | chlorine | s-heterocyclic |
| Lactobionic acid | ether | cyano | | furan | bromine | chlorine | s-heterocyclic | pyridine |
| Lactobionic acid | ketone | peroxide | epoxide | | | heterocyclic-S | iodine | ester |
| Lauric acid | ester | ether | cyano | | furan | bromine | chlorine | s-heterocyclic |
| Leucine | ester | ether | cyano | | furan | bromine | chlorine | s-heterocyclic |
| Leucine | ester | ether | cyano | | furan | bromine | chlorine | s-heterocyclic |
| Lysine | ester | ether | cyano | | furan | bromine | chlorine | s-heterocyclic |
| Lysine | ester | ether | cyano | | furan | bromine | chlorine | s-heterocyclic |
| Maleic | ester | ether | cyano | | furan | bromine | chlorine | s-heterocyclic |
| Malic Acid | ester | ether | cyano | | furan | bromine | chlorine | s-heterocyclic |
| Malic Acid | ester | ether | cyano | | furan | bromine | chlorine | s-heterocyclic |
| Malonic | ester | ether | cyano | | furan | bromine | chlorine | s-heterocyclic |
| Mandelic Acid | ester | ether | cyano | | furan | bromine | chlorine | s-heterocyclic |
| Mandelic Acid | ester | ether | cyano | | furan | bromine | chlorine | s-heterocyclic |
| Methionine | ester | ether | cyano | | furan | bromine | chlorine | s-heterocyclic |
| Methionine | ester | ether | cyano | | furan | bromine | chlorine | s-heterocyclic |
| Methionine | ketone | peroxide | epoxide | Ag | Se | heterocyclic-S | iodine | ester |
| Nicotinamide | thiol | n-heterocyclic ring | thione-disulfide | pyrrolidindione | iodine | hydrazone | thiocyanate | *bromine |
| Nicotinamide | ester | ether | cyano | | furan | bromine | chlorine | s-heterocyclic |
| Nicotinic Acid | ester | ether | cyano | | furan | bromine | chlorine | s-heterocyclic |
| Nicotinic Acid | thiol | n-heterocyclic ring | thione-disulfide | pyrrolidindione | iodine | hydrazone | thiocyanate | *bromine |
| Orotic acid | ester | ether | cyano | | furan | bromine | chlorine | s-heterocyclic |
| Orotic acid | ester | ether | cyano | | furan | bromine | chlorine | s-heterocyclic |
| Oxalic acid | ester | ether | cyano | | furan | bromine | chlorine | s-heterocyclic |
| Palmitic acid | ester | ether | cyano | | furan | bromine | chlorine | s-heterocyclic |
| Pamoic acid | ester | ether | cyano | | furan | bromine | chlorine | s-heterocyclic |
| Pamoic acid | ether | cyano | | furan | bromine | chlorine | s-heterocyclic | pyridine |
| Pamoic acid | iodine | ketone | sulfonic acid | sulfate | phosphate | phosphonic acid | carboxylic acid | nitro |
| Phenylalanine | ester | ether | cyano | | furan | bromine | chlorine | s-heterocyclic |
| Phenylalanine | ester | ether | cyano | | furan | bromine | chlorine | s-heterocyclic |
| Piperazine | ester | ether | cyano | | furan | bromine | chlorine | s-heterocyclic |
| Procaine | ester | ether | cyano | | furan | bromine | chlorine | s-heterocyclic |
| Procaine | ester | ether | cyano | | furan | bromine | chlorine | s-heterocyclic |
| Proline | ester | ether | cyano | | furan | bromine | chlorine | s-heterocyclic |
| Proline | ester | ether | cyano | | furan | bromine | chlorine | s-heterocyclic |
| p-Toluenesulfonic acid | | | | | | | | |
| Pyridoxamine | ester | ether | cyano | | furan | bromine | chlorine | s-heterocyclic |
| Pyridoxamine | ester | ether | cyano | | furan | bromine | chlorine | s-heterocyclic |
| Pyridoxamine | thiol | n-heterocyclic ring | thione-disulfide | | iodine | hydrazone | thiocyanate | *bromine |
| Pyridoxine (4-Pyridoxic Acid) | thiol | n-heterocyclic ring | thione-disulfide | pyrrolidindione | iodine | hydrazone | thiocyanate | *bromine |
| Pyridoxine (4-Pyridoxic Acid) | ester | ether | cyano | | furan | bromine | chlorine | s-heterocyclic |
| Pyroglutamic acid | ester | ether | cyano | | furan | bromine | chlorine | s-heterocyclic |
| Pyroglutamic acid | ester | ether | cyano | | furan | bromine | chlorine | s-heterocyclic |
| Quercetin | ester | ether | cyano | | furan | bromine | chlorine | s-heterocyclic |
| Quercetin | iodine | ketone | sulfonic acid | sulfate | phosphate | phosphonic acid | carboxylic acid | nitro |
| Quercetin | ketone | peroxide | epoxide | | | heterocyclic-S | iodine | ester |
| Resveratrol | ester | ether | cyano | | furan | bromine | chlorine | s-heterocyclic |

TABLE II-continued

| Resveratrol | iodine | ketone | sulfonic acid | sulfate | phosphate | phosphonic acid | carboxylic acid | nitro |
|---|---|---|---|---|---|---|---|---|
| Saccharin | ester | ether | cyano | | furan | bromine | chlorine | s-heterocyclic |
| Saccharin | ester | ether | cyano | | furan | bromine | chlorine | s-heterocyclic |
| Saccharin | ester | ether | cyano | | furan | bromine | chlorine | s-heterocyclic |
| Salicylic Acid | ester | ether | cyano | | furan | bromine | chlorine | s-heterocyclic |
| Salicylic Acid | ester | ether | cyano | | furan | bromine | chlorine | s-heterocyclic |
| Salicylic Acid, 4-amino | ester | ether | cyano | | furan | bromine | chlorine | s-heterocyclic |
| Salicylic Acid, 4-amino | ether | cyano | | furan | bromine | chlorine | s-heterocyclic | pyridine |
| Salicylic Acid, 4-amino | ester | ether | cyano | | furan | bromine | chlorine | s-heterocyclic |
| Sebacic acid | ester | ether | cyano | | furan | bromine | chlorine | s-heterocyclic |
| Serine | ester | ether | cyano | | furan | bromine | chlorine | s-heterocyclic |
| Serine | ester | ether | cyano | | furan | bromine | chlorine | s-heterocyclic |
| Serine | ester | ether | cyano | | furan | bromine | chlorine | s-heterocyclic |
| Stearic acid | ester | ether | cyano | | furan | bromine | chlorine | s-heterocyclic |
| Succinic Acid | ester | ether | cyano | | furan | bromine | chlorine | s-heterocyclic |
| Tartaric Acid | ester | ether | cyano | | furan | bromine | chlorine | s-heterocyclic |
| Threonine | ester | ether | cyano | | furan | bromine | chlorine | s-heterocyclic |
| Threonine | ester | ether | cyano | | furan | bromine | chlorine | s-heterocyclic |
| Threonine | ester | ether | cyano | | furan | bromine | chlorine | s-heterocyclic |
| Tris | ester | ether | cyano | | furan | bromine | chlorine | s-heterocyclic |
| Tris | ester | ether | cyano | | furan | bromine | chlorine | s-heterocyclic |
| Tryptophan | ester | ether | cyano | | furan | bromine | chlorine | s-heterocyclic |
| Tryptophan | ester | ether | cyano | | furan | bromine | chlorine | s-heterocyclic |
| Tryptophan | thiol | n-heterocyclic ring | thione-disulfide | pyrrolidindione | iodine | hydrazone | thiocyanate | *bromine |
| Tyrosine | ester | ether | cyano | | furan | bromine | chlorine | s-heterocyclic |
| Tyrosine | ester | ether | cyano | | furan | bromine | chlorine | s-heterocyclic |
| Tyrosine | ester | ether | cyano | | furan | bromine | chlorine | s-heterocyclic |
| Urea | ester | ether | cyano | | furan | bromine | chlorine | s-heterocyclic |
| Urea | ester | ether | cyano | | furan | bromine | chlorine | s-heterocyclic |
| Urea | ester | ether | cyano | | furan | bromine | chlorine | s-heterocyclic |
| Valine | ester | ether | cyano | | furan | bromine | chlorine | s-heterocyclic |
| Valine | ester | ether | cyano | | furan | bromine | chlorine | s-heterocyclic |
| Vitamin K5 | ester | ether | cyano | | furan | bromine | chlorine | s-heterocyclic |
| Vitamin K5 | ester | ether | cyano | | furan | bromine | chlorine | s-heterocyclic |
| Xylitol | ester | ether | cyano | | furan | bromine | chlorine | s-heterocyclic |

| Co-crystal Former | Interacting Group | | | | | | |
|---|---|---|---|---|---|---|---|
| 1,5-Napthalene-disulfonic Acid | | | | | | | |
| 1-Hydroxy-2-naphthoic acid | cyano | n-heterocyclic | ketone | phosphate ester | | fluorine | carbamate |
| 1-Hydroxy-2-naphthoic acid | cyano | n-heterocyclic | ketone | phosphate ester | | fluorine | carbamate |
| 4-Aminobenzoic Acid | pyridine | cyano | n-heterocyclic | ketone | phosphate ester | | fluorine |
| 4-Aminobenzoic Acid | pyridine | cyano | n-heterocyclic | ketone | phosphate ester | | fluorine |
| 4-aminopyridine | pyridine | cyano | n-heterocyclic | ketone | phosphate ester | | fluorine |
| 4-aminopyridine | | hydroxamic acid | cyano | carboxamide | *sulfonic acid | *phosphoric acid | N-oxide |
| 4-Chlorobenzene-Sulfonic Acid | | | | | | | |
| 4-ethoxyphenyl Urea | pyridine | cyano | n-heterocyclic | ketone | phosphate ester | | fluorine |
| 4-ethoxyphenyl Urea | pyridine | cyano | n-heterocyclic | ketone | phosphate ester | | fluorine |
| 7-oxo-DHEA | cyano | n-heterocyclic | ketone | phosphate ester | | fluorine | carbamate |
| 7-oxo-DHEA | pyridine | cyano | n-heterocyclic | ketone | phosphate ester | | fluorine |
| Acesulfame | | | | | | | |
| Acesulfame | pyridine | cyano | n-heterocyclic | ketone | phosphate ester | | fluorine |
| Acetohydroxamic Acid | pyridine | cyano | n-heterocyclic | ketone | phosphate ester | | fluorine |
| Acetohydroxamic Acid | pyridine | cyano | n-heterocyclic | ketone | phosphate ester | | fluorine |
| Acetohydroxamic Acid | pyridine | cyano | n-heterocyclic | ketone | phosphate ester | | fluorine |
| Adenine | pyridine | cyano | n-heterocyclic | ketone | phosphate ester | | fluorine |
| Adenine | | hydroxamic acid | cyano | carboxamide | sulfonic acid | *phosphoric acid | N-oxide |
| Adipic acid | pyridine | cyano | n-heterocyclic | ketone | phosphate ester | | fluorine |
| Alanine | pyridine | cyano | n-heterocyclic | ketone | phosphate ester | | fluorine |
| Alanine | pyridine | cyano | n-heterocyclic | ketone | phosphate ester | | fluorine |
| Allopurinaol | pyridine | cyano | n-heterocyclic | ketone | phosphate ester | | fluorine |
| Allopurinaol | pyridine | cyano | n-heterocyclic | ketone | phosphate ester | | fluorine |
| Arginine | pyridine | cyano | n-heterocyclic | ketone | phosphate ester | | fluorine |
| Arginine | pyridine | cyano | n-heterocyclic | ketone | phosphate ester | | fluorine |
| Ascorbic Acid | pyridine | cyano | n-heterocyclic | ketone | phosphate ester | | fluorine |
| Ascorbic Acid | pyridine | cyano | n-heterocyclic | ketone | phosphate ester | | fluorine |
| Ascorbic Acid | pyridine | cyano | n-heterocyclic | ketone | phosphate ester | | fluorine |
| Asparagine | pyridine | cyano | n-heterocyclic | ketone | phosphate ester | | fluorine |
| Asparagine | pyridine | cyano | n-heterocyclic | ketone | phosphate ester | | fluorine |
| Asparagine | pyridine | cyano | n-heterocycfic | ketone | phosphate ester | | fluorine |
| Aspartic Acid | pyridine | cyano | n-heterocyclic | ketone | phosphate ester | | fluorine |
| Aspartic Acid | pyridine | cyano | n-heterocyclic | ketone | phosphate ester | | fluorine |
| Benzenesulfonic Acid | | | | | | | |
| Benzoic Acid | pyridine | cyano | n-heterocyclic | ketone | phosphate ester | | fluorine |
| Caffeine | pyridine | cyano | n-heterocyclic | ketone | phosphate ester | | fluorine |
| Camphoric acid | pyridine | cyano | n-heterocyclic | ketone | phosphate ester | | fluorine |

TABLE II-continued

| | | | | | | |
|---|---|---|---|---|---|---|
| Capric acid | pyridine | cyano | n-heterocyclic | ketone | phosphate ester | fluorine |
| Genistein | pyridine | cyano | n-heterocyclic | ketone | phosphate ester | fluorine |
| Genistein | sulfone | analine | | | | |
| Genistein | ether | carboxylic acid | sulfate | sulfone | | alcohol |
| Cinnamic acid | pyridine | cyano | n-heterocyclic | ketone | phosphate ester | fluorine |
| Citric Acid | pyridine | cyano | n-heterocyclic | ketone | phosphate ester | fluorine |
| Citric Acid | pyridine | cyano | n-heterocyclic | ketone | phosphate ester | fluorine |
| Clemizole | | hydroxamic acid | cyano | carboxamide | *sulfonic acid | *phosphoric acid | N-oxide |
| Cyclamic Acid | pyridine | cyano | n-heterocyclic | ketone | phosphate ester | fluorine |
| Cyclamic Acid | | | | | | |
| Cysteine | pyridine | cyano | n-heterocyclic | ketone | phosphate ester | fluorine |
| Cysteine | pyridine | cyano | n-heterocyclic | ketone | phosphate ester | fluorine |
| Cysteine | | | | | | |
| Dimethylglycine | pyridine | cyano | n-heterocyclic | ketone | phosphate ester | fluorine |
| Dimethylglycine | pyridine | cyano | n-heterocyclic | ketone | phosphate ester | fluorine |
| D-ribose | ether | carboxylic acid | sulfate | sulfone | | alcohol |
| D-ribose | pyridine | cyano | n-heterocyclic | ketone | phosphate ester | fluorine |
| Fumaric Acid | pyridine | cyano | n-heterocyclic | ketone | phosphate ester | fluorine |
| Galactaric acid | pyridine | cyano | n-heterocyclic | ketone | phosphate ester | fluorine |
| Galactaric acid | cyano | n-heterocyclic | ketone | phosphate ester | | fluorine | carbamate |
| Chrysin | pyridine | cyano | n-heterocyclic | ketone | phosphate ester | fluorine |
| Chrysin | sulfone | analine | | | | |
| Chrysin | ether | carboxylic acid | sulfate | sulfone | | alcohol |
| Gentisic acid | pyridine | cyano | n-heterocyclic | ketone | phosphate ester | fluorine |
| Gentisic acid | sulfone | analine | | | | |
| Glucamine, N-methyl | cyano | n-heterocyclic | ketone | phosphate ester | | fluorine | carbamate |
| Glucamine, N-methyl | pyridine | cyano | n-heterocyclic | ketone | phosphate ester | fluorine |
| Gluconic Acid | pyridine | cyano | n-heterocyclic | ketone | phosphate ester | fluorine |
| Gluconic Acid | pyridine | cyano | n-heterocyclic | ketone | phosphate ester | fluorine |
| Glucosamine | pyridine | cyano | n-heterocyclic | ketone | phosphate ester | fluorine |
| Glucuronic acid | pyridine | cyano | n-heterocyclic | ketone | phosphate ester | fluorine |
| Glucuronic acid | cyano | n-heterocyclic | ketone | phosphate ester | | fluorine | carbamate |
| Glucuronic acid | pyridine | cyano | n-heterocyclic | ketone | phosphate ester | fluorine |
| Glutamic Acid | pyridine | cyano | n-heterocyclic | ketone | phosphate ester | fluorine |
| Glutamic Acid | pyridine | cyano | n-heterocyclic | ketone | phosphate ester | fluorine |
| Glutamine | pyridine | cyano | n-heterocyclic | ketone | phosphate ester | fluorine |
| Glutamine | pyridine | cyano | n-heterocyclic | ketone | phosphate ester | fluorine |
| Glutamine | pyridine | cyano | n-heterocyclic | ketone | phosphate ester | fluorine |
| Glutaric Acid | pyridine | cyano | n-heterocyclic | ketone | phosphate ester | fluorine |
| Glycine | pyridine | cyano | n-heterocyclic | ketone | phosphate ester | fluorine |
| Glycine | pyridine | cyano | n-heterocyclic | ketone | phosphate ester | fluorine |
| Glycolic Acid | pyridine | cyano | n-heterocyclic | ketone | phosphate ester | fluorine |
| Glycolic Acid | pyridine | cyano | n-heterocyclic | ketone | phosphate ester | fluorine |
| Hippuric Acid | pyridine | cyano | n-heterocyclic | ketone | phosphate ester | fluorine |
| Hippuric Acid | pyridine | cyano | n-heterocyclic | ketone | phosphate ester | fluorine |
| Hippuric Acid | pyridine | cyano | n-heterocyclic | ketone | phosphate ester | fluorine |
| Histidine | pyridine | cyano | n-heterocyclic | ketone | phosphate ester | fluorine |
| Histidine | pyridine | cyano | n-heterocyclic | ketone | phosphate ester | fluorine |
| Histidine | | | | | | |
| Hydroquinone | pyridine | cyano | n-heterocyclic | ketone | phosphate ester | fluorine |
| Hydroquinone | sulfone | analine | | | | |
| Imidazole | pyridine | cyano | n-heterocyclic | ketone | phosphate ester | fluorine |
| Ipriflavone | ether | carboxylic acid | sulfate | sulfone | | alcohol |
| Ipriflavone | pyridine | cyano | n-heterocyclic | ketone | phosphate ester | fluorine |
| Isoleucine | pyridine | cyano | n-heterocyclic | ketone | phosphate ester | fluorine |
| Isoleucine | pyridine | cyano | n-heterocyclic | ketone | phosphate ester | fluorine |
| lactobionic acid | pyridine | cyano | n-heterocyclic | ketone | phosphate ester | fluorine |
| Lactobionic acid | cyano | n-heterocyclic | ketone | phosphate ester | | fluorine | carbamate |
| Lactobionic acid | ether | carboxylic acid | sulfate | sulfone | | alcohol |
| Lauric acid | pyridine | cyano | n-heterocyclic | ketone | phosphate ester | fluorine |
| Leucine | pyridine | cyano | n-heterocyclic | ketone | phosphate ester | fluorine |
| Leucine | pyridine | cyano | n-heterocyclic | ketone | phosphate ester | fluorine |
| Lysine | pyridine | cyano | n-heterocyclic | ketone | phosphate ester | fluorine |
| Lysine | pyridine | cyano | n-heterocyclic | ketone | phosphate ester | fluorine |
| Maleic | pyridine | cyano | n-heterocyclic | ketone | phosphate ester | fluorine |
| Malic Acid | pyridine | cyano | n-heterocyclic | ketone | phosphate ester | fluorine |
| Malic Acid | pyridine | cyano | n-heterocyclic | ketone | phosphate ester | fluorine |
| Malonic | pyridine | cyano | n-heterocyclic | ketone | phosphate ester | fluorine |
| Mandelic Acid | pyridine | cyano | n-heterocyclic | ketone | phosphate ester | fluorine |
| Mandelic Acid | pyridine | cyano | n-heterocyclic | ketone | phosphate ester | fluorine |
| Methionine | pyridine | cyano | n-heterocyclic | ketone | phosphate ester | fluorine |
| Methionine | pyridine | cyano | n-heterocyclic | ketone | phosphate ester | fluorine |
| Methionine | ether | carboxylic acid | sulfate | sulfone | | alcohol |
| Nicotinamide | | hydroxamic acid | cyano | carboxamide | *sulfonic acid | *phosphoric acid | N-oxide |
| Nicotinamide | pyridine | cyano | n-heterocyclic | ketone | phosphate ester | fluorine |
| Nicotinic Acid | pyridine | cyano | n-heterocyclic | ketone | phosphate ester | fluorine |
| Nicotinic Acid | | hydroxamic acid | cyano | carboxamide | *sulfonic acid | *phosphoric acid | N-oxide |
| Orotic acid | pyridine | cyano | n-heterocyclic | ketone | phosphate ester | fluorine |
| Orotic acid | pyridine | cyano | n-heterocyclic | ketone | phosphate ester | fluorine |

TABLE II-continued

| | | | | | | |
|---|---|---|---|---|---|---|
| Oxalic acid | pyridine | cyano | n-heterocyclic | ketone | phosphate ester | fluorine |
| Palmitic acid | pyridine | cyano | n-heterocyclic | ketone | phosphate ester | fluorine |
| Pamoic acid | pyridine | cyano | n-heterocyclic | ketone | phosphate ester | fluorine |
| Pamoic acid | cyano | n-heterocyclic | ketone | phosphate ester | fluorine | carbamate |
| Pamoic acid | sulfone | analine | | | | |
| Phenylalanine | pyridine | cyano | n-heterocyclic | ketone | phosphate ester | fluorine |
| Phenylalanine | pyridine | cyano | n-heterocyclic | ketone | phosphate ester | fluorine |
| Piperazine | pyridine | cyano | n-heterocyclic | ketone | phosphate ester | fluorine |
| Procaine | pyridine | cyano | n-heterocyclic | ketone | phosphate ester | fluorine |
| Procaine | pyridine | cyano | n-heterocyclic | ketone | phosphate ester | fluorine |
| Proline | pyridine | cyano | n-heterocyclic | ketone | phosphate ester | fluorine |
| Proline | pyridine | cyano | n-heterocyclic | ketone | phosphate ester | fluorine |
| p-Toluenesulfonic acid | | | | | | |
| Pyridoxamine | pyridine | cyano | n-heterocyclic | ketone | phosphate ester | fluorine |
| Pyridoxamine | pyridine | cyano | n-heterocyclic | ketone | phosphate ester | fluorine |
| Pyridoxamine | | hydroxamic acid | cyano | carboxamade | *sulfonic acid | *phosphoric acid | N-oxide |
| Pyridoxine | | hydroxamic acid | cyano | carboxamide | *sulfonic acid | *phosphoric acid | N-oxide |
| (4-Pyridoxic Acid) | | | | | | |
| Pyridoxine | pyridine | cyano | n-heterocyclic | ketone | phosphate ester | fluorine |
| (4-Pyridoxic Acid) | | | | | | |
| Pyroglutamic acid | pyridine | cyano | n-heterocyclic | ketone | phosphate ester | fluorine |
| Pyroglutamic acid | pyridine | cyano | n-heterocyclic | ketone | phosphate ester | fluorine |
| Quercetin | pyridine | cyano | n-heterocyclic | ketone | phosphate ester | fluorine |
| Quercetin | sulfone | analine | | | | |
| Quercetin | ether | carboxylic acid | sulfate | sulfone | | alcohol |
| Resveratrol | pyridine | cyano | n-heterocyclic | ketone | phosphate ester | fluorine |
| Resveratrol | sulfone | analine | | | | |
| Saccharin | pyridine | cyano | n-heterocyclic | ketone | phosphate ester | fluorine |
| Saccharin | pyridine | cyano | n-heterociic | ketone | phosphate ester | fluorine |
| Saccharin | | | | | | |
| Saccharin | pyridine | cyano | n-heterocyclic | ketone | phosphate ester | fluorine |
| Salicylic Acid | pyridine | cyano | n-heterocyclic | ketone | phosphate ester | fluorine |
| Salicylic Acid | pyridine | cyano | n-heterocyclic | ketone | phosphate ester | fluorine |
| Salicylic Acid, 4-amino | pyridine | cyano | n-heterociic | ketone | phosphate ester | fluorine |
| Salicylic Acid, 4-amino | cyano | n-heterocyclic | ketone | phosphate ester | fluorine | carbamate |
| Salicylic Acid, 4-amino | pyridine | cyano | n-heterocyclic | ketone | phosphate ester | fluorine |
| Sebacic acid | pyridine | cyano | n-heterocyclic | ketone | phosphate ester | fluorine |
| Serine | pyridine | cyano | n-heterocyclic | ketone | phosphate ester | fluorine |
| Serine | pyridine | cyano | n-heterocyclic | ketone | phosphate ester | fluorine |
| Serine | pyridine | cyano | n-heterocyclic | ketone | phosphate ester | fluorine |
| Stearic acid | pyridine | cyano | n-heterocyclic | ketone | phosphate ester | fluorine |
| Succinic Acid | pyridine | cyano | n-heterocyclic | ketone | phosphate ester | fluorine |
| Tartaric Acid | pyridine | cyano | n-heterocyclic | ketone | phosphate ester | fluorine |
| Threonine | pyridine | cyano | n-heterocyclic | ketone | phosphate ester | fluorine |
| Threonine | pyridine | cyano | n-heterocyclic | ketone | phosphate ester | fluorine |
| Threonine | pyridine | cyano | n-heterocyclic | ketone | phosphate ester | fluorine |
| Tris | pyridine | cyano | n-heterocyclic | ketone | phosphate ester | fluorine |
| Tris | pyridine | cyano | n-heterocyclic | ketone | phosphate ester | fluorine |
| Tryptophan | pyridine | cyano | n-heterocyclic | ketone | phosphate ester | fluorine |
| Tryptophan | pyridine | cyano | n-heterocyclic | ketone | phosphate ester | fluorine |
| Tryptophan | | hydroxamic acid | cyano | carboxamide | *sulfonic acid | *phosphoric acid | N-oxide |
| Tyrosine | pyridine | cyano | n-heterocyllc | ketone | phosphate ester | fluorine |
| Tyrosine | pyridine | cyano | n-heterocyclic | ketone | phosphate ester | fluorine |
| Tyrosine | pyridine | cyano | n-heterocyclic | ketone | phosphate ester | fluorine |
| Urea | pyridine | cyano | n-heterocyclic | ketone | phosphate ester | fluorine |
| Urea | pyridine | cyano | n-heterocyclic | ketone | phosphate ester | fluorine |
| Urea | pyridine | cyano | n-heterocyclic | ketone | phosphate ester | fluorine |
| Valine | pyridine | cyano | n-heterocyclic | ketone | phosphate ester | fluorine |
| Valine | pyridine | cyano | n-heterocyclic | ketone | phosphate ester | fluorine |
| Vitamin K5 | pyridine | cyano | n-heterocyclic | ketone | phosphate ester | fluorine |
| Vitamin K5 | pyridine | cyano | n-heterocyclic | ketone | phosphate ester | fluorine |
| Xylitol | pyridine | cyano | n-heterocyclic | ketone | phosphate ester | fluorine |

| Co-crystal Former | Interacting Group | | | | | | | |
|---|---|---|---|---|---|---|---|---|
| 1,5-Napthalene-disulfonic Acid | | | | | | | | |
| 1-Hydroxy-2-naphthoic acid | imidazole | BF4 | | | | | | |
| 1-Hydroxy-2-naphthoic acid | imidazole | BF4 | | | | | | |
| 4-Aminobenzoic Acid | carbamate | imidazole | BF4 | | N-SO2 | thiourea | iodine | |
| 4-Aminobenzoic Acid | carbamate | imidazole | BF4 | | N-SO2 | thiourea | iodine | |
| 4-aminopyridine | carbamate | imidazole | BF4 | | N-SO2 | thiourea | iodine | |
| 4-aminopyridine | ester | ether | fluorine | acetate | thione | dithiadiazocyclo-pentadienyl | | |
| 4-Chlorobenzene-Sulfonic Acid | | | | | | | | |
| 4-ethoxyphenyl Urea | carbamate | imidazole | BF4 | | N-SO2 | thiourea | iodine | epoxide peroxide |
| 4-ethoxyphenyl Urea | carbamate | imidazole | BF4 | | N-SO2 | thiourea | iodine | |
| 7-oxo-DHEA | imidazole | BF4 | | | | | | |
| 7-oxo-DHEA | carbamate | imidazole | BF4 | | N-SO2 | thiourea | iodine | |
| Acesulfame | | | | | | | | |

TABLE II-continued

| | | | | | | | | | | |
|---|---|---|---|---|---|---|---|---|---|---|
| Acesulfame | carbamate | imidazole | BF4 | | | N-SO2 | thiourea | iodine | epoxide | peroxide |
| Acetohydroxamic Acid | carbamate | imidazole | BF4 | | | N-SO2 | thiourea | iodine | epoxide | peroxide |
| Acetohydroxamic Acid | carbamate | imidazole | BF4 | | | N-SO2 | thiourea | iodine | | |
| Acetohydroxamic Acid | carbamate | imidazole | BF4 | | | N-SO2 | thiourea | iodine | epoxide | |
| Adenine | carbamate | imidazole | BF4 | | | N-SO2 | thiourea | iodine | | |
| Adenine | ester | ether | fluorine | acetate | thione | dithiadiazocyclo-pentadienyl | | | | |
| Adipic acid | carbamate | imidazole | BF4 | | | N-SO2 | thiourea | iodine | | |
| Alanine | carbamate | imidazole | BF4 | | | N-SO2 | thiourea | iodine | | |
| Alanine | carbamate | imidazole | BF4 | | | N-SO2 | thiourea | iodine | | |
| Allopurinaol | carbamate | imidazole | BF4 | | | N-SO2 | thiourea | iodine | epoxide | |
| Allopurinaol | carbamate | imidazole | BF4 | | | N-SO2 | thiourea | iodine | | |
| Arginine | carbamate | imidazole | BF4 | | | N-SO2 | thiourea | iodine | | |
| Arginine | carbamate | imidazole | BF4 | | | N-SO2 | thiourea | iodine | | |
| Ascorbic Acid | carbamate | imidazole | BF4 | | | N-SO2 | thiourea | iodine | | |
| Ascorbic Acid | carbamate | imidazole | BF4 | | | N-SO2 | thiourea | iodine | epoxide | |
| Ascorbic Acid | carbamate | imidazole | BF4 | | | N-SO2 | thiourea | iodine | | |
| Asparagine | carbamate | imidazole | BF4 | | | N-SO2 | thiourea | iodine | | |
| Asparagine | carbamate | imidazole | BF4 | | | N-SO2 | thiourea | iodine | epoxide | peroxide |
| Asparagine | carbamate | imidazole | BF4 | | | N-SO2 | thiourea | iodine | | |
| Aspartic Acid | carbamate | imidazole | BF4 | | | N-SO2 | thiourea | iodine | | |
| Aspartic Acid | carbamate | imidazole | BF4 | | | N-SO2 | thiourea | iodine | | |
| Benzenesulfonic Acid | | | | | | | | | | |
| Benzoic Acid | carbamate | imidazole | BF4 | | | N-SO2 | thiourea | iodine | | |
| Caffeine | carbamate | imidazole | BF4 | | | N-SO2 | thiourea | iodine | | |
| Camphoric acid | carbamate | imidazole | BF4 | | | N-SO2 | thiourea | iodine | | |
| Capric acid | carbamate | imidazole | BF4 | | | N-SO2 | thiourea | iodine | | |
| Genistein | carbamate | imidazole | BF4 | | | N-SO2 | thiourea | iodine | | |
| Genistein | | | | | | | | | | |
| Genistein | phospphate | cyanamide | | | | | | | | |
| Cinnamic acid | carbamate | imidazole | BF4 | | | N-SO2 | thiourea | iodine | | |
| Citric Acid | carbamate | imidazole | BF4 | | | N-SO2 | thiourea | iodine | epoxide | |
| Citric Acid | carbamate | imidazole | BF4 | | | N-SO2 | thiourea | iodine | | |
| Clemizole | ester | ether | fluorine | acetate | thione | dithiadiazocyclo-pentadienyl | | | | |
| Cyclamic Acid | carbamate | imidazole | BF4 | | | N-SO2 | thiourea | iodine | | |
| Cyclamic Acid | | | | | | | | | | |
| Cysteine | carbamate | imidazole | BF4 | | | N-SO2 | thiourea | iodine | | |
| Cysteine | carbamate | imidazole | BF4 | | | N-SO2 | thiourea | iodine | | |
| Cysteine | | | | | | | | | | |
| Dimethylglycine | carbamate | imidazole | BF4 | | | N-SO2 | thiourea | iodine | | |
| Dimethylglycine | carbamate | imidazole | BF4 | | | N-SO2 | thiourea | iodine | | |
| D-ribose | phospphate | cyanamide | | | | | | | | |
| D-ribose | carbamate | imidazole | BF4 | | | N-SO2 | thiourea | iodine | epoxide | |
| Fumaric Acid | carbamate | imidazole | BF4 | | | N-SO2 | thiourea | iodine | | |
| Galactaric acid | carbamate | imidazole | BF4 | | | N-SO2 | thiourea | iodine | | |
| Galactaric acid | imidazole | BF4 | | | | | | | | |
| Chrysin | carbamate | imidazole | BF4 | | | N-SO2 | thiourea | iodine | | |
| Chrysin | | | | | | | | | | |
| Chrysin | phospphate | cyanamide | | | | | | | | |
| Gentisic acid | carbamate | imidazole | BF4 | | | N-SO2 | thiourea | iodine | | |
| Gentisic acid | | | | | | | | | | |
| Glucamine, N-methyl | imidazole | BF4 | | | | | | | | |
| Glucamine, N-methyl | carbamate | imidazole | BF4 | | | N-SO2 | thioursa | iodine | | |
| Gluconic Acid | carbamate | imidazole | BF4 | | | N-SO2 | thiourea | iodine | epoxide | |
| Gluconic Acid | carbamate | imidazole | BF4 | | | N-SO2 | thiourea | iodine | | |
| Glucosamine | carbamate | imidazole | BF4 | | | N-SO2 | thiourea | iodine | epoxide | |
| Glucuronic acid | carbamate | Imidazole | BF4 | | | N-SO2 | thiourea | iodine | | |
| Glucuronic acid | imidazole | BF4 | | | | | | | | |
| Glucuronic acid | carbamate | imidazole | BF4 | alkane | aromatic | N-SO2 | thiourea | iodine | epoxide | |
| Glutamic Acid | carbamate | imidazole | BF4 | | | N-SO2 | thiourea | iodine | | |
| Glutamic Acid | carbamate | imidazole | BF4 | | | N-SO2 | thiourea | iodine | | |
| Glutamine | carbamate | imidazole | BF4 | | | N-SO2 | thiourea | iodine | | |
| Glutamine | carbamate | imidazole | BF4 | | | N-SO2 | thiourea | iodine | epoxide | peroxide |
| Glutamine | carbamate | imidazole | BF4 | | | N-SO2 | thiourea | iodine | | |
| Glutaric Acid | carbamate | imidazole | BF4 | | | N-SO2 | thiourea | iodine | | |
| Glycine | carbamate | imidazole | BF4 | | | N-SO2 | thiourea | iodine | | |
| Glycine | carbamate | imidazole | BF4 | | | N-SO2 | thiourea | iodine | | |
| Glycolic Acid | carbamate | imidazole | BF4 | | | N-SO2 | thiourea | iodine | epoxide | |
| Glycolic Acid | carbamate | imidazole | BF4 | | | N-SO2 | thioures | iodine | | |
| Hippuric Acid | carbamate | imidazole | BF4 | | | N-SO2 | thiourea | iodine | epoxide | peroxide |
| Hippuric Acid | carbamate | imidazole | BF4 | | | N-SO2 | thiourea | iodine | | |
| Hippuric Acid | carbamate | imidazole | BF4 | | | N-SO2 | thiourea | iodine | | |
| Histidine | carbamate | imidazole | BF4 | | | N-SO2 | thiourea | iodine | | |
| Histidine | carbamate | imidazole | BF4 | | | N-SO2 | thiourea | iodine | | |
| Histidine | | | | | | | | | | |

TABLE II-continued

| | | | | | | | | | |
|---|---|---|---|---|---|---|---|---|---|
| Hydroquinone | carbamate | imidazole | BF4 | | | N-SO2 | thiourea | iodine | epoxide |
| Hydroquinone | | | | | | | | | |
| Imidazole | carbamate | imidazole | BF4 | | | N-SO2 | thiourea | iodine | |
| Ipriflavone | phosphate | cyanamide | | | | | | | |
| Ipriflavone | carbamate | imidazole | BF4 | | | N-SO2 | thiourea | iodine | |
| Isoleucine | carbamate | imidazole | BF4 | | | N-SO2 | thiourea | iodine | |
| Isoleucine | carbamate | imidazole | BF4 | | | N-SO2 | thiourea | iodine | |
| lactobionic acid | carbamate | imidazole | BF4 | | | N-SO2 | thiourea | iodine | |
| Lactobionic acid | imidazole | BF4 | | | | | | | |
| Lactobionic acid | phospphate | cyanamide | | | | | | | |
| Lauric acid | carbamate | imidazole | BF4 | | | N-SO2 | thiourea | iodine | |
| Leucine | carbamate | imidazole | BF4 | | | N-SO2 | thiourea | iodine | |
| Leucine | carbamate | imidazole | BF4 | | | N-SO2 | thiourea | iodine | |
| Lysine | carbamate | imidazole | BF4 | | | N-SO2 | thiourea | iodine | |
| Lysine | carbamate | imidazole | BF4 | | | N-SO2 | thiourea | iodine | |
| Maleic | carbamate | imidazole | BF4 | | | N-SO2 | thiourea | iodine | |
| Malic Acid | carbamate | imidazole | BF4 | | | N-SO2 | thiourea | iodine | epoxide |
| Malic Acid | carbamate | imidazole | BF4 | | | N-SO2 | thiourea | iodine | |
| Malonic | carbamate | imidazole | BF4 | | | N-SO2 | thiourea | iodine | |
| Mandelic Acid | carbamate | imidazole | BF4 | | | N-SO2 | thiourea | iodine | epoxide |
| Mandelic Acid | carbamate | imidazole | BF4 | | | N-SO2 | thiourea | iodine | |
| Methionine | carbamate | imidazole | BF4 | | | N-SO2 | thiourea | iodine | |
| Methionine | carbamate | imidazole | BF4 | | | N-SO2 | thiourea | iodine | |
| Methionine | phospphate | | | | | | | | |
| Nicotinamide | ester | ether | fluorine | acetate | thione | dithiadiazocyclopentadienyl | | | |
| Nicotinamide | carbamate | imidazole | BF4 | | | N-SO2 | thiourea | iodine | epoxide peroxide |
| Nicotinic Acid | carbamate | imidazole | BF4 | | | N-SO2 | thiourea | iodine | |
| Nicotinic Acid | ester | ether | fluorine | acetate | thione | dithiadiazocyclopentadienyl | | | |
| Orotic acid | carbamate | imidazole | BF4 | | | N-SO2 | thiourea | iodine | |
| Orotic acid | carbamate | imidazole | BF4 | | | N-SO2 | thiourea | iodine | epoxide peroxide |
| Oxalic acid | carbamate | imidazole | BF4 | | | N-SO2 | thiourea | iodine | |
| Palmitic acid | carbamate | imidazole | BF4 | | | N-SO2 | thiourea | iodine | |
| Pamoic acid | carbamate | imidazole | BF4 | | | N-SO2 | thiourea | iodine | |
| Pamoic acid | imidazole | BF4 | | | | | | | |
| Pamoic acid | | | | | | | | | |
| Phenylalanine | carbamate | imidazole | BF4 | | | N-SO2 | thiourea | iodine | |
| Phenylalanine | carbamate | imidazole | BF4 | | | N-SO2 | thiourea | iodine | |
| Piperazine | carbamate | imidazole | BF4 | | | N-SO2 | thiourea | iodine | |
| Procaine | carbamate | imidazole | BF4 | | | N-SO2 | thioursa | iodine | |
| Procaine | carbamate | imidazole | BF4 | | | N-SO2 | thiourea | iodine | |
| Proline | carbamate | imidazole | BF4 | | | N-SO2 | thiourea | iodine | |
| Proline | carbamate | imidazole | BF4 | | | N-SO2 | thiourea | iodine | |
| p-Toluenesulfonic acid | | | | | | | | | |
| Pyridoxamine | carbamate | imidazole | BF4 | | | N-SO2 | thiourea | iodine | epoxide |
| Pyridoxamine | carbamate | imidazole | BF4 | | | N-SO2 | thiourea | iodine | |
| Pyridoxamine | ester | ether | fluorine | acetate | thione | dithiadiazocyclopentadienyl | | | |
| Pyridoxine (4-Pyridoxic Acid) | ester | ether | fluorine | acetate | thione | dithiadiazocyclopentadienyl | | | |
| Pyridoxine (4-Pyridoxic Acid) | carbamate | imidazole | BF4 | | | N-SO2 | thiourea | iodine | epoxide |
| Pyroglutamic acid | carbamate | imidazole | BF4 | | | N-SO2 | thiourea | iodine | |
| Pyroglutamic acid | carbamate | imidazole | BF4 | | | N-SO2 | thiourea | iodine | epoxide peroxide |
| Quercetin | carbamate | imidazole | BF4 | | | N-SO2 | thiourea | iodine | |
| Quercetin | | | | | | | | | |
| Quercetin | phosphate | cyanamide | | | | | | | |
| Resveratrol | carbamate | imidazole | BF4 | | | N-SO2 | thiourea | iodine | |
| Resveratrol | | | | | | | | | |
| Saccharin | carbamate | imidazole | BF4 | | | N-SO2 | thiourea | iodine | epoxide peroxide |
| Saccharin | carbamate | imidazole | BF4 | | | N-SO2 | thiourea | iodine | |
| Saccharin | | | | | | | | | |
| Saccharin | carbamate | imidazole | BF4 | | | N-SO2 | thiourea | iodine | |
| Salicylic Acid | carbamate | imidazole | BF4 | | | N-SO2 | thiourea | iodine | |
| Salicylic Acid | carbamate | imidazole | BF4 | | | N-SO2 | thiourea | iodine | epoxide |
| Salicylic Acid, 4-amino | carbamate | imidazole | BF4 | | | N-SO2 | thiourea | iodine | |
| Salicylic Acid, 4-amino | imidazole | BF4 | | | | | | | |
| Salicylic Acid, 4-amino | carbamate | imidazole | BF4 | | | N-SO2 | thiourea | iodine | |
| Sebacic acid | carbamate | imidazole | BF4 | | | N-SO2 | thiourea | iodine | |
| Serine | carbamate | imidazole | BF4 | | | N-SO2 | thiourea | iodine | |
| Serine | carbamate | imidazole | BF4 | | | N-SO2 | thiourea | iodine | |
| Serine | carbamate | imidazole | BF4 | | | N-SO2 | thiourea | iodine | epoxide |
| Stearic acid | carbamate | imidazole | BF4 | | | N-SO2 | thiourea | iodine | |
| Succinic Acid | carbamate | imidazole | BF4 | | | N-SO2 | thiourea | iodine | |
| Tartaric Acid | carbamate | imidazole | BF4 | | | N-SO2 | thiourea | iodine | |
| Threonine | carbamate | imidazole | BF4 | | | N-SO2 | thiourea | iodine | |

TABLE II-continued

| | | | | | | | | | |
|---|---|---|---|---|---|---|---|---|---|
| Threonine | carbamate | imidazole | BF4 | | N-SO2 | thiourea | iodine | | |
| Threonine | carbamate | imidazole | BF4 | | N-SO2 | thiourea | iodine | epoxide | |
| Tris | carbamate | imidazole | BF4 | | N-SO2 | thiourea | iodine | | |
| Tris | carbamate | imidazole | BF4 | | N-SO2 | thiourea | iodine | epoxide | |
| Tryptophan | carbamate | imidazole | BF4 | | N-SO2 | thiourea | iodine | | |
| Tryptophan | carbamate | imidazole | BF4 | | N-SO2 | thiourea | iodine | | |
| Tryptophan | ester | ether | fluorine | acetate | thione | dithiadiazocyclo-pentadienyl | | | |
| Tyrosine | carbamate | imidazole | BF4 | | N-SO2 | thiourea | iodine | | |
| Tyrosine | carbamate | imidazole | BF4 | | N-SO2 | thiourea | iodine | | |
| Tyrosine | carbamate | imidazole | BF4 | | N-SO2 | thiourea | iodine | epoxide | |
| Urea | carbamate | imidazole | BF4 | | N-SO2 | thiourea | iodine | | |
| Urea | carbamate | imidazole | BF4 | | N-SO2 | thiourea | iodine | | |
| Urea | carbamate | imidazole | BF4 | | N-SO2 | thiourea | iodine | epoxide | peroxide |
| Valine | carbamate | imidazole | BF4 | | N-SO2 | thiourea | iodine | | |
| Valine | carbamate | imidazole | BF4 | | N-SO2 | thiourea | iodine | | |
| Vitamin K5 | carbamate | imidazole | BF4 | | N-SO2 | thiourea | iodine | | |
| Vitamin K5 | carbamate | imidazole | BF4 | | N-SO2 | thiourea | iodine | epoxide | |
| Xylitol | carbamate | imidazole | BF4 | | N-SO2 | thiourea | iodine | epoxide | |

TABLE III

| Functional Group | Functional Group Structure | Interacting Group | | | | | |
|---|---|---|---|---|---|---|---|
| pyridine | (pyridine structure) | *alcohol | pyridinium | *amide | nitro | *amine | *carboxilic acid |
| Imidazole | (imidazole structure) | imidazole | chlorine | acetamide | carboxylate | thione | nitro |
| Hydroxamic acid | (hydroxamic acid structure) | hydroxamic acid | alcohol | phosphinic ester | alkane | pyridine | amide |
| peroxide | R—O—OH | ester | peroxide | amide | ether | alkane | N-heterocycle |
| epoxide | (epoxide structure) | alkane | bromine | alcohol | ester | epoxide | amide |
| thioester | (thioester structure) | aromatic | thioester | alkane | sulfamide | hydroxy | bromine |
| thioketone | (thioketone structure) | alkane | thioketone | ketone | SULFAMIDE | AMINE | thiol |

| Functional Group | | | | | | | | | | |
|---|---|---|---|---|---|---|---|---|---|---|
| pyridine | *sulfonamide | *ketone | ether | triazole | alkane | ammonium | oxime | *chlorine | alkyne | thiol |
| Imidazole | cyanamide | ketone | cyano | carboxilic acid | alcohol | alkane | thiol | amine | phosphinic acid hemihydrate | chlorine |
| Hydroxamic acid | sulfonamide | carboxylate | phosphine | amine | aromatic | | | | | |
| peroxide | aromatic | alcohol | pyrimidine-dione | analine | thiazole | peroxy acid | ketone | carboxilic acid | azide oxide | phosphine |
| epoxide | alkene | hydrazone | aromatic | thioether | ketone | aldehyde | chlorine | carboxilic acid | alkyne | |
| thioester | iodine | amine | cyano | thioketone | amide | | chlorine | nitro | | |
| thioketone | sulfoxide | oxo | chlorine | bromine | AROMATIC | alkene | sulfone | iodine | AZOXY | potassium |
| pyridine | n-heterocyclic ring | thionedisulfide | pyrroli-dindione | iodine | hydrazone | thiocyanate | *bromine | aromatic | hydroxamic acid | cyano |

TABLE III-continued

| | | | | | | | | | |
|---|---|---|---|---|---|---|---|---|---|
| Imidazole | sulfonyl | sulfoxide | amide | fluorine ester | sulfonate | | | | |
| Hydroxamic acid | | | | | | | | | |
| peroxide | sulfonamide | analine | | | | | | | |
| epoxide | ammonium | fluorine | nitro | amine | cyano | | | | |
| thioester | | | | | | | | | |
| thioketone | epoxide | n-oxide | cyano | iron | cobalt | amine | sulfate | | |
| pyridine | carboxamide | *sulfonic acid | *phosphoric acid | N-oxide | ester | ether | fluorine | acetate | thione | dithiadiazocyclopentadienyl |
| imidazole | | | | | | | | | |
| Hydroxamic acid | | | | | | | | | |
| peroxide | | | | | | | | | |
| epoxide | | | | | | | | | |
| thioester | | | | | | | | | |
| thioketone | | | | | | | | | |
| pyridine | | | | | | | | | |
| imidazole | | | | | | | | | |
| Hydroxamic acid | | | | | | | | | |
| peroxide | | | | | | | | | |
| epoxide | | | | | | | | | |
| thioester | | | | | | | | | |
| thioketone | | | | | | | | | |

| Functional Group | Functional Group Structure | Interacting Group | | | | | |
|---|---|---|---|---|---|---|---|
| nitrate ester | —O—NO$_2$ | aromatic | amide | alkane | chlorine | nitrate ester | bromine |
| Thiophosphate ester-O | —O—P(=S)(O⁻)—OH | amine | imidazole | cyclic amide | | | |
| Phosphate ester | —O—P(=O)(O⁻)—OH | aromatic | alcohol | phosphate ester | aromatic N-ring | pyridine | analine |
| Ketone | R—C(=O)—R | alcohol | ketone | thiol | amide | amine | analine |
| Aldehyde | R—C(=O)—H | alcohol | ketone | thiol | amide | amine | analine |
| Thiol | R—SH | carboxylic acid | sodium | aldehyde | ketone | aromatic-N | cadmium |
| Alcohol | R—OH | alcohol | ketone | thiol | amide | amine | analine |

| Functional Group | | | | | | | | | |
|---|---|---|---|---|---|---|---|---|---|
| nitrate ester | alcohol | ether | acetate | | | | | | |
| Thiophosphate ester-O | | | | | | | | | |
| Phosphate ester | amine | | sodium | potassium | lithium | carboxylic acid | amide | alkane | |
| Ketone | phenol | phosphate | sulfate | sulfone | nitrate | pyridine | aromatic | carboxilic acid | metals | aldehyde |
| Aldehyde | phenol | phosphate | sulfate | sulfone | nitrate | pyridine | aromatic | carboxilic acid | metals | aldehyde |
| Thiol | alkane | arsenic | chlorine | alcohol | potassium | Ru | aromatic | Rb | Sb | |
| Alcohol | phenol | phosphate | sulfate | sulfone | nitrate | pyridine | aromatic | carboxilic acid | metals | aldehyde |

TABLE III-continued

| | | | | | | | | | | |
|---|---|---|---|---|---|---|---|---|---|---|
| nitrate ester | | | | | | | | | | |
| Thiophosphate ester-O | | | | | | | | | | |
| Phosphate ester | | | | | | | | | | |
| Ketone | ester | ether | cyano | | furan | bromine | chlorine | s-heterocyclic | pyridine | cyano |
| Aldehyde | ester | ether | cyano | | furan | bromine | chlorine | s-heterocyclic | pyridine | cyano |
| Thiol | | | | | | | | | | |
| Alcohol | ester | ether | cyano | | furan | bromine | chlorine | s-heterocyclic | pyridine | cyano |
| nitrate ester | | | | | | | | | | |
| Thiophosphate ester-O | | | | | | | | | | |
| Phosphate ester | | | | | | | | | | |
| Ketone | n-heterocyclic | ketone | phosphate ester | fluorine | carbamate | imidazole | BF4 | alkane | aromatic | N-SO2 |
| Aldehyde | n-heteracyclic | ketone | phosphate ester | fluorine | carbamate | imidazole | BF4 | alkane | aromatic | N-SO2 |
| Thiol | | | | | | | | | | |
| Alcohol | n-heterocyclic | ketone | phosphate | fluorine | carbamate | imidazole | BF4 | alkane | aromatic | N-SO2 |
| nitrate ester | | | | | | | | | | |
| Thiophosphate ester-O | | | | | | | | | | |
| Phosphate ester | | | | | | | | | | |
| Ketone | thiourea | iodine | | | | | | | | |
| Aldehyde | thiourea | iodine | epoxide | | | | | | | |
| Thiol | | | | | | | | | | |
| Alcohol | thiourea | iodine | epoxide | | | | | | | |

| Functional Group | Functional Group Structure | Interacting Group | | | | | | |
|---|---|---|---|---|---|---|---|---|
| Thioether | R—S—R | aromatic-N | amide | amine | aromatic_s | Sp2 amine | sulfoxide | |
| Ether | R—O—R | aromatic-N | amide | amine | aromatic_s | Sp2 amine | sulfoxide | |
| Cyanamide | N—C≡N | cyano | amine | potassium | aromatic-N | bromine | sodium | |
| Thiocyanate | —S—C≡N | aromatic-S | ester | ether | | | | |
| sP2 amine | NH=CR2 | thioether | ether | metals | MoOCl4 | BF4 | bromine | |
| Amine primary | R—NH2 | alcohol | ketone | thiol | amide | amine | analine | |
| Amine secondary | R2—NH | alcohol | ketone | thiol | amide | amine | analine | |

| Functional Group | | | | | | | | | | |
|---|---|---|---|---|---|---|---|---|---|---|
| Thioether | chlorate | chlorine | alkyne | cyano | ester | amine | nitro | nitrate | bromine | aldehyde |
| Ether | chlorate | chlorine | alkyne | cyano | ester | amine | nitro | nitrate | bromine | aldehyde |
| Cyanamide | imidazole | ether | n-heterocyclic | alcohol | cesium | Ag | | | | |
| Thiocyanate | | | | | | | | | | |
| sP2 amine | chlorine | | Sp2 amine | sulfate | Osmium | | | | | |
| Amine primary | phenol | phosphate | sulfate | sulfone | nitrate | pyridine | aromatic | carboxilic acid | metals | aldehyde |
| Amine secondary | phenol | phosphate | sulfate | sulfone | nitrate | pyridine | aromatic | carboxilic acid | metals | aldehyde |
| Thioether | ketone | peroxide | epoxide | Ag | Se | heterocyclic-S | iodine | ester | ether | carboxylic acid |
| Ether | ketone | peroxide | epoxide | Ag | Se | heterocyclic-S | iodine | ester | ether | carboxylic acid |
| Cyanamide | | | | | | | | | | |
| Thiocyanate | | | | | | | | | | |
| sP2 amine | | | | | | | | | | |
| Amine | ester | ether | cyano | | furan | bromine | chlorine | s-hetero- | pyridine | cyano |

TABLE III-continued

| | | | | | | | | | | |
|---|---|---|---|---|---|---|---|---|---|---|
| primary Amine | ester | ether | cyano | | furan | cyclic bromine | chlorine | s-hetero-cyclic | pyridine | cyano |
| secondary | | | | | | | | | | |
| Thioether | sulfate | sulfone | alkane | alcohol | | phospphate | | | | |
| Ether | sulfate | sulfone | alkane | alcohol | | phospphate | cyanamide | | | |
| Cyanamide | | | | | | | | | | |
| Thiocyanate | | | | | | | | | | |
| sP2 amine | | | | | | | | | | |
| Amine primary | n-heterocyclic | ketone | phosphate ester | fluorine | carbamate | imidazole | BF4 | alkane | aromatic | N-SO2 |
| Amine secondary | n-heterocyclic | ketone | phosphate | fluorine | carbamate | imidazole | BF4 | alkane | aromatic | N-SO2 |
| Thioether | | | | | | | | | | |
| Ether | | | | | | | | | | |
| Cyanamide | | | | | | | | | | |
| Thiocyanate | | | | | | | | | | |
| sP2 amine | | | | | | | | | | |
| Amine primary | thiourea | iodine | | | | | | | | |
| Amine secondary | thiourea | iodine | | | | | | | | |

| Functional Group | Functional Group Structure | Interacting Group | | | | | |
|---|---|---|---|---|---|---|---|
| Amine tertiary | $R_3-N$ | alcohol | ketone | thiol | amide | amine | analine |
| Amide | $R-C(=O)-NH_2$ | alcohol | ketone | thiol | amide | amine | analine |
| Sulfonic acid | $R-S(=O)(=O)-O^-$ | pyridine | ketone | aldehyde | ether | ester | amide |
| Phosphinic acid | $R-P(=O)(R)-O^-$ | alkane | potassium | lithium | n-heterocyclic | oxime | amide |
| Phosphonic acid | $R-P(=O)(OH)-O^-$ | alkane | potassium | lithium | n-heterocyclic | oxime | amide |
| Carboxylic acid | $R-C(=O)-OH$ | alcohol | ketone | thiol | amide | amine | analine |

| Functional Group | | | | | | | | | |
|---|---|---|---|---|---|---|---|---|---|
| Amine tertiary | phenol | phosphate | sulfate | sulfone | nitrate | pyridine | aromatic | carboxilic acid | metals | aldehyde |
| Amide | phenol | phosphate | sulfate | sulfone | nitrate | pyridine | aromatic | carboxilic acid | metals | aldehyde |
| Sulfonic acid | carboxilic acid | amine | metals | thioether | | sulfate | alcohol | | | |
| Phosphinic acid | phenol | aromatic | amine | alcohol | | metals | | | | |
| Phosphonic acid | phenol | aromatic | amine | alcohol | | metals | carboxilic acid | Sp2 amine | analine | ether |
| Carboxylic acid | phenol | phosphate | sulfate | sulfone | nitrate | pyridine | aromatic | carboxilic acid | metals | aldehyde |
| Amine tertiary | ester | ether | cyano | | furan | bromine | chlorine | s-hetero-cyclic | pyridine | cyano |
| Amide | ester | ether | cyano | | furan | bromine | chlorine | s-hetero-cyclic | pyridine | cyano |
| Sulfonic acid | | | | | | | | | | |
| Phosphinic acid | | | | | | | | | | |
| Phosphonic acid | phosphonic acid | aromatic-N | ketone | aldehyde | imidazole | | | | | |
| Carboxylic | ester | ether | cyano | | furan | bromine | chlorine | s-hetero- | pyridine | cyano |

TABLE III-continued

| | | | | | | | | | | | |
|---|---|---|---|---|---|---|---|---|---|---|---|
| acid | | | | | | | | | cyclic | | |
| Amine tertiary | n-heterocyclic | ketone | phosphate ester | fluorine | carbamate | imidazole | BF4 | alkane | aromatic | N-SO2 |
| Amide | n-heterocyclic | ketone | phosphate ester | fluorine | carbamate | imidazole | BF4 | alkane | aromatic | N-SO2 |
| Sulfonic acid | | | | | | | | | | |
| Phosphinic acid | | | | | | | | | | |
| Phosphonic acid | | | | | | | | | | |
| Carboxylic acid | n-heterocyclic | ketone | phosphate ester | fluorine | carbamate | imidazole | BF4 | alkane | aromatic | N-SO2 |
| Amine tertiary | thiourea | iodine | | | | | | | | |
| Amide | thiourea | iodine | epoxide | peroxide | | | | | | |
| Sulfonic acid | | | | | | | | | | |
| Phosphinic acid | | | | | | | | | | |
| Phosphonic acid | | | | | | | | | | |
| Carboxylic acid | thiourea | iodine | | | | | | | | |

| Functional Group | Functional Group Structure | | | Interacting Group | | | | |
|---|---|---|---|---|---|---|---|---|
| Sulfate ester | $\mathrm{-O-\overset{\overset{O}{\|\|}}{\underset{\underset{O}{\|\|}}{S}}-O^-}$ | pyridine | ketone | aldehyde | ether | ester | amide | |
| Oxime | C=N—OH | alcohol | alkane | amine | amide | ether | ester | |
| Nitrile | —C≡N | metal | ketone | phenol | alcohol | | cyano | |
| Diazo | RH$_2$C—N=N—CH$_2$R | Oxime | | | | | | |
| Nitro | NO$_2$ | pyridine | ketone | aldehyde | ether | ester | amide | |
| S-hetorocyclic ring | (S-containing 5-membered ring with n—n) | alcohol | thioketone | thioether | s-heterocyclic | ketone | aromatic | |
| Thiophene | (thiophene ring) | chlorine | fluorine | amide | ketone | NO | SO | |

| Functional Group | | | | | | | | | | | |
|---|---|---|---|---|---|---|---|---|---|---|---|
| Sulfate ester | carboxilic acid | amine | metals | thioether | sulfate | alcohol | | | | | |
| Oxime | pyridine | n-aromatic | chlorate | chlorine | Sp2-N | diazo | thioketone | cyano | n-oxide | ketone | |
| Nitrile | amine | analine | bromine | amide | alkane | carboxylic acid | chlorine | n-hetero-cyclic | aromatic | potassium | |
| Diazo | | | | | | | | | | | |
| Nitro | carboxilic acid | amine | metals | thioether | sulfate | alcohol | | | | | |
| S-heterocyclic ring | alkene | amine | chlorine | BF4 | sulfate | ester | NO | ether | amide | iodine | |
| Thiophene | CO | | | | | | | | | | |
| Sulfate ester | | | | | | | | | | | |
| Oxime | aldehyde | carboxylic acid | bromine | aromatic | pyridine | BF4 | | | | | |
| Nitrile | aldehyde | thioether | pyridine | n-aromatic | bromine | ether | s-aromatic | thiophene | | | |
| Diazo | | | | | | | | | | | |
| Nitro | | | | | | | | | | | |
| S-hetero-cyclic ring | carboxylic acid | sodium | cyano | chloride | furan | | | | | | |
| Thiophene | | | | | | | | | | | |
| Sulfate ester | | | | | | | | | | | |
| Oxime | | | | | | | | | | | |
| Nitrile | | | | | | | | | | | |

TABLE III-continued

Diazo
Nitro
S-heterocyclic ring
Thiophene
Sulfate ester
Oxime
Nitrile
Diazo
Nitro
S-heterocyclic ring
Thiophene

| Functional Group | Functional Group Structure | Interacting Group | | | | | |
|---|---|---|---|---|---|---|---|
| N-heterocyclic ring | (structure) | alcohol | thioketone | thioether | s-heterocyclic | ketone | aromatic |
| O-heterocyclic ring | (structure) | alcohol | thioketone | thioether | s-heterocyclic | ketone | aromatic |
| Pyrrole | (structure) | chlorine | fluorine | amide | ketone | NO | SO |
| Furan | (structure) | s-heterocyclic | | | | | |

| Functional Group | | | | | | | | | |
|---|---|---|---|---|---|---|---|---|---|
| N-heterocyclic ring | alkene | amine | chlorine | BF4 | sulfate | ester | NO | ether | amide | iodine |
| O-heterocyclic ring | alkene | amine | chlorine | BF4 | sulfate | ester | NO | ether | amide | iodine |
| Pyrrole | CO | imidazole | pyridine | n-aromatic | aldehyde | carboxylic acid | sulfate | chlorine | bromine | oxime |
| Furan | | | | | | | | | | |
| N-heterocyclic ring | carboxylic acid | sodium | cyano | chloride | aldehyde | | | | | |
| O-heterocyclic ring | carboxylic acid | sodium | cyano | chloride | aldehyde | | | | | |
| Pyrrole | alcohol | phenol | ester | ether | | | | | | |
| Furan | | | | | | | | | | |
| N-heterocyclic ring | | | | | | | | | | |
| O-heterocyclic ring | | | | | | | | | | |
| Pyrrole | | | | | | | | | | |
| Furan | | | | | | | | | | |
| N-heterocyclic ring | | | | | | | | | | |

TABLE III-continued

O-hetero-
cyclic
ring
Pyrrole
Furan

What is claimed is:

1. A co-crystal comprising modafinil and a co-crystal former selected from the group consisting of: malonic acid, glycolic acid, fumaric acid, tartaric acid, citric acid, succinic acid, gentisic acid, oxalic acid, 1-hydroxy-2-naphthoic acid, orotic acid, glutaric acid, L-tartaric acid, palmitic acid, L-proline, salicylic acid, lauric acid, L-malic acid, and maleic acid.

2. The co-crystal according to claim 1, wherein:
   (a) the co-crystal is characterized by a powder X-ray diffraction pattern comprising peaks expressed in terms of 2-theta angles, wherein:
      (i) said co-crystal is a modafinil:malonic acid co-crystal and said X-ray diffraction pattern comprises peaks at 5.08, 9.28, and 16.81 degrees;
      (ii) said co-crystal is a modafinil:malonic acid co-crystal and said X-ray diffraction pattern comprises peaks at 16.81, 18.27, and 19.45 degrees;
      (iii) said co-crystal is a modafinil:malonic acid co-crystal and said X-ray diffraction pattern comprises peaks at 9.28, 19.45, and 22.83 degrees;
      (iv) said co-crystal is a modafinil:malonic acid co-crystal and said X-ray diffraction pattern comprises peaks at 5.08 and 9.28 degrees;
      (v) said co-crystal is a modafinil:malonic acid co-crystal and said X-ray diffraction pattern comprises peaks at 16.81 and 19.45 degrees;
      (vi) said co-crystal is a modafinil:malonic acid co-crystal and said X-ray diffraction pattern comprises peaks at 18.27 and 22.83 degrees;
      (vii) said co-crystal is a modafinil:malonic acid co-crystal and said X-ray diffraction pattern comprises a peak at 5.08 degrees;
      (viii) said co-crystal is a modafinil:malonic acid co-crystal and said X-ray diffraction pattern comprises a peak at 9.28 degrees; or
      (ix) said co-crystal is a modafinil:malonic acid co-crystal and said X-ray diffraction pattern comprises a peak at 16.81 degrees;
   (b) the co-crystal is characterized by a DSC thermogram, wherein said co-crystal is a modafinil:malonic acid co-crystal and said DSC thermogram comprises an endothermic transition at about 116 degrees C.; or
   (c) the co-crystal is characterized by a Raman spectrum comprising peaks expressed in terms of cm$^{-1}$, wherein:
      (i) said co-crystal is a modafinil:malonic acid co-crystal and said Raman spectrum comprises peaks at 1004, 633, and 265;
      (ii) said co-crystal is a modafinil:malonic acid co-crystal and said Raman spectrum comprises peaks at 1032, 1601, and 767;
      (iii) said co-crystal is a modafinil:malonic acid co-crystal and said Raman spectrum comprises peaks at 1004 and 633;
      (iv) said co-crystal is a modafinil:malonic acid co-crystal and said Raman spectrum comprises peaks at 1183 and 767; or
      (v) said co-crystal is a modafinil:malonic acid co-crystal and said Raman spectrum comprises peaks at 1601 and 718.

3. The co-crystal according to claim 1, wherein the co-crystal is characterized by a powder X-ray diffraction pattern comprising peaks expressed in terms of 2-theta angles, wherein:
   (a) said co-crystal is a modafinil:glycolic acid co-crystal and said X-ray diffraction pattern comprises peaks at 9.51, 15.97, and 20.03 degrees;
   (b) said co-crystal is a modafinil:glycolic acid co-crystal and said X-ray diffraction pattern comprises peaks at 14.91, 19.01, and 22.75 degrees;
   (c) said co-crystal is a modafinil:glycolic acid co-crystal and said X-ray diffraction pattern comprises peaks at 15.97, 25.03, and 25.71 degrees;
   (d) said co-crystal is a modafinil:glycolic acid co-crystal and said X-ray diffraction pattern comprises peaks at 9.51 and 15.97 degrees;
   (e) said co-crystal is a modafinil:glycolic acid co-crystal and said X-ray diffraction pattern comprises peaks at 20.03 and 25.03 degrees;
   (f) said co-crystal is a modafinil:glycolic acid co-crystal and said X-ray diffraction pattern comprises peaks at 15.97 and 25.03 degrees;
   (g) said co-crystal is a modafinil:glycolic acid co-crystal and said X-ray diffraction pattern comprises a peak at 9.51 degrees;
   (h) said co-crystal is a modafinil:glycolic acid co-crystal and said X-ray diffraction pattern comprises a peak at 15.97 degrees; or
   (i) said co-crystal is a modafinil:glycolic acid co-crystal and said X-ray diffraction pattern comprises a peak at 20.03 degrees.

4. The co-crystal according to claim 1, wherein:
   (a) the co-crystal is characterized by a powder X-ray diffraction pattern comprising peaks expressed in terms of 2-theta angles, wherein:
      (i) said co-crystal is a modafinil:maleic acid co-crystal and said X-ray diffraction pattern comprises peaks at 4.69, 6.15, and 9.61 degrees;
      (ii) said co-crystal is a modafinil:maleic acid co-crystal and said X-ray diffraction pattern comprises peaks at 10.23, 19.97, and 21.83 degrees;
      (iii) said co-crystal is a modafinil:maleic acid co-crystal and said X-ray diffraction pattern comprises peaks at 4.69, 10.23, and 21.83 degrees;
      (iv) said co-crystal is a modafinil:maleic acid co-crystal and said X-ray diffraction pattern comprises peaks at 4.69 and 19.97 degrees;
      (v) said co-crystal is a modafinil:maleic acid co-crystal and said X-ray diffraction pattern comprises peaks at 6.15 and 9.61 degrees;
      (vi) said co-crystal is a modafinil:maleic acid co-crystal and said X-ray diffraction pattern comprises peaks at 4.69 and 6.15 degrees;

(vii) said co-crystal is a modafinil:maleic acid co-crystal and said X-ray diffraction pattern comprises a peak at 4.69 degrees;

(viii) said co-crystal is a modafinil:maleic acid co-crystal and said X-ray diffraction pattern comprises a peak at 9.61 degrees; or (ix) said co-crystal is a modafinil:maleic acid co-crystal and said X-ray diffraction pattern comprises a peak at 19.97 degrees; or (b) the co-crystal is characterized by a DSC thermogram, wherein said co-crystal is a modafinil:maleic acid co-crystal and said DSC thermogram comprises an endothermic transition at about 168 degrees C.

5. The co-crystal according to claim 1, wherein the co-crystal is characterized by a powder X-ray diffraction pattern comprising peaks expressed in terms of 2-theta angles, wherein:

(a) said co-crystal is a modafinil:L-tartaric acid co-crystal and said X-ray diffraction pattern comprises peaks at 6.10, 14.33, and 20.71 degrees;

(b) said co-crystal is a modafinil:L-tartaric acid co-crystal and said X-ray diffraction pattern comprises peaks at 16.93, 20.15, and 22.49 degrees;

(c) said co-crystal is a modafinil:L-tartaric acid co-crystal and said X-ray diffraction pattern comprises peaks at 16.93, 20.71, and 29.72 degrees;

(d) said co-crystal is a modafinil:L-tartaric acid co-crystal and said X-ray diffraction pattern comprises peaks at 6.10 and 20.15 degrees;

(e) said co-crystal is a modafinil:L-tartaric acid co-crystal and said X-ray diffraction pattern comprises peaks at 14.33 and 20.71 degrees;

(f) said co-crystal is a modafinil:L-tartaric acid co-crystal and said X-ray diffraction pattern comprises peaks at 7.36 and 25.04 degrees;

(g) said co-crystal is a modafinil:L-tartaric acid co-crystal and said X-ray diffraction pattern comprises a peak at 6.10 degrees;

(h) said co-crystal is a modafinil:L-tartaric acid co-crystal and said X-ray diffraction pattern comprises a peak at 16.93 degrees; or (i) said co-crystal is a modafinil:L-tartaric acid co-crystal and said X-ray diffraction pattern comprises a peak at 20.71 degrees.

6. The co-crystal according to claim 1, wherein the co-crystal is characterized by a powder X-ray diffraction pattern comprising peaks expressed in terms of 2-theta angles, wherein:

(a) said co-crystal is a modafinil:citric acid co-crystal and said X-ray diffraction pattern comprises peaks at 5.29, 7.29, and 9.31 degrees;

(b) said co-crystal is a modafinil:citric acid co-crystal and said X-ray diffraction pattern comprises peaks at 12.41, 13.29, and 14.61 degrees;

(c) said co-crystal is a modafinil:citric acid co-crystal and said X-ray diffraction pattern comprises peaks at 17.29, 17.97, and 21.37 degrees;

(d) said co-crystal is a modafinil:citric acid co-crystal and said X-ray diffraction pattern comprises peaks at 5.29 and 17.29 degrees;

(e) said co-crystal is a modafinil:citric acid co-crystal and said X-ray diffraction pattern comprises peaks at 7.29 and 9.31 degrees;

(f) said co-crystal is a modafinil:citric acid co-crystal and said X-ray diffraction pattern comprises peaks at 12.41 and 21.37 degrees;

(g) said co-crystal is a modafinil:citric acid co-crystal and said X-ray diffraction pattern comprises a peak at 5.29 degrees;

(h) said co-crystal is a modafinil:citric acid co-crystal and said X-ray diffraction pattern comprises a peak at 7.29 degrees; or (i) said co-crystal is a modafinil:citric acid co-crystal and said X-ray diffraction pattern comprises a peak at 12.41 degrees.

7. The co-crystal according to claim 1, wherein:

(a) the co-crystal is characterized by a powder X-ray diffraction pattern comprising peaks expressed in terms of 2-theta angles, wherein:

(i) said co-crystal is a modafinil:succinic acid co-crystal and said X-ray diffraction pattern comprises peaks at 5.45, 9.93, and 17.99 degrees;

(ii) said co-crystal is a modafinil:succinic acid co-crystal and said X-ray diffraction pattern comprises peaks at 19.95, 21.95, and 25.07 degrees;

(iii) said co-crystal is a modafinil:succinic acid co-crystal and said X-ray diffraction pattern comprises peaks at 5.45, 17.99, and 21.35 degrees;

(iv) said co-crystal is a modafinil:succinic acid co-crystal and said X-ray diffraction pattern comprises peaks at 5.45 and 9.93 degrees;

(v) said co-crystal is a modafinil:succinic acid co-crystal and said X-ray diffraction pattern comprises peaks at 17.99 and 21.95 degrees;

(vi) said co-crystal is a modafinil:succinic acid co-crystal and said X-ray diffraction pattern comprises peaks at 9.93 and 19.95 degrees;

(vii) said co-crystal is a modafinil:succinic acid co-crystal and said X-ray diffraction pattern comprises a peak at 5.45 degrees;

(viii) said co-crystal is a modafinil:succinic acid co-crystal and said X-ray diffraction pattern comprises a peak at 9.93 degrees; or (ix) said co-crystal is a modafinil:succinic acid co-crystal and said X-ray diffraction pattern comprises a peak at 17.99 degrees; or (b) the co-crystal is characterized by a DSC thermogram, wherein said co-crystal is a modafinil:succinic acid co-crystal and said DSC thermogram comprises an endothermic transition at about 149 degrees C.

8. The co-crystal according to claim 1, wherein the co-crystal is characterized by a powder X-ray diffraction pattern comprising peaks expressed in terms of 2-theta angles, wherein:

(a) said co-crystal is a modafinil:DL-tartaric acid co-crystal and said X-ray diffraction pattern comprises peaks at 4.75, 9.53, and 15.83 degrees;

(b) said co-crystal is a modafinil:DL-tartaric acid co-crystal and said X-ray diffraction pattern comprises peaks at 17.61, 20.25, and 22.55 degrees;

(c) said co-crystal is a modafinil:DL-tartaric acid co-crystal and said X-ray diffraction pattern comprises peaks at 10.07, 17.61, and 21.53 degrees;

(d) said co-crystal is a modafinil:DL-tartaric acid co-crystal and said X-ray diffraction pattern comprises peaks at 4.75 and 15.83 degrees;

(e) said co-crystal is a modafinil:DL-tartaric acid co-crystal and said X-ray diffraction pattern comprises peaks at 9.53 and 17.61 degrees;

(f) said co-crystal is a modafinil:DL-tartaric acid co-crystal and said X-ray diffraction pattern comprises peaks at 21.53 and 22.55 degrees;

(g) said co-crystal is a modafinil:DL-tartaric acid co-crystal and said X-ray diffraction pattern comprises a peak at 4.75 degrees;

(h) said co-crystal is a modafinil:DL-tartaric acid co-crystal and said X-ray diffraction pattern comprises a peak at 9.53 degrees; or (i) said co-crystal is a modafinil:DL-tartaric acid co-crystal and said X-ray diffraction pattern comprises a peak at 15.83 degrees.

9. The co-crystal according to claim 1, wherein the co-crystal is characterized by a powder X-ray diffraction pattern comprising peaks expressed in terms of 2-theta angles, wherein:

(a) said co-crystal is a modafinil:fumaric acid co-crystal and said X-ray diffraction pattern comprises peaks at 5.45, 9.95, and 18.03 degrees;

(b) said co-crystal is a modafinil:fumaric acid co-crystal and said X-ray diffraction pattern comprises peaks at 15.93, 18.81, and 21.95 degrees;

(c) said co-crystal is a modafinil:fumaric acid co-crystal and said X-ray diffraction pattern comprises peaks at 9.95, 19.93, and 23.09 degrees;

(d) said co-crystal is a modafinil:fumaric acid co-crystal and said X-ray diffraction pattern comprises peaks at 5.45 and 9.95 degrees;

(e) said co-crystal is a modafinil:fumaric acid co-crystal and said X-ray diffraction pattern comprises peaks at 5.45 and 18.03 degrees;

(f) said co-crystal is a modafinil:fumaric acid co-crystal and said X-ray diffraction pattern comprises peaks at 15.93 and 21.95 degrees;

(g) said co-crystal is a modafinil:fumaric acid co-crystal and said X-ray diffraction pattern comprises a peak at 5.45 degrees;

(h) said co-crystal is a modafinil:fumaric acid co-crystal and said X-ray diffraction pattern comprises a peak at 9.95 degrees; or (i) said co-crystal is a modafinil:fumaric acid co-crystal and said X-ray diffraction pattern comprises a peak at 18.03 degrees.

10. The co-crystal according to claim 9, wherein the co-crystal is modafinil:fumaric acid Form I.

11. The co-crystal according to claim 1, wherein the co-crystal is characterized by a powder X-ray diffraction pattern comprising peaks expressed in terms of 2-theta angles, wherein:

(a) said co-crystal is a modafinil:fumaric acid co-crystal and said X-ray diffraction pattern comprises peaks at 6.47, 8.57, and 9.99 degrees;

(b) said co-crystal is a modafinil:fumaric acid co-crystal and said X-ray diffraction pattern comprises peaks at 13.89, 14.53, and 20.79 degrees;

(c) said co-crystal is a modafinil:fumaric acid co-crystal and said X-ray diffraction pattern comprises peaks at 16.45, 18.39, and 20.05 degrees;

(d) said co-crystal is a modafinil:fumaric acid co-crystal and said X-ray diffraction pattern comprises peaks at 6.47 and 20.79 degrees;

(e) said co-crystal is a modafinil:fumaric acid co-crystal and said X-ray diffraction pattern comprises peaks at 9.99 and 14.53 degrees;

(f) said co-crystal is a modafinil:fumaric acid co-crystal and said X-ray diffraction pattern comprises peaks at 13.89 and 20.05 degrees;

(g) said co-crystal is a modafinil:fumaric acid co-crystal and said X-ray diffraction pattern comprises a peak at 6.47 degrees;

(h) said co-crystal is a modafinil:fumaric acid co-crystal and said X-ray diffraction pattern comprises a peak at 13.89 degrees; or (i) said co-crystal is a modafinil:fumaric acid co-crystal and said X-ray diffraction pattern comprises a peak at 20.79 degrees.

12. The co-crystal according to claim 11, wherein the co-crystal is modafinil:fumaric acid Form II.

13. The co-crystal according to claim 1, wherein the co-crystal is characterized by a powder X-ray diffraction pattern comprising peaks expressed in terms of 2-theta angles, wherein:

(a) said co-crystal is a modafinil:gentisic acid co-crystal and said X-ray diffraction pattern comprises peaks at 6.96, 12.92, and 14.76 degrees;

(b) said co-crystal is a modafinil:gentisic acid co-crystal and said X-ray diffraction pattern comprises peaks at 14.76, 18.26, and 20.10 degrees;

(c) said co-crystal is a modafinil:gentisic acid co-crystal and said X-ray diffraction pattern comprises peaks at 6.96, 17.40, and 20.94 degrees;

(d) said co-crystal is a modafinil:gentisic acid co-crystal and said X-ray diffraction pattern comprises peaks at 6.96 and 14.76 degrees;

(e) said co-crystal is a modafinil:gentisic acid co-crystal and said X-ray diffraction pattern comprises peaks at 12.92 and 17.40 degrees;

(f) said co-crystal is a modafinil:gentisic acid co-crystal and said X-ray diffraction pattern comprises peaks at 6.96 and 18.26 degrees;

(g) said co-crystal is a modafinil:gentisic acid co-crystal and said X-ray diffraction pattern comprises a peak at 6.96 degrees;

(h) said co-crystal is a modafinil:gentisic acid co-crystal and said X-ray diffraction pattern comprises a peak at 14.76 degrees; or (i) said co-crystal is a modafinil:gentisic acid co-crystal and said X-ray diffraction pattern comprises a peak at 18.26 degrees.

14. The co-crystal according to claim 1, wherein the co-crystal is characterized by a powder X-ray diffraction pattern comprising peaks expressed in terms of 2-theta angles, wherein:

(a) said co-crystal is a modafinil:oxalic acid co-crystal and said X-ray diffraction pattern comprises peaks at 5.98, 17.54, and 19.68 degrees;

(b) said co-crystal is a modafinil:oxalic acid co-crystal and said X-ray diffraction pattern comprises peaks at 13.68, 14.80, and 21.12 degrees;

(c) said co-crystal is a modafinil:oxalic acid co-crystal and said X-ray diffraction pattern comprises peaks at 17.54, 19.68, and 21.86 degrees;

(d) said co-crystal is a modafinil:oxalic acid co-crystal and said X-ray diffraction pattern comprises peaks at 5.98 and 19.68 degrees;

(e) said co-crystal is a modafinil:oxalic acid co-crystal and said X-ray diffraction pattern comprises peaks at 13.68 and 14.80 degrees;

(f) said co-crystal is a modafinil:oxalic acid co-crystal and said X-ray diffraction pattern comprises peaks at 5.98 and 17.54 degrees;

(g) said co-crystal is a modafinil:oxalic acid co-crystal and said X-ray diffraction pattern comprises a peak at 5.98 degrees;

(h) said co-crystal is a modafinil:oxalic acid co-crystal and said X-ray diffraction pattern comprises a peak at 19.68 degrees; or (i) said co-crystal is a modafinil:oxalic acid co-crystal and said X-ray diffraction pattern comprises a peak at 17.54 degrees.

15. The co-crystal according to claim 1, wherein the co-crystal is characterized by a powder X-ray diffraction pattern comprising peaks expressed in terms of 2-theta angles, wherein:
   (a) said co-crystal is a modafinil:1-hydroxy-2-naphthoic acid co-crystal and said X-ray diffraction pattern comprises peaks at 5.72, 7.10, and 14.16 degrees;
   (b) said co-crystal is a modafinil:1-hydroxy-2-naphthoic acid co-crystal and said X-ray diffraction pattern comprises peaks at 11.48, 15.66, and 20.26 degrees;
   (c) said co-crystal is a modafinil:1-hydroxy-2-naphthoic acid co-crystal and said X-ray diffraction pattern comprises peaks at 5.72, 7.10, and 20.26 degrees;
   (d) said co-crystal is a modafinil:1-hydroxy-2-naphthoic acid co-crystal and said X-ray diffraction pattern comprises peaks at 5.72 and 7.10 degrees;
   (e) said co-crystal is a modafinil:1-hydroxy-2-naphthoic acid co-crystal and said X-ray diffraction pattern comprises peaks at 14.16 and 20.26 degrees;
   (f) said co-crystal is a modafinil:1-hydroxy-2-naphthoic acid co-crystal and said X-ray diffraction pattern comprises peaks at 5.72 and 14.16 degrees;
   (g) said co-crystal is a modafinil:1-hydroxy-2-naphthoic acid co-crystal and said X-ray diffraction pattern comprises a peak at 5.72 degrees;
   (h) said co-crystal is a modafinil:1-hydroxy-2-naphthoic acid co-crystal and said X-ray diffraction pattern comprises a peak at 7.10 degrees; or
   (i) said co-crystal is a modafinil:1-hydroxy-2-naphthoic acid co-crystal and said X-ray diffraction pattern comprises a peak at 14.16 degrees.

16. The co-crystal according to claim 1, wherein:
   (a) the co-crystal is characterized by a powder X-ray diffraction pattern comprising peaks expressed in terms of 2-theta angles, wherein:
      (i) said co-crystal is a modafinil:malonic acid co-crystal and said X-ray diffraction pattern comprises peaks at 5.04, 9.26, and 16.73 degrees;
      (ii) said co-crystal is a modafinil:malonic acid co-crystal and said X-ray diffraction pattern comprises peaks at 18.23, 19.37, and 22.74 degrees;
      (iii) said co-crystal is a modafinil:malonic acid co-crystal and said X-ray diffraction pattern comprises peaks at 5.04, 16.73, and 19.37 degrees;
      (iv) said co-crystal is a modafinil:malonic acid co-crystal and said X-ray diffraction pattern comprises peaks at 5.04 and 9.26 degrees;
      (v) said co-crystal is a modafinil:malonic acid co-crystal and said X-ray diffraction pattern comprises peaks at 16.73 and 19.37 degrees;
      (vi) said co-crystal is a modafinil:malonic acid co-crystal and said X-ray diffraction pattern comprises peaks at 9.26 and 18.23 degrees;
      (vii) said co-crystal is a modafinil:malonic acid co-crystal and said X-ray diffraction pattern comprises a peak at 5.04 degrees;
      (viii) said co-crystal is a modafinil:malonic acid co-crystal and said X-ray diffraction pattern comprises a peak at 9.26 degrees; or
      (ix) said co-crystal is a modafinil:malonic acid co-crystal and said X-ray diffraction pattern comprises a peak at 19.37 degrees; or
   (b) the co-crystal is characterized by a DSC thermogram, wherein said co-crystal is a modafinil:malonic acid co-crystal and said DSC thermogram comprises an endothermic transition at about 115 degrees C.

17. The co-crystal according to claim 16, wherein the modafinil is R-(−)-modafinil.

18. The co-crystal according to claim 1, wherein:
   (a) the co-crystal is characterized by a powder X-ray diffraction pattern comprising peaks expressed in terms of 2-theta angles, wherein:
      (i) said co-crystal is a modafinil:succinic acid co-crystal and said X-ray diffraction pattern comprises peaks at 5.36, 9.83, and 17.88 degrees;
      (ii) said co-crystal is a modafinil:succinic acid co-crystal and said X-ray diffraction pattern comprises peaks at 15.80, 19.87, and 21.85 degrees;
      (iii) said co-crystal is a modafinil:succinic acid co-crystal and said X-ray diffraction pattern comprises peaks at 5.36, 9.83, and 21.85 degrees;
      (iv) said co-crystal is a modafinil:succinic acid co-crystal and said X-ray diffraction pattern comprises peaks at 5.36 and 9.83 degrees;
      (v) said co-crystal is a modafinil:succinic acid co-crystal and said X-ray diffraction pattern comprises peaks at 17.88 and 19.87 degrees;
      (vi) said co-crystal is a modafinil:succinic acid co-crystal and said X-ray diffraction pattern comprises peaks at 9.83 and 15.80 degrees;
      (vii) said co-crystal is a modafinil:succinic acid co-crystal and said X-ray diffraction pattern comprises a peak at 5.36 degrees;
      (viii) said co-crystal is a modafinil:succinic acid co-crystal and said X-ray diffraction pattern comprises a peak at 9.83 degrees; or
      (ix) said co-crystal is a modafinil:succinic acid co-crystal and said X-ray diffraction pattern comprises a peak at 17.88 degrees; or
   (b) the co-crystal is characterized by a DSC thermogram, wherein said co-crystal is a modafinil:succinic acid co-crystal and said DSC thermogram comprises an endothermic transition at about 145 degrees C.

19. The co-crystal according to claim 18, wherein the modafinil is R-(−)-modafinil.

20. The co-crystal according to claim 1, wherein:
   (a) the co-crystal is characterized by a powder X-ray diffraction pattern comprising peaks expressed in terms of 2-theta angles, wherein:
      (i) said co-crystal is a modafinil:citric acid co-crystal and said X-ray diffraction pattern comprises peaks at 5.18, 7.23, and 9.23 degrees;
      (ii) said co-crystal is a modafinil:citric acid co-crystal and said X-ray diffraction pattern comprises peaks at 12.32, 13.23, and 17.25 degrees;
      (iii) said co-crystal is a modafinil:citric acid co-crystal and said X-ray diffraction pattern comprises peaks at 9.23, 17.92, and 21.30 degrees;
      (iv) said co-crystal is a modafinil:citric acid co-crystal and said X-ray diffraction pattern comprises peaks at 5.18 and 9.23 degrees;
      (v) said co-crystal is a modafinil:citric acid co-crystal and said X-ray diffraction pattern comprises peaks at 7.23 and 13.23 degrees;
      (vi) said co-crystal is a modafinil:citric acid co-crystal and said X-ray diffraction pattern comprises peaks at 17.25 and 17.92 degrees;
      (vii) said co-crystal is a modafinil:citric acid co-crystal and said X-ray diffraction pattern comprises a peak at 5.18 degrees;

(viii) said co-crystal is a modafinil:citric acid co-crystal and said X-ray diffraction pattern comprises a peak at 7.23 degrees; or (ix) said co-crystal is a modafinil:citric acid co-crystal and said X-ray diffraction pattern comprises a peak at 9.23 degrees; or (b) the co-crystal is characterized by a DSC thermogram, wherein said co-crystal is a modafinil:citric acid co-crystal and said DSC thermogram comprises an endothermic transition at about 89 degrees C.

21. The co-crystal according to claim 20, wherein the modafinil is R-(−)-modafinil.

22. The co-crystal according to claim 1, wherein the co-crystal is characterized by a powder X-ray diffraction pattern comprising peaks expressed in terms of 2-theta angles, wherein:

(a) said co-crystal is a modafinil:1-hydroxy-2-naphthoic acid co-crystal and said X-ray diffraction pattern comprises peaks at 5.27, 8.85, and 10.60 degrees;

(b) said co-crystal is a modafinil:1-hydroxy-2-naphthoic acid co-crystal and said X-ray diffraction pattern comprises peaks at 10.60, 14.47, and 21.20 degrees;

(c) said co-crystal is a modafinil:1-hydroxy-2-naphthoic acid co-crystal and said X-ray diffraction pattern comprises peaks at 5.27, 14.47, and 23.03 degrees;

(d) said co-crystal is a modafinil:1-hydroxy-2-naphthoic acid co-crystal and said X-ray diffraction pattern comprises peaks at 5.27 and 8.85 degrees;

(e) said co-crystal is a modafinil:1-hydroxy-2-naphthoic acid co-crystal and said X-ray diffraction pattern comprises peaks at 10.60 and 23.03 degrees;

(f) said co-crystal is a modafinil:1-hydroxy-2-naphthoic acid co-crystal and said X-ray diffraction pattern comprises peaks at 14.47 and 21.20 degrees;

(g) said co-crystal is a modafinil:1-hydroxy-2-naphthoic acid co-crystal and said X-ray diffraction pattern comprises a peak at 5.27 degrees;

(h) said co-crystal is a modafinil:1-hydroxy-2-naphthoic acid co-crystal and said X-ray diffraction pattern comprises a peak at 8.85 degrees; or (i) said co-crystal is a modafinil:1-hydroxy-2-naphthoic acid co-crystal and said X-ray diffraction pattern comprises a peak at 14.47 degrees.

23. The co-crystal according to claim 22, wherein the modafinil is R-(−)-modafinil.

24. The co-crystal according to claim 1, wherein the co-crystal is characterized by a powder X-ray diffraction pattern comprising peaks expressed in terms of 2-theta angles, wherein:

(a) said co-crystal is a modafinil:DL-tartaric acid co-crystal and said X-ray diffraction pattern comprises peaks at 4.67, 15.41, and 19.46 degrees;

(b) said co-crystal is a modafinil:DL-tartaric acid co-crystal and said X-ray diffraction pattern comprises peaks at 17.97, 19.46, and 22.91 degrees;

(c) said co-crystal is a modafinil:DL-tartaric acid co-crystal and said X-ray diffraction pattern comprises peaks at 4.67, 22.91, and 24.63 degrees;

(d) said co-crystal is a modafinil:DL-tartaric acid co-crystal and said X-ray diffraction pattern comprises peaks at 4.67 and 19.46 degrees;

(e) said co-crystal is a modafinil:DL-tartaric acid co-crystal and said X-ray diffraction pattern comprises peaks at 17.97 and 22.91 degrees;

(f) said co-crystal is a modafinil:DL-tartaric acid co-crystal and said X-ray diffraction pattern comprises peaks at 15.41 and 24.63 degrees;

(g) said co-crystal is a modafinil:DL-tartaric acid co-crystal and said X-ray diffraction pattern comprises a peak at 4.67 degrees;

(h) said co-crystal is a modafinil:DL-tartaric acid co-crystal and said X-ray diffraction pattern comprises a peak at 19.46 degrees; or (i) said co-crystal is a modafinil:DL-tartaric acid co-crystal and said X-ray diffraction pattern comprises a peak at 22.91 degrees.

25. The co-crystal according to claim 24, wherein the modafinil is R-(−)-modafinil.

26. The co-crystal according to claim 1, wherein the co-crystal is characterized by a powder X-ray diffraction pattern comprising peaks expressed in terms of 2-theta angles, wherein:

(a) said co-crystal is a modafinil:orotic acid co-crystal and said X-ray diffraction pattern comprises peaks at 9.77, 17.85, and 20.52 degrees;

(b) said co-crystal is a modafinil:orotic acid co-crystal and said X-ray diffraction pattern comprises peaks at 17.85, 24.03, and 26.80 degrees;

(c) said co-crystal is a modafinil:orotic acid co-crystal and said X-ray diffraction pattern comprises peaks at 9.77, 20.52, and 24.03 degrees;

(d) said co-crystal is a modafinil:orotic acid co-crystal and said X-ray diffraction pattern comprises peaks at 9.77 and 17.85 degrees;

(e) said co-crystal is a modafinil:orotic acid co-crystal and said X-ray diffraction pattern comprises peaks at 17.85 and 24.03 degrees;

(f) said co-crystal is a modafinil:orotic acid co-crystal and said X-ray diffraction pattern comprises peaks at 9.77 and 26.80 degrees;

(g) said co-crystal is a modafinil:orotic acid co-crystal and said X-ray diffraction pattern comprises a peak at 9.77 degrees;

(h) said co-crystal is a modafinil:orotic acid co-crystal and said X-ray diffraction pattern comprises a peak at 17.85 degrees; or (i) said co-crystal is a modafinil:orotic acid co-crystal and said X-ray diffraction pattern comprises a peak at 24.03 degrees.

27. The co-crystal according to claim 26, wherein the modafinil is R-(−)-modafinil.

28. A pharmaceutical composition comprising a modafinil solvate wherein the solvent is selected from the group consisting of: acetic acid, tetrahydrofuran, 1,4-dioxane, methanol, nitromethane, acetone, o-xylene, benzene, ethanol, benzyl alcohol, isopropanol, acetonitrile, and toluene.

29. The pharmaceutical composition of claim 28 wherein the composition is a solvate form and is characterized by a powder X-ray diffraction pattern comprising peaks expressed in terms of 2-theta angles, wherein:

(a) said form is a modafinil acetic acid solvate and said X-ray diffraction pattern comprises peaks at 6.17, 9.63, and 19.99 degrees;

(b) said form is a modafinil acetic acid solvate and said X-ray diffraction pattern comprises peaks at 6.17 and 9.63 degrees;

(c) said form is a modafinil acetic acid solvate and said X-ray diffraction pattern comprises peaks at 19.99 and 21.83 degrees;

(d) said form is a modafinil acetic acid solvate and said X-ray diffraction pattern comprises peaks at 9.63 and 19.99 degrees; or (e) said form is a modafinil acetic acid solvate and said X-ray diffraction pattern comprises a peak at 6.17 degrees.

30. The pharmaceutical composition of claim 28 wherein the composition is a solvate form and is characterized by a powder X-ray diffraction pattern comprising peaks expressed in terms of 2-theta angles, wherein:
(a) said form is a modafinil tetrahydrofuran solvate and said X-ray diffraction pattern comprises peaks at 6.97, 9.79, and 10.97 degrees;
(b) said form is a modafinil tetrahydrofuran solvate and said X-ray diffraction pattern comprises peaks at 10.97 and 20.59 degrees;
(c) said form is a modafinil tetrahydrofuran solvate and said X-ray diffraction pattern comprises peaks at 9.79 and 19.03 degrees;
(d) said form is a modafinil tetrahydrofuran solvate and said X-ray diffraction pattern comprises peaks at 6.97 and 16.19 degrees; or
(e) said form is a modafinil tetrahydrofuran solvate and said X-ray diffraction pattern comprises a peak at 6.97 degrees.

31. The pharmaceutical composition of claim 28 wherein the composition is a solvate form and is characterized by a powder X-ray diffraction pattern comprising peaks expressed in terms of 2-theta angles, wherein:
(a) said form is a modafinil 1,4-dioxane solvate and said X-ray diffraction pattern comprises peaks at 6.93, 9.85, and 10.97 degrees;
(b) said form is a modafinil 1,4-dioxane solvate and said X-ray diffraction pattern comprises peaks at 6.93 and 20.65 degrees;
(c) said form is a modafinil 1,4-dioxane solvate and said X-ray diffraction pattern comprises peaks at 10.97 and 18.97 degrees;
(d) said form is a modafinil 1,4-dioxane solvate and said X-ray diffraction pattern comprises peaks at 16.19 and 23.33 degrees; or
(e) said form is a modafinil 1,4-dioxane solvate and said X-ray diffraction pattern comprises a peak at 6.93 degrees.

32. The pharmaceutical composition of claim 28 wherein the composition is a solvate form and is characterized by a powder X-ray diffraction pattern comprising peaks expressed in terms of 2-theta angles, wherein:
(a) said form is a modafinil methanol solvate and said X-ray diffraction pattern comprises peaks at 6.15, 9.89, and 20.07 degrees;
(b) said form is a modafinil methanol solvate and said X-ray diffraction pattern comprises peaks at 6.15 and 9.89 degrees;
(c) said form is a modafinil methanol solvate and said X-ray diffraction pattern comprises peaks at 12.25 and 17.97 degrees;
(d) said form is a modafinil methanol solvate and said X-ray diffraction pattern comprises peaks at 20.07 and 21.85 degrees; or
(e) said form is a modafinil methanol solvate and said X-ray diffraction pattern comprises a peak at 6.15 degrees.

33. The pharmaceutical composition of claim 28 wherein the composition is a solvate form and is characterized by a powder X-ray diffraction pattern comprising peaks expressed in terms of 2-theta angles, wherein:
(a) said form is a modafinil nitromethane solvate and said X-ray diffraction pattern comprises peaks at 6.17, 9.77, and 20.07 degrees;
(b) said form is a modafinil nitromethane solvate and said X-ray diffraction pattern comprises peaks at 12.29 and 15.89 degrees;
(c) said form is a modafinil nitromethane solvate and said X-ray diffraction pattern comprises peaks at 6.17 and 20.07 degrees;
(d) said form is a modafinil nitromethane solvate and said X-ray diffraction pattern comprises peaks at 9.77 and 22.17 degrees; or
(e) said form is a modafinil nitromethane solvate and said X-ray diffraction pattern comprises a peak at 6.17 degrees.

34. The pharmaceutical composition of claim 28 wherein the composition is a solvate form and is characterized by a powder X-ray diffraction pattern comprising peaks expressed in terms of 2-theta angles, wherein:
(a) said form is a modafinil acetone solvate and said X-ray diffraction pattern comprises peaks at 6.11, 9.53, and 15.81 degrees;
(b) said form is a modafinil acetone solvate and said X-ray diffraction pattern comprises peaks at 6.11 and 9.53 degrees;
(c) said form is a modafinil acetone solvate and said X-ray diffraction pattern comprises peaks at 15.81 and 20.03 degrees;
(d) said form is a modafinil acetone solvate and said X-ray diffraction pattern comprises peaks at 18.11 and 21.63 degrees; or
(e) said form is a modafinil acetone solvate and said X-ray diffraction pattern comprises a peak at 6.11 degrees.

35. The co-crystal of claim 1, wherein the modafinil is R-(−)-modafinil.

36. The co-crystal of claim 1, wherein the modafinil is S-(+)-modafinil.

37. A method for treating a subject suffering from excessive daytime sleepiness associated with narcolepsy, multiple sclerosis related fatigue, infertility, eating disorders, attention deficit hyperactivity disorder (ADHD), Parkinson's disease, incontinence, sleep apnea, or myopathies, which comprises administering to a subject a therapeutically effective amount of a co-crystal comprising modafinil.

38. The method according to claim 37, wherein the subject is a human subject.

39. The pharmaceutical composition of claim 28 wherein the composition is a solvate form and is characterized by a powder X-ray diffraction pattern comprising peaks expressed in terms of 2-theta angles, wherein:
(a) said form is a R-(−)-modafinil benzyl alcohol solvate and said X-ray diffraction pattern comprises peaks at 7.76, 18.57, and 21.53 degrees;
(b) said form is a R-(−)-modafinil benzyl alcohol solvate and said X-ray diffraction pattern comprises peaks at 5.77 and 7.76 degrees;
(c) said form is a R-(−)-modafinil benzyl alcohol solvate and said X-ray diffraction pattern comprises peaks at 18.57 and 21.53 degrees;
(d) said form is a R-(−)-modafinil benzyl alcohol solvate and said X-ray diffraction pattern comprises peaks at 10.48 and 27.73 degrees; or
(e) said form is a R-(−)-modafinil benzyl alcohol solvate and said X-ray diffraction pattern comprises a peak at 7.76 degrees.

40. The pharmaceutical composition of claim 28 wherein the composition is a solvate form and is characterized by a powder X-ray diffraction pattern comprising peaks expressed in terms of 2-theta angles, wherein:

(a) said form is a R-(−)-modafinil isopropanol solvate and said X-ray diffraction pattern comprises peaks at 5.76, 7.77, and 21.53 degrees;

(b) said form is a R-(−)-modafinil isopropanol solvate and said X-ray diffraction pattern comprises peaks at 10.49 and 18.58 degrees;

(c) said form is a R-(−)-modafinil isopropanol solvate and said X-ray diffraction pattern comprises peaks at 7.77 and 18.58 degrees;

(d) said form is a R-(−)-modafinil isopropanol solvate and said X-ray diffraction pattern comprises peaks at 5.76 and 15.79 degrees; or (e) said form is a R-(−)-modafinil isopropanol solvate and said X-ray diffraction pattern comprises a peak at 7.77 degrees.

41. The pharmaceutical composition of claim 28 wherein the composition is a solvate form and is characterized by a powder X-ray diffraction pattern comprising peaks expressed in terms of 2-theta angles, wherein:

(a) said form is a R-(−)-modafinil acetonitrile solvate and said X-ray diffraction pattern comprises peaks at 6.17, 8.16, and 21.86 degrees;

(b) said form is a R-(−)-modafinil acetonitrile solvate and said X-ray diffraction pattern comprises peaks at 6.17 and 11.19 degrees;

(c) said form is a R-(−)-modafinil acetonitrile solvate and said X-ray diffraction pattern comprises peaks at 8.16 and 10.19 degrees;

(d) said form is a R-(−)-modafinil acetonitrile solvate and said X-ray diffraction pattern comprises peaks at 6.17 and 8.16 degrees; or (e) said form is a R-(−)-modafinil acetonitrile solvate and said X-ray diffraction pattern comprises a peak at 6.17 degrees.

42. The pharmaceutical composition of claim 28 wherein the composition is a solvate form and is characterized by a powder X-ray diffraction pattern comprising peaks expressed in terms of 2-theta angles, wherein:

(a) said form is a R-(−)-modafinil ethanol solvate and said X-ray diffraction pattern comprises peaks at 6.13, 9.59, and 20.05 degrees;

(b) said form is a R-(−)-modafinil ethanol solvate and said X-ray diffraction pattern comprises peaks at 15.69 and 21.55 degrees;

(c) said form is a R-(−)-modafinil ethanol solvate and said X-ray diffraction pattern comprises peaks at 9.59 and 20.05 degrees;

(d) said form is a R-(−)-modafinil ethanol solvate and said X-ray diffraction pattern comprises peaks at 6.13 and 15.69 degrees; or (e) said form is a R-(−)-modafinil ethanol solvate and said X-ray diffraction pattern comprises a peak at 6.13 degrees.

43. The co-crystal according to claim 1, wherein the co-crystal is characterized by a powder X-ray diffraction pattern comprising peaks expressed in terms of 2-theta angles, wherein:

(a) said co-crystal is a modafinil:gentisic acid co-crystal and said X-ray diffraction pattern comprises peaks at 7.07, 9.07, and 12.31 degrees;

(b) said co-crystal is a modafinil-gentisic acid co-crystal and said X-ray diffraction pattern comprises peaks at 9.07, 18.39, and 21.27 degrees;

(c) said co-crystal is a modafinil:gentisic acid co-crystal and said X-ray diffraction pattern comprises peaks at 17.63, 23.57, and 26.93 degrees;

(d) said co-crystal is a modafinil:gentisic acid co-crystal and said X-ray diffraction pattern comprises peaks at 9.07 and 16.03 degrees;

(e) said co-crystal is a modafinil:gentisic acid co-crystal and said X-ray diffraction pattern comprises peaks at 7.51 and 21.27 degrees;

(f) said co-crystal is a modafinil:gentisic acid co-crystal and said X-ray diffraction pattern comprises peaks at 7.07 and 7.51 degrees;

(g) said co-crystal is a modafinil:gentisic acid co-crystal and said X-ray diffraction pattern comprises a peak at 9.07 degrees;

(h) said co-crystal is a modafinil:gentisic acid co-crystal and said X-ray diffraction pattern comprises a peak at 7.07 degrees;

(i) said co-crystal is a modafinil:gentisic acid co-crystal and said X-ray diffraction pattern comprises a peak at 16.03 degrees;

(j) said co-crystal is a modafinil:gentisic acid co-crystal and said X-ray diffraction pattern comprises peaks at 7.07, 9.07, 16.03, 18.39, 21.27, and 23.57 degrees; or (k) said co-crystal is a modafinil:gentisic acid co-crystal and said X-ray diffraction pattern comprises peaks at 7.51, 12.31, 14.09, 16.03, 17.63, and 23.57 degrees.

44. The co-crystal according to claim 1, wherein the co-crystal is characterized by a powder X-ray diffraction pattern comprising peaks expressed in terms of 2-theta angles, wherein:

(a) said co-crystal is a modafinil:glutaric acid co-crystal and said X-ray diffraction pattern comprises peaks at 9.78, 18.92, and 21.36 degrees;

(b) said co-crystal is a modafinil:glutaric acid co-crystal and said X-ray diffraction pattern comprises peaks at 20.50, 22.25, and 23.87 degrees;

(c) said co-crystal is a modafinil:glutaric acid co-crystal and said X-ray diffraction pattern comprises peaks at 8.67, 19.74, and 27.16 degrees;

(d) said co-crystal is a modafinil:glutaric acid co-crystal and said X-ray diffraction pattern comprises peaks at 8.67 and 18.92 degrees;

(e) said co-crystal is a modafinil:glutaric acid co-crystal and said X-ray diffraction pattern comprises peaks at 9.78 and 20.50 degrees;

(f) said co-crystal is a modafinil:glutaric acid co-crystal and said X-ray diffraction pattern comprises peaks at 21.36 and 23.87 degrees;

(g) said co-crystal is a modafinil:glutaric acid co-crystal and said X-ray diffraction pattern comprises a peak at 23.87 degrees;

(h) said co-crystal is a modafinil:glutaric acid co-crystal and said X-ray diffraction pattern comprises a peak at 8.67 degrees;

(i) said co-crystal is a modafinil:glutaric acid co-crystal and said X-ray diffraction pattern comprises a peak at 9.78 degrees;

(j) said co-crystal is a modafinil:glutaric acid co-crystal and said X-ray diffraction pattern comprises peaks at 8.67, 9.78, 18.92, 20.50, and 23.87 degrees; or (k) said co-crystal is a modafinil:glutaric acid co-crystal and said X-ray diffraction pattern comprises peaks at 18.92, 20.50, 21.36, 22.25, and 23.87 degrees.

45. The co-crystal according to claim 1, wherein the co-crystal is characterized by a powder X-ray diffraction pattern comprising peaks expressed in terms of 2-theta angles, wherein:

(a) said co-crystal is a modafinil:citric acid co-crystal and said X-ray diffraction pattern comprises peaks at 7.06, 9.10, and 17.95 degrees;
(b) said co-crystal is a modafinil:citric acid co-crystal and said X-ray diffraction pattern comprises peaks at 12.43, 13.18, and 20.85 degrees;
(c) said co-crystal is a modafinil:citric acid co-crystal and said X-ray diffraction pattern comprises peaks at 5.23, 7.06, and 9.10 degrees;
(d) said co-crystal is a modafinil:citric acid co-crystal and said X-ray diffraction pattern comprises peaks at 5.23 and 12.43 degrees;
(e) said co-crystal is a modafinil:citric acid co-crystal and said X-ray diffraction pattern comprises peaks at 9.10 and 17.95 degrees;
(f) said co-crystal is a modafinil:citric acid co-crystal and said X-ray diffraction pattern comprises peaks at 9.10 and 12.43 degrees;
(g) said co-crystal is a modafinil:citric acid co-crystal and said X-ray diffraction pattern comprises a peak at 7.06 degrees;
(h) said co-crystal is a modafinil:citric acid co-crystal and said X-ray diffraction pattern comprises a peak at 9.10 degrees;
(i) said co-crystal is a modafinil:citric acid co-crystal and said X-ray diffraction pattern comprises a peak at 17.95 degrees;
(j) said co-crystal is a modafinil:citric acid co-crystal and said X-ray diffraction pattern comprises peaks at 7.06, 12.43, 13.18, 17.95, and 20.85 degrees; or
(k) said co-crystal is a modafinil:citric acid co-crystal and said X-ray diffraction pattern comprises peaks at 7.06, 9.10, 17.95, 21.39, and 22.96 degrees.

46. The co-crystal according to claim 1, wherein the co-crystal is characterized by a powder X-ray diffraction pattern comprising peaks expressed in terms of 2-theta angles, wherein:
(a) said co-crystal is a modafinil:L-tartaric acid co-crystal and said X-ray diffraction pattern comprises peaks at 4.56, 10.33, and 17.29 degrees;
(b) said co-crystal is a modafinil:L-tartaric acid co-crystal and said X-ray diffraction pattern comprises peaks at 17.29, 19.91, and 21.13 degrees;
(c) said co-crystal is a modafinil:L-tartaric acid co-crystal and said X-ray diffraction pattern comprises peaks at 4.56, 14.45, and 19.91 degrees;
(d) said co-crystal is a modafinil:L-tartaric acid co-crystal and said X-ray diffraction pattern comprises peaks at 4.56 and 10.33 degrees;
(e) said co-crystal is a modafinil:L-tartaric acid co-crystal and said X-ray diffraction pattern comprises peaks at 17.29 and 19.91 degrees;
(f) said co-crystal is a modafinil:L-tartaric acid co-crystal and said X-ray diffraction pattern comprises peaks at 19.91 and 21.13 degrees;
(g) said co-crystal is a modafinil:L-tartaric acid co-crystal and said X-ray diffraction pattern comprises a peak at 4.56 degrees;
(h) said co-crystal is a modafinil:L-tartaric acid co-crystal and said X-ray diffraction pattern comprises a peak at 10.33 degrees;
(i) said co-crystal is a modafinil:L-tartaric acid co-crystal and said X-ray diffraction pattern comprises a peak at 19.91 degrees; or
(j) said co-crystal is a modafinil:L-tartaric acid co-crystal and said X-ray diffraction pattern comprises peaks at 4.56, 10.33, 17.29, 19.91, and 21.13 degrees.

47. The co-crystal according to claim 1, wherein the co-crystal is characterized by a powder X-ray diffraction pattern comprising peaks expressed in terms of 2-theta angles, wherein:
(a) said co-crystal is a modafinil:oxalic acid co-crystal and said X-ray diffraction pattern comprises peaks at 5.99, 14.73, and 17.38 degrees;
(b) said co-crystal is a modafinil:oxalic acid co-crystal and said X-ray diffraction pattern comprises peaks at 17.38, 18.64, and 28.85 degrees;
(c) said co-crystal is a modafinil:oxalic acid co-crystal and said X-ray diffraction pattern comprises peaks at 14.73, 18.64, and 25.66 degrees;
(d) said co-crystal is a modafinil:oxalic acid co-crystal and said X-ray diffraction pattern comprises peaks at 5.99 and 14.73 degrees;
(e) said co-crystal is a modafinil:oxalic acid co-crystal and said X-ray diffraction pattern comprises peaks at 17.38 and 18.64 degrees;
(f) said co-crystal is a modafinil:oxalic acid co-crystal and said X-ray diffraction pattern comprises peaks at 5.99 and 28.85 degrees;
(g) said co-crystal is a modafinil:oxalic acid co-crystal and said X-ray diffraction pattern comprises a peak at 5.99 degrees;
(h) said co-crystal is a modafinil:oxalic acid co-crystal and said X-ray diffraction pattern comprises a peak at 14.73 degrees;
(i) said co-crystal is a modafinil:oxalic acid co-crystal and said X-ray diffraction pattern comprises a peak at 28.85 degrees; or
(j) said co-crystal is a modafinil:oxalic acid co-crystal and said X-ray diffraction pattern comprises peaks at 5.99, 14.73, 17.38, 18.64, and 28.85 degrees.

48. The co-crystal according to claim 1, wherein the co-crystal is characterized by a powder X-ray diffraction pattern comprising peaks expressed in terms of 2-theta angles, wherein:
(a) said co-crystal is a modafinil:palmitic acid co-crystal and said X-ray diffraction pattern comprises peaks at 3.80, 6.55, and 7.66 degrees;
(b) said co-crystal is a modafinil:palmitic acid co-crystal and said X-ray diffraction pattern comprises peaks at 10.24, 19.48, and 21.09 degrees;
(c) said co-crystal is a modafinil:palmitic acid co-crystal and said X-ray diffraction pattern comprises peaks at 3.80, 19.48, and 23.99 degrees;
(d) said co-crystal is a modafinil:palmitic acid co-crystal and said X-ray diffraction pattern comprises peaks at 3.80 and 6.55 degrees;
(e) said co-crystal is a modafinil:palmitic acid co-crystal and said X-ray diffraction pattern comprises peaks at 6.55 and 7.66 degrees;
(f) said co-crystal is a modafinil:palmitic acid co-crystal and said X-ray diffraction pattern comprises peaks at 19.48 and 23.99 degrees;
(g) said co-crystal is a modafinil:palmitic acid co-crystal and said X-ray diffraction pattern comprises a peak at 3.80 degrees;
(h) said co-crystal is a modafinil:palmitic acid co-crystal and said X-ray diffraction pattern comprises a peak at 6.55 degrees;
(i) said co-crystal is a modafinil:palmitic acid co-crystal and said X-ray diffraction pattern comprises a peak at 7.66 degrees;

(j) said co-crystal is a modafinil:palmitic acid co-crystal and said X-ray diffraction pattern comprises peaks at 3.80, 7.66, 10.24, and 19.48 degrees; or (k) said co-crystal is a modafinil:palmitic acid co-crystal and said X-ray diffraction pattern comprises peaks at 3.80, 6.55, 7.66, 10.24, 19.48, and 23.99 degrees.

49. The co-crystal according to claim 1, wherein the co-crystal is characterized by a powder X-ray diffraction pattern comprising peaks expressed in terms of 2-theta angles, wherein:

(a) said co-crystal is a modafinil:L-proline co-crystal and said X-ray diffraction pattern comprises peaks at 6.52, 8.53, and 10.25 degrees;

(b) said co-crystal is a modafinil:L-proline co-crystal and said X-ray diffraction pattern comprises peaks at 19.06, 22.75, and 25.08 degrees;

(c) said co-crystal is a modafinil:L-proline co-crystal and said X-ray diffraction pattern comprises peaks at 6.52, 10.25, and 19.06 degrees;

(d) said co-crystal is a modafinil:L-proline co-crystal and said X-ray diffraction pattern comprises peaks at 6.52 and 8.53 degrees;

(e) said co-crystal is a modafinil:L-proline co-crystal and said X-ray diffraction pattern comprises peaks at 6.52 and 10.25 degrees;

(f) said co-crystal is a modafinil:L-proline co-crystal and said X-ray diffraction pattern comprises peaks at 19.06 and 22.29 degrees;

(g) said co-crystal is a modafinil:L-proline co-crystal and said X-ray diffraction pattern comprises a peak at 6.52 degrees;

(h) said co-crystal is a modafinil:L-proline co-crystal and said X-ray diffraction pattern comprises a peak at 8.53 degrees;

(i) said co-crystal is a modafinil:L-proline co-crystal and said X-ray diffraction pattern comprises a peak at 19.06 degrees;

(j) said co-crystal is a modafinil:L-proline co-crystal and said X-ray diffraction pattern comprises peaks at 6.52, 10.25, 19.06, 22.75, and 25.08 degrees; or (k) said co-crystal is a modafinil:L-proline co-crystal and said X-ray diffraction pattern comprises peaks at 8.53, 10.25, 19.06, 22.29, and 25.08 degrees.

50. The co-crystal according to claim 1, wherein the co-crystal is characterized by a powder X-ray diffraction pattern comprising peaks expressed in terms of 2-theta angles, wherein:

(a) said co-crystal is a modafinil:salicylic acid co-crystal and said X-ray diffraction pattern comprises peaks at 8.92, 10.85, and 17.07 degrees;

(b) said co-crystal is a modafinil:salicylic acid co-crystal and said X-ray diffraction pattern comprises peaks at 12.18, 21.24, and 23.32 degrees;

(c) said co-crystal is a modafinil:salicylic acid co-crystal and said X-ray diffraction pattern comprises peaks at 8.92, 18.81, and 25.22 degrees;

(d) said co-crystal is a modafinil:salicylic acid co-crystal and said X-ray diffraction pattern comprises peaks at 8.92 and 10.85 degrees;

(e) said co-crystal is a modafinil:salicylic acid co-crystal and said X-ray diffraction pattern comprises peaks at 17.07 and 21.24 degrees;

(f) said co-crystal is a modafinil:salicylic acid co-crystal and said X-ray diffraction pattern comprises peaks at 23.32 and 25.22 degrees;

(g) said co-crystal is a modafinil:salicylic acid co-crystal and said X-ray diffraction pattern comprises a peak at 8.92 degrees;

(h) said co-crystal is a modafinil:salicylic acid co-crystal and said X-ray diffraction pattern comprises a peak at 10.85 degrees;

(i) said co-crystal is a modafinil:salicylic acid co-crystal and said X-ray diffraction pattern comprises a peak at 21.24 degrees;

(j) said co-crystal is a modafinil:salicylic acid co-crystal and said X-ray diffraction pattern comprises peaks at 8.92, 12.18, 17.07, 21.24, and 23.32 degrees; or (k) said co-crystal is a modafinil:salicylic acid co-crystal and said X-ray diffraction pattern comprises peaks at 10.85, 14.04, 21.24, and 23.32 degrees.

51. The co-crystal according to claim 1, wherein the co-crystal is characterized by a powder X-ray diffraction pattern comprising peaks expressed in terms of 2-theta angles, wherein:

(a) said co-crystal is a modafinil:lauric acid co-crystal and said X-ray diffraction pattern comprises peaks at 3.12, 6.55, and 10.24 degrees;

(b) said co-crystal is a modafinil:lauric acid co-crystal and said X-ray diffraction pattern comprises peaks at 6.55, 13.97, and 17.62 degrees;

(c) said co-crystal is a modafinil:lauric acid co-crystal and said X-ray diffraction pattern comprises peaks at 3.12, 21.38, and 23.81 degrees;

(d) said co-crystal is a modafinil:lauric acid co-crystal and said X-ray diffraction pattern comprises peaks at 3.12 and 6.55 degrees;

(e) said co-crystal is a modafinil:lauric acid co-crystal and said X-ray diffraction pattern comprises peaks at 10.24 and 17.62 degrees;

(f) said co-crystal is a modafinil:lauric acid co-crystal and said X-ray diffraction pattern comprises peaks at 21.38 and 23.81 degrees;

(g) said co-crystal is a modafinil:lauric acid co-crystal and said X-ray diffraction pattern comprises a peak at 3.12 degrees;

(h) said co-crystal is a modafinil:lauric acid co-crystal and said X-ray diffraction pattern comprises a peak at 6.55 degrees;

(i) said co-crystal is a modafinil:lauric acid co-crystal and said X-ray diffraction pattern comprises a peak at 21.38 degrees;

(j) said co-crystal is a modafinil:lauric acid co-crystal and said X-ray diffraction pattern comprises peaks at 3.12, 10.24, 16.40, 19.02, and 21.38 degrees; or (k) said co-crystal is a modafinil:lauric acid co-crystal and said X-ray diffraction pattern comprises peaks at 3.12, 6.55, 10.24, 21.38, and 23.81 degrees.

52. The co-crystal according to claim 1, wherein the co-crystal is characterized by a powder X-ray diffraction pattern comprising peaks expressed in terms of 2-theta angles, wherein:

(a) said co-crystal is a modafinil:L-malic acid co-crystal and said X-ray diffraction pattern comprises peaks at 4.62, 9.32, and 19.30 degrees;

(b) said co-crystal is a modafinil:L-malic acid co-crystal and said X-ray diffraction pattern comprises peaks at 9.32, 10.32, and 21.48 degrees;

(c) said co-crystal is a modafinil:L-malic acid co-crystal and said X-ray diffraction pattern comprises peaks at 19.30, 21.48, and 24.26 degrees;

(d) said co-crystal is a modafinil:L-malic acid co-crystal and said X-ray diffraction pattern comprises peaks at 4.62 and 9.32 degrees;

(e) said co-crystal is a modafinil:L-malic acid co-crystal and said X-ray diffraction pattern comprises peaks at 9.32 and 10.32 degrees;

(f) said co-crystal is a modafinil:L-malic acid co-crystal and said X-ray diffraction pattern comprises peaks at 19.30 and 21.48 degrees;

(g) said co-crystal is a modafinil:L-malic acid co-crystal and said X-ray diffraction pattern comprises a peak at 4.62 degrees;

(h) said co-crystal is a modafinil:L-malic acid co-crystal and said X-ray diffraction pattern comprises a peak at 9.32 degrees;

(i) said co-crystal is a modafinil:L-malic acid co-crystal and said X-ray diffraction pattern comprises a peak at 19.30 degrees;

(j) said co-crystal is a modafinil:L-malic acid co-crystal and said X-ray diffraction pattern comprises peaks at 4.62, 15.83, 17.38, 19.30, and 21.48 degrees; or (k) said co-crystal is a modafinil:L-malic acid co-crystal and said X-ray diffraction pattern comprises peaks at 9.32, 10.32, 17.38, 19.30, 21.48, and 24.26 degrees.

53. Form VII modafinil as characterized by a powder X-ray diffraction pattern comprising peaks expressed in terms of 2-theta angles, characterized by any one, any two, any three, any four, any five, or any six or more of the peaks in the following figure including, but not limited to, 5.47, 9.99, 15.73, 17.85, 18.77, 20.05, 21.23, 22.05, 23.15, and 25.13 degrees.

* * * * *

UNITED STATES PATENT AND TRADEMARK OFFICE
CERTIFICATE OF CORRECTION

| | | |
|---|---|---|
| PATENT NO. | : 7,566,805 B2 | Page 1 of 1 |
| APPLICATION NO. | : 10/570405 | |
| DATED | : July 28, 2009 | |
| INVENTOR(S) | : Hickey et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 146 days.

Signed and Sealed this
Twenty-second Day of November, 2011

David J. Kappos
*Director of the United States Patent and Trademark Office*